United States Patent
Wadamoto

(10) Patent No.: US 12,071,396 B2
(45) Date of Patent: Aug. 27, 2024

(54) METHOD FOR PREPARING AROMATIC AMINO ACID DERIVATIVE

(71) Applicant: Chugai Seiyaku Kabushiki Kaisha, Tokyo (JP)

(72) Inventor: Manabu Wadamoto, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 406 days.

(21) Appl. No.: 17/437,535

(22) PCT Filed: Mar. 13, 2020

(86) PCT No.: PCT/JP2020/011012
§ 371 (c)(1),
(2) Date: Sep. 9, 2021

(87) PCT Pub. No.: WO2020/189540
PCT Pub. Date: Sep. 24, 2020

(65) Prior Publication Data
US 2022/0144762 A1  May 12, 2022

(30) Foreign Application Priority Data

Mar. 15, 2019 (JP) ................. 2019-048394
May 27, 2019 (JP) ................. 2019-098657
Sep. 30, 2019 (JP) ................. 2019-178503
Dec. 6, 2019 (JP) ................. 2019-221297

(51) Int. Cl.
| | |
|---|---|
| C07C 269/06 | (2006.01) |
| C07D 209/48 | (2006.01) |
| C07D 213/55 | (2006.01) |
| C07D 239/26 | (2006.01) |
| C07D 263/18 | (2006.01) |

(52) U.S. Cl.
CPC .......... *C07C 269/06* (2013.01); *C07D 209/48* (2013.01); *C07D 213/55* (2013.01); *C07D 239/26* (2013.01); *C07D 263/18* (2013.01); *C07C 2603/18* (2017.05)

(58) Field of Classification Search
None
See application file for complete search history.

(56) References Cited

U.S. PATENT DOCUMENTS

| | | |
|---|---|---|
| 4,859,736 A | 8/1989 | Rink |
| 5,057,415 A | 10/1991 | Schuetz et al. |
| 5,059,679 A | 10/1991 | Yajima et al. |
| 7,288,372 B2 | 10/2007 | Olejnik et al. |
| 7,439,222 B2 | 10/2008 | Guinn et al. |
| 8,518,666 B2 | 8/2013 | Wang et al. |
| 8,809,280 B2 | 8/2014 | Strom et al. |
| 9,133,245 B2 | 9/2015 | Gao et al. |
| 9,409,952 B2 | 8/2016 | Kariyuki et al. |
| 9,701,993 B2 | 7/2017 | Suga et al. |
| 10,711,268 B2 | 7/2020 | Murakami et al. |
| 10,815,489 B2 | 10/2020 | Ohta et al. |
| 11,492,369 B2 | 11/2022 | Nomura et al. |
| 11,542,299 B2 | 1/2023 | Nomura et al. |
| 11,732,002 B2 | 8/2023 | Iwasaki et al. |
| 11,787,836 B2 | 10/2023 | Nomura et al. |
| 11,891,457 B2 | 2/2024 | Kariyuki et al. |
| 2003/0219780 A1 | 11/2003 | Olejnik et al. |
| 2005/0165217 A1 | 7/2005 | Guinn et al. |
| 2008/0044854 A1 | 2/2008 | Wang et al. |
| 2008/0221303 A1 | 9/2008 | Katzhendler et al. |
| 2010/0137561 A1 | 6/2010 | Chen |
| 2010/0292435 A1 | 11/2010 | Chen et al. |
| 2013/0035296 A1 | 2/2013 | Strom et al. |
| 2013/0217599 A1 | 8/2013 | Suga et al. |
| 2014/0194369 A1 | 7/2014 | Gao et al. |
| 2015/0080549 A1 | 3/2015 | Kariyuki et al. |
| 2016/0272964 A1 | 9/2016 | Murakami et al. |
| 2016/0311858 A1 | 10/2016 | Kariyuki et al. |
| 2018/0127761 A1 | 5/2018 | Ohta et al. |
| 2019/0338050 A1 | 11/2019 | Nakano et al. |
| 2020/0040372 A1 | 2/2020 | Tanaka et al. |
| 2020/0131669 A1 | 4/2020 | Muraoka et al. |
| 2020/0277327 A1 | 9/2020 | Nomura et al. |
| 2020/0339623 A1 | 10/2020 | Nomura et al. |
| 2021/0061860 A1 | 3/2021 | Kariyuki et al. |
| 2021/0087572 A1 | 3/2021 | Ohta et al. |
| 2022/0017456 A1 | 1/2022 | Ishizawa |
| 2022/0024972 A1 | 1/2022 | Iwasaki et al. |
| 2022/0205009 A1 | 6/2022 | Shinohara et al. |
| 2022/0411462 A1 | 12/2022 | Hou et al. |
| 2023/0026641 A1 | 1/2023 | Nomura et al. |
| 2023/0056969 A1 | 2/2023 | Kondo et al. |

(Continued)

FOREIGN PATENT DOCUMENTS

| | | |
|---|---|---|
| EP | 1277755 A1 | 1/2003 |
| EP | 1424395 A1 | 6/2004 |

(Continued)

OTHER PUBLICATIONS

U.S. Appl. No. 14/368,564, filed Jun. 25, 2014, Kariyuki et al.
U.S. Appl. No. 15/166,550, filed May 27, 2016, Kariyuki et al.
U.S. Appl. No. 15/557,532, filed Sep. 12, 2017, Ohta et al.
U.S. Appl. No. 16/081,522, filed Jul. 8, 2019, Nakano et al.
U.S. Appl. No. 16/479,736, filed Jul. 22, 2019, Tanaka et al.
U.S. Appl. No. 16/619,388, filed Dec. 4, 2019, Nomura et al.
U.S. Appl. No. 16/771,335, filed Jun. 10, 2020, Nomura et al.

(Continued)

*Primary Examiner* — Zinna Northington Davis

(74) *Attorney, Agent, or Firm* — Nixon & Vanderhye P.C.

(57) ABSTRACT

The present invention provides methods of efficiently producing various optically active aromatic amino acid derivatives by reacting, using an additive, a specific ester compound with an aromatic halide and zinc in the presence of a catalyst. The present invention also provides amino acid derivatives that can be produced by the methods.

31 Claims, No Drawings

(56) References Cited

U.S. PATENT DOCUMENTS

| | | |
|---|---|---|
| 2023/0108274 A1 | 4/2023 | Kagotani et al. |
| 2023/0138226 A1 | 5/2023 | Nomura et al. |
| 2023/0151060 A1 | 5/2023 | Tanada et al. |
| 2023/0295221 A1 | 9/2023 | Iwasaki et al. |
| 2023/0303619 A1 | 9/2023 | Iwasaki et al. |
| 2023/0406879 A1 | 12/2023 | Nomura et al. |
| 2024/0052340 A1 | 2/2024 | Nishimura et al. |
| 2024/0067674 A1 | 2/2024 | Sekita et al. |

FOREIGN PATENT DOCUMENTS

| | | |
|---|---|---|
| EP | 1964916 A1 | 9/2008 |
| EP | 2088202 A1 | 8/2009 |
| EP | 2141175 A1 | 1/2010 |
| EP | 2177533 A1 | 4/2010 |
| EP | 2380596 A1 | 10/2011 |
| EP | 2492344 A1 | 8/2012 |
| EP | 2610348 A1 | 7/2013 |
| EP | 2615455 A1 | 7/2013 |
| EP | 2088202 B1 | 8/2013 |
| EP | 2647720 A1 | 10/2013 |
| EP | 2813512 A1 | 12/2014 |
| EP | 2492344 B1 | 4/2016 |
| EP | 3031915 A1 | 6/2016 |
| EP | 2141175 B1 | 7/2016 |
| EP | 3031915 B1 | 3/2019 |
| EP | 2813512 B1 | 3/2021 |
| JP | S57159747 A | 10/1982 |
| JP | S60169451 A | 9/1985 |
| JP | S62289 A | 1/1987 |
| JP | S62143698 A | 6/1987 |
| JP | S63260946 A | 10/1988 |
| JP | H01222795 A | 9/1989 |
| JP | H01250396 A | 10/1989 |
| JP | H0259146 B2 | 12/1990 |
| JP | H0681759 B2 | 10/1994 |
| JP | 2513775 B2 | 7/1996 |
| JP | 2001048866 A | 2/2001 |
| JP | 2003508408 A | 3/2003 |
| JP | 2003551199 A | 10/2003 |
| JP | 2005095013 A | 4/2005 |
| JP | 2007319064 A | 12/2007 |
| JP | 2008125396 A | 6/2008 |
| JP | 2009096791 A | 5/2009 |
| JP | 2009528824 A | 8/2009 |
| JP | 4490663 B2 | 6/2010 |
| JP | 4502293 B2 | 7/2010 |
| JP | 2011139667 A | 7/2011 |
| JP | 2012506909 A | 3/2012 |
| JP | 2012510486 A | 5/2012 |
| JP | 2012525348 A | 10/2012 |
| JP | 5200241 B2 | 6/2013 |
| JP | 5592893 B2 | 9/2014 |
| JP | 5808882 B2 | 11/2015 |
| JP | 2018509172 A | 4/2018 |
| WO | WO-9831700 A1 | 7/1998 |
| WO | WO-0181325 A2 | 11/2001 |
| WO | WO-02085923 A2 | 10/2002 |
| WO | WO-03014354 A1 | 2/2003 |
| WO | WO-03068990 A1 | 8/2003 |
| WO | WO-03089454 A2 | 10/2003 |
| WO | WO-2005063791 A2 | 7/2005 |
| WO | WO-2007066627 A1 | 6/2007 |
| WO | WO-2007103307 A2 | 9/2007 |
| WO | WO-2007120614 A2 | 10/2007 |
| WO | WO-2008117833 A1 | 10/2008 |
| WO | WO-2010053050 A1 | 5/2010 |
| WO | WO2010062590 A2 | 6/2010 |
| WO | WO-2010063604 A1 | 6/2010 |
| WO | WO-2010125079 A2 | 11/2010 |
| WO | WO-2011049157 A1 | 4/2011 |
| WO | WO-2011051692 A1 | 5/2011 |
| WO | WO-2011058122 A1 | 5/2011 |
| WO | WO-2012026566 A1 | 3/2012 |
| WO | WO-2012033154 A1 | 3/2012 |
| WO | WO-2012074130 A1 | 6/2012 |
| WO | WO-2012122059 A1 | 9/2012 |
| WO | WO-2013100132 A1 | 7/2013 |
| WO | WO-2014033466 A1 | 3/2014 |
| WO | WO-2014181888 A1 | 11/2014 |
| WO | WO-2015019192 A2 | 2/2015 |
| WO | WO-2015019999 A1 | 2/2015 |
| WO | WO-2015155676 A1 | 10/2015 |
| WO | WO2015179434 A1 | 11/2015 |
| WO | WO-2015185162 A1 | 12/2015 |
| WO | WO-2016115168 A1 | 7/2016 |
| WO | WO-2016148044 A1 | 9/2016 |
| WO | WO-2016154675 A1 | 10/2016 |
| WO | WO-2017150732 A1 | 9/2017 |
| WO | WO-2017181061 A1 | 10/2017 |
| WO | WO-2018100561 A1 | 6/2018 |
| WO | WO-2018143145 A1 | 8/2018 |
| WO | WO-2018225851 A1 | 12/2018 |
| WO | WO-2018225864 A1 | 12/2018 |
| WO | WO-2019117274 A1 | 6/2019 |
| WO | WO-2020095983 A1 | 5/2020 |
| WO | WO-2020111238 A1 | 6/2020 |
| WO | WO-2020122182 A1 | 6/2020 |
| WO | WO-2020138336 A1 | 7/2020 |

OTHER PUBLICATIONS

U.S. Appl. No. 17/011,815, filed Sep. 3, 2020, Kariyuki et al.
U.S. Appl. No. 17/024,944, filed Sep. 18, 2020, Ohta et al.
U.S. Appl. No. 17/291,099, filed Jun. 3, 2021, Ishizawa.
U.S. Appl. No. 17/297,231, filed May 26, 2021, Iwasaki et al.
U.S. Appl. No. 17/312,296, filed Jun. 9, 2021, Muraoka et al.
U.S. Appl. No. 17/417,822, filed Jun. 24, 2021, Shinohara et al.
Afonso, A., et al., "Solid-Phase Synthesis of Biaryl Cyclic Peptides Containing a 3-Aryltyrosine," European Journal of Organic Chemistry, 2012(31):6204-6211 (2012).
Alakhov, Y.B., et al., "Butylation of the Tryptophan Indole Ring: A Side Reaction During the Removal of t-butyloxycarbonyl and t-butyl Protecting Groups in Peptide Synthesis," Journal of the Chemical Society D: Chemical Communications, 7:406b-407 (1970).
Albericio, F., et al., "Fmoc Methodology: Cleavage from the Resin and Final Deprotection," Amino Acids, Peptides and Proteins in Organic Chemistry, 3:349-369 (2011).
Alex, A., et al., "Intramolecular Hydrogen Bonding to Improve Membrane Permeability and Absorption in Beyond Rule of Five Chemical Space," Medicinal Chemistry Communication, 2(7):669-674 (2011).
Alvaro, et al., "A Novel Activity of Immobilized Penicillin G Acylase: Removal of Benzyloxycarbonyl Amino Protecting Group," Biocatalysis and Biotransformation, 18(3):253-258 (2000).
Bastiaans, et al., "Flexible and Convergent Total Synthesis of Cyclotheonamide B," The Journal of Organic Chemistry, 62(12):3880-3889 (1997).
Beck, J.G., et al., "Intestinal Permeability of Cyclic Peptides: Common Key Backbone Motifs Identified," Journal of the American Chemical Society, 134(29):12125-12133 (2012).
Behrendt, R., et al., "Advances in Fmoc Solid-Phase Peptide Synthesis," Journal of Peptide Science, 22(1):4-27 (2016).
Bock, J.E., et al., "Getting in Shape: Controlling Peptide Bioactivity and Bioavailability Using Conformational Constraints," ACS Chemical Biology, 8(3):488-499 (2013).
Bockus, A.T., et al., "Form and Function in Cyclic Peptide Natural Products: A Pharmacokinetic Perspective," Current Topics in Medicinal Chemistry, 13(7):821-836 (2013).
Bolek, S. and Ignatowska, J., "Ring opening reactions of cyclic sulfamidates. Synthesis of β-fluoroaryl alanines and derivatives of 4,4-difluoroglutamic acid," Journal of Fluorine Chemistry, 27:13-21 (2019).
Brunner, J., "Biosynthetic Incorporation of Non-natural Amino Acids into Proteins," Chemical Society Reviews, 22(3):183-189 (1993).
Burkholder, T. P., et al., "Acid-catalyzed O-allylation of β-Hydroxy-α-Amino Acids: An Entry into Conformationally Constrained Dipeptide Surrogates," Bioorganic & Medicinal Chemistry Letters, 2(6):579-582 (1992).

(56) References Cited

OTHER PUBLICATIONS

Carpino, L.A., et al., "Dramatically Enhanced N→O Acyl Migration During the Trifluoroacetic Acid-based Deprotection Step in Solid Phase Peptide Synthesis," Tetrahedron Letters, 46(8):1361-1364 (2005).
Chatterjee, J., et al., "N-Methylation of Peptides: A New Perspective in Medicinal Chemistry," Accounts of Chemical Research, 41(10):1331-1342 (2008).
Chen, C.C., et al., "A Mild Removal of Fmoc Group Using Sodium Azide," Amino Acids, 46(2):367-374 (2014).
Chen, J.F., et al., "Effect of Alanine-293 Replacement on the Activity, ATP Binding, and Editing of *Escherichia coli* Leucyl-tRNA Synthetase," Biochemistry, 40(5):1144-1149 (2001).
Chen, S., et al., "Structurally Diverse Cyclisation Linkers Impose Different Backbone Conformations in Bicyclic Peptides," Chembiochem, 13(7):1032-1038 (2012).
Cox, A.D., et al., "Drugging the Undruggable RAS: Mission possible?," Nature Reviews Drug Discovery, 13(11):828-851 (2014).
Creighton, C.J., et al., "Mechanistic Studies of an Unusual Amide Bond Scission," Journal of the American Chemical Society, 121(29):6786-6791 (1999).
Cudic, M. and Fields, G.B., "Solid-Phase Peptide Synthesis," Molecular Biomethods Handbook, 515-546 (2008).
Cusack, S., et al., "The 2 A Crystal Structure of Leucyl-tRNA Synthetase and Its Complex With a Leucyl-Adenylate Analogue," The EMBO Journal, 19(10):2351-2361 (2000).
Dailler, et al., "Divergent Synthesis of Aeruginosas Based on a C(sp(3))-H Activation Strategy," Chemistry, 21(26):9370-9379 (2015).
Dawson, P.E., et al., "Synthesis of Proteins by Native Chemical Ligation," Science, 266(5186):776-779 (1994).
Doi, Y., et al., "Elongation Factor Tu Mutants Expand Amino Acid Tolerance of Protein Biosynthesis System," Journal of the American Chemical Society, 129(46):14458-14462 (2007).
Doublie, S., et al., "Tryptophanyl-tRNA Synthetase Crystal Structure Reveals an Unexpected Homology to Tyrosyl-tRNA Synthetase," Structure, 3(1):17-31 (1995).
Eberhard, H. and Seitz, O., "N—O-Acyl Shift in Fmoc-Based Synthesis of Phosphopeptides," Organic & Biomolecular Chemistry, 6(8):1349-1355 (2008).
Fang, W.J., et al., "Deletion of Ac-NMePhe(1) from [NMePhe(1)]arodyn Under Acidic Conditions, Part 1: Effects of Cleavage Conditions and N-terminal Functionality," Biopolymers 96(1):97-102 (2011).
Frankel, A., et al., "Encodamers: Unnatural Peptide Oligomers Encoded in RNA," Chemistry & Biology, 10(11):1043-1050 (2003).
Fujii, N., et al., "Trimethylsilyl Trifluoromethanesulphonate as a Useful Deprotecting Reagent in Both Solution and Solid Phase Peptide Syntheses," Journal of the Chemical Society, 4:274-275 (1987).
Fujino, M., et al., "Further Studies on the Use of Multi-substituted Benzenesulfonyl Groups for Protection of the Guanidino Function of Arginine," Chemical and Pharmaceutical Bulletin, 29(10):2825-2831 (1981).
Fujino, T., et al., "Reevaluation of the D-Amino Acid Compatibility With the Elongation Event in Translation," Journal of the American Chemical Society, 135(5):1830-1837 (2013).
Fujino, T., et al., "Ribosomal Synthesis of Peptides with Multiple beta-Amino Acids," Journal of the American Chemical Society, 138(6):1962-1969 (2016).
Fukai, S., et al., "Mechanism of Molecular Interactions for tRNA(Val) Recognition by Valyl-tRNA Synthetase," RNA, 9(1):100-111 (2003).
Fukai, S., et al., "Structural Basis for Double-Sieve Discrimination of L-Valine From L-Isoleucine and L-Threonine by the Complex of tRNA(Val) and Valyl-tRNA Synthetase," Cell, 103(5):793-803 (2000).
Fukunaga, R. and Yokoyama, S., "Structural Basis for Non-Cognate Amino Acid Discrimination by the Valyl-tRNA Synthetase Editing Domain," The Journal of Biological Chemistry, 280(33):29937-29945 (2005).

Ganesan, A., "The Impact of Natural Products Upon Modern Drug Discovery," Current Opinion in Chemical Biology, 12(3):306-317 (2008).
GenBank, "Valine-tRNA ligase [Thermus thermophilus]," Accession No. P96142, accessed on Jan. 27, 2021.
Gilon, C., et al., "Backbone Cyclization: A New Method for Conferring Conformational Constraint on Peptides," Biopolymers, 31(6):745-750 (1991).
Goto, et al., "Ribosomal Synthesis of Combinatorial Polypeptides Containing Unusual Amino Acid Blocks," Kagaku Kogyo, 58(4):255-262 (2007).
Goto, Y. and Suga, H., "Translation Initiation With Initiator tRNA Charged With Exotic Peptides," Journal of the American Chemical Society, 131(14):5040-5041 (2009).
Goto, Y., et al., "Flexizymes for Genetic Code Reprogramming," Nature Protocols, 6(6):779-790 (2011).
Gravestock, et al., "Novel branched isocyanides as useful building blocks in the Passerini-amine deprotection-acyl migration (PADAM) synthesis of potential HIV-1 protease inhibitors," Tetrahedron Letters, 53(26):3225-3229 (2012).
Grosjean, H. and Bjork, G.R., "Enzymatic Conversion of Cytidine to Lysidine in Anticodon of Bacterial Isoleucyl-tRNA-an Alternative Way of RNA Editing," Trends in Biochemical Sciences, 29(4):165-168 (2004).
Hartman, M.C.T., et al., "An Expanded Set of Amino Acid Analogs for the Ribosomal Translation of Unnatural Peptides," PLoS One, 2(10):e972 (2007).
Hartman, M.C.T., et al., "Enzymatic Aminoacylation of tRNA With Unnatural Amino Acids," Proceedings of the National Academy of Sciences of the United States of America, 103(12):4356-4361 (2006).
Hayashi, G., et al., "Ribosomal Synthesis of Nonstandard Cyclic Peptides and Its Application to Drug Discovery," The Journal of Japanese Biochemical Society, 82(6):505-514 (2010).
Hecht, S.M., et al., ""Chemical Aminoacylation" of tRNA's," The Journal of Biological Chemistry, 253(13):4517-4520 (1978).
Heinis, C., et al., "Phage-Encoded Combinatorial Chemical Libraries Based on Bicyclic Peptides," Nature Chemical Biology, 5(7):502-507 (2009).
Higuchi, T. and Suga, H., "Programmed Synthesis of Natural Product-Like Non-Standard Peptides Using the Translation System and Its Application," Journal of Synthetic Organic Chemistry, 68(3):217-227 (2010).
Hoogenboom, H.R., "Selecting and Screening Recombinant Antibody Libraries," Nature Biotechnology, 23(9):1105-1116 (2005).
Hountondji, C., et al., "Crucial Role of Conserved Lysine 277 in the Fidelity of tRNA Aminoacylation by *Escherichia coli* Valyl-tRNA Synthetase," Biochemistry, 41(50):14856-14865 (2002).
Hountondji, C., et al., "Valyl-tRNA Synthetase From *Escherichia coli* MALDI-MS Identification of the Binding Sites for L-Valine or for Noncognate Amino Acids Upon Qualitative Comparative Labeling With Reactive Amino-Acid Analogs," European Journal of Biochemistry, 267(15):4789-4798 (2000).
Hruby, V.J., et al., "Emerging Approaches in the Molecular Design of Receptor-Selective Peptide Ligands: Conformational, Topographical and Dynamic Considerations," The Biochemical Journal, 268(2):249-262 (1990).
Ikeuchi, Y., et al., "Agmatine-conjugated Cytidine in a tRNA Anticodon Is Essential for AUA Decoding in Archaea," Nature Chemical Biology, 6(4):277-282 (2010).
Ikeuchi, Y., et al., "Molecular Mechanism of Lysidine Synthesis That Determines tRNA Identity and Codon Recognition," Molecular Cell, 19(2):235-246 (2005).
Isidro-Llobet, A., et al., "Amino Acid-Protecting Groups," Chemical Reviews, 109(6):2455-2504 (2009).
Itoh, Y., et al., "Crystallographic and Mutational Studies of Seryl-tRNA Synthetase From the Archaeon Pyrococcus Horikoshii," RNA Biology, 5(3):169-177 (2008).
Iwane, Y., et al., "Expanding the Amino Acid Repertoire of Ribosomal Polypeptide Synthesis via the Artificial Division of Codon Boxes," Nature Chemistry, 8(4):317-325 (2016).

(56) References Cited

OTHER PUBLICATIONS

Jaradat, D.M.M., "Thirteen Decades of Peptide Synthesis: Key Developments in Solid Phase Peptide Synthesis and Amide Bond Formation Utilized in Peptide Ligation," Amino Acids, 50(1):39-68 (2018).
Jones, A.B., et al., "A Formal Synthesis of FK-506. Exploration of Some Alternatives to Macrolactamization," The Journal of Organic Chemistry, 55(9):2786-2797 (1990).
Josephson, K., et al., "mRNA Display: From Basic Principles to Macrocycle Drug Discovery," Drug Discovery Today, 19(4):388-399 (2014).
Josephson, K., et al., "Ribosomal Synthesis of Unnatural Peptides," Journal of the American Chemical Society, 127(33):11727-11735 (2005).
Kato, et al., Yakubutsutaishagaku. 2nd edition, pp. 9-13 (2000).
Kato, et al., Yakubutsutaishagaku. 3rd edition, pp. 43-46 (2010).
Katoh, T., et al., "Ribosomal Synthesis of Backbone Macrocyclic Peptides," Chemical Communications, 47(36):9946-9958 (2011).
Kawakami, T. and Aimoto, S., "Sequential Peptide Ligation by Using a Controlled Cysteinyl Prolyl Ester (CPE) Autoactivating Unit," Tetrahedron Letters, 48(11):1903-1905 (2007).
Kawakami, T., et al., "Diverse Backbone-Cyclized Peptides via Codon Reprogramming," Nature Chemical Biology, 5(12):888-890 (2009).
Kawakami, T., et al., "In Vitro Selection of Multiple Libraries Created by Genetic Code Reprogramming to Discover Macrocyclic Peptides That Antagonize VEGFR2 Activity in Living Cells," ACS Chemical Biology, 8(6):1205-1214 (2013).
Kawakami, T., et al., "Incorporation of Electrically Charged N-alkyl Amino Acids Into Ribosomally Synthesized Peptides via Posttranslational Conversion," Chemical Science, 5(3):887-893 (2014).
Kawakami, T., et al., "Messenger RNA-Programmed Incorporation of Multiple N-Methyl-Amino Acids Into Linear and Cyclic Peptides," Chemistry & Biology, 15(1):32-42 (2008).
Kawakami, T., et al., "Ribosomal Synthesis of Polypeptoids and Peptoid-Peptide Hybrids," Journal of the American Chemical Society, 130(50):16861-16863 (2008).
Kiho, T., et al., "Total Synthesis of Pleofugin A, a Potent Inositol Phosphorylceramide Synthase Inhibitor," Organic Letters, 20(15):4637-4640 (2018).
Kleineweischede, R. and Hackenberger, C.P., "Chemoselective Peptide Cyclization by Traceless Staudinger Ligation," Angewandte Chemie (International ed. in English), 47(32):5984-5988 (2008).
Kobayashi, T., et al., "Recognition of Non-Alpha-Amino Substrates by pyrrolysyl-tRNA Synthetase," Journal of Molecular Biology, 385(5):1352-1360 (2009).
Kopina, B.J. and Lauhon, C.T., "Efficient Preparation of 2,4-diaminopyrimidine Nucleosides: Total Synthesis of Lysidine and Agmatidine," Organic Letters, 14(16):4118-4121 (2012).
Kuhn, B., et al., "Intramolecular Hydrogen Bonding in Medicinal Chemistry," Journal of Medicinal Chemistry, 53(6):2601-2611 (2010).
Lajoie, M.J., et al., "Overcoming Challenges in Engineering the Genetic Code," Journal of Molecular Biology, 428(5PtB):1004-1021 (2016).
Lassak, J., et al., "Stall No More at Polyproline Stretches With the Translation Elongation Factors EF-P and IF-5A," Molecular Microbiology, 99(2):219-235 (2016).
Laufer, B., et al., "The Impact of Amino Acid Side Chain Mutations in Conformational Design of Peptides and Proteins," Chemistry, 16(18):5385-5390 (2010).
Lee, K.W. and Briggs, J.M., "Molecular Modeling Study of the Editing Active Site of *Escherichia coli* leucyl-tRNA Synthetase: Two Amino Acid Binding Sites in the Editing Domain," Proteins, 54(4):693-704 (2004).
Lejeune, V., et al., "Towards a Selective Boc Deprotection on Acid Cleavable Wang Resin," Tetrahedron Letters, 44(25):4757-4759 (2003).
Li, S., et al., "In Vitro Selection of mRNA Display Libraries Containing an Unnatural Amino Acid," Journal of the American Chemical Society, 124(34):9972-9973 (2002).
Li, X., et al., "Salicylaldehyde Ester-Induced Chemoselective Peptide Ligations: Enabling Generation of Natural Peptidic Linkages at the Serine/Threonine Sites," Organic Letters, 12(8):1724-1727 (2010).
Liniger, M., et al., "Total Synthesis and Characterization of 7-Hypoquinuclidonium Tetrafluoroborate and 7-Hypoquinuclidone BF3 Complex," Journal of the American Chemical Society, 138(3):969-974 (2016).
Liu, D.R., et al., "Engineering a tRNA and aminoacyl-tRNA Synthetase for the Site-Specific Incorporation of Unnatural Amino Acids Into Proteins in Vivo," Proceedings of the National Academy of Sciences of the United States of America, 94(19):10092-10097 (1997).
Liu, Z., et al., "N-Boc Deprotection and Isolation Method for Water-soluble Zwitterionic Compounds," The Journal of Organic Chemistry, 79(23):11792-11796 (2014).
Lodder, M., et al., "The N-Pentenoyl Protecting Group for Aminoacyl-tRNAs," Methods, 36(3):245-251 (2005).
Loos, P., et al., "Unified Azoline and Azole Syntheses by Optimized Aza☐Wittig Chemistry," European Journal of Organic Chemistry, 2013(16):3290-3315 (2013).
Lundquist, J.T. and Pelletier, J.C., "Improved Solid-Phase Peptide Synthesis Method Utilizing Alpha-Azide-Protected Amino Acids," Organic Letters, 3(5):781-783 (2001).
Luo, D., et al., "Total Synthesis of the Potent Marine-Derived Elastase Inhibitor Lyngbyastatin 7 and in Vitro Biological Evaluation in Model Systems for Pulmonary Diseases," The Journal of Organic Chemistry, 81(2):532-544 (2016).
Maini, R., et al., "Protein Synthesis With Ribosomes Selected for the Incorporation of beta-Amino Acids," Biochemistry, 54(23):3694-3706 (2015).
Maini, R., et al., "Ribosome-Mediated Synthesis of Natural Product-Like Peptides via Cell-Free Translation," Current Opinion in Chemical Biology, 34:44-52 (2016).
Malhotra, R., et al., "Efficient Asymmetric Synthesis of N-Protected-B-Aryloxyamino Acids Via Regioselective Ring Opening of Serine Sulfamidate Carboxylic Acid," Organic & Biomolecular Chemistry, 12(33):6507-6515 (2014).
Manfredini, S., et al., "Design And Synthesis of Phosphonoacetic Acid (PPA) Ester and Amide Bioisosters of Ribofuranosylnucleoside Diphosphates as Potential Ribonucleotide Reductase Inhibitors and Evaluation of Their Enzyme Inhibitory, Cytostatic and Antiviral Activity," Antiviral Chemistry and Chemotherapy, 14(4):183-194 (2003).
Mangold, S.L., et al., "Z-Selective Olefin Metathesis on Peptides: Investigation of Side-Chain Influence, Preorganization, and Guidelines in Substrate Selection," Journal of the American Chemical Society, 136(35):12469-12478 (2014).
Marcucci, E., et al., "Solid-Phase Synthesis of NMe-IB-01212, a Highly N-Methylated Cyclic Peptide," Organic Letters, 14(2):612-615 (2012).
Mas-Moruno, C., et al., "Cilengitide: The First Anti-Angiogenic Small Molecule Drug Candidate Design, Synthesis, and Clinical Evaluation," Anti-Cancer Agents in Medicinal Chemistry, 10(10):753-768 (2010).
Meinnel, T., et al., "Methionine as Translation Start Signal: A Review of the Enzymes of the Pathway in *Escherichia coli*," Biochimie, 75(12):1061-1075 (1993).
Mermershtain, I., et al., "Idiosyncrasy and Identity in the Prokaryotic Phe-system: Crystal Structure of *E. coli* phenylalanyl-tRNA Synthetase Complexed With Phenylalanine and AMP," Protein Science, 20(1):160-167 (2011).
Merryman, C. and Green, R., "Transformation of Aminoacyl tRNAs for the in Vitro Selection of "Drug-Like" Molecules," Chemistry & Biology, 11(4):575-582 (2004).
Millward, S.W., et al., "A General Route for Post-Translational Cyclization of mRNA Display Libraries," Journal of the American Chemical Society, 127(41):14142-14143 (2005).
Millward, S.W., et al., "Design of Cyclic Peptides That Bind Protein Surfaces With Antibody-Like Affinity," ACS Chemical Biology, 2(9):625-634 (2007).
Montalbetti, C.A.G.N. and Falque, V., "Amide Bond Formation and Peptide Coupling," Tetrahedron, 61(46):10827-10852 (2005).

(56) References Cited

OTHER PUBLICATIONS

Morieux, P., et al., "The Structure-Activity Relationship of the 3-Oxy Site in the Anticonvulsant (R)-N-Benzyl 2-Acetamido-3-Methoxypropionamide," Journal of Medicinal Chemistry, 53(15):5716-5726 (2010).

Muramatsu, T., et al., "A Novel Lysine-Substituted Nucleoside in The First Position of the Anticodon of Minor Isoleucine tRNA from *Escherichia coli*," The Journal of Biological Chemistry, 263(19):9261-9267 (1988).

Navo, C.D., et al., "Oxygen by Carbon Replacement at the Glycosidic Linkage Modulates the Sugar Conformation in Tn Antigen Mimics," ACS Omega, 3(12):18142-18152 (2018).

Niida, A., et al., "Investigation of the Structural Requirements of K-Ras(G12D) Selective Inhibitory Peptide KRpep-2d Using Alanine Scans and Cysteine Bridging," Bioorganic & Medicinal Chemistry Letters, 27(12):2757-2761 (2017).

Ohta, A., et al., "Synthesis of Polyester by Means of Genetic Code Reprogramming," Chemistry & Biology, 14(12):1315-1322 (2007).

Ohtsuki, T., et al., "Phototriggered Protein Syntheses by Using (7-diethylaminocoumarin-4-yl) Methoxycarbonyl-Caged Aminoacyl tRNAs," Nature communications, 7:12501 (2016).

Ohwada, T., et al., "On the Planarity of Amide Nitrogen. Intrinsic Pyramidal Nitrogen of N-acyl-7-azabicyclo[2.2.1 ]heptanes," Tetrahedron Letters, 39(8):865-868 (1998).

Orain, D., et al., "Protecting Groups in Solid-Phase Organic Synthesis," Journal of Combinatorial Chemistry, 4(1):1-16 (2002).

Osawa, T., et al., "Structural Basis of tRNA Agmatinylation Essential for AUA Codon Decoding," Nature Structural & Molecular Biology, 18(11):1275-1280 (2011).

Ostrem, J.M.L., et al., "Direct Small-Molecule Inhibitors of KRAS: From Structural Insights to Mechanism-Based Design," Nature Reviews Drug discovery, 15(11):771-785 (2016).

Ovadia, O., et al., "Improvement of Drug-Like Properties of Peptides: The Somatostatin Paradigm," Expert Opinion on Drug Discovery, 5(7):655-671 (2010).

Parthasarathy, R., et al., "Sortase A as a Novel Molecular "Stapler" for Sequence-Specific Protein Conjugation," Bioconjugate Chemistry, 18(2):469-476 (2007).

Peacock, J.R., et al., "Amino Acid-Dependent Stability of the Acyl Linkage in aminoacyl-tRNA," RNA, 20(6):758-764 (2014).

Perona, J.J. and Hadd, A., "Structural Diversity and Protein Engineering of the aminoacyl-tRNA Synthetases," Biochemistry, 51(44):8705-8729 (2012).

Peschke, B., et al., "New Highly Potent Dipeptidic Growth Hormone Secretagogues with Low Molecular Weight," European Journal of Medicinal Chemistry, 35(6):599-618 (2000).

Piszkiewicz, D., et al., "Anomalous Cleavage of Aspartyl-Proline Peptide Bonds During Amino Acid Sequence Determinations," Biochemical and Biophysical Research Communications, 40(5):1173-1178 (1970).

Rader, A.F.B., et al., "Orally Active Peptides: Is There a Magic Bullet?," Angewandte Chemie, 57(44):14414-14438 (2018).

Rafi, S.B., et al., "Predicting and Improving The Membrane Permeability of Peptidic Small Molecules," Journal of Medicinal Chemistry, 55(7):3163-3169 (2012).

Reddy, P.R., et al., "Synthesis of Small Cyclic Peptides via Intramolecular Heck Reactions," Tetrahedron Letters, 44(2):353-356 (2003).

Rezai, T., et al., "Testing the Conformational Hypothesis of Passive Membrane Permeability Using Synthetic Cyclic Peptide Diastereomers," Journal of the American Chemical Society, 128(8):2510-2511 (2006).

Rodriguez, H., et al., "A Convenient Microwave-Enhanced Solid-phase Synthesis of Short Chain N-Methyl-Rich Peptides," Journal of Peptide Science, 16(3):136-140 (2010).

Roodbeen, R., et al., "Microwave Heating in the Solid-Phase Synthesis of N-Methylated Peptides: When Is Room Temperature Better?," European Journal of Organic Chemistry, 2012(36):7106-7111 (2012).

Sakamoto, K., et al., "K-Ras(G12D)-Selective Inhibitory Peptides Generated by Random Peptide T7 Phage Display Technology," Biochemical and Biophysical Research Communications, 484(3):605-611 (2017).

Salowe, S.P., et al., "The Catalytic Flexibility of Trnaile-Lysidine Synthetase Can Generate Alternative tRNA Substrates for Isoleucyl-tRNA Synthetase," The Journal of Biological Chemistry, 284(15):9656-9662 (2009).

Samatar, A.A., et al., "Targeting RAS-ERK Signalling in Cancer: Promises and Challenges," Nature reviews. Drug Discovery, 13(12):928-942 (2014).

Sang-Aroon, W., et al., "Theoretical Study on Isomerization and Peptide Bond Cleavage at Aspartic Residue," Journal of Molecular Modeling, 19(9):3627-3636 (2013).

Sankaranarayanan, R., et al., "The Structure of threonyl-tRNA synthetase-tRNA(Thr) Complex Enlightens Its Repressor Activity and Reveals an Essential Zinc Ion in the Active Site," Cell, 97(3):371-381 (1999).

Satyanarayanajois, S.D. and Hill, R.A., "Medicinal Chemistry for 2020," Future Medicinal Chemistry, 3(14):1765-1786 (2011).

Schlippe, Y.V.G., et al., "In Vitro Selection of Highly Modified Cyclic Peptides That Act as Tight Binding Inhibitors," Journal of the American Chemical Society, 134(25):10469-10477 (2012).

Sever, S., et al., "*Escherichia coli* tryptophanyl-tRNA Synthetase Mutants Selected for Tryptophan Auxotrophy Implicate the Dimer Interface in Optimizing Amino Acid Binding," Biochemistry, 35(1):32-40 (1996).

Shimizu, Y., et al., "Cell-Free Translation Reconstituted With Purified Components," Nature Biotechnology, 19(8):751-755 (2001).

Shukla, G.S. and Krag, D.N., "Phage-Displayed Combinatorial Peptide Libraries in Fusion to Beta-Lactamase as Reporter for an Accelerated Clone Screening: Potential Uses of Selected Enzyme-Linked Affinity Reagents in Downstream Applications," Combinatorial Chemistry & High Throughput Screening, 13(1):75-87 (2010).

Sogabe, S., et al., "Crystal Structure of a Human K-Ras G12D Mutant in Complex with GDP and the Cyclic Inhibitory Peptide KRpep-2d," ACS Medicinal Chemistry Letters, 8(7):732-736 (2017).

Starosta, A.L., et al., "A Conserved Proline Triplet in Val-tRNA Synthetase and the Origin of Elongation Factor P," Cell Reports, 9(2):476-483 (2014).

Stetsenko, D.A., et al., "Removal of Acid-Labile Protecting or Anchoring Groups in the Presence of Polyfluorinated Alcohol: Application to Solid-Phase Peptide Synthesis," Russian Journal of Bioorganic Chemistry, 42(2):143-152 (2016).

Struck, A., et al., "An Enzyme Cascade for Selective Modification of Tyrosine Residues in Structurally Diverse Peptides and Proteins," Journal of the American Chemical Society, 138(9):3038-3045 (2016).

Subtelny, A.O., et al., "Optimal Codon Choice Can Improve the Efficiency and Fidelity of N-methyl Amino Acid Incorporation Into Peptides by In-Vitro Translation," Angewandte Chemie (International ed. in English), 50(14):3164-3167 (2011).

Subtelny, A.O., et al., "Ribosomal Synthesis of N-Methyl Peptides," Journal of the American Chemical Society, 130(19):6131-6136 (2008).

Suenaga, K., et al., "Aurilide, A Cytotoxic Depsipeptide From the Sea Hare *Dolabella auricularia*: Isolation, Structure Determination, Synthesis, and Biological Activity," Tetrahedron, 60(38):8509-8527 (2004).

Suenaga, K., et al., "Synthesis and Cytotoxicity of Aurilide Analogs," Bioorganic & Medicinal Chemistry Letters, 18(14):3902-3905 (2008).

Suzuki, T., et al., "Discovery and Characterization of tRNAIle Lysidine Synthetase (TilS)," FEBS Letters, 584(2):272-277 (2010).

Suzuki, T., "How to Decipher AUA Codon in Archaea," Kagaku to Seibutsu, 50(1):36-43 (2012).

Tam, J.P., et al., "Cyclohexyl Ester as a New Protecting Group for Aspartyl Peptides to Minimize Aspartimide Formation in Acidic and Basic Treatments," Tetrahedron Letters, 20(42):4033-4036 (1979).

Tan, Z., et al., "Amino Acid Backbone Specificity of the *Escherichia coli* Translation Machinery," Journal of the American Chemical Society, 126(40):12752-12753 (2004).

(56) References Cited

OTHER PUBLICATIONS

Teixido, M., et al., "Solid-Phase Synthesis and Characterization of N-Methyl-Rich Peptides," The Journal of Peptide Research, 65(2):153-166 (2005).
Terasaka, et al., "Construction of Nonstandard Peptide Library by Genetic Code Reprogramming and Bioactive Peptide Discovery," Experimental Medicine, 29(7):1063-1070 (2011).
Terasaka, N., et al., "Recent Developments of Engineered Translational Machineries for the Incorporation of Non-Canonical Amino Acids Into Polypeptides," International Journal of Molecular Sciences, 16(3):6513-6531 (2015).
Tsuda, et al., "Amino Acids, Peptides and Proteins in Organic Chemistry," 3:201-406, 495-517, 549-569 (2011).
Tsukiji, S. and Nagamune, T., "Sortase-mediated Ligation: A Gift From Gram-positive Bacteria to Protein Engineering," Chembiochem, 10(5):787-798 (2009).
Urban, J., et al., "Lability of N-alkylated Peptides Towards TFA Cleavage," International Journal of Peptide and Protein Research, 47(3):182-189 (1996).
Vaisar, T. and Urban, J., "Gas-Phase Fragmentation of Protonated Mono-n-Methylated Peptides. Analogy With Solution-Phase Acid-Catalyzed Hydrolysis," Journal of Mass Spectrometry, 33(6):505-524 (1998).
Van Der Auwera, C.V.D., et al., "Easy Cleavage of C'-Terminal Iminoacids from Peptide Acids through Acidic Hydrolysis," International Journal of Peptide and Protein Research, 31(2):186-191 (1988).
Wang, J., et al., "Kinetics of Ribosome-Catalyzed Polymerization Using Artificial Aminoacyl-tRNA Substrates Clarifies Inefficiencies and Improvements," ACS Chemical Biology, 10(10):2187-2192 (2015).
Wang, T., et al., "Revisiting Oxytocin through the Medium of Isonitriles," Journal of the American Chemical Society, 134(32):13244-13247 (2012).
Weber, F., et al., "A Potato Mitochondrial Isoleucine tRNA is Coded for by a Mitochondrial Gene Possessing a Methionine Anticodon," Nucleic Acids Research, 18(17):5027-5030 (1990).
Wells, J.A. and McClendon, C.L., "Reaching for High-Hanging Fruit in Drug Discovery at Protein-Protein Interfaces," Nature, 450(7172):1001-1009 (2007).
Wenschuh, H., et al., "Stepwise Automated Solid Phase Synthesis of Naturally Occurring Peptaibols Using FMOC Amino Acid Fluorides," The Journal of Organic Chemistry, 60(2):405-410 (1995).
Wermuth, C. G., editor, "The Practice of Medicinal Chemistry," 2nd Edition, Academic Press, pp. 52-53 (2003), English translation of Wermuth, C. G., editor, "The Practice of Medicinal Chemistry," 2nd Edition, vol. 1, p. 87 (2003).
White, C.J. and Yudin, A.K., "Contemporary Strategies for Peptide Macrocyclization," Nature Chemistry, 3(7):509-524 (2011).
White, T.R., et al., "On-Resin N-methylation of Cyclic Peptides for Discovery of Orally Bioavailable Scaffolds," Nature Chemical Biology, 7(11):810-817 (2011).
Wu, J., et al., "Intrinsic Basicity of Oligomeric Peptides that Contain Glycine, Alanine, and Valine—the Effects of the Alkyl Side Chain on Proton Transfer Reactions," Journal of the American Society for Mass Spectrometry, 6(2):91-101 (1995).
Wu, N., et al., "A Genetically Encoded Photocaged Amino Acid," Journal of the American Chemical Society, 126(44):14306-14307 (2004).
Yajima, et al., "New Strategy for the Chemical Synthesis of Proteins," Tetrahedron, 44(3):805-819 (1988).
Yamagishi, Y., et al., "Natural Product-Like Macrocyclic N-Methyl-Peptide Inhibitors Against a Ubiquitin Ligase Uncovered From a Ribosome-Expressed De Novo Library," Chemistry & Biology, 18(12):1562-1570 (2011).
Yamanoi, K., et al., "Synthesis of Trans and cis-α-(carboxycyclopropyl) Glycines Novel Neuroinhibitory Amino Acids as L-Glutamate Analogue," Tetrahedron Letters, 29(10):1181-1184 (1988).
Yanagisawa, T., et al., "Multistep Engineering of Pyrrolysyl-tRNA Synthetase to Genetically Encode N(epsilon)-(o-azidobenzyloxycarbonyl) Lysine for Site-Specific Protein Modification," Chemistry & Biology, 15(11):1187-1197 (2008).
Yang, Y., "Side Reactions in Peptide Synthesis," pp. 1-31 (2015).
Yang, Y., Side Reactions in Peptide Synthesis, pp. 246 (2016).
Yao, G., et al., "Efficient Synthesis and Stereochemical Revision of Coibamide A," Journal of American Chemical Society, 137(42):13488-13491 (2015).
Zhai, Y. and Martinis, S.A., "Two Conserved Threonines Collaborate in the *Escherichia coli* Leucyl-tRNA Synthetase Amino Acid Editing Mechanism," Biochemistry, 44(47):15437-15443 (2005).
Zhang, A.J., et al., "A Method for Removal of N-BOC Protecting Groups from Substrates on TFA-Sensitive Resins," Tetrahedron Letters, 39(41):7439-7442 (1998).
Zhang, B., et al., "Specificity of Translation for N-Alkyl Amino Acids," Journal of the American Chemical Society, 129(37):11316-11317 (2007).
Zhang, K., et al., "Ab Initio Studies of Neutral and Protonated Triglycines: Comparison of Calculated and Experimental Gas-Phase Basicity," Journal of the American Chemical Society, 116(25):11512-11521 (1994).
U.S. Appl. No. 07/251,176, filed Sep. 30, 1988, Hans-Jurgen et al.
U.S. Appl. No. 10/345,664, filed Jan. 16, 2003, Olejnik et al.
U.S. Appl. No. 11/682,272, filed Mar. 5, 2007, Wang et al.
U.S. Appl. No. 13/505,625, filed Oct. 22, 2012, Strom et al.
U.S. Appl. No. 14/125,906, filed Mar. 10, 2014, Gao et al.
U.S. Appl. No. 14/368,564, filed Jun. 25, 2014, Kariyuki et al., related application.
U.S. Appl. No. 15/166,550, filed May 27, 2016, Kariyuki et al., related application.
U.S. Appl. No. 15/557,532, filed Sep. 12, 2017, Ohta et al., related application.
U.S. Appl. No. 16/081,522, filed Jul. 8, 2019, Nakano et al., related application.
U.S. Appl. No. 16/479,736, filed Jul. 22, 2019, Tanaka et al., related application.
U.S. Appl. No. 16/619,014, filed Dec. 3, 2019, Muraoka et al.
U.S. Appl. No. 16/619,388, filed Dec. 4, 2019, Nomura et al, related application.
U.S. Appl. No. 16/771,335, filed Jun. 10, 2020, Nomura et al., related application.
U.S. Appl. No. 17/011,815, filed Sep. 3, 2020, Kariyuki et al., related application.
U.S. Appl. No. 17/024,944, filed Sep. 18, 2020, Ohta et al., related application.
U.S. Appl. No. 17/291,099, filed Jun. 3, 2021, Ishizawa, related application.
U.S. Appl. No. 17/297,231, filed May 26, 2021, Iwasaki et al., related application.
U.S. Appl. No. 17/312,296, filed Jun. 9, 2021, Muraoka et al., related application.
U.S. Appl. No. 17/417,822, filed Jun. 24, 2021, Shinohara et al., related application.
Cornella, J., et al., "Practical Ni-Catalyzed Aryl-Alkyl Cross-Coupling of Secondary Redox-Active Esters," J Am Chem Soc., 138:2174-2177 (2016).
Gracia, S. R., et al., "Synthesis of chemically modified bioactive peptides: recent advances, challenges and developments for medicinal chemistry," Future Med Chem., 1(7):1289-1310 (2009).
Huihui, K. M. M., et al., "Decarboxylative Cross-Electrophile Coupling of N-Hydroxyphthalimide Esters with Aryl Iodides," J Am Chem Soc., 138(15):5016-5019 (2016).
Lenzi, A., et al., "Synthesis of N-Boc-α-amino acids with nucleobase residues as building blocks for the preparation of chiral PNA (peptidic nucleic acids)," Tetrahedron Letters, 36(10):1713-1716 (1995).
Li, H., et al., "Ni-Catalyzed Electrochemical Decarboxylative C—C Couplings in Batch and Continuous Flow," Org Lett., 20:1338-1341 (2018).
Miyake, A., et al., "Design and Synthesis of N-[N-(S)-1-Ethoxycarbonyl-3-pheylpropyl]-L-alanyl]-N-(indan-2-yl)glycine (CV-3317), a New, Potent Angiotensin Converting Enzyme Inhibitor," Chem Pharm Bull., 34(7):2852-2858 (1986).

(56) References Cited

OTHER PUBLICATIONS

Murashige, R., et al., "Asymmetric and efficient synthesis of homopheylalanine derivatives via Friedel-Crafts reaction with trifluoromethanesulfonic acid," Tetrahedron Letters, 49(46):6566-6568 (2008).
Toriyama, F., et al., "Redox-Active Esters in Fe-Catalyzed C—C Coupling," J Am Chem Soc., 138(35):11132-11135 (2016).
Wang, S., et al., "Iridium/f-Amphox-Catalyzed Asymmetric Hydrogenation of Styrylglyoxylamides," Synlett., 29(16):2203-2207 (2018).
Watanabe, E., et al., "A Practical Method for Continuous Production of sp3-rich Compounds from (Hetero) Aryl Halides and Redox-Active Esters," Chem Eur J., 26:186-191 (2020).
U.S. Appl. No. 16/619,014, filed Dec. 3, 2019, Muraoka et al., related application.
U.S. Appl. No. 17/773,733, filed May 2, 2022, Tanada et al., related application.
U.S. Appl. No. 17/773,734, filed May 2, 2022, Nomura et al., related application.
U.S. Appl. No. 17/738,283, filed May 6, 2022, Hou et al., related application.
U.S. Appl. No. 17/788,506, filed Jun. 23, 2022, Kondo et al., related application.
U.S. Appl. No. 17/787,809, filed Jun. 21, 2022, Kagotani et al., related application.
U.S. Appl. No. 17/976,942, filed Oct. 31, 2022, Nomura et al., related application.
U.S. Appl. No. 17/928,759, filed Nov. 30, 2022, Iwasaki et al., related application.
U.S. Appl. No. 18/010,608, filed Dec. 15, 2022, Nishimura et al., related application.
U.S. Appl. No. 18/203,371, filed May 30, 2023, Iwasaki et al., related application.
U.S. Appl. No. 18/268,737, filed Jun. 21, 2023, Morita et al., related application.
U.S. Appl. No. 18/269,334, filed Jun. 23, 2023, Sekita et al., related application.
U.S. Appl. No. 18/459,998, filed Sep. 1, 2023, Nomura et al., related application.
U.S. Appl. No. 18/460,300, filed Sep. 1, 2023, Kariyuki et al., related application.
U.S. Appl. No. 18/289,451, filed Nov. 3, 2023, Tanada et al., related application.
U.S. Appl. No. 18/289,592, filed Nov. 6, 2023, Kawada et al., related application.

METHOD FOR PREPARING AROMATIC AMINO ACID DERIVATIVE

CROSS-REFERENCE TO RELATED APPLICATIONS

This application is a U.S. National Phase of PCT Application No. PCT/JP2020/011012, filed Mar. 13, 2020, which claims the benefit of Japanese Patent Application Nos. 2019-048394, filed Mar. 15, 2019; 2019-098657, filed May 27, 2019; 2019-178503, filed Sep. 30, 2019; and 2019-221297, filed Dec. 6, 2019, each of which is incorporated herein by reference in its entirety.

TECHNICAL FIELD

The present invention relates to aromatic amino acid derivatives useful as drug intermediates, and production methods thereof.

BACKGROUND ART

Access to a tough target, which is represented by inhibition of a protein-protein interaction, may be done better by middle-molecular weight compounds (molecular weight: 500 to 2000) than low molecular weight compounds. Furthermore, middle-molecular weight compounds may be superior to antibodies in that they can transfer into cells. Among middle-molecular weight compounds that have physiological activity, peptide drugs are valuable molecular species, with 40 or more peptide drugs having already been commercially available (NPL 1). Representative examples of such peptide drugs include cyclosporin A and polymyxin B. Focusing on their structures, it can be found that they are peptide compounds containing several unnatural amino acids. An unnatural amino acid refers to an amino acid that is not naturally encoded on mRNA, and it is highly interesting that unnatural amino acids are contained in naturally-occurring cyclosporin A and polymyxin B, and in addition, their pharmacological activity is expressed through the interaction between the structural sites of such unnatural amino acids and an in vivo action site. An example of unnatural amino acids that interact with an in vivo action site includes the homophenylalanine partial structure of an angiotensin-converting enzyme inhibitor represented by delapril (NPL 2).

From the above, it can be said that for drug discovery research and drug manufacture, it is important to establish efficient and versatile methods of producing aromatic amino acid derivatives represented by homophenylalanine derivatives.

The following methods are known as methods of producing optically active aromatic amino acids.

The following (1) to (5) are methods of obtaining an optically active aromatic amino acid by inducing an asymmetric center from a prochiral starting material or methods of optically resolving a DL-mixture of an aromatic amino acid:

(1) a method in which a highly reactive halogenated aralkyl compound represented by benzyl bromide is enantioselectively added to a glycine derivative or an alanine derivative by using an optically active phase transfer catalyst (PTL 1);

(2) a method in which a highly reactive halogenated aralkyl compound represented by benzyl bromide is diastereoselectively added to optically active oxazolidinone that is derived from glycine (PTL 2);

(3) a method in which an α-amino acid is produced from α-keto acid by an enzymatic process (PTL 3);

(4) an optical resolution method, in which a DL-mixture of N-acetyl aromatic amino acid is deacetylated by an acylase in an L-aromatic amino acid selective manner (PTL 4); and (5) a method in which a homophenylalanine derivative is produced from an optically active alcohol obtained by an asymmetric reduction of a styrylglyoxylic acid derivative, which is a key reaction (NPL 3).

The following (6) to (9) are methods of producing an optically active aromatic amino acid of interest by introducing a functional group into a starting optically active amino acid:

(6) a method of production from an aromatic halide and a zinc reagent derived from optically active serine, in the presence of a palladium catalyst (PTL 5);

(7) a method of production from an aromatic iodide and an N-hydroxyphthalimide ester derived from aspartic acid or glutamic acid, in the presence of a nickel catalyst (NPL 4);

(8) a method of production from an aromatic zinc reagent and an N-hydroxyphthalimide ester derived from aspartic acid or glutamic acid, in the presence of a nickel catalyst (NPL 5); and (9) a method in which the side chain of aspartic acid is arylated by a Friedel-Crafts reaction, and then a homophenylalanine derivative is produced (NPL 6).

CITATION LIST

Patent Literature

[PTL 1] Japanese Patent Application Kokai Publication (JP-A) 2001-48866
[PTL 2] JP-A (Kokai) 2009-96791
[PTL 3] JP-A (Kokai) S62-000289
[PTL 4] JP-A (Kokai) S60-169451
[PTL 5] Japanese Patent Application Kohyo Publication (JP-A) 2012-506909

Non-Patent Literature

[NPL 1] Future Med. Chem. 2009, 1, 1289-1310.
[NPL 2] Chem. Pharm. Bull., 1986, 34(7), 2852-2858.
[NPL 3] Synlett, 2018, 29, 2203-2207.
[NPL 4] J. Am. Chem. Soc., 2016, 138, 5016-5019.
[NPL 5] J. Am. Chem. Soc., 2016, 138, 2174-2177.
[NPL 6] Tetrahedron Lett., 2008, 49, 6566-6568.

SUMMARY OF INVENTION

Technical Problem

The present invention provides efficient and versatile methods of producing aromatic amino acid derivatives.

In the methods of PTL 1 or PTL 2, the halogenated aralkyl compound used as an electrophilic reagent needs to be stable under basic conditions. The electrophilic reagent used therein is necessarily a highly reactive reagent such that a carbon-carbon bond is efficiently formed, which limits the reagents capable of being subjected to such reaction conditions. Therefore, the methods cannot be said to be versatile as a method of producing an aromatic amino acid derivative.

The method described in PTL 3 requires that D-ketocarboxylic acid subjected to an enzymatic process should be stably supplied and that an enzyme having high substrate specificity suitable for the □-ketocarboxylic acid should be produced for each intended aromatic amino acid derivative, and thus the method is not suitable as a versatile method of producing an aromatic amino acid derivative.

In the method described in PTL 4, when producing a plurality of aromatic amino acid derivatives each having different amino acid side chains, it is necessary to use, as raw materials, racemic acylated aromatic amino acid derivatives corresponding to the respective aromatic amino acid derivatives to be produced. Moreover, it is also necessary to produce a hydrolase capable of selectively hydrolyzing aromatic amino acid derivatives each having different side chain structures. More specifically, both a racemic starting material and a hydrolase corresponding to the type of an aromatic amino acid derivative are required, and this makes versatility as the production method poor.

The method described in PTL 5 is not efficient because a multi-step reaction is required to prepare the zinc reagent from raw-material serine.

The method described in NPL 3 is problematic as an industrial reaction in that the asymmetric reduction reaction, which is a key reaction, requires a hydrogen stream of 20 atm. Moreover, the styrylglyoxylic acid derivative used in the asymmetric reduction reaction is limited to an amide form and needs to be converted to a carboxylic acid form or an ester form useful as a drug intermediate, and thus the method is not efficient.

In the method described in NPL 4, raw materials used are an aromatic iodide and an N-hydroxyphthalimide ester (NHPI ester), which is readily prepared from aspartic acid, glutamic acid, or the like, and the method can be regarded as a versatile method from the view that various aromatic amino acid derivatives can be produced by changing aromatic iodides to be used. However, in the method described in this document, an excess of an NHPI ester form of an amino acid needs to be used, which may generate, as by-products, a plurality of amino acid derivatives derived from the excess amino acid. Such by-products have physical properties similar to the intended aromatic amino acid derivative, thereby possibly causing difficulty in obtaining a high-quality aromatic amino acid derivative. Furthermore, among aromatic halides, only aromatic iodides are applicable to this method, and there remains a problem with respect to substrate universality. Specifically, while the reaction proceeds in a laboratory scale, the method of producing a phenylalanine derivative and a homophenylalanine derivative described in NPL 4 requires an excess of an NHPI ester form of aspartic acid or an NHPI ester form of glutamic acid relative to the aromatic iodides. Moreover, it has been found that the reaction does not proceed under reaction conditions for using a stirring blade(s) that is employed in industrial-scale reactions.

In the method described in NPL 5, it is possible to use, as a raw material, an N-hydroxyphthalimide ester (NHPI ester) that is readily prepared from glutamic acid; however, since it is troublesome to prepare the aromatic zinc compound that requires strict anhydrous conditions, the method can be said to be problematic as an industrial production method.

In the method described in NPL 6, the aryl group that can be introduced by a Friedel-Crafts reaction is limited to electron-rich aryl groups.

As mentioned above, to date, there has been no known efficient and versatile method of industrially producing an optically active aromatic amino acid derivative, which involves industrially desirable conditions.

An objective of the present invention is to provide efficient and versatile methods of producing an optically active aromatic amino acid derivative from a readily available optically active amino acid using an industrial facility, and optically active aromatic amino acid derivatives that can be produced by the method and that can be used as a raw material of middle-molecular weight compounds.

Solution to Problem

As a result of dedicated research on methods of producing an optically active aromatic amino acid derivative, the present inventors have found reaction conditions for reacting a specific ester compound with an aromatic halide and a reducing agent in the presence of a catalyst. Specifically, the present inventors have found efficient methods of producing an optically active aromatic amino acid derivative by using an additive, the method being applicable to reaction conditions for utilizing an industrially commonly used stirring blade(s). Moreover, the present inventors have found highly versatile methods capable of producing various optically active aromatic amino acid derivatives from a common ester compound by changing aromatic halides used in the reaction, and thus completed the present invention.

In one non-limiting specific embodiment, the present invention encompasses the following:

[1] a method of producing a compound represented by Formula I, a salt of the compound, or a solvate of the compound or the salt:

Formula I

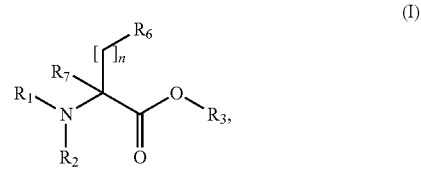

wherein $R_1$ is hydrogen or a protecting group for an amino group;

$R_2$ is hydrogen or $C_1$-$C_6$ alkyl, and $R_3$ is hydrogen or a protecting group for a carboxyl group, or $R_2$ and $R_3$ together form a divalent protecting group;

$R_6$ is optionally substituted $C_6$-$C_{10}$ aryl or optionally substituted heteroaryl;

$R_7$ is hydrogen or $C_1$-$C_4$ alkyl; and n is 1 or 2, the method comprising the step of mixing a compound represented by Formula II, a salt of the compound, or a solvate of the compound or the salt with a reducing agent, an additive, and $R_6$—X (wherein $R_6$ is the same as $R_6$ of the compound represented by Formula I, and X is halogen, OTf, or OMs) in the presence of a solvent and a catalyst to obtain the compound represented by Formula I, the salt of the compound, or the solvate of the compound or the salt:

Formula II

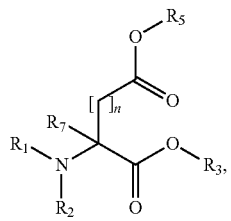

wherein
R₁, R₂, R₃, R₇, and n are the same as R₁, R₂, R₃, R₇, and n of the compound represented by Formula I, respectively;
R₅ is selected from the group consisting of:

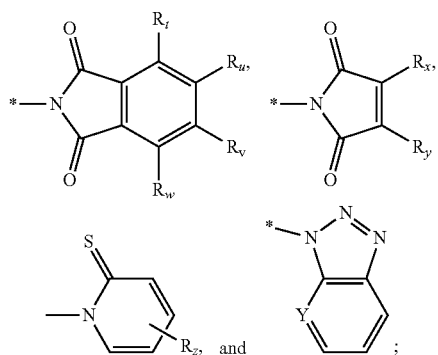

$R_t$, $R_u$, $R_v$, and $R_w$ are independently hydrogen, halogen, or nitro;
$R_x$ and $R_y$ are independently hydrogen, $C_1$-$C_4$ alkyl, or optionally substituted phenyl;
$R_z$ is hydrogen, $C_1$-$C_4$ alkyl, or halogen;
Y is CH or N; and
* indicates a point of bonding;
[2] the method of [1], wherein $R_1$ is a protecting group for an amino group, and the protecting group for an amino group is selected from the group consisting of Fmoc, Boc, Alloc, Cbz, Teoc, and trifluoroacetyl;
[3] the method of [1] or [2], wherein $R_3$ is a protecting group for a carboxyl group, and the protecting group for a carboxyl group is selected from the group consisting of methyl, ethyl, t-Bu, benzyl, trityl, cumyl, methoxytrityl, and 2-(trimethylsilyl)ethyl;
[4] the method of [1] or [2], wherein
$R_2$ and $R_3$ together form a divalent protecting group, the divalent protecting group is —(CR₈R₉)—, and Formula I is represented by Formula IA:

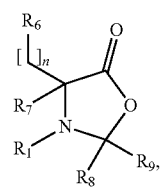

wherein
R₁, R₆, R₇, and n are the same as R₁, R₆, R₇, and n of the compound represented by Formula I, respectively; and
R₈ and R₉ are independently hydrogen, $C_1$-$C_4$ alkyl, or $C_6$-$C_{10}$ aryl, or R₈ and R₉ together form oxo (=O);
[5] the method of any one of [1] to [4], wherein the additive is a silyl compound represented by Formula A:

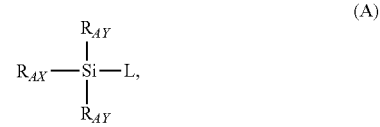

[wherein
$R_{AX}$ and $R_{AY}$ are independently selected from the group consisting of $C_1$-$C_4$ alkyl, $C_1$-$C_4$ alkoxy, and phenyl; and
L is selected from the group consisting of —Cl, —Br, —I, and —OTf] or 1,2-dibromoethane;
[6] the method of [5], wherein the silyl compound is selected from the group consisting of TMSCl, TMSBr, TMSI, TMSOTf, TBDMSCl, TESCl, TIPSCl, TBDPSCl, and chlorotriethoxysilane;
[7] the method of any one of [1] to [6], wherein R₅ is:

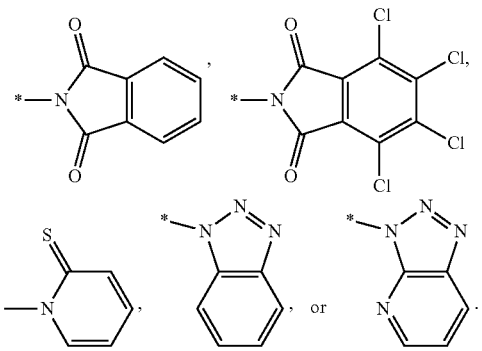

[8] the method of any one of [1] to [7], wherein X is iodine or bromine, and R₆ is optionally substituted phenyl or optionally substituted pyridyl;
[9-1] the method of [8], wherein the optionally substituted phenyl or the optionally substituted pyridyl is substituted with 0 to 3 substituents independently selected from the group consisting of $C_1$-$C_4$ alkyl, $C_1$-$C_4$ haloalkyl, $C_1$-$C_4$ alkoxy, $C_1$-$C_4$ haloalkoxy, $C_2$-$C_6$ alkenyloxy, halogen, $C_3$-$C_8$ cycloalkyl, —NR$_p$R$_q$ (wherein R$_p$ and R$_q$ are independently hydrogen or $C_1$-$C_4$ alkyl), —CONR$_r$R$_s$ (wherein R$_r$ and R$_s$ are independently selected from the group consisting of hydrogen, hydroxy, protected hydroxy, $C_1$-$C_4$ alkyl, and $C_1$-$C_4$ alkylsulfonyl), and cyclic boryl;
[9-2] the method of [9-1], wherein the optionally substituted phenyl or the optionally substituted pyridyl is substituted with one $C_1$-$C_4$ alkyl; one —CONR$_r$R$_s$; one $C_1$-$C_4$ haloalkyl and one or two halogens; two $C_1$-$C_4$ alkoxy groups; one $C_1$-$C_4$ alkoxy and one or two halogens; or one —CONR$_r$R$_s$ and one $C_1$-$C_4$ alkoxy;
[9-3] the method of [9-2], wherein the optionally substituted phenyl or the optionally substituted pyridyl is substituted with one methyl; one methyl((tetrahydro- 2H-pyran-2-yl)oxy)carbamoyl; one trifluoromethyl and one or two fluorines; one trifluoromethyl and one or two chlorines; one trifluoromethyl, one fluorine, and one chlorine; two methoxy groups; one methoxy and one or two fluorines; one methylaminocarbonyl and one methoxy; or one methylsulfonylaminocarbonyl and one methoxy;

[10] the method of any one of [1] to [9-3], wherein the catalyst is:
(a) a metal;
(b) formed by mixing a metal and a possible ligand compound therefor;
(c) a complex of a metal and a ligand therefor; or
(d) formed by further mixing, with the complex of a metal and a ligand therefor, a possible ligand compound for the metal, and wherein the metal is nickel, chromium, iron, copper, palladium or a salt of these metals, or is a solvate of nickel, chromium, iron, copper, palladium or a salt of these metals; [11] the method of [10], wherein the metal is selected from the group consisting of $NiBr_2$, $NiI_2$, $NiCl_2$, $NiF_2$, $Ni(OAc)_2$, $Ni(acac)_2$, $Ni(OTf)_2$, $NiCO_3$, $Ni(NO_3)_2$, $NiSO_4$, $(NH_4)_2Ni(SO_4)_2$, allyl(cyclopentadienyl)nickel(II), bis(cyclopentadienyl)nickel, and bis(cyclooctadienyl)nickel, or is a solvate of these metals;

[12] the method of [10] or [11], wherein the possible ligand compound is selected from:
a compound represented by Formula B:

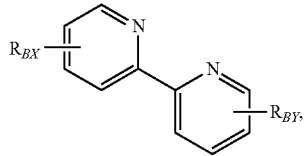

wherein $R_{BX}$ and $R_{BY}$ are independently selected from hydrogen, $C_1$-$C_4$ alkyl, $C_1$-$C_4$ alkoxy, heterocyclyl, and $C_6$-$C_{10}$ aryl;
a compound represented by Formula C:

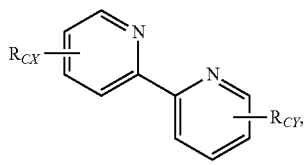

wherein $R_{CX}$ and $R_{CY}$ are independently selected from hydrogen, $C_1$-$C_4$ alkyl, $C_6$-$C_{10}$ aryl, and heteroaryl;
a compound represented by Formula D:

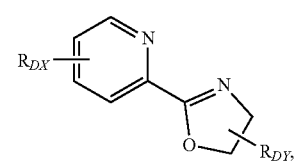

wherein $R_{DX}$ and $R_{DY}$ are independently selected from hydrogen, $C_1$-$C_4$ alkyl, $C_1$-$C_4$ haloalkyl, and $C_6$-$C_{10}$ aryl;
a compound represented by Formula E:

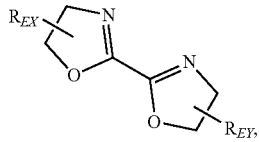

wherein $R_{EX}$ and $R_{EY}$ are independently selected from hydrogen, $C_1$-$C_4$ alkyl, $C_6$-$C_{10}$ aryl $C_1$-$C_6$ alkyl, and $C_6$-$C_{10}$ aryl;
a compound represented by Formula F:

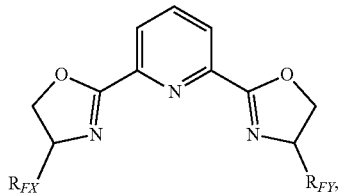

wherein $R_{FX}$ and $R_{FY}$ are independently selected from hydrogen, $C_1$-$C_4$ alkyl, and $C_6$-$C_{10}$ aryl; and
a compound represented by Formula G:

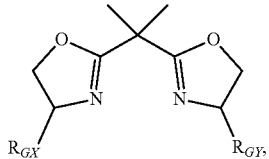

wherein $R_{GX}$ and $R_{GY}$ are independently selected from hydrogen, $C_1$-$C_4$ alkyl, $C_6$-$C_{10}$ aryl $C_1$-$C_6$ alkyl, and $C_6$-$C_{10}$ aryl;

[13] the method of [10], wherein the catalyst is a complex of a metal and a ligand therefor, and the complex of a metal and a ligand therefor is selected from the group consisting of tetrakis(triphenylphosphine)nickel(0), bis(triphenylphosphine)nickel(II) dichloride, bis(tricyclohexylphosphine)nickel(II) dichloride, dibromobis(triphenylphosphine)nickel(II), bis[(2-dimethylamino)phenyl]aminenickel(II) chloride, cis-[2,2'-bis(diphenylphosphino)-1,1'-binaphthyl](2-methylphenyl)nickel(II) chloride, and [1,2-bis(diphenylphosphino)ethane]dichloronickel(II);

[14] the method of any one of [1] to [13], wherein the reducing agent is selected from the group consisting of zinc, manganese, iron, and magnesium;

[15] the method of any one of [1] to [14], wherein
(a) the compound represented by Formula II, the salt of the compound, or the solvate of the compound or the salt, the reducing agent, and $R_6$—X are mixed in the presence of the solvent and the catalyst, and then the additive is mixed therewith;

(b) the reducing agent and the additive are mixed in the presence of the solvent and the catalyst, and then the compound represented by Formula II, the salt of the compound, or the solvate of the compound or the salt, and $R_6$—X are mixed therewith; or (c) the reducing agent is mixed with the solvent and the catalyst, and then the compound represented by Formula II, the salt of the compound, or the solvate of the compound or the salt, $R_6$—X, and the additive are mixed therewith;

[16] the method of any one of [1] to [15], wherein 1 to 500 mol % of the additive is used relative to the compound represented by Formula II, the salt of the compound, or the solvate of the compound or the salt;

[17] the method of any one of [1] to [16], wherein the step is carried out at a reaction temperature of −10° C. to 70° C.;

[18] a method of producing a compound represented by Formula III, a salt of the compound, or a solvate of the compound or the salt:

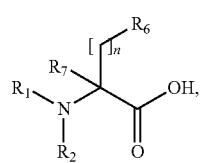

(III)

wherein $R_1$, $R_6$, $R_7$, and n are the same as $R_1$, $R_6$, $R_7$, and n of the compound represented by Formula I, respectively, and $R_2$ is hydrogen or $C_1$-$C_6$ alkyl, the method comprising the steps of:
following the method of any one of [1] to [17] to produce the compound represented by Formula I, the salt of the compound, or the solvate of the compound or the salt; and
when $R_3$ is a protecting group for a carboxyl group, removing the protecting group from the compound represented by Formula I, the salt of the compound, or the solvate of the compound or the salt, to obtain the compound represented by Formula III, the salt of the compound, or the solvate of the compound or the salt;

[19] a method of producing a compound represented by Formula IV, a salt of the compound, or a solvate of the compound or the salt:

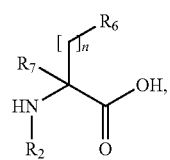

(IV)

wherein $R_6$, $R_7$, and n are the same as $R_6$, $R_7$, and n of the compound represented by Formula I, respectively, and $R_2$ is hydrogen or $C_1$-$C_6$ alkyl, the method comprising the steps of:
following the method of any one of [1] to [17] to produce the compound represented by Formula I, the salt of the compound, or the solvate of the compound or the salt; and when $R_1$ is a protecting group for an amino group and $R_3$ is a protecting group for a carboxyl group, removing these protecting groups to obtain the compound represented by Formula IV, the salt of the compound, or the solvate of the compound or the salt;

[20] a method of producing a compound represented by Formula V, a salt of the compound, or a solvate of the compound or the salt:

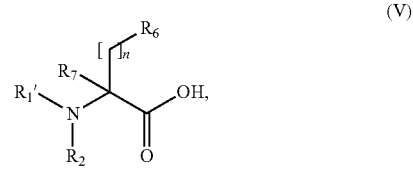

(V)

wherein $R_2$, $R_6$, $R_7$, and n are the same as $R_2$, $R_6$, $R_7$, and n of the compound represented by Formula IV, respectively; and $R_1'$ is a protecting group for an amino group, the method comprising the steps of:
following the method of [19] to produce the compound represented by Formula IV, the salt of the compound, or the solvate of the compound or the salt, and introducing $R_1'$ into the compound represented by Formula IV, the salt of the compound, or the solvate of the compound or the salt to obtain the compound represented by Formula V, the salt of the compound, or the solvate of the compound or the salt;

[21] a method of producing a compound represented by Formula VI, a salt of the compound, or a solvate of the compound or the salt:

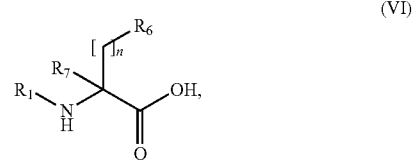

(VI)

wherein $R_1$, $R_6$, $R_7$, and n are the same as $R_1$, $R_6$, $R_7$, and n of the compound represented by Formula I, respectively, the method comprising the steps of:
following the method of any one of [4] to [17] to produce the compound represented by Formula IA, the salt of the compound, or the solvate of the compound or the salt; and opening the oxazolidinone ring of the compound represented by Formula IA to obtain the compound represented by Formula VI, the salt of the compound, or the solvate of the compound or the salt;

[22] a compound, a salt of the compound, or a solvate of the compound or the salt produced by the method of any one of [1] to [21];

[23] an amino acid derivative represented by Formula I, a salt of the amino acid derivative, or a solvate of the amino acid derivative or the salt:

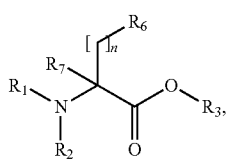

(I)

wherein
- $R_1$ is hydrogen or a protecting group for an amino group;
- $R_2$ is hydrogen or $C_1$-$C_6$ alkyl, and $R_3$ is hydrogen or a protecting group for a carboxyl group, or $R_2$ and $R_3$ together form a divalent protecting group;
- $R_6$ is optionally substituted $C_6$-$C_{10}$ aryl or optionally substituted heteroaryl;
- $R_7$ is hydrogen or $C_1$-$C_4$ alkyl; and
- n is 1 or 2;

[24] the amino acid derivative, the salt of the amino acid derivative, or the solvate of the amino acid derivative or the salt of [23], wherein R1 is a protecting group for an amino group, and the protecting group for an amino group is selected from the group consisting of Fmoc, Boc, Alloc, Cbz, Teoc, and trifluoroacetyl;

[25] the amino acid derivative, the salt of the amino acid derivative, or the solvate of the amino acid derivative or the salt of [23] or [24], wherein $R_3$ is a protecting group for a carboxyl group, and the protecting group for a carboxyl group is selected from the group consisting of methyl, ethyl, t-Bu, benzyl, trityl, cumyl, methoxytrityl, and 2-(trimethylsilyl)ethyl;

[26] the amino acid derivative, the salt of the amino acid derivative, or the solvate of the amino acid derivative or the salt of [23] or [24], wherein $R_2$ and $R_3$ together form a divalent protecting group, the divalent protecting group is —($CR_8R_9$)—, and Formula I is represented by Formula IA:

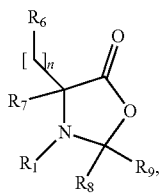

(IA)

wherein
- $R_1$, $R_6$, $R_7$, and n are the same as $R_1$, $R_6$, $R_7$, and n of the compound represented by Formula I, respectively; and
- $R_8$ and $R_9$ are independently hydrogen, $C_1$-$C_4$ alkyl, or $C_6$-$C_{10}$ aryl, or $R_8$ and $R_9$ together form oxo (=O);

[27] the amino acid derivative, the salt of the amino acid derivative, or the solvate of the amino acid derivative or the salt of any one of [23] to [26], wherein $R_6$ is optionally substituted phenyl or optionally substituted pyridyl;

[28] the amino acid derivative, the salt of the amino acid derivative, or the solvate of the amino acid derivative or the salt of [27], wherein the optionally substituted phenyl or the optionally substituted pyridyl is substituted with 0 to 3 substituents independently selected from the group consisting of $C_1$-$C_4$ alkyl, $C_1$-$C_4$ haloalkyl, $C_1$-$C_4$ alkoxy, $C_1$-$C_4$ haloalkoxy, $C_2$-$C_6$ alkenyloxy, halogen, $C_3$-$C_8$ cycloalkyl, —NRpRq (wherein Rp and Rq are independently hydrogen or $C_1$-$C_4$ alkyl), —CONRrRs (wherein Rr and Rs are independently selected from the group consisting of hydrogen, hydroxy, protected hydroxy, $C_1$-$C_4$ alkyl, and $C_1$-$C_4$ alkylsulfonyl), and cyclic boryl;

[29] the amino acid derivative, the salt of the amino acid derivative, or the solvate of the amino acid derivative or the salt of [28], wherein the optionally substituted phenyl or the optionally substituted pyridyl is substituted with one $C_1$-$C_4$ alkyl; one —CONRrRs; one $C_1$-$C_4$ haloalkyl and one or two halogens; two $C_1$-$C_4$ alkoxy groups; one $C_1$-$C_4$ alkoxy and one or two halogens; or one —CONRrRs and one $C_1$-$C_4$ alkoxy;

[30] the amino acid derivative, the salt of the amino acid derivative, or the solvate of the amino acid derivative or the salt of [29], wherein the optionally substituted phenyl or the optionally substituted pyridyl is substituted with one methyl; one methyl((tetrahydro-2H-pyran-2-yl)oxy)carbamoyl; one trifluoromethyl and one or two fluorines; one trifluoromethyl and one or two chlorines; one trifluoromethyl, one fluorine, and one chlorine; two methoxy groups; one methoxy and one or two fluorines; one methylaminocarbonyl and one methoxy; or one methylsulfonylaminocarbonyl and one methoxy;

[31] an amino acid derivative selected from the group consisting of below, a salt of the amino acid derivative, or a solvate of the amino acid derivative or the salt:
(1-1) benzyl 2-((tert-butoxycarbonyl)amino)-4-(3-chloro-4-(trifluoromethyl)phenyl)butanoate,
(1-2) tert-butyl 2-((tert-butoxycarbonyl)amino)-4-(3-chloro-4-(trifluoromethyl)phenyl)butanoate,
(1-3) benzyl 2-((((9H-fluoren-9-yl)methoxy)carbonyl)amino)-4-(3-chloro-4-(trifluoromethyl)phenyl)butanoate,
(1-4) tert-butyl 2-((((9H-fluoren-9-yl)methoxy)carbonyl)amino)-4-(3-chloro-4-(trifluoromethyl)phenyl)butanoate,
(1-5) benzyl 2-(((benzyloxy)carbonyl)amino)-4-(3-chloro-4-(trifluoromethyl)phenyl)butanoate,
(1-6) tert-butyl 2-(((benzyloxy)carbonyl)amino)-4-(3-chloro-4-(trifluoromethyl)phenyl)butanoate,
(1-7) benzyl 2-((tert-butoxycarbonyl)(methyl)amino)-4-(3-chloro-4-(trifluoromethyl)phenyl)butanoate,
(1-8) tert-butyl 2-((tert-butoxycarbonyl)(methyl)amino)-4-(3-chloro-4-(trifluoromethyl)phenyl)butanoate,
(1-9) benzyl 2-((((9H-fluoren-9-yl)methoxy)carbonyl)(methyl)amino)-4-(3-chloro-4-(trifluoromethyl)phenyl)butanoate,
(1-10) tert-butyl 2-((((9H-fluoren-9-yl)methoxy)carbonyl)(methyl)amino)-4-(3-chloro-4-(trifluoromethyl)phenyl)butanoate,
(1-11) benzyl 2-(((benzyloxy)carbonyl)(methyl)amino)-4-(3-chloro-4-(trifluoromethyl)phenyl)butanoate,
(1-12) tert-butyl 2-(((benzyloxy)carbonyl)(methyl)amino)-4-(3-chloro-4-(trifluoromethyl)phenyl)butanoate,
(1-13) 2-((tert-butoxycarbonyl)amino)-4-(3-chloro-4-(trifluoromethyl)phenyl)butanoic acid,
(1-14) 2-((((9H-fluoren-9-yl)methoxy)carbonyl)amino)-4-(3-chloro-4-(trifluoromethyl)phenyl)butanoic acid, (1-15) 2-(((benzyloxy)carbonyl)amino)-4-(3-chloro-4-(trifluoromethyl)phenyl)butanoic acid,
(1-16) 2-((tert-butoxycarbonyl)(methyl)amino)-4-(3-chloro-4-(trifluoromethyl)phenyl)butanoic acid,
(1-17) 2-((((9H-fluoren-9-yl)methoxy)carbonyl)(methyl)amino)-4-(3-chloro-4-(trifluoromethyl)phenyl)butanoic acid,
(1-18) 2-(((benzyloxy)carbonyl)(methyl)amino)-4-(3-chloro-4-(trifluoromethyl)phenyl)butanoic acid,
(1-19) 2-amino-4-(3-chloro-4-(trifluoromethyl)phenyl)butanoic acid,
(1-20) 4-(3-chloro-4-(trifluoromethyl)phenyl)-2-(methylamino)butanoic acid,
(1-21) benzyl 2-((tert-butoxycarbonyl)amino)-3-(3-chloro-4-(trifluoromethyl)phenyl)propanoate,
(1-22) tert-butyl 2-((tert-butoxycarbonyl)amino)-3-(3-chloro-4-(trifluoromethyl)phenyl)propanoate,
(1-23) benzyl 2-((((9H-fluoren-9-yl)methoxy)carbonyl)amino)-3-(3-chloro-4-(trifluoromethyl)phenyl)propanoate,
(1-24) tert-butyl 2-((((9H-fluoren-9-yl)methoxy)carbonyl)amino)-3-(3-chloro-4-(trifluoromethyl)phenyl)propanoate,
(1-25) benzyl 2-(((benzyloxy)carbonyl)amino)-3-(3-chloro-4-(trifluoromethyl)phenyl)propanoate,
(1-26) tert-butyl 2-(((benzyloxy)carbonyl)amino)-3-(3-chloro-4-(trifluoromethyl)phenyl)propanoate,
(1-27) benzyl 2-((tert-butoxycarbonyl)(methyl)amino)-3-(3-chloro-4-(trifluoromethyl)phenyl)propanoate,
(1-28) tert-butyl 2-((tert-butoxycarbonyl)(methyl)amino)-3-(3-chloro-4-(trifluoromethyl)phenyl)propanoate,
(1-29) benzyl 2-((((9H-fluoren-9-yl)methoxy)carbonyl)(methyl)amino)-3-(3-chloro-4-(trifluoromethyl)phenyl)propanoate,
(1-30) tert-butyl 2-((((9H-fluoren-9-yl)methoxy)carbonyl)(methyl)amino)-3-(3-chloro-4-(trifluoromethyl)phenyl)propanoate,
(1-31) benzyl 2-(((benzyloxy)carbonyl)(methyl)amino)-3-(3-chloro-4-(trifluoromethyl)phenyl)propanoate,
(1-32) tert-butyl 2-(((benzyloxy)carbonyl)(methyl)amino)-3-(3-chloro-4-(trifluoromethyl)phenyl)propanoate,
(1-33) 2-((tert-butoxycarbonyl)amino)-3-(3-chloro-4-(trifluoromethyl)phenyl)propanoic acid,
(1-34) 2-((((9H-fluoren-9-yl)methoxy)carbonyl)amino)-3-(3-chloro-4-(trifluoromethyl)phenyl)propanoic acid,
(1-35) 2-(((benzyloxy)carbonyl)amino)-3-(3-chloro-4-(trifluoromethyl)phenyl)propanoic acid,
(1-36) 2-((tert-butoxycarbonyl)(methyl)amino)-3-(3-chloro-4-(trifluoromethyl)phenyl)propanoic acid,
(1-37) 2-((((9H-fluoren-9-yl)methoxy)carbonyl)(methyl)amino)-3-(3-chloro-4-(trifluoromethyl)phenyl)propanoic acid,
(1-38) 2-(((benzyloxy)carbonyl)(methyl)amino)-3-(3-chloro-4-(trifluoromethyl)phenyl)propanoic acid,
(1-39) 2-amino-3-(3-chloro-4-(trifluoromethyl)phenyl)propanoic acid,
(1-40) 3-(3-chloro-4-(trifluoromethyl)phenyl)-2-(methylamino)propanoic acid,
(2-1) tert-butyl 2-((((9H-fluoren-9-yl)methoxy)carbonyl)amino)-4-phenylbutanoate,
(2-2) tert-butyl 2-((((9H-fluoren-9-yl)methoxy)carbonyl)amino)-4-(o-tolyl)butanoate,
(2-3) tert-butyl 2-((((9H-fluoren-9-yl)methoxy)carbonyl)amino)-4-(m-tolyl)butanoate,
(2-4) tert-butyl 2-((((9H-fluoren-9-yl)methoxy)carbonyl)amino)-4-(p-tolyl)butanoate,
(2-5) tert-butyl 2-((((9H-fluoren-9-yl)methoxy)carbonyl)amino)-4-(4-ethylphenyl)butanoate,
(2-6) tert-butyl 2-((((9H-fluoren-9-yl)methoxy)carbonyl)amino)-4-(2-chlorophenyl)butanoate,
(2-7) tert-butyl 2-((((9H-fluoren-9-yl)methoxy)carbonyl)amino)-4-(3-chlorophenyl)butanoate,
(2-8) tert-butyl 2-((((9H-fluoren-9-yl)methoxy)carbonyl)amino)-4-(4-chlorophenyl)butanoate,
(2-9) tert-butyl 2-((((9H-fluoren-9-yl)methoxy)carbonyl)amino)-4-(2-fluorophenyl)butanoate,
(2-10) tert-butyl 2-((((9H-fluoren-9-yl)methoxy)carbonyl)amino)-4-(3-fluorophenyl)butanoate,
(2-11) tert-butyl 2-((((9H-fluoren-9-yl)methoxy)carbonyl)amino)-4-(4-fluorophenyl)butanoate,
(2-12) tert-butyl 2-((((9H-fluoren-9-yl)methoxy)carbonyl)amino)-4-(2-cyclopropylphenyl)butanoate,
(2-13) tert-butyl 2-((((9H-fluoren-9-yl)methoxy)carbonyl)amino)-4-(3-cyclopropylphenyl)butanoate,
(2-14) tert-butyl 2-((((9H-fluoren-9-yl)methoxy)carbonyl)amino)-4-(4-cyclopropylphenyl)butanoate,
(2-15) tert-butyl 2-((((9H-fluoren-9-yl)methoxy)carbonyl)amino)-4-(2-(trifluoromethyl)phenyl)butanoate,
(2-16) tert-butyl 2-((((9H-fluoren-9-yl)methoxy)carbonyl)amino)-4-(3-(trifluoromethyl)phenyl)butanoate,
(2-17) tert-butyl 2-((((9H-fluoren-9-yl)methoxy)carbonyl)amino)-4-(4-(trifluoromethyl)phenyl)butanoate,
(2-18) tert-butyl 2-((((9H-fluoren-9-yl)methoxy)carbonyl)amino)-4-(2-isopropylphenyl)butanoate,
(2-19) tert-butyl 2-((((9H-fluoren-9-yl)methoxy)carbonyl)amino)-4-(3-isopropylphenyl)butanoate,
(2-20) tert-butyl 2-((((9H-fluoren-9-yl)methoxy)carbonyl)amino)-4-(4-isopropylphenyl)butanoate,
(2-21) tert-butyl 2-((((9H-fluoren-9-yl)methoxy)carbonyl)amino)-4-(2-methoxyphenyl)butanoate,
(2-22) tert-butyl 2-((((9H-fluoren-9-yl)methoxy)carbonyl)amino)-4-(3-methoxyphenyl)butanoate,
(2-23) tert-butyl 2-((((9H-fluoren-9-yl)methoxy)carbonyl)amino)-4-(4-methoxyphenyl)butanoate,
(2-24) tert-butyl 2-((((9H-fluoren-9-yl)methoxy)carbonyl)amino)-4-(2-(allyloxy)phenyl)butanoate,
(2-25) tert-butyl 2-((((9H-fluoren-9-yl)methoxy)carbonyl)amino)-4-(3-(allyloxy)phenyl)butanoate,
(2-26) tert-butyl 2-((((9H-fluoren-9-yl)methoxy)carbonyl)amino)-4-(4-(allyloxy)phenyl)butanoate,
(2-27) tert-butyl 2-((((9H-fluoren-9-yl)methoxy)carbonyl)amino)-4-(4-isopropoxyphenyl)butanoate,
(2-28) tert-butyl 2-((((9H-fluoren-9-yl)methoxy)carbonyl)amino)-4-(3-fluoro-4-(trifluoromethyl)phenyl)butanoate,
(2-29) tert-butyl 2-((((9H-fluoren-9-yl)methoxy)carbonyl)amino)-4-(2-fluoro-4-(trifluoromethyl)phenyl)butanoate,
(2-30) tert-butyl 2-((((9H-fluoren-9-yl)methoxy)carbonyl)amino)-4-(3,4-dimethoxyphenyl)butanoate,
(2-31) tert-butyl 2-((((9H-fluoren-9-yl)methoxy)carbonyl)amino)-4-(2-fluoro-4-methoxyphenyl)butanoate,
(2-32) tert-butyl 2-((((9H-fluoren-9-yl)methoxy)carbonyl)amino)-4-(3-fluoro-4-methoxyphenyl)butanoate,
(2-33) tert-butyl 2-((((9H-fluoren-9-yl)methoxy)carbonyl)amino)-4-(3,5-difluoro-4-methoxyphenyl)butanoate, (2-34) tert-butyl 2-((((9H-fluoren-9-yl)methoxy)carbonyl)amino)-4-(3,5-difluoro-4-(trifluoromethyl)phenyl)butanoate,
(2-35) tert-butyl 2-((((9H-fluoren-9-yl)methoxy)carbonyl)amino)-4-(3-methoxy-4-(methylcarbamoyl)phenyl)butanoate,
(2-36) tert-butyl 2-((((9H-fluoren-9-yl)methoxy)carbonyl)amino)-4-(4-methoxy-3-(methylcarbamoyl)phenyl)butanoate,
(2-37) tert-butyl 2-((((9H-fluoren-9-yl)methoxy)carbonyl)amino)-4-(3-methoxy-4-((methylsulfonyl)carbamoyl)phenyl)butanoate,
(2-38) tert-butyl 2-((((9H-fluoren-9-yl)methoxy)carbonyl)amino)-4-(4-(methyl((tetrahydro-2H-pyran-2-yl)oxy)carbamoyl)phenyl)butanoate,
(2-39) tert-butyl 2-((((9H-fluoren-9-yl)methoxy)carbonyl)amino)-4-(3-methoxy-4-(((tetrahydro-2H-pyran-2-yl)oxy)carbamoyl)phenyl)butanoate,
(2-40) tert-butyl 2-((((9H-fluoren-9-yl)methoxy)carbonyl)amino)-4-(pyridin-2-yl)butanoate,
(2-41) tert-butyl 2-((((9H-fluoren-9-yl)methoxy)carbonyl)amino)-4-(pyridin-3-yl)butanoate,
(2-42) tert-butyl 2-((((9H-fluoren-9-yl)methoxy)carbonyl)amino)-4-(pyridin-4-yl)butanoate,
(2-43) tert-butyl 2-((((9H-fluoren-9-yl)methoxy)carbonyl)amino)-4-(6-methylpyridin-3-yl)butanoate,
(2-44) tert-butyl 2-((((9H-fluoren-9-yl)methoxy)carbonyl)amino)-4-(5-methylpyridin-3-yl)butanoate,
(2-45) tert-butyl 2-((((9H-fluoren-9-yl)methoxy)carbonyl)amino)-4-(4-methylpyridin-3-yl)butanoate,
(2-46) tert-butyl 2-((((9H-fluoren-9-yl)methoxy)carbonyl)amino)-4-(6-methoxypyridin-3-yl)butanoate,
(2-47) tert-butyl 2-((((9H-fluoren-9-yl)methoxy)carbonyl)amino)-4-(5-methoxypyridin-3-yl)butanoate,
(2-48) tert-butyl 2-((((9H-fluoren-9-yl)methoxy)carbonyl)amino)-4-(5-fluoropyridin-3-yl)butanoate,
(2-49) tert-butyl 2-((((9H-fluoren-9-yl)methoxy)carbonyl)amino)-4-(5-chloropyridin-3-yl)butanoate,
(2-50) tert-butyl 2-((((9H-fluoren-9-yl)methoxy)carbonyl)amino)-4-(5-bromopyridin-3-yl)butanoate,
(2-51) tert-butyl 2-((((9H-fluoren-9-yl)methoxy)carbonyl)amino)-4-(5-iodopyridin-3-yl)butanoate,
(2-52) tert-butyl 2-((((9H-fluoren-9-yl)methoxy)carbonyl)amino)-4-(2-(methylamino)pyridin-4-yl)butanoate,
(2-53) tert-butyl 2-((((9H-fluoren-9-yl)methoxy)carbonyl)amino)-4-(2-(dimethylamino)pyridin-4-yl)butanoate,
(2-54) tert-butyl 2-((((9H-fluoren-9-yl)methoxy)carbonyl)amino)-4-(pyrimidin-5-yl)butanoate,
(3-1) tert-butyl 2-((((9H-fluoren-9-yl)methoxy)carbonyl)(methyl)amino)-4-phenylbutanoate,
(3-2) tert-butyl 2-((((9H-fluoren-9-yl)methoxy)carbonyl)(methyl)amino)-4-(o-tolyl)butanoate,
(3-3) tert-butyl 2-((((9H-fluoren-9-yl)methoxy)carbonyl)(methyl)amino)-4-(m-tolyl)butanoate,
(3-4) tert-butyl 2-((((9H-fluoren-9-yl)methoxy)carbonyl)(methyl)amino)-4-(p-tolyl)butanoate,
(3-5) tert-butyl 2-((((9H-fluoren-9-yl)methoxy)carbonyl)(methyl)amino)-4-(4-ethylphenyl)butanoate,
(3-6) tert-butyl 2-((((9H-fluoren-9-yl)methoxy)carbonyl)(methyl)amino)-4-(2-chlorophenyl)butanoate,
(3-7) tert-butyl 2-((((9H-fluoren-9-yl)methoxy)carbonyl)(methyl)amino)-4-(3-chlorophenyl)butanoate,
(3-8) tert-butyl 2-((((9H-fluoren-9-yl)methoxy)carbonyl)(methyl)amino)-4-(4-chlorophenyl)butanoate,
(3-9) tert-butyl 2-((((9H-fluoren-9-yl)methoxy)carbonyl)(methyl)amino)-4-(2-fluorophenyl)butanoate,
(3-10) tert-butyl 2-((((9H-fluoren-9-yl)methoxy)carbonyl)(methyl)amino)-4-(3-fluorophenyl)butanoate,
(3-11) tert-butyl 2-((((9H-fluoren-9-yl)methoxy)carbonyl)(methyl)amino)-4-(4-fluorophenyl)butanoate,
(3-12) tert-butyl 2-((((9H-fluoren-9-yl)methoxy)carbonyl)(methyl)amino)-4-(2-cyclopropylphenyl)butanoate,
(3-13) tert-butyl 2-((((9H-fluoren-9-yl)methoxy)carbonyl)(methyl)amino)-4-(3-cyclopropylphenyl)butanoate,
(3-14) tert-butyl 2-((((9H-fluoren-9-yl)methoxy)carbonyl)(methyl)amino)-4-(4-cyclopropylphenyl)butanoate,
(3-15) tert-butyl 2-((((9H-fluoren-9-yl)methoxy)carbonyl)(methyl)amino)-4-(2-(trifluoromethyl)phenyl)butanoate,
(3-16) tert-butyl 2-((((9H-fluoren-9-yl)methoxy)carbonyl)(methyl)amino)-4-(3-(trifluoromethyl)phenyl)butanoate,
(3-17) tert-butyl 2-((((9H-fluoren-9-yl)methoxy)carbonyl)(methyl)amino)-4-(4-(trifluoromethyl)phenyl)butanoate,
(3-18) tert-butyl 2-((((9H-fluoren-9-yl)methoxy)carbonyl)(methyl)amino)-4-(2-isopropylphenyl)butanoate,
(3-19) tert-butyl 2-((((9H-fluoren-9-yl)methoxy)carbonyl)(methyl)amino)-4-(3-isopropylphenyl)butanoate,
(3-20) tert-butyl 2-((((9H-fluoren-9-yl)methoxy)carbonyl)(methyl)amino)-4-(4-isopropylphenyl)butanoate,
(3-21) tert-butyl 2-((((9H-fluoren-9-yl)methoxy)carbonyl)(methyl)amino)-4-(2-methoxyphenyl)butanoate,
(3-22) tert-butyl 2-((((9H-fluoren-9-yl)methoxy)carbonyl)(methyl)amino)-4-(3-methoxyphenyl)butanoate,
(3-23) tert-butyl 2-((((9H-fluoren-9-yl)methoxy)carbonyl)(methyl)amino)-4-(4-methoxyphenyl)butanoate,
(3-24) tert-butyl 2-((((9H-fluoren-9-yl)methoxy)carbonyl)(methyl)amino)-4-(2-(allyloxy)phenyl)butanoate,
(3-25) tert-butyl 2-((((9H-fluoren-9-yl)methoxy)carbonyl)(methyl)amino)-4-(3-(allyloxy)phenyl)butanoate,
(3-26) tert-butyl 2-((((9H-fluoren-9-yl)methoxy)carbonyl)(methyl)amino)-4-(4-(allyloxy)phenyl)butanoate,
(3-27) tert-butyl 2-((((9H-fluoren-9-yl)methoxy)carbonyl)(methyl)amino)-4-(4-isopropoxyphenyl)butanoate,
(3-28) tert-butyl 2-((((9H-fluoren-9-yl)methoxy)carbonyl)(methyl)amino)-4-(3-fluoro-4-(trifluoromethyl)phenyl)butanoate,
(3-29) tert-butyl 2-((((9H-fluoren-9-yl)methoxy)carbonyl)(methyl)amino)-4-(2-fluoro-4-(trifluoromethyl)phenyl)butanoate,
(3-30) tert-butyl 2-((((9H-fluoren-9-yl)methoxy)carbonyl)(methyl)amino)-4-(3,4-dimethoxyphenyl)butanoate,
(3-31) tert-butyl 2-((((9H-fluoren-9-yl)methoxy)carbonyl)(methyl)amino)-4-(2-fluoro-4-methoxyphenyl)butanoate,
(3-32) tert-butyl 2-((((9H-fluoren-9-yl)methoxy)carbonyl)(methyl)amino)-4-(3-fluoro-4-methoxyphenyl)butanoate, (3-33) tert-butyl 2-((((9H-fluoren-9-yl)methoxy)carbonyl)(methyl)amino)-4-(3,5-difluoro-4-methoxyphenyl)butanoate,
(3-34) tert-butyl 2-((((9H-fluoren-9-yl)methoxy)carbonyl)(methyl)amino)-4-(3,5-difluoro-4-(trifluoromethyl)phenyl)butanoate,
(3-35) tert-butyl 2-((((9H-fluoren-9-yl)methoxy)carbonyl)(methyl)amino)-4-(3-methoxy-4-(methylcarbamoyl)phenyl)butanoate,
(3-36) tert-butyl 2-((((9H-fluoren-9-yl)methoxy)carbonyl)(methyl)amino)-4-(4-methoxy-3-(methylcarbamoyl)phenyl)butanoate,
(3-37) tert-butyl 2-((((9H-fluoren-9-yl)methoxy)carbonyl)(methyl)amino)-4-(3-methoxy-4-((methylsulfonyl)carbamoyl)phenyl)butanoate,
(3-38) tert-butyl 2-((((9H-fluoren-9-yl)methoxy)carbonyl)(methyl)amino)-4-(4-(methyl((tetrahydro-2H-pyran-2-yl)oxy)carbamoyl)phenyl)butanoate,
(3-39) tert-butyl 2-((((9H-fluoren-9-yl)methoxy)carbonyl)(methyl)amino)-4-(3-methoxy-4-(((tetrahydro-2H-pyran-2-yl)oxy)carbamoyl)phenyl)butanoate,
(3-40) tert-butyl 2-((((9H-fluoren-9-yl)methoxy)carbonyl)(methyl)amino)-4-(pyridin-2-yl)butanoate,
(3-41) tert-butyl 2-((((9H-fluoren-9-yl)methoxy)carbonyl)(methyl)amino)-4-(pyridin-3-yl)butanoate,
(3-42) tert-butyl 2-((((9H-fluoren-9-yl)methoxy)carbonyl)(methyl)amino)-4-(pyridin-4-yl)butanoate,
(3-43) tert-butyl 2-((((9H-fluoren-9-yl)methoxy)carbonyl)(methyl)amino)-4-(6-methylpyridin-3-yl)butanoate,
(3-44) tert-butyl 2-((((9H-fluoren-9-yl)methoxy)carbonyl)(methyl)amino)-4-(5-methylpyridin-3-yl)butanoate,
(3-45) tert-butyl 2-((((9H-fluoren-9-yl)methoxy)carbonyl)(methyl)amino)-4-(4-methylpyridin-3-yl)butanoate,
(3-46) tert-butyl 2-((((9H-fluoren-9-yl)methoxy)carbonyl)(methyl)amino)-4-(6-methoxypyridin-3-yl)butanoate,
(3-47) tert-butyl 2-((((9H-fluoren-9-yl)methoxy)carbonyl)(methyl)amino)-4-(5-methoxypyridin-3-yl)butanoate,
(3-48) tert-butyl 2-((((9H-fluoren-9-yl)methoxy)carbonyl)(methyl)amino)-4-(5-fluoropyridin-3-yl)butanoate,
(3-49) tert-butyl 2-((((9H-fluoren-9-yl)methoxy)carbonyl)(methyl)amino)-4-(5-chloropyridin-3-yl)butanoate,
(3-50) tert-butyl 2-((((9H-fluoren-9-yl)methoxy)carbonyl)(methyl)amino)-4-(5-bromopyridin-3-yl)butanoate,
(3-51) tert-butyl 2-((((9H-fluoren-9-yl)methoxy)carbonyl)(methyl)amino)-4-(5-iodopyridin-3-yl)butanoate,
(3-52) tert-butyl 2-((((9H-fluoren-9-yl)methoxy)carbonyl)(methyl)amino)-4-(2-(methylamino)pyridin-4-yl)butanoate,
(3-53) tert-butyl 2-((((9H-fluoren-9-yl)methoxy)carbonyl)(methyl)amino)-4-(2-(dimethylamino)pyridin-4-yl)butanoate,
(3-54) tert-butyl 2-((((9H-fluoren-9-yl)methoxy)carbonyl)(methyl)amino)-4-(pyrimidin-5-yl)butanoate,
(4-1) tert-butyl (((9H-fluoren-9-yl)methoxy)carbonyl)phenylalaninate,
(4-2) tert-butyl 2-((((9H-fluoren-9-yl)methoxy)carbonyl)amino)-3-(o-tolyl)propanoate,
(4-3) tert-butyl 2-((((9H-fluoren-9-yl)methoxy)carbonyl)amino)-3-(m-tolyl)propanoate,
(4-4) tert-butyl 2-((((9H-fluoren-9-yl)methoxy)carbonyl)amino)-3-(p-tolyl)propanoate,
(4-5) tert-butyl 2-((((9H-fluoren-9-yl)methoxy)carbonyl)amino)-3-(4-ethylphenyl)propanoate,
(4-6) tert-butyl 2-((((9H-fluoren-9-yl)methoxy)carbonyl)amino)-3-(2-chlorophenyl)propanoate,
(4-7) tert-butyl 2-((((9H-fluoren-9-yl)methoxy)carbonyl)amino)-3-(3-chlorophenyl)propanoate,
(4-8) tert-butyl 2-((((9H-fluoren-9-yl)methoxy)carbonyl)amino)-3-(4-chlorophenyl)propanoate,
(4-9) tert-butyl 2-((((9H-fluoren-9-yl)methoxy)carbonyl)amino)-3-(2-fluorophenyl)propanoate,
(4-10) tert-butyl 2-((((9H-fluoren-9-yl)methoxy)carbonyl)amino)-3-(3-fluorophenyl)propanoate,
(4-11) tert-butyl 2-((((9H-fluoren-9-yl)methoxy)carbonyl)amino)-3-(4-fluorophenyl)propanoate,
(4-12) tert-butyl 2-((((9H-fluoren-9-yl)methoxy)carbonyl)amino)-3-(2-cyclopropylphenyl)propanoate,
(4-13) tert-butyl 2-((((9H-fluoren-9-yl)methoxy)carbonyl)amino)-3-(3-cyclopropylphenyl)propanoate,
(4-14) tert-butyl 2-((((9H-fluoren-9-yl)methoxy)carbonyl)amino)-3-(4-cyclopropylphenyl)propanoate,
(4-15) tert-butyl 2-((((9H-fluoren-9-yl)methoxy)carbonyl)amino)-3-(2-(trifluoromethyl)phenyl)propanoate,
(4-16) tert-butyl 2-((((9H-fluoren-9-yl)methoxy)carbonyl)amino)-3-(3-(trifluoromethyl)phenyl)propanoate,
(4-17) tert-butyl 2-((((9H-fluoren-9-yl)methoxy)carbonyl)amino)-3-(4-(trifluoromethyl)phenyl)propanoate,
(4-18) tert-butyl 2-((((9H-fluoren-9-yl)methoxy)carbonyl)amino)-3-(2-isopropylphenyl)propanoate,
(4-19) tert-butyl 2-((((9H-fluoren-9-yl)methoxy)carbonyl)amino)-3-(3-isopropylphenyl)propanoate,
(4-20) tert-butyl 2-((((9H-fluoren-9-yl)methoxy)carbonyl)amino)-3-(4-isopropylphenyl)propanoate,
(4-21) tert-butyl 2-((((9H-fluoren-9-yl)methoxy)carbonyl)amino)-3-(2-methoxyphenyl)propanoate,
(4-22) tert-butyl 2-((((9H-fluoren-9-yl)methoxy)carbonyl)amino)-3-(3-methoxyphenyl)propanoate,
(4-23) tert-butyl 2-((((9H-fluoren-9-yl)methoxy)carbonyl)amino)-3-(4-methoxyphenyl)propanoate,
(4-24) tert-butyl 2-((((9H-fluoren-9-yl)methoxy)carbonyl)amino)-3-(2-(allyloxy)phenyl)propanoate,
(4-25) tert-butyl 2-((((9H-fluoren-9-yl)methoxy)carbonyl)amino)-3-(3-(allyloxy)phenyl)propanoate,
(4-26) tert-butyl 2-((((9H-fluoren-9-yl)methoxy)carbonyl)amino)-3-(4-(allyloxy)phenyl)propanoate,
(4-27) tert-butyl 2-((((9H-fluoren-9-yl)methoxy)carbonyl)amino)-3-(4-isopropoxyphenyl)propanoate,
(4-28) tert-butyl 2-((((9H-fluoren-9-yl)methoxy)carbonyl)amino)-3-(3-fluoro-4-(trifluoromethyl)phenyl)propanoate,
(4-29) tert-butyl 2-((((9H-fluoren-9-yl)methoxy)carbonyl)amino)-3-(2-fluoro-4-(trifluoromethyl)phenyl)propanoate,
(4-30) tert-butyl 2-((((9H-fluoren-9-yl)methoxy)carbonyl)amino)-3-(3,4-dimethoxyphenyl)propanoate,
(4-31) tert-butyl 2-((((9H-fluoren-9-yl)methoxy)carbonyl)amino)-3-(2-fluoro-4-methoxyphenyl)propanoate,
(4-32) tert-butyl 2-((((9H-fluoren-9-yl)methoxy)carbonyl)amino)-3-(3-fluoro-4-methoxyphenyl)propanoate, (4-33) tert-butyl 2-((((9H-fluoren-9-yl)methoxy)carbonyl)amino)-3-(3,5-difluoro-4-methoxyphenyl)propanoate,
(4-34) tert-butyl 2-((((9H-fluoren-9-yl)methoxy)carbonyl)amino)-3-(3,5-difluoro-4-(trifluoromethyl)phenyl)propanoate,
(4-35) tert-butyl 2-((((9H-fluoren-9-yl)methoxy)carbonyl)amino)-3-(3-methoxy-4-(methylcarbamoyl)phenyl)propanoate,
(4-36) tert-butyl 2-((((9H-fluoren-9-yl)methoxy)carbonyl)amino)-3-(4-methoxy-3-(methylcarbamoyl)phenyl)propanoate,
(4-37) tert-butyl 2-((((9H-fluoren-9-yl)methoxy)carbonyl)amino)-3-(3-methoxy-4-((methylsulfonyl)carbamoyl)phenyl)propanoate,
(4-38) tert-butyl 2-((((9H-fluoren-9-yl)methoxy)carbonyl)amino)-3-(4-(methyl((tetrahydro-2H-pyran-2-yl)oxy)carbamoyl)phenyl)propanoate,
(4-39) tert-butyl 2-((((9H-fluoren-9-yl)methoxy)carbonyl)amino)-3-(3-methoxy-4-(((tetrahydro-2H-pyran-2-yl)oxy)carbamoyl)phenyl)propanoate,
(4-40) tert-butyl 2-((((9H-fluoren-9-yl)methoxy)carbonyl)amino)-3-(pyridin-2-yl)propanoate,
(4-41) tert-butyl 2-((((9H-fluoren-9-yl)methoxy)carbonyl)amino)-3-(pyridin-3-yl)propanoate,
(4-42) tert-butyl 2-((((9H-fluoren-9-yl)methoxy)carbonyl)amino)-3-(pyridin-4-yl)propanoate,
(4-43) tert-butyl 2-((((9H-fluoren-9-yl)methoxy)carbonyl)amino)-3-(6-methylpyridin-3-yl)propanoate,
(4-44) tert-butyl 2-((((9H-fluoren-9-yl)methoxy)carbonyl)amino)-3-(5-methylpyridin-3-yl)propanoate,
(4-45) tert-butyl 2-((((9H-fluoren-9-yl)methoxy)carbonyl)amino)-3-(4-methylpyridin-3-yl)propanoate,
(4-46) tert-butyl 2-((((9H-fluoren-9-yl)methoxy)carbonyl)amino)-3-(6-methoxypyridin-3-yl)propanoate,
(4-47) tert-butyl 2-((((9H-fluoren-9-yl)methoxy)carbonyl)amino)-3-(5-methoxypyridin-3-yl)propanoate,
(4-48) tert-butyl 2-((((9H-fluoren-9-yl)methoxy)carbonyl)amino)-3-(5-fluoropyridin-3-yl)propanoate,
(4-49) tert-butyl 2-((((9H-fluoren-9-yl)methoxy)carbonyl)amino)-3-(5-chloropyridin-3-yl)propanoate,
(4-50) tert-butyl 2-((((9H-fluoren-9-yl)methoxy)carbonyl)amino)-3-(5-bromopyridin-3-yl)propanoate,
(4-51) tert-butyl 2-((((9H-fluoren-9-yl)methoxy)carbonyl)amino)-3-(5-iodopyridin-3-yl)propanoate,
(4-52) tert-butyl 2-((((9H-fluoren-9-yl)methoxy)carbonyl)amino)-3-(2-(methylamino)pyridin-4-yl)propanoate,
(4-53) tert-butyl 2-((((9H-fluoren-9-yl)methoxy)carbonyl)amino)-3-(2-(dimethylamino)pyridin-4-yl)propanoate,
(4-54) tert-butyl 2-((((9H-fluoren-9-yl)methoxy)carbonyl)amino)-3-(pyrimidin-5-yl) propanoate,
(5-1) tert-butyl N-methyl(((9H-fluoren-9-yl)methoxy)carbonyl)phenylalaninate,
(5-2) tert-butyl 2-((((9H-fluoren-9-yl)methoxy)carbonyl)(methyl)amino)-3-(o-tolyl)propanoate,
(5-3) tert-butyl 2-((((9H-fluoren-9-yl)methoxy)carbonyl)(methyl)amino)-3-(m-tolyl)propanoate,
(5-4) tert-butyl 2-((((9H-fluoren-9-yl)methoxy)carbonyl)(methyl)amino)-3-(p-tolyl)propanoate,
(5-5) tert-butyl 2-((((9H-fluoren-9-yl)methoxy)carbonyl)(methyl)amino)-3-(4-ethylphenyl)propanoate,
(5-6) tert-butyl 2-((((9H-fluoren-9-yl)methoxy)carbonyl)(methyl)amino)-3-(2-chlorophenyl)propanoate,
(5-7) tert-butyl 2-((((9H-fluoren-9-yl)methoxy)carbonyl)(methyl)amino)-3-(3-chlorophenyl)propanoate,
(5-8) tert-butyl 2-((((9H-fluoren-9-yl)methoxy)carbonyl)(methyl)amino)-3-(4-chlorophenyl)propanoate,
(5-9) tert-butyl 2-((((9H-fluoren-9-yl)methoxy)carbonyl)(methyl)amino)-3-(2-fluorophenyl)propanoate,
(5-10) tert-butyl 2-((((9H-fluoren-9-yl)methoxy)carbonyl)(methyl)amino)-3-(3-fluorophenyl)propanoate,
(5-11) tert-butyl 2-((((9H-fluoren-9-yl)methoxy)carbonyl)(methyl)amino)-3-(4-fluorophenyl)propanoate,
(5-12) tert-butyl 2-((((9H-fluoren-9-yl)methoxy)carbonyl)(methyl)amino)-3-(2-cyclopropylphenyl)propanoate,
(5-13) tert-butyl 2-((((9H-fluoren-9-yl)methoxy)carbonyl)(methyl)amino)-3-(3-cyclopropylphenyl)propanoate,
(5-14) tert-butyl 2-((((9H-fluoren-9-yl)methoxy)carbonyl)(methyl)amino)-3-(4-cyclopropylphenyl)propanoate,
(5-15) tert-butyl 2-((((9H-fluoren-9-yl)methoxy)carbonyl)(methyl)amino)-3-(2-(trifluoromethyl)phenyl)propanoate,
(5-16) tert-butyl 2-((((9H-fluoren-9-yl)methoxy)carbonyl)(methyl)amino)-3-(3-(trifluoromethyl)phenyl)propanoate,
(5-17) tert-butyl 2-((((9H-fluoren-9-yl)methoxy)carbonyl)(methyl)amino)-3-(4-(trifluoromethyl)phenyl)propanoate,
(5-18) tert-butyl 2-((((9H-fluoren-9-yl)methoxy)carbonyl)(methyl)amino)-3-(2-isopropylphenyl)propanoate,
(5-19) tert-butyl 2-((((9H-fluoren-9-yl)methoxy)carbonyl)(methyl)amino)-3-(3-isopropylphenyl)propanoate,
(5-20) tert-butyl 2-((((9H-fluoren-9-yl)methoxy)carbonyl)(methyl)amino)-3-(4-isopropylphenyl)propanoate,
(5-21) tert-butyl 2-((((9H-fluoren-9-yl)methoxy)carbonyl)(methyl)amino)-3-(2-methoxyphenyl)propanoate,
(5-22) tert-butyl 2-((((9H-fluoren-9-yl)methoxy)carbonyl)(methyl)amino)-3-(3-methoxyphenyl)propanoate,
(5-23) tert-butyl 2-((((9H-fluoren-9-yl)methoxy)carbonyl)(methyl)amino)-3-(4-methoxyphenyl)propanoate,
(5-24) tert-butyl 2-((((9H-fluoren-9-yl)methoxy)carbonyl)(methyl)amino)-3-(2-(allyloxy)phenyl)propanoate,
(5-25) tert-butyl 2-((((9H-fluoren-9-yl)methoxy)carbonyl)(methyl)amino)-3-(3-(allyloxy)phenyl)propanoate,
(5-26) tert-butyl 2-((((9H-fluoren-9-yl)methoxy)carbonyl)(methyl)amino)-3-(4-(allyloxy)phenyl)propanoate,
(5-27) tert-butyl 2-((((9H-fluoren-9-yl)methoxy)carbonyl)(methyl)amino)-3-(4-isopropoxyphenyl)propanoate,
(5-28) tert-butyl 2-((((9H-fluoren-9-yl)methoxy)carbonyl)(methyl)amino)-3-(3-fluoro-4-(trifluoromethyl)phenyl)propanoate,
(5-29) tert-butyl 2-((((9H-fluoren-9-yl)methoxy)carbonyl)(methyl)amino)-3-(2-fluoro-4-(trifluoromethyl)phenyl)propanoate,
(5-30) tert-butyl 2-((((9H-fluoren-9-yl)methoxy)carbonyl)(methyl)amino)-3-(3,4-dimethoxyphenyl)propanoate, (5-31) tert-butyl 2-((((9H-fluoren-9-yl)methoxy)carbonyl)(methyl)amino)-3-(2-fluoro-4-methoxyphenyl)propanoate,
(5-32) tert-butyl 2-((((9H-fluoren-9-yl)methoxy)carbonyl)(methyl)amino)-3-(3-fluoro-4-methoxyphenyl)propanoate,
(5-33) tert-butyl 2-((((9H-fluoren-9-yl)methoxy)carbonyl)(methyl)amino)-3-(3,5-difluoro-4-methoxyphenyl)propanoate,
(5-34) tert-butyl 2-((((9H-fluoren-9-yl)methoxy)carbonyl)(methyl)amino)-3-(3,5-difluoro-4-(trifluoromethyl)phenyl)propanoate,
(5-35) tert-butyl 2-((((9H-fluoren-9-yl)methoxy)carbonyl)(methyl)amino)-3-(3-methoxy-4-(methylcarbamoyl)phenyl)propanoate,
(5-36) tert-butyl 2-((((9H-fluoren-9-yl)methoxy)carbonyl)(methyl)amino)-3-(4-methoxy-3-(methylcarbamoyl)phenyl)propanoate,
(5-37) tert-butyl 2-((((9H-fluoren-9-yl)methoxy)carbonyl)(methyl)amino)-3-(3-methoxy-4-((methylsulfonyl)carbamoyl)phenyl)propanoate,
(5-38) tert-butyl 2-((((9H-fluoren-9-yl)methoxy)carbonyl)(methyl)amino)-3-(4-(methyl((tetrahydro-2H-pyran-2-yl)oxy)carbamoyl)phenyl)propanoate,
(5-39) tert-butyl 2-((((9H-fluoren-9-yl)methoxy)carbonyl)(methyl)amino)-3-(3-methoxy-4-(((tetrahydro-2H-pyran-2-yl)oxy)carbamoyl)phenyl)propanoate,
(5-40) tert-butyl 2-((((9H-fluoren-9-yl)methoxy)carbonyl)(methyl)amino)-3-(pyridin-2-yl)propanoate,
(5-41) tert-butyl 2-((((9H-fluoren-9-yl)methoxy)carbonyl)(methyl)amino)-3-(pyridin-3-yl)propanoate,
(5-42) tert-butyl 2-((((9H-fluoren-9-yl)methoxy)carbonyl)(methyl)amino)-3-(pyridin-4-yl)propanoate,
(5-43) tert-butyl 2-((((9H-fluoren-9-yl)methoxy)carbonyl)(methyl)amino)-3-(6-methylpyridin-3-yl)propanoate,
(5-44) tert-butyl 2-((((9H-fluoren-9-yl)methoxy)carbonyl)(methyl)amino)-3-(5-methylpyridin-3-yl)propanoate,
(5-45) tert-butyl 2-((((9H-fluoren-9-yl)methoxy)carbonyl)(methyl)amino)-3-(4-methylpyridin-3-yl)propanoate,
(5-46) tert-butyl 2-((((9H-fluoren-9-yl)methoxy)carbonyl)(methyl)amino)-3-(6-methoxypyridin-3-yl)propanoate,
(5-47) tert-butyl 2-((((9H-fluoren-9-yl)methoxy)carbonyl)(methyl)amino)-3-(5-methoxypyridin-3-yl)propanoate,
(5-48) tert-butyl 2-((((9H-fluoren-9-yl)methoxy)carbonyl)(methyl)amino)-3-(5-fluoropyridin-3-yl)propanoate,
(5-49) tert-butyl 2-((((9H-fluoren-9-yl)methoxy)carbonyl)(methyl)amino)-3-(5-chloropyridin-3-yl)propanoate,
(5-50) tert-butyl 2-((((9H-fluoren-9-yl)methoxy)carbonyl)(methyl)amino)-3-(5-bromopyridin-3-yl)propanoate,
(5-51) tert-butyl 2-((((9H-fluoren-9-yl)methoxy)carbonyl)(methyl)amino)-3-(5-iodopyridin-3-yl)propanoate,
(5-52) tert-butyl 2-((((9H-fluoren-9-yl)methoxy)carbonyl)(methyl)amino)-3-(2-(methylamino)pyridin-4-yl)propanoate,
(5-53) tert-butyl 2-((((9H-fluoren-9-yl)methoxy)carbonyl)(methyl)amino)-3-(2-(dimethylamino)pyridin-4-yl)propanoate,
(5-54) tert-butyl 2-((((9H-fluoren-9-yl)methoxy)carbonyl)(methyl)amino)-3-(pyrimidin-5-yl)propanoate,
(6-1) 2-((((9H-fluoren-9-yl)methoxy)carbonyl)amino)-4-phenylbutanoic acid,
(6-2) 2-((((9H-fluoren-9-yl)methoxy)carbonyl)amino)-4-(o-tolyl)butanoic acid,
(6-3) 2-((((9H-fluoren-9-yl)methoxy)carbonyl)amino)-4-(m-tolyl)butanoic acid,
(6-4) 2-((((9H-fluoren-9-yl)methoxy)carbonyl)amino)-4-(p-tolyl)butanoic acid,
(6-5) 2-((((9H-fluoren-9-yl)methoxy)carbonyl)amino)-4-(4-ethylphenyl)butanoic acid,
(6-6) 2-((((9H-fluoren-9-yl)methoxy)carbonyl)amino)-4-(2-chlorophenyl)butanoic acid,
(6-7) 2-((((9H-fluoren-9-yl)methoxy)carbonyl)amino)-4-(3-chlorophenyl)butanoic acid,
(6-8) 2-((((9H-fluoren-9-yl)methoxy)carbonyl)amino)-4-(4-chlorophenyl)butanoic acid,
(6-9) 2-((((9H-fluoren-9-yl)methoxy)carbonyl)amino)-4-(2-fluorophenyl)butanoic acid,
(6-10) 2-((((9H-fluoren-9-yl)methoxy)carbonyl)amino)-4-(3-fluorophenyl)butanoic acid,
(6-11) 2-((((9H-fluoren-9-yl)methoxy)carbonyl)amino)-4-(4-fluorophenyl)butanoic acid,
(6-12) 2-((((9H-fluoren-9-yl)methoxy)carbonyl)amino)-4-(2-cyclopropylphenyl)butanoic acid,
(6-13) 2-((((9H-fluoren-9-yl)methoxy)carbonyl)amino)-4-(3-cyclopropylphenyl)butanoic acid,
(6-14) 2-((((9H-fluoren-9-yl)methoxy)carbonyl)amino)-4-(4-cyclopropylphenyl)butanoic acid,
(6-15) 2-((((9H-fluoren-9-yl)methoxy)carbonyl)amino)-4-(2-(trifluoromethyl)phenyl)butanoic acid,
(6-16) 2-((((9H-fluoren-9-yl)methoxy)carbonyl)amino)-4-(3-(trifluoromethyl)phenyl)butanoic acid,
(6-17) 2-((((9H-fluoren-9-yl)methoxy)carbonyl)amino)-4-(4-(trifluoromethyl)phenyl)butanoic acid,
(6-18) 2-((((9H-fluoren-9-yl)methoxy)carbonyl)amino)-4-(2-isopropylphenyl)butanoic acid,
(6-19) 2-((((9H-fluoren-9-yl)methoxy)carbonyl)amino)-4-(3-isopropylphenyl)butanoic acid,
(6-20) 2-((((9H-fluoren-9-yl)methoxy)carbonyl)amino)-4-(4-isopropylphenyl)butanoic acid,
(6-21) 2-((((9H-fluoren-9-yl)methoxy)carbonyl)amino)-4-(2-methoxyphenyl)butanoic acid,
(6-22) 2-((((9H-fluoren-9-yl)methoxy)carbonyl)amino)-4-(3-methoxyphenyl)butanoic acid,
(6-23) 2-((((9H-fluoren-9-yl)methoxy)carbonyl)amino)-4-(4-methoxyphenyl)butanoic acid,
(6-24) 2-((((9H-fluoren-9-yl)methoxy)carbonyl)amino)-4-(2-(allyloxy)phenyl)butanoic acid,
(6-25) 2-((((9H-fluoren-9-yl)methoxy)carbonyl)amino)-4-(3-(allyloxy)phenyl)butanoic acid,
(6-26) 2-((((9H-fluoren-9-yl)methoxy)carbonyl)amino)-4-(4-(allyloxy)phenyl)butanoic acid,
(6-27) 2-((((9H-fluoren-9-yl)methoxy)carbonyl)amino)-4-(4-isopropoxyphenyl)butanoic acid,
(6-28) 2-((((9H-fluoren-9-yl)methoxy)carbonyl)amino)-4-(3-fluoro-4-(trifluoromethyl)phenyl)butanoic acid,
(6-29) 2-((((9H-fluoren-9-yl)methoxy)carbonyl)amino)-4-(2-fluoro-4-(trifluoromethyl)phenyl)butanoic acid,
(6-30) 2-((((9H-fluoren-9-yl)methoxy)carbonyl)amino)-4-(3,4-dimethoxyphenyl)butanoic acid,
(6-31) 2-((((9H-fluoren-9-yl)methoxy)carbonyl)amino)-4-(2-fluoro-4-methoxyphenyl)butanoic acid, (6-32) 2-((((9H-fluoren-9-yl)methoxy)carbonyl) amino)-4-(3-fluoro-4-methoxyphenyl)butanoic acid,
(6-33) 2-((((9H-fluoren-9-yl)methoxy)carbonyl) amino)-4-(3,5-difluoro-4-methoxyphenyl)butanoic acid,
(6-34) 2-((((9H-fluoren-9-yl)methoxy)carbonyl) amino)-4-(3,5-difluoro-4-(trifluoromethyl)phenyl) butanoic acid,
(6-35) 2-((((9H-fluoren-9-yl)methoxy)carbonyl) amino)-4-(3-methoxy-4-(methylcarbamoyl)phenyl) butanoic acid,
(6-36) 2-((((9H-fluoren-9-yl)methoxy)carbonyl) amino)-4-(4-methoxy-3-(methylcarbamoyl)phenyl) butanoic acid,
(6-37) 2-((((9H-fluoren-9-yl)methoxy)carbonyl) amino)-4-(3-methoxy-4-((methylsulfonyl)carbamoyl)phenyl)butanoic acid,
(6-38) 2-((((9H-fluoren-9-yl)methoxy)carbonyl) amino)-4-(4-(methyl((tetrahydro-2H-pyran-2-yl) oxy)carbamoyl)phenyl)butanoic acid,
(6-39) 2-((((9H-fluoren-9-yl)methoxy)carbonyl) amino)-4-(3-methoxy-4-(((tetrahydro-2H-pyran-2-yl)oxy)carbamoyl)phenyl)butanoic acid,
(6-40) 2-((((9H-fluoren-9-yl)methoxy)carbonyl) amino)-4-(pyridin-2-yl)butanoic acid,
(6-41) 2-((((9H-fluoren-9-yl)methoxy)carbonyl) amino)-4-(pyridin-3-yl)butanoic acid,
(6-42) 2-((((9H-fluoren-9-yl)methoxy)carbonyl) amino)-4-(pyridin-4-yl)butanoic acid,
(6-43) 2-((((9H-fluoren-9-yl)methoxy)carbonyl) amino)-4-(6-methylpyridin-3-yl)butanoic acid,
(6-44) 2-((((9H-fluoren-9-yl)methoxy)carbonyl) amino)-4-(5-methylpyridin-3-yl)butanoic acid,
(6-45) 2-((((9H-fluoren-9-yl)methoxy)carbonyl) amino)-4-(4-methylpyridin-3-yl)butanoic acid,
(6-46) 2-((((9H-fluoren-9-yl)methoxy)carbonyl) amino)-4-(6-methoxypyridin-3-yl)butanoic acid,
(6-47) 2-((((9H-fluoren-9-yl)methoxy)carbonyl) amino)-4-(5-methoxypyridin-3-yl)butanoic acid,
(6-48) 2-((((9H-fluoren-9-yl)methoxy)carbonyl) amino)-4-(5-fluoropyridin-3-yl)butanoic acid,
(6-49) 2-((((9H-fluoren-9-yl)methoxy)carbonyl) amino)-4-(5-chloropyridin-3-yl)butanoic acid,
(6-50) 2-((((9H-fluoren-9-yl)methoxy)carbonyl) amino)-4-(5-bromopyridin-3-yl)butanoic acid,
(6-51) 2-((((9H-fluoren-9-yl)methoxy)carbonyl) amino)-4-(5-iodopyridin-3-yl)butanoic acid,
(6-52) 2-((((9H-fluoren-9-yl)methoxy)carbonyl) amino)-4-(2-(methylamino)pyridin-4-yl)butanoic acid,
(6-53) 2-((((9H-fluoren-9-yl)methoxy)carbonyl) amino)-4-(2-(dimethylamino)pyridin-4-yl)butanoic acid,
(6-54) 2-((((9H-fluoren-9-yl)methoxy)carbonyl) amino)-4-(pyrimidin-5-yl)butanoic acid,
(7-1) 2-((((9H-fluoren-9-yl)methoxy)carbonyl) (methyl)amino)-4-phenylbutanoic acid,
(7-2) 2-((((9H-fluoren-9-yl)methoxy)carbonyl) (methyl)amino)-4-(o-tolyl)butanoic acid,
(7-3) 2-((((9H-fluoren-9-yl)methoxy)carbonyl) (methyl)amino)-4-(m-tolyl)butanoic acid,
(7-4) 2-((((9H-fluoren-9-yl)methoxy)carbonyl) (methyl)amino)-4-(p-tolyl)butanoic acid,
(7-5) 2-((((9H-fluoren-9-yl)methoxy)carbonyl) (methyl)amino)-4-(4-ethylphenyl)butanoic acid,
(7-6) 2-((((9H-fluoren-9-yl)methoxy)carbonyl) (methyl)amino)-4-(2-chlorophenyl)butanoic acid,
(7-7) 2-((((9H-fluoren-9-yl)methoxy)carbonyl) (methyl)amino)-4-(3-chlorophenyl)butanoic acid,
(7-8) 2-((((9H-fluoren-9-yl)methoxy)carbonyl) (methyl)amino)-4-(4-chlorophenyl)butanoic acid,
(7-9) 2-((((9H-fluoren-9-yl)methoxy)carbonyl) (methyl)amino)-4-(2-fluorophenyl)butanoic acid,
(7-10) 2-((((9H-fluoren-9-yl)methoxy)carbonyl) (methyl)amino)-4-(3-fluorophenyl)butanoic acid,
(7-11) 2-((((9H-fluoren-9-yl)methoxy)carbonyl) (methyl)amino)-4-(4-fluorophenyl)butanoic acid,
(7-12) 2-((((9H-fluoren-9-yl)methoxy)carbonyl) (methyl)amino)-4-(2-cyclopropylphenyl)butanoic acid,
(7-13) 2-((((9H-fluoren-9-yl)methoxy)carbonyl) (methyl)amino)-4-(3-cyclopropylphenyl)butanoic acid,
(7-14) 2-((((9H-fluoren-9-yl)methoxy)carbonyl) (methyl)amino)-4-(4-cyclopropylphenyl)butanoic acid,
(7-15) 2-((((9H-fluoren-9-yl)methoxy)carbonyl) (methyl)amino)-4-(2-(trifluoromethyl)phenyl)butanoic acid,
(7-16) 2-((((9H-fluoren-9-yl)methoxy)carbonyl) (methyl)amino)-4-(3-(trifluoromethyl)phenyl)butanoic acid,
(7-17) 2-((((9H-fluoren-9-yl)methoxy)carbonyl) (methyl)amino)-4-(4-(trifluoromethyl)phenyl)butanoic acid,
(7-18) 2-((((9H-fluoren-9-yl)methoxy)carbonyl) (methyl)amino)-4-(2-isopropylphenyl)butanoic acid,
(7-19) 2-((((9H-fluoren-9-yl)methoxy)carbonyl) (methyl)amino)-4-(3-isopropylphenyl)butanoic acid,
(7-20) 2-((((9H-fluoren-9-yl)methoxy)carbonyl) (methyl)amino)-4-(4-isopropylphenyl)butanoic acid,
(7-21) 2-((((9H-fluoren-9-yl)methoxy)carbonyl) (methyl)amino)-4-(2-methoxyphenyl)butanoic acid,
(7-22) 2-((((9H-fluoren-9-yl)methoxy)carbonyl) (methyl)amino)-4-(3-methoxyphenyl)butanoic acid,
(7-23) 2-((((9H-fluoren-9-yl)methoxy)carbonyl) (methyl)amino)-4-(4-methoxyphenyl)butanoic acid,
(7-24) 2-((((9H-fluoren-9-yl)methoxy)carbonyl) (methyl)amino)-4-(2-(allyloxy)phenyl)butanoic acid,
(7-25) 2-((((9H-fluoren-9-yl)methoxy)carbonyl) (methyl)amino)-4-(3-(allyloxy)phenyl)butanoic acid,
(7-26) 2-((((9H-fluoren-9-yl)methoxy)carbonyl) (methyl)amino)-4-(4-(allyloxy)phenyl)butanoic acid,
(7-27) 2-((((9H-fluoren-9-yl)methoxy)carbonyl) (methyl)amino)-4-(4-isopropoxyphenyl)butanoic acid,
(7-28) 2-((((9H-fluoren-9-yl)methoxy)carbonyl) (methyl)amino)-4-(3-fluoro-4-(trifluoromethyl)phenyl)butanoic acid,
(7-29) 2-((((9H-fluoren-9-yl)methoxy)carbonyl) (methyl)amino)-4-(2-fluoro-4-(trifluoromethyl)phenyl)butanoic acid,
(7-30) 2-((((9H-fluoren-9-yl)methoxy)carbonyl) (methyl)amino)-4-(3,4-dimethoxyphenyl)butanoic acid,
(7-31) 2-((((9H-fluoren-9-yl)methoxy)carbonyl) (methyl)amino)-4-(2-fluoro-4-methoxyphenyl)butanoic acid,
(7-32) 2-((((9H-fluoren-9-yl)methoxy)carbonyl) (methyl)amino)-4-(3-fluoro-4-methoxyphenyl)butanoic acid, (7-33) 2-((((9H-fluoren-9-yl)methoxy)carbonyl)(methyl)amino)-4-(3,5-difluoro-4-methoxyphenyl)butanoic acid,
(7-34) 2-((((9H-fluoren-9-yl)methoxy)carbonyl)(methyl)amino)-4-(3,5-difluoro-4-(trifluoromethyl)phenyl)butanoic acid,
(7-35) 2-((((9H-fluoren-9-yl)methoxy)carbonyl)(methyl)amino)-4-(3-methoxy-4-(methylcarbamoyl)phenyl)butanoic acid,
(7-36) 2-((((9H-fluoren-9-yl)methoxy)carbonyl)(methyl)amino)-4-(4-methoxy-3-(methylcarbamoyl)phenyl)butanoic acid,
(7-37) 2-((((9H-fluoren-9-yl)methoxy)carbonyl)(methyl)amino)-4-(3-methoxy-4-((methylsulfonyl)carbamoyl)phenyl)butanoic acid,
(7-38) 2-((((9H-fluoren-9-yl)methoxy)carbonyl)(methyl)amino)-4-(4-(methyl((tetrahydro-2H-pyran-2-yl)oxy)carbamoyl)phenyl)butanoic acid,
(7-39) 2-((((9H-fluoren-9-yl)methoxy)carbonyl)(methyl)amino)-4-(3-methoxy-4-(((tetrahydro-2H-pyran-2-yl)oxy)carbamoyl)phenyl)butanoic acid,
(7-40) 2-((((9H-fluoren-9-yl)methoxy)carbonyl)(methyl)amino)-4-(pyridin-2-yl)butanoic acid,
(7-41) 2-((((9H-fluoren-9-yl)methoxy)carbonyl)(methyl)amino)-4-(pyridin-3-yl)butanoic acid,
(7-42) 2-((((9H-fluoren-9-yl)methoxy)carbonyl)(methyl)amino)-4-(pyridin-4-yl)butanoic acid,
(7-43) 2-((((9H-fluoren-9-yl)methoxy)carbonyl)(methyl)amino)-4-(6-methylpyridin-3-yl)butanoic acid,
(7-44) 2-((((9H-fluoren-9-yl)methoxy)carbonyl)(methyl)amino)-4-(5-methylpyridin-3-yl)butanoic acid,
(7-45) 2-((((9H-fluoren-9-yl)methoxy)carbonyl)(methyl)amino)-4-(4-methylpyridin-3-yl)butanoic acid,
(7-46) 2-((((9H-fluoren-9-yl)methoxy)carbonyl)(methyl)amino)-4-(6-methoxypyridin-3-yl)butanoic acid,
(7-47) 2-((((9H-fluoren-9-yl)methoxy)carbonyl)(methyl)amino)-4-(5-methoxypyridin-3-yl)butanoic acid,
(7-48) 2-((((9H-fluoren-9-yl)methoxy)carbonyl)(methyl)amino)-4-(5-fluoropyridin-3-yl)butanoic acid,
(7-49) 2-((((9H-fluoren-9-yl)methoxy)carbonyl)(methyl)amino)-4-(5-chloropyridin-3-yl)butanoic acid,
(7-50) 2-((((9H-fluoren-9-yl)methoxy)carbonyl)(methyl)amino)-4-(5-bromopyridin-3-yl)butanoic acid,
(7-51) 2-((((9H-fluoren-9-yl)methoxy)carbonyl)(methyl)amino)-4-(5-iodopyridin-3-yl)butanoic acid,
(7-52) 2-((((9H-fluoren-9-yl)methoxy)carbonyl)(methyl)amino)-4-(2-(methylamino)pyridin-4-yl)butanoic acid,
(7-53) 2-((((9H-fluoren-9-yl)methoxy)carbonyl)(methyl)amino)-4-(2-(dimethylamino)pyridin-4-yl)butanoic acid,
(7-54) 2-((((9H-fluoren-9-yl)methoxy)carbonyl)(methyl)amino)-4-(pyrimidin-5-yl)butanoic acid,
(8-1) (((9H-fluoren-9-yl)methoxy)carbonyl)phenylalanine,
(8-2) 2-((((9H-fluoren-9-yl)methoxy)carbonyl)amino)-3-(o-tolyl)propanoic acid,
(8-3) 2-((((9H-fluoren-9-yl)methoxy)carbonyl)amino)-3-(m-tolyl)propanoic acid,
(8-4) 2-((((9H-fluoren-9-yl)methoxy)carbonyl)amino)-3-(p-tolyl)propanoic acid,
(8-5) 2-((((9H-fluoren-9-yl)methoxy)carbonyl)amino)-3-(4-ethylphenyl)propanoic acid,
(8-6) 2-((((9H-fluoren-9-yl)methoxy)carbonyl)amino)-3-(2-chlorophenyl)propanoic acid,
(8-7) 2-((((9H-fluoren-9-yl)methoxy)carbonyl)amino)-3-(3-chlorophenyl)propanoic acid,
(8-8) 2-((((9H-fluoren-9-yl)methoxy)carbonyl)amino)-3-(4-chlorophenyl)propanoic acid,
(8-9) 2-((((9H-fluoren-9-yl)methoxy)carbonyl)amino)-3-(2-fluorophenyl)propanoic acid,
(8-10) 2-((((9H-fluoren-9-yl)methoxy)carbonyl)amino)-3-(3-fluorophenyl)propanoic acid,
(8-11) 2-((((9H-fluoren-9-yl)methoxy)carbonyl)amino)-3-(4-fluorophenyl)propanoic acid,
(8-12) 2-((((9H-fluoren-9-yl)methoxy)carbonyl)amino)-3-(2-cyclopropylphenyl)propanoic acid,
(8-13) 2-((((9H-fluoren-9-yl)methoxy)carbonyl)amino)-3-(3-cyclopropylphenyl)propanoic acid,
(8-14) 2-((((9H-fluoren-9-yl)methoxy)carbonyl)amino)-3-(4-cyclopropylphenyl)propanoic acid,
(8-15) 2-((((9H-fluoren-9-yl)methoxy)carbonyl)amino)-3-(2-(trifluoromethyl)phenyl)propanoic acid,
(8-16) 2-((((9H-fluoren-9-yl)methoxy)carbonyl)amino)-3-(3-(trifluoromethyl)phenyl)propanoic acid,
(8-17) 2-((((9H-fluoren-9-yl)methoxy)carbonyl)amino)-3-(4-(trifluoromethyl)phenyl)propanoic acid,
(8-18) 2-((((9H-fluoren-9-yl)methoxy)carbonyl)amino)-3-(2-isopropylphenyl)propanoic acid,
(8-19) 2-((((9H-fluoren-9-yl)methoxy)carbonyl)amino)-3-(3-isopropylphenyl)propanoic acid,
(8-20) 2-((((9H-fluoren-9-yl)methoxy)carbonyl)amino)-3-(4-isopropylphenyl)propanoic acid,
(8-21) 2-((((9H-fluoren-9-yl)methoxy)carbonyl)amino)-3-(2-methoxyphenyl)propanoic acid,
(8-22) 2-((((9H-fluoren-9-yl)methoxy)carbonyl)amino)-3-(3-methoxyphenyl)propanoic acid,
(8-23) 2-((((9H-fluoren-9-yl)methoxy)carbonyl)amino)-3-(4-methoxyphenyl)propanoic acid,
(8-24) 2-((((9H-fluoren-9-yl)methoxy)carbonyl)amino)-3-(2-(allyloxy)phenyl)propanoic acid,
(8-25) 2-((((9H-fluoren-9-yl)methoxy)carbonyl)amino)-3-(3-(allyloxy)phenyl)propanoic acid,
(8-26) 2-((((9H-fluoren-9-yl)methoxy)carbonyl)amino)-3-(4-(allyloxy)phenyl)propanoic acid,
(8-27) 2-((((9H-fluoren-9-yl)methoxy)carbonyl)amino)-3-(4-isopropoxyphenyl)propanoic acid,
(8-28) 2-((((9H-fluoren-9-yl)methoxy)carbonyl)amino)-3-(3-fluoro-4-(trifluoromethyl)phenyl)propanoic acid,
(8-29) 2-((((9H-fluoren-9-yl)methoxy)carbonyl)amino)-3-(2-fluoro-4-(trifluoromethyl)phenyl)propanoic acid,
(8-30) 2-((((9H-fluoren-9-yl)methoxy)carbonyl)amino)-3-(3,4-dimethoxyphenyl)propanoic acid,
(8-31) 2-((((9H-fluoren-9-yl)methoxy)carbonyl)amino)-3-(2-fluoro-4-methoxyphenyl)propanoic acid,
(8-32) 2-((((9H-fluoren-9-yl)methoxy)carbonyl)amino)-3-(3-fluoro-4-methoxyphenyl)propanoic acid, (8-33) 2-((((9H-fluoren-9-yl)methoxy)carbonyl) amino)-3-(3,5-difluoro-4-methoxyphenyl)propanoic acid,
(8-34) 2-((((9H-fluoren-9-yl)methoxy)carbonyl) amino)-3-(3,5-difluoro-4-(trifluoromethyl)phenyl) propanoic acid,
(8-35) 2-((((9H-fluoren-9-yl)methoxy)carbonyl) amino)-3-(3-methoxy-4-(methylcarbamoyl)phenyl) propanoic acid,
(8-36) 2-((((9H-fluoren-9-yl)methoxy)carbonyl) amino)-3-(4-methoxy-3-(methylcarbamoyl)phenyl) propanoic acid,
(8-37) 2-((((9H-fluoren-9-yl)methoxy)carbonyl) amino)-3-(3-methoxy-4-((methylsulfonyl)carbamoyl)phenyl)propanoic acid,
(8-38) 2-((((9H-fluoren-9-yl)methoxy)carbonyl) amino)-3-(4-(methyl((tetrahydro-2H-pyran-2-yl) oxy)carbamoyl)phenyl)propanoic acid,
(8-39) 2-((((9H-fluoren-9-yl)methoxy)carbonyl) amino)-3-(3-methoxy-4-(((tetrahydro-2H-pyran-2-yl)oxy)carbamoyl)phenyl)propanoic acid,
(8-40) 2-((((9H-fluoren-9-yl)methoxy)carbonyl) amino)-3-(pyridin-2-yl)propanoic acid,
(8-41) 2-((((9H-fluoren-9-yl)methoxy)carbonyl) amino)-3-(pyridin-3-yl)propanoic acid,
(8-42) 2-((((9H-fluoren-9-yl)methoxy)carbonyl) amino)-3-(pyridin-4-yl)propanoic acid,
(8-43) 2-((((9H-fluoren-9-yl)methoxy)carbonyl) amino)-3-(6-methylpyridin-3-yl)propanoic acid,
(8-44) 2-((((9H-fluoren-9-yl)methoxy)carbonyl) amino)-3-(5-methylpyridin-3-yl)propanoic acid,
(8-45) 2-((((9H-fluoren-9-yl)methoxy)carbonyl) amino)-3-(4-methylpyridin-3-yl)propanoic acid,
(8-46) 2-((((9H-fluoren-9-yl)methoxy)carbonyl) amino)-3-(6-methoxypyridin-3-yl)propanoic acid,
(8-47) 2-((((9H-fluoren-9-yl)methoxy)carbonyl) amino)-3-(5-methoxypyridin-3-yl)propanoic acid,
(8-48) 2-((((9H-fluoren-9-yl)methoxy)carbonyl) amino)-3-(5-fluoropyridin-3-yl)propanoic acid,
(8-49) 2-((((9H-fluoren-9-yl)methoxy)carbonyl) amino)-3-(5-chloropyridin-3-yl)propanoic acid,
(8-50) 2-((((9H-fluoren-9-yl)methoxy)carbonyl) amino)-3-(5-bromopyridin-3-yl)propanoic acid,
(8-51) 2-((((9H-fluoren-9-yl)methoxy)carbonyl) amino)-3-(5-iodopyridin-3-yl)propanoic acid,
(8-52) 2-((((9H-fluoren-9-yl)methoxy)carbonyl) amino)-3-(2-(methylamino)pyridin-4-yl)propanoic acid,
(8-53) 2-((((9H-fluoren-9-yl)methoxy)carbonyl) amino)-3-(2-(dimethylamino)pyridin-4-yl)propanoic acid,
(8-54) 2-((((9H-fluoren-9-yl)methoxy)carbonyl) amino)-3-(pyrimidin-5-yl)propanoic acid,
(9-1) N-(((9H-fluoren-9-yl)methoxy)carbonyl)-N-methylphenylalanine,
(9-2) 2-((((9H-fluoren-9-yl)methoxy)carbonyl) (methyl)amino)-3-(o-tolyl)propanoic acid,
(9-3) 2-((((9H-fluoren-9-yl)methoxy)carbonyl) (methyl)amino)-3-(m-tolyl)propanoic acid,
(9-4) 2-((((9H-fluoren-9-yl)methoxy)carbonyl) (methyl)amino)-3-(p-tolyl)propanoic acid,
(9-5) 2-((((9H-fluoren-9-yl)methoxy)carbonyl) (methyl)amino)-3-(4-ethylphenyl)propanoic acid,
(9-6) 2-((((9H-fluoren-9-yl)methoxy)carbonyl) (methyl)amino)-3-(2-chlorophenyl)propanoic acid,
(9-7) 2-((((9H-fluoren-9-yl)methoxy)carbonyl) (methyl)amino)-3-(3-chlorophenyl)propanoic acid,
(9-8) 2-((((9H-fluoren-9-yl)methoxy)carbonyl) (methyl)amino)-3-(4-chlorophenyl)propanoic acid,
(9-9) 2-((((9H-fluoren-9-yl)methoxy)carbonyl) (methyl)amino)-3-(2-fluorophenyl)propanoic acid,
(9-10) 2-((((9H-fluoren-9-yl)methoxy)carbonyl) (methyl)amino)-3-(3-fluorophenyl)propanoic acid,
(9-11) 2-((((9H-fluoren-9-yl)methoxy)carbonyl) (methyl)amino)-3-(4-fluorophenyl)propanoic acid,
(9-12) 2-((((9H-fluoren-9-yl)methoxy)carbonyl) (methyl)amino)-3-(2-cyclopropylphenyl)propanoic acid,
(9-13) 2-((((9H-fluoren-9-yl)methoxy)carbonyl) (methyl)amino)-3-(3-cyclopropylphenyl)propanoic acid,
(9-14) 2-((((9H-fluoren-9-yl)methoxy)carbonyl) (methyl)amino)-3-(4-cyclopropylphenyl)propanoic acid,
(9-15) 2-((((9H-fluoren-9-yl)methoxy)carbonyl) (methyl)amino)-3-(2-(trifluoromethyl)phenyl)propanoic acid,
(9-16) 2-((((9H-fluoren-9-yl)methoxy)carbonyl) (methyl)amino)-3-(3-(trifluoromethyl)phenyl)propanoic acid,
(9-17) 2-((((9H-fluoren-9-yl)methoxy)carbonyl) (methyl)amino)-3-(4-(trifluoromethyl)phenyl)propanoic acid,
(9-18) 2-((((9H-fluoren-9-yl)methoxy)carbonyl) (methyl)amino)-3-(2-isopropylphenyl)propanoic acid,
(9-19) 2-((((9H-fluoren-9-yl)methoxy)carbonyl) (methyl)amino)-3-(3-isopropylphenyl)propanoic acid,
(9-20) 2-((((9H-fluoren-9-yl)methoxy)carbonyl) (methyl)amino)-3-(4-isopropylphenyl)propanoic acid,
(9-21) 2-((((9H-fluoren-9-yl)methoxy)carbonyl) (methyl)amino)-3-(2-methoxyphenyl)propanoic acid,
(9-22) 2-((((9H-fluoren-9-yl)methoxy)carbonyl) (methyl)amino)-3-(3-methoxyphenyl)propanoic acid,
(9-23) 2-((((9H-fluoren-9-yl)methoxy)carbonyl) (methyl)amino)-3-(4-methoxyphenyl)propanoic acid,
(9-24) 2-((((9H-fluoren-9-yl)methoxy)carbonyl) (methyl)amino)-3-(2-(allyloxy)phenyl)propanoic acid,
(9-25) 2-((((9H-fluoren-9-yl)methoxy)carbonyl) (methyl)amino)-3-(3-(allyloxy)phenyl)propanoic acid,
(9-26) 2-((((9H-fluoren-9-yl)methoxy)carbonyl) (methyl)amino)-3-(4-(allyloxy)phenyl)propanoic acid,
(9-27) 2-((((9H-fluoren-9-yl)methoxy)carbonyl) (methyl)amino)-3-(4-isopropoxyphenyl)propanoic acid,
(9-28) 2-((((9H-fluoren-9-yl)methoxy)carbonyl) (methyl)amino)-3-(3-fluoro-4-(trifluoromethyl)phenyl)propanoic acid,
(9-29) 2-((((9H-fluoren-9-yl)methoxy)carbonyl) (methyl)amino)-3-(2-fluoro-4-(trifluoromethyl)phenyl)propanoic acid,
(9-30) 2-((((9H-fluoren-9-yl)methoxy)carbonyl) (methyl)amino)-3-(3,4-dimethoxyphenyl)propanoic acid, (9-31) 2-((((9H-fluoren-9-yl)methoxy)carbonyl)(methyl)amino)-3-(2-fluoro-4-methoxyphenyl)propanoic acid,
(9-32) 2-((((9H-fluoren-9-yl)methoxy)carbonyl)(methyl)amino)-3-(3-fluoro-4-methoxyphenyl)propanoic acid,
(9-33) 2-((((9H-fluoren-9-yl)methoxy)carbonyl)(methyl)amino)-3-(3,5-difluoro-4-methoxyphenyl)propanoic acid,
(9-34) 2-((((9H-fluoren-9-yl)methoxy)carbonyl)(methyl)amino)-3-(3,5-difluoro-4-(trifluoromethyl)phenyl)propanoic acid,
(9-35) 2-((((9H-fluoren-9-yl)methoxy)carbonyl)(methyl)amino)-3-(3-methoxy-4-(methylcarbamoyl)phenyl)propanoic acid,
(9-36) 2-((((9H-fluoren-9-yl)methoxy)carbonyl)(methyl)amino)-3-(4-methoxy-3-(methylcarbamoyl)phenyl)propanoic acid,
(9-37) 2-((((9H-fluoren-9-yl)methoxy)carbonyl)(methyl)amino)-3-(3-methoxy-4-((methylsulfonyl)carbamoyl)phenyl)propanoic acid,
(9-38) 2-((((9H-fluoren-9-yl)methoxy)carbonyl)(methyl)amino)-3-(4-(methyl((tetrahydro-2H-pyran-2-yl)oxy)carbamoyl)phenyl)propanoic acid,
(9-39) 2-((((9H-fluoren-9-yl)methoxy)carbonyl)(methyl)amino)-3-(3-methoxy-4-(((tetrahydro-2H-pyran-2-yl)oxy)carbamoyl)phenyl)propanoic acid,
(9-40) 2-((((9H-fluoren-9-yl)methoxy)carbonyl)(methyl)amino)-3-(pyridin-2-yl)propanoic acid,
(9-41) 2-((((9H-fluoren-9-yl)methoxy)carbonyl)(methyl)amino)-3-(pyridin-3-yl)propanoic acid,
(9-42) 2-((((9H-fluoren-9-yl)methoxy)carbonyl)(methyl)amino)-3-(pyridin-4-yl)propanoic acid,
(9-43) 2-((((9H-fluoren-9-yl)methoxy)carbonyl)(methyl)amino)-3-(6-methylpyridin-3-yl)propanoic acid,
(9-44) 2-((((9H-fluoren-9-yl)methoxy)carbonyl)(methyl)amino)-3-(5-methylpyridin-3-yl)propanoic acid,
(9-45) 2-((((9H-fluoren-9-yl)methoxy)carbonyl)(methyl)amino)-3-(4-methylpyridin-3-yl)propanoic acid,
(9-46) 2-((((9H-fluoren-9-yl)methoxy)carbonyl)(methyl)amino)-3-(6-methoxypyridin-3-yl)propanoic acid,
(9-47) 2-((((9H-fluoren-9-yl)methoxy)carbonyl)(methyl)amino)-3-(5-methoxypyridin-3-yl)propanoic acid,
(9-48) 2-((((9H-fluoren-9-yl)methoxy)carbonyl)(methyl)amino)-3-(5-fluoropyridin-3-yl)propanoic acid,
(9-49) 2-((((9H-fluoren-9-yl)methoxy)carbonyl)(methyl)amino)-3-(5-chloropyridin-3-yl)propanoic acid,
(9-50) 2-((((9H-fluoren-9-yl)methoxy)carbonyl)(methyl)amino)-3-(5-bromopyridin-3-yl)propanoic acid,
(9-51) 2-((((9H-fluoren-9-yl)methoxy)carbonyl)(methyl)amino)-3-(5-iodopyridin-3-yl)propanoic acid,
(9-52) 2-((((9H-fluoren-9-yl)methoxy)carbonyl)(methyl)amino)-3-(2-(methylamino)pyridin-4-yl)propanoic acid,
(9-53) 2-((((9H-fluoren-9-yl)methoxy)carbonyl)(methyl)amino)-3-(2-(dimethylamino)pyridin-4-yl)propanoic acid,
(9-54) 2-((((9H-fluoren-9-yl)methoxy)carbonyl)(methyl)amino)-3-(pyrimidin-5-yl)propanoic acid,
(10-1) 2-amino-4-phenylbutanoic acid,
(10-2) 2-amino-4-(o-tolyl)butanoic acid,
(10-3) 2-amino-4-(m-tolyl)butanoic acid,
(10-4) 2-amino-4-(p-tolyl)butanoic acid,
(10-5) 2-amino-4-(4-ethylphenyl)butanoic acid,
(10-6) 2-amino-4-(2-chlorophenyl)butanoic acid,
(10-7) 2-amino-4-(3-chlorophenyl)butanoic acid,
(10-8) 2-amino-4-(4-chlorophenyl)butanoic acid,
(10-9) 2-amino-4-(2-fluorophenyl)butanoic acid,
(10-10) 2-amino-4-(3-fluorophenyl)butanoic acid,
(10-11) 2-amino-4-(4-fluorophenyl)butanoic acid,
(10-12) 2-amino-4-(2-cyclopropylphenyl)butanoic acid,
(10-13) 2-amino-4-(3-cyclopropylphenyl)butanoic acid,
(10-14) 2-amino-4-(4-cyclopropylphenyl)butanoic acid,
(10-15) 2-amino-4-(2-(trifluoromethyl)phenyl)butanoic acid,
(10-16) 2-amino-4-(3-(trifluoromethyl)phenyl)butanoic acid,
(10-17) 2-amino-4-(4-(trifluoromethyl)phenyl)butanoic acid,
(10-18) 2-amino-4-(2-isopropylphenyl)butanoic acid,
(10-19) 2-amino-4-(3-isopropylphenyl)butanoic acid,
(10-20) 2-amino-4-(4-isopropylphenyl)butanoic acid,
(10-21) 2-amino-4-(2-methoxyphenyl)butanoic acid,
(10-22) 2-amino-4-(3-methoxyphenyl)butanoic acid,
(10-23) 2-amino-4-(4-methoxyphenyl)butanoic acid,
(10-24) 2-amino-4-(2-(allyloxy)phenyl)butanoic acid,
(10-25) 2-amino-4-(3-(allyloxy)phenyl)butanoic acid,
(10-26) 2-amino-4-(4-(allyloxy)phenyl)butanoic acid,
(10-27) 2-amino-4-(4-isopropoxyphenyl)butanoic acid,
(10-28) 2-amino-4-(3-fluoro-4-(trifluoromethyl)phenyl)butanoic acid,
(10-29) 2-amino-4-(2-fluoro-4-(trifluoromethyl)phenyl)butanoic acid,
(10-30) 2-amino-4-(3,4-dimethoxyphenyl)butanoic acid,
(10-31) 2-amino-4-(2-fluoro-4-methoxyphenyl)butanoic acid,
(10-32) 2-amino-4-(3-fluoro-4-methoxyphenyl)butanoic acid,
(10-33) 2-amino-4-(3,5-difluoro-4-methoxyphenyl)butanoic acid,
(10-34) 2-amino-4-(3,5-difluoro-4-(trifluoromethyl)phenyl)butanoic acid,
(10-35) 2-amino-4-(3-methoxy-4-(methylcarbamoyl)phenyl)butanoic acid,
(10-36) 2-amino-4-(4-methoxy-3-(methylcarbamoyl)phenyl)butanoic acid,
(10-37) 2-amino-4-(3-methoxy-4-((methylsulfonyl)carbamoyl)phenyl)butanoic acid,
(10-38) 2-amino-4-(4-(methyl((tetrahydro-2H-pyran-2-yl)oxy)carbamoyl)phenyl)butanoic acid,
(10-39) 2-amino-4-(3-methoxy-4-(((tetrahydro-2H-pyran-2-yl)oxy)carbamoyl)phenyl)butanoic acid,
(10-40) 2-amino-4-(pyridin-2-yl)butanoic acid,
(10-41) 2-amino-4-(pyridin-3-yl)butanoic acid,
(10-42) 2-amino-4-(pyridin-4-yl)butanoic acid,
(10-43) 2-amino-4-(6-methylpyridin-3-yl)butanoic acid,
(10-44) 2-amino-4-(5-methylpyridin-3-yl)butanoic acid, (10-45) 2-amino-4-(4-methylpyridin-3-yl)butanoic acid,
(10-46) 2-amino-4-(6-methoxypyridin-3-yl)butanoic acid,
(10-47) 2-amino-4-(5-methoxypyridin-3-yl)butanoic acid,
(10-48) 2-amino-4-(5-fluoropyridin-3-yl)butanoic acid,
(10-49) 2-amino-4-(5-chloropyridin-3-yl)butanoic acid,
(10-50) 2-amino-4-(5-bromopyridin-3-yl)butanoic acid,
(10-51) 2-amino-4-(5-iodopyridin-3-yl)butanoic acid,
(10-52) 2-amino-4-(2-(methylamino)pyridin-4-yl)butanoic acid,
(10-53) 2-amino-4-(2-(dimethylamino)pyridin-4-yl)butanoic acid,
(10-54) 2-amino-4-(pyrimidin-5-yl)butanoic acid,
(11-1) 2-(methylamino)-4-phenylbutanoic acid,
(11-2) 2-(methylamino)-4-(o-tolyl)butanoic acid,
(11-3) 2-(methylamino)-4-(m-tolyl)butanoic acid,
(11-4) 2-(methylamino)-4-(p-tolyl)butanoic acid,
(11-5) 2-(methylamino)-4-(4-ethylphenyl)butanoic acid,
(11-6) 2-(methylamino)-4-(2-chlorophenyl)butanoic acid,
(11-7) 2-(methylamino)-4-(3-chlorophenyl)butanoic acid,
(11-8) 2-(methylamino)-4-(4-chlorophenyl)butanoic acid,
(11-9) 2-(methylamino)-4-(2-fluorophenyl)butanoic acid,
(11-10) 2-(methylamino)-4-(3-fluorophenyl)butanoic acid,
(11-11) 2-(methylamino)-4-(4-fluorophenyl)butanoic acid,
(11-12) 2-(methylamino)-4-(2-cyclopropylphenyl)butanoic acid,
(11-13) 2-(methylamino)-4-(3-cyclopropylphenyl)butanoic acid,
(11-14) 2-(methylamino)-4-(4-cyclopropylphenyl)butanoic acid,
(11-15) 2-(methylamino)-4-(2-(trifluoromethyl)phenyl)butanoic acid,
(11-16) 2-(methylamino)-4-(3-(trifluoromethyl)phenyl)butanoic acid,
(11-17) 2-(methylamino)-4-(4-(trifluoromethyl)phenyl)butanoic acid,
(11-18) 2-(methylamino)-4-(2-isopropylphenyl)butanoic acid,
(11-19) 2-(methylamino)-4-(3-isopropylphenyl)butanoic acid,
(11-20) 2-(methylamino)-4-(4-isopropylphenyl)butanoic acid,
(11-21) 2-(methylamino)-4-(2-methoxyphenyl)butanoic acid,
(11-22) 2-(methylamino)-4-(3-methoxyphenyl)butanoic acid,
(11-23) 2-(methylamino)-4-(4-methoxyphenyl)butanoic acid,
(11-24) 2-(methylamino)-4-(2-(allyloxy)phenyl)butanoic acid,
(11-25) 2-(methylamino)-4-(3-(allyloxy)phenyl)butanoic acid,
(11-26) 2-(methylamino)-4-(4-(allyloxy)phenyl)butanoic acid,
(11-27) 2-(methylamino)-4-(4-isopropoxyphenyl)butanoic acid,
(11-28) 2-(methylamino)-4-(3-fluoro-4-(trifluoromethyl)phenyl)butanoic acid,
(11-29) 2-(methylamino)-4-(2-fluoro-4-(trifluoromethyl)phenyl)butanoic acid,
(11-30) 2-(methylamino)-4-(3,4-dimethoxyphenyl)butanoic acid,
(11-31) 2-(methylamino)-4-(2-fluoro-4-methoxyphenyl)butanoic acid,
(11-32) 2-(methylamino)-4-(3-fluoro-4-methoxyphenyl)butanoic acid,
(11-33) 2-(methylamino)-4-(3,5-difluoro-4-methoxyphenyl)butanoic acid,
(11-34) 2-(methylamino)-4-(3,5-difluoro-4-(trifluoromethyl)phenyl)butanoic acid,
(11-35) 2-(methylamino)-4-(3-methoxy-4-(methylcarbamoyl)phenyl)butanoic acid,
(11-36) 2-(methylamino)-4-(4-methoxy-3-(methylcarbamoyl)phenyl)butanoic acid,
(11-37) 2-(methylamino)-4-(3-methoxy-4-((methylsulfonyl)carbamoyl)phenyl)butanoic acid,
(11-38) 2-(methylamino)-4-(4-(methyl((tetrahydro-2H-pyran-2-yl)oxy)carbamoyl)phenyl)butanoic acid,
(11-39) 2-(methylamino)-4-(3-methoxy-4-((tetrahydro-2H-pyran-2-yl)oxy)carbamoyl)phenyl)butanoic acid,
(11-40) 2-(methylamino)-4-(pyridin-2-yl)butanoic acid,
(11-41) 2-(methylamino)-4-(pyridin-3-yl)butanoic acid,
(11-42) 2-(methylamino)-4-(pyridin-4-yl)butanoic acid,
(11-43) 2-(methylamino)-4-(6-methylpyridin-3-yl)butanoic acid,
(11-44) 2-(methylamino)-4-(5-methylpyridin-3-yl)butanoic acid,
(11-45) 2-(methylamino)-4-(4-methylpyridin-3-yl)butanoic acid,
(11-46) 2-(methylamino)-4-(6-methoxypyridin-3-yl)butanoic acid,
(11-47) 2-(methylamino)-4-(5-methoxypyridin-3-yl)butanoic acid,
(11-48) 2-(methylamino)-4-(5-fluoropyridin-3-yl)butanoic acid,
(11-49) 2-(methylamino)-4-(5-chloropyridin-3-yl)butanoic acid,
(11-50) 2-(methylamino)-4-(5-bromopyridin-3-yl)butanoic acid,
(11-51) 2-(methylamino)-4-(5-iodopyridin-3-yl)butanoic acid,
(11-52) 2-(methylamino)-4-(2-(methylamino)pyridin-4-yl)butanoic acid,
(11-53) 2-(methylamino)-4-(2-(dimethylamino)pyridin-4-yl)butanoic acid,
(11-54) 2-(methylamino)-4-(pyrimidin-5-yl)butanoic acid,
(12-1) phenylalanine,
(12-2) 2-amino-3-(o-tolyl)propanoic acid,
(12-3) 2-amino-3-(m-tolyl)propanoic acid,
(12-4) 2-amino-3-(p-tolyl)propanoic acid,
(12-5) 2-amino-3-(4-ethylphenyl)propanoic acid,
(12-6) 2-amino-3-(2-chlorophenyl)propanoic acid,
(12-7) 2-amino-3-(3-chlorophenyl)propanoic acid,
(12-8) 2-amino-3-(4-chlorophenyl)propanoic acid,
(12-9) 2-amino-3-(2-fluorophenyl)propanoic acid,
(12-10) 2-amino-3-(3-fluorophenyl)propanoic acid,
(12-11) 2-amino-3-(4-fluorophenyl)propanoic acid, (12-12) 2-amino-3-(2-cyclopropylphenyl)propanoic acid,
(12-13) 2-amino-3-(3-cyclopropylphenyl)propanoic acid,
(12-14) 2-amino-3-(4-cyclopropylphenyl)propanoic acid,
(12-15) 2-amino-3-(2-(trifluoromethyl)phenyl)propanoic acid,
(12-16) 2-amino-3-(3-(trifluoromethyl)phenyl)propanoic acid,
(12-17) 2-amino-3-(4-(trifluoromethyl)phenyl)propanoic acid,
(12-18) 2-amino-3-(2-isopropylphenyl)propanoic acid,
(12-19) 2-amino-3-(3-isopropylphenyl)propanoic acid,
(12-20) 2-amino-3-(4-isopropylphenyl)propanoic acid,
(12-21) 2-amino-3-(2-methoxyphenyl)propanoic acid,
(12-22) 2-amino-3-(3-methoxyphenyl)propanoic acid,
(12-23) 2-amino-3-(4-methoxyphenyl)propanoic acid,
(12-24) 2-amino-3-(2-(allyloxy)phenyl)propanoic acid,
(12-25) 2-amino-3-(3-(allyloxy)phenyl)propanoic acid,
(12-26) 2-amino-3-(4-(allyloxy)phenyl)propanoic acid,
(12-27) 2-amino-3-(4-isopropoxyphenyl)propanoic acid,
(12-28) 2-amino-3-(3-fluoro-4-(trifluoromethyl)phenyl)propanoic acid,
(12-29) 2-amino-3-(2-fluoro-4-(trifluoromethyl)phenyl)propanoic acid,
(12-30) 2-amino-3-(3,4-dimethoxyphenyl)propanoic acid,
(12-31) 2-amino-3-(2-fluoro-4-methoxyphenyl)propanoic acid,
(12-32) 2-amino-3-(3-fluoro-4-methoxyphenyl)propanoic acid,
(12-33) 2-amino-3-(3,5-difluoro-4-methoxyphenyl)propanoic acid,
(12-34) 2-amino-3-(3,5-difluoro-4-(trifluoromethyl)phenyl)propanoic acid,
(12-35) 2-amino-3-(3-methoxy-4-(methylcarbamoyl)phenyl)propanoic acid,
(12-36) 2-amino-3-(4-methoxy-3-(methylcarbamoyl)phenyl)propanoic acid,
(12-37) 2-amino-3-(3-methoxy-4-((methylsulfonyl)carbamoyl)phenyl)propanoic acid,
(12-38) 2-amino-3-(4-(methyl((tetrahydro-2H-pyran-2-yl)oxy)carbamoyl)phenyl)propanoic acid,
(12-39) 2-amino-3-(3-methoxy-4-(((tetrahydro-2H-pyran-2-yl)oxy)carbamoyl)phenyl)propanoic acid,
(12-40) 2-amino-3-(pyridin-2-yl)propanoic acid,
(12-41) 2-amino-3-(pyridin-3-yl)propanoic acid,
(12-42) 2-amino-3-(pyridin-4-yl)propanoic acid,
(12-43) 2-amino-3-(6-methylpyridin-3-yl)propanoic acid,
(12-44) 2-amino-3-(5-methylpyridin-3-yl)propanoic acid,
(12-45) 2-amino-3-(4-methylpyridin-3-yl)propanoic acid,
(12-46) 2-amino-3-(6-methoxypyridin-3-yl)propanoic acid,
(12-47) 2-amino-3-(5-methoxypyridin-3-yl)propanoic acid,
(12-48) 2-amino-3-(5-fluoropyridin-3-yl)propanoic acid,
(12-49) 2-amino-3-(5-chloropyridin-3-yl)propanoic acid,
(12-50) 2-amino-3-(5-bromopyridin-3-yl)propanoic acid,
(12-51) 2-amino-3-(5-iodopyridin-3-yl)propanoic acid,
(12-52) 2-amino-3-(2-(methylamino)pyridin-4-yl)propanoic acid,
(12-53) 2-amino-3-(2-(dimethylamino)pyridin-4-yl)propanoic acid,
(12-54) 2-amino-3-(pyrimidin-5-yl)propanoic acid,
(13-1) methylphenylalanine,
(13-2) 2-(methylamino)-3-(o-tolyl)propanoic acid,
(13-3) 2-(methylamino)-3-(m-tolyl)propanoic acid,
(13-4) 2-(methylamino)-3-(p-tolyl)propanoic acid,
(13-5) 2-(methylamino)-3-(4-ethylphenyl)propanoic acid,
(13-6) 2-(methylamino)-3-(2-chlorophenyl)propanoic acid,
(13-7) 2-(methylamino)-3-(3-chlorophenyl)propanoic acid,
(13-8) 2-(methylamino)-3-(4-chlorophenyl)propanoic acid,
(13-9) 2-(methylamino)-3-(2-fluorophenyl)propanoic acid,
(13-10) 2-(methylamino)-3-(3-fluorophenyl)propanoic acid,
(13-11) 2-(methylamino)-3-(4-fluorophenyl)propanoic acid,
(13-12) 2-(methylamino)-3-(2-cyclopropylphenyl)propanoic acid,
(13-13) 2-(methylamino)-3-(3-cyclopropylphenyl)propanoic acid,
(13-14) 2-(methylamino)-3-(4-cyclopropylphenyl)propanoic acid,
(13-15) 2-(methylamino)-3-(2-(trifluoromethyl)phenyl)propanoic acid,
(13-16) 2-(methylamino)-3-(3-(trifluoromethyl)phenyl)propanoic acid,
(13-17) 2-(methylamino)-3-(4-(trifluoromethyl)phenyl)propanoic acid,
(13-18) 2-(methylamino)-3-(2-isopropylphenyl)propanoic acid,
(13-19) 2-(methylamino)-3-(3-isopropylphenyl)propanoic acid,
(13-20) 2-(methylamino)-3-(4-isopropylphenyl)propanoic acid,
(13-21) 2-(methylamino)-3-(2-methoxyphenyl)propanoic acid,
(13-22) 2-(methylamino)-3-(3-methoxyphenyl)propanoic acid,
(13-23) 2-(methylamino)-3-(4-methoxyphenyl)propanoic acid,
(13-24) 2-(methylamino)-3-(2-(allyloxy)phenyl)propanoic acid,
(13-25) 2-(methylamino)-3-(3-(allyloxy)phenyl)propanoic acid,
(13-26) 2-(methylamino)-3-(4-(allyloxy)phenyl)propanoic acid,
(13-27) 2-(methylamino)-3-(4-isopropoxyphenyl)propanoic acid,
(13-28) 2-(methylamino)-3-(3-fluoro-4-(trifluoromethyl)phenyl)propanoic acid,
(13-29) 2-(methylamino)-3-(2-fluoro-4-(trifluoromethyl)phenyl)propanoic acid,
(13-30) 2-(methylamino)-3-(3,4-dimethoxyphenyl)propanoic acid,
(13-31) 2-(methylamino)-3-(2-fluoro-4-methoxyphenyl)propanoic acid,
(13-32) 2-(methylamino)-3-(3-fluoro-4-methoxyphenyl)propanoic acid,
(13-33) 2-(methylamino)-3-(3,5-difluoro-4-methoxyphenyl)propanoic acid, (13-34) 2-(methylamino)-3-(3,5-difluoro-4-(trifluoromethyl)phenyl)propanoic acid,
(13-35) 2-(methylamino)-3-(3-methoxy-4-(methylcarbamoyl)phenyl)propanoic acid,
(13-36) 2-(methylamino)-3-(4-methoxy-3-(methylcarbamoyl)phenyl)propanoic acid,
(13-37) 2-(methylamino)-3-(3-methoxy-4-((methylsulfonyl)carbamoyl)phenyl)propanoic acid,
(13-38) 2-(methylamino)-3-(4-(methyl((tetrahydro-2H-pyran-2-yl)oxy)carbamoyl)phenyl)propanoic acid,
(13-39) 2-(methylamino)-3-(3-methoxy-4-(((tetrahydro-2H-pyran-2-yl)oxy)carbamoyl)phenyl)propanoic acid,
(13-40) 2-(methylamino)-3-(pyridin-2-yl)propanoic acid,
(13-41) 2-(methylamino)-3-(pyridin-3-yl)propanoic acid,
(13-42) 2-(methylamino)-3-(pyridin-4-yl)propanoic acid,
(13-43) 2-(methylamino)-3-(6-methylpyridin-3-yl)propanoic acid,
(13-44) 2-(methylamino)-3-(5-methylpyridin-3-yl)propanoic acid,
(13-45) 2-(methylamino)-3-(4-methylpyridin-3-yl)propanoic acid,
(13-46) 2-(methylamino)-3-(6-methoxypyridin-3-yl)propanoic acid,
(13-47) 2-(methylamino)-3-(5-methoxypyridin-3-yl)propanoic acid,
(13-48) 2-(methylamino)-3-(5-fluoropyridin-3-yl)propanoic acid,
(13-49) 2-(methylamino)-3-(5-chloropyridin-3-yl)propanoic acid,
(13-50) 2-(methylamino)-3-(5-bromopyridin-3-yl)propanoic acid,
(13-51) 2-(methylamino)-3-(5-iodopyridin-3-yl)propanoic acid,
(13-52) 2-(methylamino)-3-(2-(methylamino)pyridin-4-yl)propanoic acid,
(13-53) 2-(methylamino)-3-(2-(dimethylamino)pyridin-4-yl)propanoic acid,
(13-54) 2-(methylamino)-3-(pyrimidin-5-yl)propanoic acid,
(14-1) tert-butyl 2-((((9H-fluoren-9-yl)methoxy)carbonyl)(ethyl)amino)-3-(p-tolyl)propanoate,
(14-2) benzyl 2-((((9H-fluoren-9-yl)methoxy)carbonyl)(ethyl)amino)-3-(p-tolyl)propanoate,
(14-3) tert-butyl 2-((tert-butoxycarbonyl)(ethyl)amino)-3-(p-tolyl)propanoate,
(14-4) benzyl 2-((tert-butoxycarbonyl)(ethyl)amino)-3-(p-tolyl)propanoate,
(14-5) tert-butyl 2-(((benzyloxy)carbonyl)(ethyl)amino)-3-(p-tolyl)propanoate,
(14-6) benzyl 2-(((benzyloxy)carbonyl)(ethyl)amino)-3-(p-tolyl)propanoate,
(14-7) tert-butyl 2-(((allyloxy)carbonyl)(ethyl)amino)-3-(p-tolyl)propanoate,
(14-8) benzyl 2-(((allyloxy)carbonyl)(ethyl)amino)-3-(p-tolyl)propanoate,
(14-9) tert-butyl 2-(ethyl((2-(trimethylsilyl)ethoxy)carbonyl)amino)-3-(p-tolyl)propanoate,
(14-10) benzyl 2-(ethyl((2-(trimethylsilyl)ethoxy)carbonyl)amino)-3-(p-tolyl)propanoate,
(14-11) 2-((((9H-fluoren-9-yl)methoxy)carbonyl)(ethyl)amino)-3-(p-tolyl)propanoic acid,
(14-12) 2-((tert-butoxycarbonyl)(ethyl)amino)-3-(p-tolyl)propanoic acid,
(14-13) 2-(((benzyloxy)carbonyl)(ethyl)amino)-3-(p-tolyl)propanoic acid,
(14-14) 2-(((allyloxy)carbonyl)(ethyl)amino)-3-(p-tolyl)propanoic acid,
(14-15) 2-(ethyl((2-(trimethylsilyl)ethoxy)carbonyl)amino)-3-(p-tolyl)propionic acid, and
(14-16) 2-(ethylamino)-3-(p-tolyl)propanoic acid.

Advantageous Effects of Invention

According to the present invention, optically active aromatic amino acid derivatives usable in searching for peptide drugs and/or supplying active ingredients of drugs can be efficiently produced. Moreover, since it is also possible to produce various optically active aromatic amino acid derivatives, the present invention can provide structurally varied optically active aromatic amino acid derivatives.

DESCRIPTION OF EMBODIMENTS

Abbreviation

Abbreviations used in the present invention are described below.
AA or AcONH$_4$: ammonium acetate
AcOEt: ethylacetate
Alloc group: allyloxycarbonyl group
BF$_3$·OEt$_2$: boron trifluoride-diethyl ether complex
Bn group: benzyl group
Boc group: tert-butoxycarbonyl group
Cbz group: benzyloxycarbonyl group
DCM: dichloromethane
DIC: N,N'-diisopropyl carbodiimide
DMA: N,N-dimethylacetamide
DMF: N,N-dimethylformamide
DMI: 1,3-dimethyl-2-imidazolidinone
DMPU: N,N'-dimethylpropyleneurea
DMSO: dimethylsulfoxide
dtbbpy: 4,4'-di-tert-butyl-2,2'-bipyridine
EDTA·2Na: ethylenediaminetetraacetic acid disodium
FA: formic acid
Fmoc-Cl: 9-fluorenylmethyl chloroformate
Fmoc-OSu: N-[(9H-fluoren-9-ylmethoxy)carbonyloxy]succinimide
Fmoc group: 9-fluorenylmethyloxycarbonyl group
HPLC: high performance liquid chromatography
LC/MS: liquid chromatography/mass spectrometry
MeCN: acetonitrile
Ms group: mesyl group
MTBE: methyl tert-butyl ether
NHPI: N-hydroxyphthalimide
NMP: N-methylpyrrolidone
NMR: nuclear magnetic resonance spectrum
PhSiH$_3$: phenylsilane
Ph group: phenyl group
TBDMSCl: tert-butyldimethylsilyl chloride
TBDMS group: tert-butyldimethylsilyl group
TBDPSCl: tert-butyldiphenylsilyl chloride
TBDPS group: tert-butyldiphenylsilyl group
tBu or t-Bu group: tert-butyl group
Teoc group: 2-(trimethylsilyl)ethoxycarbonyl group
TESCl: triethylsilyl chloride
TES group: triethylsilyl group
TFA: trifluoroacetic acid
TfOH: trifluoromethanesulfonic acid Tf group: trifluoromethanesulfonyl group
THF: tetrahydrofuran
TIPSCl: triisopropylsilyl chloride
TIPS group: triisopropylsilyl group
TMSBr: trimethylsilyl bromide
TMSCl: trimethylsilyl chloride
TMSI: trimethylsilyl iodide
TMSOTf: trimethylsilyl trifluoromethanesulfonate
TMS group: trimethylsilyl group
Tr group: trityl group
Ts group: tosyl group
Gly: glycine
Ala: alanine
Ser: serine
Thr: threonine
Val: valine
Leu: leucine
Ile: isoleucine
Phe: phenylalanine
Tyr: tyrosine
Trp: tryptophan
His: histidine
Glu: glutamic acid
Asp: aspartic acid
Gln: glutamine
Asn: asparagine
Cys: cysteine
Met: methionine
Lys: lysine
Arg: arginine
Pro: proline Definitions of Functional Groups and Such An example of "halogen atom" herein includes F, Cl, Br or I.

The term "alkyl" as used herein refers to a monovalent group derived by removing any one hydrogen atom from an aliphatic hydrocarbon, and covers a subset of hydrocarbyl or hydrocarbon group structures that contain hydrogen and carbon atoms, but do not contain a heteroatom (which refers to an atom other than carbon and hydrogen atoms) or an unsaturated carbon-carbon bond in the skeleton. The alkyl groups include linear or branched groups. The alkyl group is an alkyl group having 1 to 20 carbon atoms ($C_1$-$C_{20}$; hereinafter, "$C_p$-$C_q$" means that it has p to q carbon atoms), preferred examples of which include a $C_1$-$C_6$ alkyl group. Specific examples include methyl, ethyl, propyl, butyl, pentyl, hexyl, isopropyl, tert-butyl, and sec-butyl.

The term "alkoxy" as used herein refers to an oxy group to which the above-defined "alkyl" is bonded. Preferred examples include $C_1$-$C_4$ alkoxy and $C_1$-$C_3$ alkoxy. Specific examples of the alkoxy include methoxy, ethoxy, 1-propoxy, 2-propoxy, n-butoxy, i-butoxy, sec-butoxy, and tert-butoxy.

Herein, the term "alkenyl" refers to a monovalent group having at least one double bond (two adjacent $sp^2$ carbon atoms). The double bond can assume entgegen (E) or zusammen (Z) and cis or trans geometric forms depending on the arrangement of the double bond and substituents (if they exist). Examples of alkenyl include linear or branched chains, including straight chains containing internal olefins. Preferred examples thereof include $C_2$-$C_{10}$ alkenyl, and more preferably $C_2$-$C_6$ alkenyl and $C_2$-$C_4$ alkenyl. Specific examples of alkenyl include vinyl, allyl, 1-propenyl, 2-propenyl, 1-butenyl, 2-butenyl (including cis and trans forms), 3-butenyl, pentenyl, and hexenyl.

The term "alkenyloxy" as used herein means an oxy group to which the above-defined "alkenyl" is bonded, and preferred examples include $C_2$-$C_6$ alkenyloxy and $C_2$-$C_4$ alkenyloxy.

Herein, the term "alkynyl" refers to a monovalent group having at least one triple bond (two adjacent sp carbon atoms). Examples thereof include linear or branched chain alkynyl including internal alkylene. Preferred examples thereof include $C_2$-$C_{10}$ alkynyl, and more preferably $C_2$-$C_6$ alkynyl and $C_2$-$C_4$ alkynyl. Specific examples of alkynyl include ethynyl, 1-propynyl, propargyl, 3-butynyl, pentynyl, hexynyl, 3-phenyl-2-propynyl, 3-(2'-fluorophenyl)-2-propynyl, 2-hydroxy-2-propynyl, 3-(3-fluorophenyl)-2-propynyl, and 3-methyl-(5-phenyl)-4-pentynyl.

The term "alkynyloxy" as used herein means an oxy group to which the above-defined "alkynyl" is bonded, and preferred examples include $C_2$-$C_6$ alkynyloxy and $C_2$-$C_4$ alkynyloxy.

The term "haloalkyl" as used herein means a group obtained by substituting one or more hydrogen atoms of the above "alkyl" with halogen atoms, and preferred examples include $C_1$-$C_6$ haloalkyl, $C_1$-$C_4$ haloalkyl, $C_1$-$C_3$ haloalkyl, and $C_1$-$C_2$ haloalkyl.

The term "haloalkoxy" as used herein means an oxy group to which the above "haloalkyl" is bonded, and preferred examples include $C_1$-$C_4$ haloalkoxy, $C_1$-$C_3$ haloalkoxy, and $C_1$-$C_2$ haloalkoxy.

The term "fluoroalkyl" as used herein means a group obtained by substituting one or more hydrogen atoms of the "alkyl" with fluorine atoms, and preferred examples include $C_1$-$C_6$ fluoroalkyl, $C_1$-$C_4$ fluoroalkyl, $C_1$-$C_3$ fluoroalkyl, and $C_1$-$C_2$ fluoroalkyl. Specific examples of fluoroalkyl include difluoromethyl, trifluoromethyl, 2,2,2-trifluoroethyl, pentafluoroethyl, 2,2,3,3-tetrafluoropropyl, and heptafluoropropyl.

The term "fluoroalkoxy" as used herein means an oxy group to which the above "fluoroalkyl" is bonded, and preferred examples include $C_1$-$C_4$ fluoroalkoxy, $C_1$-$C_3$ fluoroalkoxy, and $C_1$-$C_2$ fluoroalkoxy. Specific examples of fluoroalkoxy include trifluoromethoxy, difluoromethoxy, 2,2,2-trifluoroethoxy, pentafluoroethoxy, 2,2,3,3-tetrafluoropropoxy, and heptafluoropropoxy.

The term "alkylsulfonyl" as used herein means a sulfonyl group to which the above "alkyl" is bonded (i.e., alkyl-$SO_2$—). Preferred examples of alkylsulfonyl include $C_1$-$C_6$ alkylsulfonyl and $C_1$-$C_4$ alkylsulfonyl, and specific examples include methylsulfonyl, ethylsulfonyl, n-propylsulfonyl, and i-propylsulfonyl.

The term "alkylsulfonylamino" as used herein means a group obtained by substituting one hydrogen atom of an amino group (—$NH_2$) with the above "alkylsulfonyl". Preferred examples of alkylsulfonylamino include $C_1$-$C_6$ alkylsulfonylamino and $C_1$-$C_4$ alkylsulfonylamino, and specific examples include methylsulfonylamino, ethylsulfonylamino, n-propylsulfonylamino, and i-propylsulfonylamino.

The term "cycloalkyl" as used herein refers to a saturated or partially saturated cyclic monovalent aliphatic hydrocarbon group, including single rings, bicyclo rings, and spiro rings. Preferred examples of cycloalkyl include $C_3$-$C_{10}$ cycloalkyl. The cycloalkyl may be partially unsaturated. Specific examples of the cycloalkyl include cyclopropyl, cyclobutyl, cyclopentyl, cyclohexyl, cycloheptyl, cyclooctyl, and bicyclo[2.2.1]heptyl.

The term "aminocarbonyl" as used herein means a group in which optionally substituted nitrogen is bonded to carbonyl (i.e., —C=O—NHR), and is also referred to as a carboxamide group. The substituent represented by R is not particularly specified, and examples include a hydroxy group, an alkyl group, and an alkylsulfonyl group. Specific examples of the substituent include methyl, ethyl, propyl, butyl, methanesulfonyl, and ethanesulfonyl.

The term "aryl" as used herein refers to a monovalent aromatic hydrocarbon ring, preferred examples of which include $C_6$-$C_{10}$ aryl. Specific examples of the aryl include phenyl, 1-naphthyl and 2-naphthyl. The aryl may be substituted with any substituent, and preferably, it may be substituted with alkyl, alkoxy, fluoroalkyl, fluoroalkoxy, oxo, aminocarbonyl, or halogen atom.

The term "heteroaryl" as used herein means an aromatic monovalent heterocyclic group having preferably 1 to 5 heteroatoms in a ring among the atoms constituting the ring. The heteroatom is preferably N, O, or S, and the number of heteroatoms is preferably 1 or 2. Heteroaryl may be partially saturated, and may be a monocyclic or fused ring (such as a bicyclic heteroaryl in which a benzene ring or a monocyclic heteroaryl ring is condensed). The number of atoms constituting the ring is preferably 5 to 10 (5- to 10-membered heteroaryl). Heteroaryl may be substituted with any substituent, and may be substituted preferably with alkyl, alkoxy, fluoroalkyl, fluoroalkoxy, oxo, aminocarbonyl, or a halogen atom. Specific examples of heteroaryl include furyl, thienyl, pyrrolyl, imidazolyl, pyrazolyl, thiazolyl, isothiazolyl, oxazolyl, isooxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, indolyl, isoindolyl, azaindolyl, indazolyl, quinolyl, isoquinolyl, cinnolinyl, quinazolinyl, quinoxalinyl, benzodioxolyl, indolizinyl, and imidazopyridyl.

Herein, the term "having a heteroatom in the ring" means that the atoms constituting the ring include a heteroatom(s). The heteroatom is preferably N, O, or S, the number of heteroatoms is preferably 1 or 2, and a 4- to 6-membered ring is preferred. Examples of such rings include aromatic hetero rings such as pyridine, and non-aromatic hetero rings such as piperidine, morpholine, pyrrolidine, and azetidine. When the heteroatom is an oxygen atom, it is represented as "having an oxygen atom in the ring" or the like, and examples of such rings include aromatic hetero rings such as furan, and non-aromatic hetero rings such as tetrahydrofuran and 1,4-dioxane. When the heteroatom is a sulfur atom, it is represented as "having a sulfur atom in the ring" or the like, and examples of such rings include aromatic hetero rings such as thiophene, and non-aromatic hetero rings such as tetrahydrothiophene. When the heteroatoms are a nitrogen atom and an oxygen atom, it is represented as "having a nitrogen atom and an oxygen atom in the ring" or the like, and examples of such rings include aromatic hetero rings such as oxazole, and non-aromatic hetero rings such as oxazoline, oxazolidine, and oxazolidinone. Furthermore, when the heteroatoms are a nitrogen atom and a sulfur atom, it is represented as "having a nitrogen atom and a sulfur atom in the ring" or the like, and examples of such rings include aromatic hetero rings such as thiazole, and non-aromatic hetero rings such as thiazoline, thiazolidine, and thiazolidinone.

Herein, the term "heterocyclic group" or "heterocyclyl" refers to a group having at least one heteroatom (such as N, O, or S) in a ring, and the ring may be aromatic or non-aromatic, i.e., may be saturated, or may be completely or partially unsaturated. The number of heteroatoms contained in the ring is preferably 1 or 2, and the ring is preferably 3- to 7-membered. The heterocyclic group may be substituted with any substituent, and may be substituted preferably with alkyl, alkoxy, fluoroalkyl, fluoroalkoxy, oxo, aminocarbonyl, a halogen atom, or aryl. Specific examples of the heterocyclic group include pyridyl, piperidino, morpholino, pyrrolidino, oxadiazolonyl, oxazolidin-2-yl, oxazolin-2-yl, aziridinyl, dihydrooxazolyl, and azetidinyl.

The term "arylalkyl (aralkyl)" as used herein is a group containing both the above-described aryl and the above-described alkyl, and means, for example, a group obtained by substituting at least one hydrogen atom of the alkyl with the aryl. Preferred examples of arylalkyl include "$C_6$-$C_{10}$ aryl $C_1$-$C_6$ alkyl", and specific examples include benzyl and phenethyl. The aryl group of arylalkyl may be substituted with any substituents, and may be substituted preferably with alkyl, alkoxy, fluoroalkyl, fluoroalkoxy, oxo, aminocarbonyl, or a halogen atom.

The term "heteroarylalkyl (heteroaralkyl)" as used herein is a group containing both heteroaryl and alkyl, and means, for example, a group obtained by substituting at least one hydrogen atom of the alkyl with heteroaryl. Preferred examples of heteroarylalkyl include "5- to 10-membered heteroaryl$C_1$-$C_6$ alkyl", and specific examples include pyridylmethyl and pyridylethyl. The heteroaryl group of heteroarylalkyl may be substituted with any substituents, and may be substituted preferably with alkyl, alkoxy, fluoroalkyl, fluoroalkoxy, oxo, aminocarbonyl, or a halogen atom.

The term "alkylene" as used herein refers to a divalent group derived by removing any one hydrogen atom from the "alkyl." Preferred examples of the alkylene include $C_1$-$C_2$ alkylene, $C_1$-$C_3$ alkylene, $C_1$-$C_4$ alkylene, $C_1$-$C_5$ alkylene, and $C_1$-$C_6$ alkylene. Specific examples of the alkylene include —$CH_2$—, —($CH_2$)$_2$—, —($CH_2$)$_3$—, $CH(CH_3)CH_2$—, —$C(CH_3)_2$—, —($CH_2$)$_4$—, $CH(CH_3)CH_2CH_2$—, —$C(CH_3)_2CH_2$—, —$CH_2CH(CH_3)CH_2$—, —$CH_2C(CH_3)_2$—, —$CH_2CH_2CH(CH_3)$—, —($CH_2$)$_5$—, and —($CH_2$)$_6$—.

The term "arylene" as used herein refers to a divalent group derived by further removing any one hydrogen atom from the aryl. The arylene may be a single ring or fused rings. The number of the ring-forming atoms is not particularly limited, but is preferably 6 to 10 ($C_6$-$C_{10}$ arylene). Specific examples of the arylene include phenylene. The arylene group may be substituted with any substituents, and may be substituted preferably with alkyl, alkoxy, fluoroalkyl, fluoroalkoxy, oxo, aminocarbonyl, or a halogen atom.

The term "heteroarylene" as used herein refers to a divalent group derived by further removing any one hydrogen atom from the heteroaryl. The heteroarylene may be a single ring or fused rings. The number of the ring-forming atoms is not particularly limited, but is preferably 5 to 10 (5- to 10-membered heteroarylene). Specific examples of the heteroarylene include imidazolediyl, pyridinediyl, oxadiazolediyl, thiazolediyl and thiadiazolediyl. The heteroarylene group may be substituted with any substituents, and may be substituted preferably with alkyl, alkoxy, fluoroalkyl, fluoroalkoxy, oxo, aminocarbonyl, or a halogen atom.

The term "fused (condensed) ring structure" as used herein refers to a cyclic structure in which in a cyclic compound having two or more rings, a plurality of rings share two or more atoms. A "fused ring structure composed of two or more aromatic rings" refers to a cyclic structure in which in a cyclic compound having two or more aromatic rings, a plurality of aromatic rings share two or more atoms. Examples of the fused ring structure include, but are not limited to, an indole skeleton, a benzofuran skeleton, a benzimidazole skeleton, a quinoline skeleton, and a bicyclo[4.4.0]decane skeleton.

Herein, the "protecting group for an amino group" includes a carbamate-type protecting group, an amide-type protecting group, an arylsulfonamide-type protecting group, an alkylamine-type protecting group, an imide-type protecting group, and such. Specific examples of the protecting group for an amino group include an Fmoc group, a Boc group, an Alloc group, a Cbz group, a Teoc group, a trifluoroacetyl group, a benzene sulfonyl group, a tosyl group, a nosyl group, a dinitronosyl group, a t-Bu group, a trityl group, a cumyl group, a benzylidene group, a 4-methoxybenzylidene group, and a diphenylmethylidene group.

Herein, the "protecting group for a carboxyl group" includes an alkyl ester-type protecting group, a benzyl ester-type protecting group, a substituted alkyl ester-type protecting group, and such. Specific examples of the protecting group for a carboxyl group include a methyl group, an ethyl group, a t-Bu group, a benzyl group, a trityl group, a cumyl group, a methoxytrityl group, a 2-(trimethylsilyl)ethyl group, a 2,2,2-trichloroethyl group, and an allyl group.

Herein, the "protecting group for hydroxy" includes an alkyl ether-type protecting group, an aralkyl ether-type protecting group, a silyl ether-type protecting group, a carbonate ester-type protecting group, and such. Specific examples of the protecting group for hydroxy include a methoxymethyl group, a benzyloxymethyl group, a tetrahydropyranyl group, a tert-butyl group, an allyl group, a 2,2,2-trichloroethyl group, a benzyl group, a 4-methoxybenzyl group, a trimethylsilyl group, a triethylsilyl group, a triisopropylsilyl group, a t-butyldimethylsilyl group, a t-butyldiphenylsilyl group, a methoxycarbonyl group, a 9-fluorenylmethoxycarbonyl group, and a 2,2,2-trichloroethoxycarbonyl group.

Herein, "protected hydroxy" means a hydroxy group protected with the protecting group for hydroxy.

In the production of the compound described herein, when the defined groups undergo undesired chemical conversion under the conditions of the performed method, the compound can be produced by means of, for example, protection and deprotection of the functional group. Here, the operations of selecting and attaching/detaching protecting groups can include, for example, the methods described in "Greene's, "Protective Groups in Organic Synthesis" (5th edition, John Wiley & Sons 2014)", and these are suitably used according to the reaction conditions. Furthermore, the order of reaction steps such as introduction of a substituent can be changed, as necessary.

Herein, when the modifying phrase "optionally substituted" is added, examples of the substituent include an alkyl group, an alkoxy group, a fluoroalkyl group, a fluoroalkoxy group, oxo, an aminocarbonyl group, an alkylsulfonyl group, an alkylsulfonylamino group, a cycloalkyl group, an aryl group, a heteroaryl group, a heterocyclyl group, an arylalkyl group, a heteroarylalkyl group, a halogen atom, a nitro group, an amino group, a monoalkylamino group, a dialkylamino group, a cyano group, a carboxyl group, an alkoxycarbonyl group, and a formyl group.

Furthermore, additional substituents may be attached to these substituents. Such additional substituents are not limited, and one or two or more may be freely selected independently from any substituents including, for example, a halogen atom, an oxygen atom, a sulfur atom, a nitrogen atom, a boron atom, a silicon atom, and a phosphorus atom. Examples include optionally substituted alkyl, alkenyl, alkynyl, aryl, heteroaryl, aralkyl, and cycloalkyl.

The compounds represented by the respective formulae of the present invention can be salts of the compounds or solvates of the compounds or the salts. Examples of the salts of the compounds represented by the respective formulae include hydrochlorides; hydrobromides; hydroiodides; phosphates; phosphonates; sulfates; sulfonates such as methanesulfonates and p-toluenesulfonates; carboxylates such as acetates, citrates, malates, tartarates, succinates, and salicylates; or alkali metal salts such as sodium salts and potassium salts; alkaline earth metal salts such as magnesium salts and calcium salts; and ammonium salts such as ammonium salts, alkylammonium salts, dialkylammonium salts, trialkylammonium salts, and tetraalkylammonium salts. These salts are produced by, for example, allowing a compound to contact with an acid or a base. The solvates of the compounds represented by the respective formulae refer to a phenomenon in which a solute molecule(s) strongly attracts a solvent molecule(s) in a solution to form one molecular group, and when the solvent is water, the solvate refers to a hydrate. The compounds represented by the respective formulae of the present invention are each also capable of, in addition to forming a solvate formed with a single solvent selected from an organic solvent such as alcohol (e.g., methanol, ethanol, 1-propanol, or 2-propanol), dimethylformamide, or diglyme, and water, forming a solvate formed with a plurality of solvents selected therefrom.

The term "amino acid" as used herein includes natural and unnatural amino acids (may also be referred to as amino acid derivatives). The term "natural amino acid" as used herein refers to Gly, Ala, Ser, Thr, Val, Leu, Ile, Phe, Tyr, Trp, His, Glu, Asp, Gln, Asn, Cys, Met, Lys, Arg, or Pro. Examples of the unnatural amino acid (amino acid derivative) include, but are not particularly limited to, β-amino acids, D-amino acids, N-substituted amino acids, α,α-disubstituted amino acids, amino acids having side chains that are different from those of natural amino acids, and hydroxycarboxylic acids. Amino acids herein may have any conformation. There is no particular limitation on the selection of amino acid side chain, but in addition to a hydrogen atom, it can be freely selected from, for example, an alkyl group, an alkenyl group, an alkynyl group, an aryl group, a heteroaryl group, an aralkyl group, a heteroaralkyl group, a cycloalkyl group, and a spiro-bonded cycloalkyl group. Each group may have a substituent, and there are no limitations on the substituent. For example, one, or two or more substituents may be freely and independently selected from any substituents including a halogen atom, an O atom, an S atom, an N atom, a B atom, an Si atom, or a P atom. Examples include an optionally substituted alkyl group, alkoxy group, alkenyl group, alkynyl group, aryl group, heteroaryl group, aralkyl group, and cycloalkyl group, or oxo, aminocarbonyl, and halogen atoms. In a non-limiting embodiment, amino acids herein may be compounds having a carboxy group and an amino group in the same molecule (even in this case, imino acids such as proline and hydroxyproline are also included in amino acids).

Substituents derived from halogen include fluoro (—F), chloro (—Cl), bromo (—Br), and iodo (—I).

Substituents derived from an O atom include hydroxy (—OH), oxy (—OR), carbonyl (—C=O—R), carboxyl (—CO$_2$H), oxycarbonyl (—C=O—OR), carbonyloxy (—O—C=O—R), thiocarbonyl (—C=O—SR), carbonylthio (—S—C=O—R), aminocarbonyl (—C=O—NHR), carbonylamino (—NH—C=O—R), oxycarbonylamino (—NH—C=O—OR), sulfonylamino (—NH—SO$_2$—R), aminosulfonyl (—SO$_2$—NHR), sulfamoylamino (—NH—SO$_2$—NHR), thiocarboxyl (—C(=O)—SH), and carboxylcarbonyl (—C(=O)—CO$_2$H).

Examples of oxy (—OR) include alkoxy, cycloalkoxy, alkenyloxy, alkynyloxy, aryloxy, heteroaryloxy, and aralkyloxy.

Examples of carbonyl (—C=O—R) include formyl (—C=O—H), alkylcarbonyl, cycloalkylcarbonyl, alkenylcarbonyl, alkynylcarbonyl, arylcarbonyl, heteroarylcarbonyl, and aralkylcarbonyl.

Examples of oxycarbonyl (—C=O—OR) include alkyloxycarbonyl, cycloalkyloxycarbonyl, alkenyloxycarbonyl, alkynyloxycarbonyl, aryloxycarbonyl, heteroaryloxycarbonyl, and aralkyloxycarbonyl.

Examples of carbonyloxy (—O—C=O—R) include alkylcarbonyloxy, cycloalkylcarbonyloxy, alkenylcarbonyloxy, alkynylcarbonyloxy, arylcarbonyloxy, heteroarylcarbonyloxy, and aralkylcarbonyloxy.

Examples of thiocarbonyl (—C=O—SR) include alkylthiocarbonyl, cycloalkylthiocarbonyl, alkenylthiocarbonyl, alkynylthiocarbonyl, arylthiocarbonyl, heteroarylthiocarbonyl, and aralkylthiocarbonyl.

Examples of carbonylthio (—S—C=O—R) include alkylcarbonylthio, cycloalkylcarbonylthio, alkenylcarbonylthio, alkynylcarbonylthio, arylcarbonylthio, heteroarylcarbonylthio, and aralkylcarbonylthio.

Examples of aminocarbonyl (—C=O—NHR) include alkylaminocarbonyl, cycloalkylaminocarbonyl, alkenylaminocarbonyl, alkynylaminocarbonyl, arylaminocarbonyl, heteroarylaminocarbonyl, and aralkylaminocarbonyl. Additional examples include compounds in which the H atom bonded to the N atom in —C=O—NHR is further replaced with alkyl, cycloalkyl, alkenyl, alkynyl, aryl, heteroaryl, or aralkyl.

Examples of carbonylamino (—NH—C=O—R) include alkylcarbonylamino, cycloalkylcarbonylamino, alkenylcarbonylamino, alkynylcarbonylamino, arylcarbonylamino, heteroarylcarbonylamino, and aralkylcarbonylamino. Additional examples include compounds in which the H atom bonded to the N atom in —NH—C=O—R is further replaced with alkyl, cycloalkyl, alkenyl, alkynyl, aryl, heteroaryl, or aralkyl.

Examples of oxycarbonylamino (—NH—C=O—OR) include alkoxycarbonylamino, cycloalkoxycarbonylamino, alkenyloxycarbonylamino, alkynyloxycarbonylamino, aryloxycarbonylamino, heteroaryloxycarbonylamino, and aralkyloxycarbonylamino. Additional examples include compounds in which the H atom bonded to the N atom in —NH—C=O—OR is further replaced with alkyl, cycloalkyl, alkenyl, alkynyl, aryl, heteroaryl, or aralkyl.

Examples of sulfonylamino (—NH—SO$_2$—R) include alkylsulfonylamino, cycloalkylsulfonylamino, alkenylsulfonylamino, alkynylsulfonylamino, arylsulfonylamino, heteroarylsulfonylamino, and aralkylsulfonylamino. Additional examples include compounds in which the H atom attached to the N atom in —NH—SO$_2$—R is further replaced with alkyl, cycloalkyl, alkenyl, alkynyl, aryl, heteroaryl, or aralkyl.

Examples of aminosulfonyl (—SO$_2$—NHR) include alkylaminosulfonyl, cycloalkylaminosulfonyl, alkenylaminosulfonyl, alkynylaminosulfonyl, arylaminosulfonyl, heteroarylaminosulfonyl, and aralkylaminosulfonyl. Additional examples include compounds in which the H atom attached to the N atom in —SO$_2$—NHR is further replaced with alkyl, cycloalkyl, alkenyl, alkynyl, aryl, heteroaryl, or aralkyl.

Examples of sulfamoylamino (—NH—SO$_2$—NHR) include alkylsulfamoylamino, cycloalkylsulfamoylamino, alkenylsulfamoylamino, alkynylsulfamoylamino, arylsulfonylamino, heteroarylsulfamoylamino, and aralkylsulfamoylamino. The two H atoms bonded to the N atoms in —NH—SO$_2$—NHR may be further replaced with substituents independently selected from the group consisting of alkyl, cycloalkyl, alkenyl, alkynyl, aryl, heteroaryl, and aralkyl, and these two substituents may form a ring.

Substituents derived from an S atom include thiol (—SH), thio (—S—R), sulfinyl (—S=O—R), sulfonyl (—S(O)$_2$—R), sulfo (—SO$_3$H), and pentafluorosulfanyl (—SF$_5$).

Examples of thio (—S—R) are selected from alkylthio, cycloalkylthio, alkenylthio, alkynylthio, arylthio, heteroarylthio, aralkylthio, and such.

Examples of sulfinyl (—S=O—R) include alkylsulfinyl, cycloalkylsulfinyl, alkenylsulfinyl, alkynylsulfinyl, arylsulfinyl, heteroarylsulfinyl, and aralkylsulfinyl.

Examples of sulfonyl (—S(O)$_2$—R) include alkylsulfonyl, cycloalkylsulfonyl, alkenylsulfonyl, alkynylsulfonyl, arylsulfonyl, heteroarylsulfonyl, and aralkylsulfonyl.

Substituents derived from an N atom include azido (—N$_3$, also called "azido group"), cyano (—CN), primary amino (—NH$_2$), secondary amino (—NH—R), tertiary amino (—NR(R')), amidino (—C(=NH)—NH$_2$), substituted amidino (—C(=NR)—NR'R''), guanidino (—NH—C(=NH)—NH$_2$), substituted guanidino (—NR—C(=NR''')—NR'R''), and aminocarbonylamino (—NR—CO—NR'R'').

Examples of secondary amino (—NH—R) include alkylamino, cycloalkylamino, alkenylamino, alkynylamino, arylamino, heteroarylamino, and aralkylamino.

Examples of tertiary amino (—NR(R')) include amino groups having any two substituents each independently selected from alkyl, cycloalkyl, alkenyl, alkynyl, aryl, heteroaryl, aralkyl and such, such as alkyl(aralkyl)amino, where any two such substituents may form a ring.

Examples of substituted amidino (—C(=NR)—NR'R'') include groups in which three substituents R, R', and R'' on the N atom are each independently selected from alkyl, cycloalkyl, alkenyl, alkynyl, aryl, heteroaryl, and aralkyl, such as alkyl(aralkyl)(aryl)amidino.

Examples of substituted guanidino (—NR—C(=NR''')—NR'R'') include groups in which R, R', R'', and R''' are each independently selected from alkyl, cycloalkyl, alkenyl, alkynyl, aryl, heteroaryl, and aralkyl, or groups in which these substituents form a ring.

Examples of aminocarbonylamino (—NR—CO—NR'R'') include groups in which R, R', and R'' are each independently selected from a hydrogen atom, alkyl, cycloalkyl, alkenyl, alkynyl, aryl, heteroaryl, and aralkyl, or groups in which these substituents form a ring.

Examples of B atom-derived substituents include boryl (—BR(R')) and dioxyboryl (—B(OR)(OR')). These two substituents, R and R', are each independently selected from alkyl, cycloalkyl, alkenyl, alkynyl, aryl, heteroaryl, and aralkyl; or they may form a ring. Specific examples include cyclic boryl groups, and more specific examples include a pinacolatoboryl group, a neopentanediolatoboryl group, and a catecholatoboryl group.

Specific examples of the substituent on the nitrogen atom of the N-substituted amino acid herein include alkyl, $C_1$-$C_6$ alkyl, $C_1$-$C_4$ alkyl, and methyl.

Examples of the "aromatic amino acid derivative" herein include, among the above amino acid derivatives, those containing an aromatic substituent in the side chain of amino acid. Specific examples of the aromatic substituent include optionally substituted aryl and optionally substituted heteroaryl.

The main-chain amino group of an amino acid may be unsubstituted (—$NH_2$) or substituted (i.e., —NHR: where R represents an optionally substituted alkyl, alkenyl, alkynyl, aryl, heteroaryl, aralkyl, or cycloalkyl, and a carbon chain bonded to the N atom and the carbon atom at α-position may form a ring, such as proline). Such an amino acid in which main-chain amino group is substituted may be referred to as "N-substituted amino acid" herein. Preferred examples of the "N-substituted amino acid" herein include, but are not limited to, N-alkyl amino acid, N—$C_1$-$C_6$ alkyl amino acid, N—$C_1$-$C_4$ alkyl amino acid, and N-methyl amino acid.

The "amino acid" as used herein includes corresponding all isotopes. In an isotope of an "amino acid", at least one atom is substituted with an atom of the same atomic number (number of protons) and different mass number (total number of protons and neutrons). Examples of the isotope contained in the "amino acid" herein include a hydrogen atom, a carbon atom, a nitrogen atom, an oxygen atom, a phosphorus atom, a sulfur atom, a fluorine atom, and a chlorine atom, including $^2H$, $^3H$, $^{13}C$, $^{14}C$, $^{15}N$, $^{17}O$, $^{18}O$, $^{32}P$, $^{35}S$, $^{18}F$, and $^{36}Cl$, respectively.

Production Methods of Compounds Represented by Formula I)

In an embodiment, the present invention relates to a method of producing a compound represented by Formula I, a salt of the compound, or a solvate of the compound or the salt:

Formula I

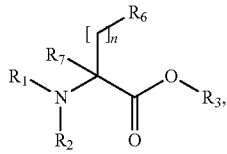

wherein $R_1$ is hydrogen or a protecting group for an amino group;

$R_2$ is hydrogen or $C_1$-$C_6$ alkyl, and $R_3$ is hydrogen or a protecting group for a carboxyl group, or $R_2$ and $R_3$ together form a divalent protecting group;

$R_6$ is optionally substituted $C_6$-$C_{10}$ aryl or optionally substituted heteroaryl;

$R_7$ is hydrogen or $C_1$-$C_4$ alkyl; and n is 1 or 2, the method comprising the step of mixing a compound represented by Formula II, a salt of the compound, or a solvate of the compound or the salt with a reducing agent, an additive, and $R_6$—X (wherein $R_6$ is the same as $R_6$ of the compound represented by Formula I, and X is halogen, OTf, or OMs) in the presence of a solvent and a catalyst to obtain the compound represented by Formula I, the salt of the compound, or the solvate of the compound or the salt:

Formula II

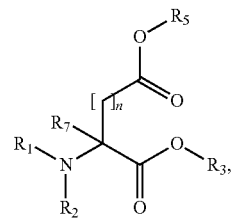

wherein $R_1$, $R_2$, $R_3$, $R_7$, and n are the same as $R_1$, $R_2$, $R_3$, $R_7$, and n of the compound represented by Formula I, respectively;

$R_5$ is selected from the group consisting of:

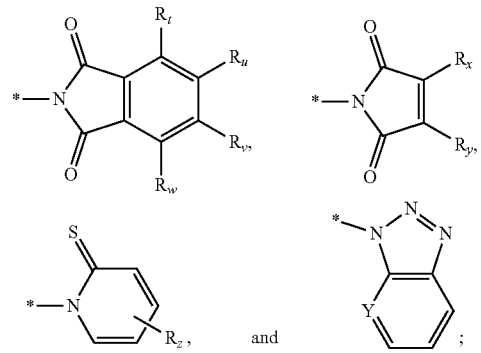

$R_t$, $R_u$, $R_v$, and $R_w$ are independently hydrogen, halogen, or nitro;

$R_x$ and $R_y$ are independently hydrogen, $C_1$-$C_4$ alkyl, or optionally substituted phenyl;

$R_z$ is hydrogen, $C_1$-$C_4$ alkyl, or halogen;

Y is CH or N; and

\* indicates a point of bonding.

In Formula I, $R_1$ is a hydrogen or a protecting group for an amino group. When $R_1$ is a protecting group for an amino group, specific examples of the protecting group include Fmoc, Boc, Alloc, Cbz, Teoc, trifluoroacetyl, a benzenesulfonyl group, a tosyl group, a nosyl group, a dinitronosyl group, a t-Bu group, a trityl group, a cumyl group, a benzylidene group, a 4-methoxybenzylidene group, and a diphenylmethylidene group, and among these, Fmoc, Boc, Alloc, Cbz, Teoc, or trifluoroacetyl is preferred.

In Formula I, $R_2$ is hydrogen or $C_1$-$C_6$ alkyl, and $R_3$ is hydrogen or a protecting group for a carboxyl group, or $R_2$ and $R_3$ together form a divalent protecting group.

When $R_2$ in Formula I is $C_1$-$C_6$ alkyl, the $C_1$-$C_6$ alkyl is preferably methyl, ethyl, propyl, butyl, or the like, and methyl or ethyl is particularly preferred.

When $R_3$ in Formula I is a protecting group for a carboxyl group, specific examples of the protecting group include methyl, ethyl, t-Bu, benzyl, trityl, cumyl, methoxytrityl, 2-(trimethylsilyl)ethyl, 2,2,2-trichloroethyl, and allyl, and among these, methyl, ethyl, t-Bu, benzyl, trityl, cumyl, methoxytrityl, or 2-(trimethylsilyl)ethyl is preferred.

When R2 and R3 together form a divalent protecting group, the divalent protecting group can be methylene optionally substituted with one or two substituents, and is preferably —($CR_8R_9$)—. When R2 and R3 together form —($CR_8R_9$)—, Formula I can be represented by formula IA:

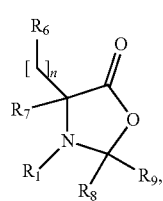

(IA)

In one embodiment, $R_8$ and $R_9$ can be independently hydrogen, $C_1$-$C_4$ alkyl, or $C_6$-$C_{10}$ aryl. More specifically, both $R_8$ and $R_9$ may be hydrogen, $C_1$-$C_4$ alkyl or $C_6$-$C_{10}$ aryl; one may be hydrogen and the other may be $C_1$-$C_4$ alkyl or $C_6$-$C_{10}$ aryl; or one may be $C_1$-$C_4$ alkyl and the other may be $C_6$-$C_{10}$ aryl. When one or both of $R_8$ and $R_9$ are $C_1$-$C_4$ alkyl, the $C_1$-$C_4$ alkyl is preferably methyl. When one or both of $R_8$ and $R_9$ are $C_6$-$C_{10}$ aryl, the $C_6$-$C_{10}$ aryl is preferably phenyl. When one or both of $R_8$ and $R_9$ are $C_1$-$C_4$ alkyl or $C_6$-$C_{10}$ aryl, the $C_1$-$C_4$ alkyl or $C_6$-$C_{10}$ aryl may have a substituent, and preferably, the $C_1$-$C_4$ alkyl is methyl and the $C_6$-$C_{10}$ aryl is phenyl. In another embodiment, $R_8$ and $R_9$ together form oxo (=O).

Specific examples of the compounds represented by Formula IA include those having the following structures:

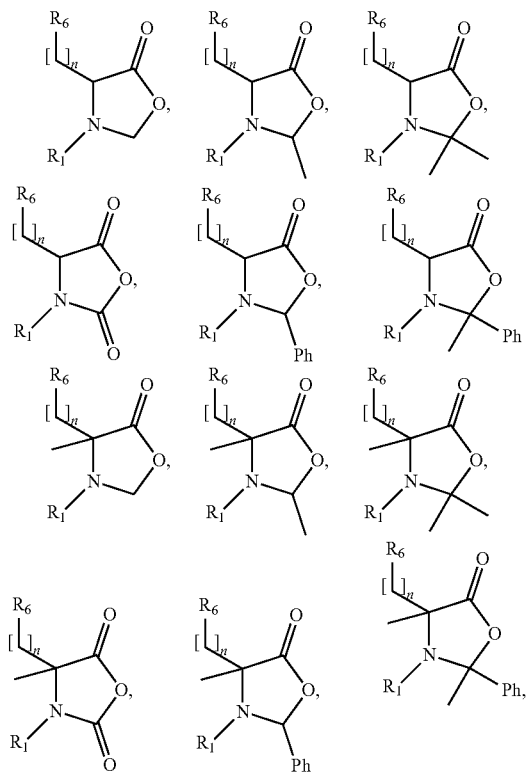

where $R_1$, $R_6$, and n in the formulae are as defined herein.

In Formula I, $R_6$ is optionally substituted $C_6$-$C_{10}$ aryl or optionally substituted heteroaryl. When $R_6$ is optionally substituted $C_6$-$C_{10}$ aryl, the $C_6$-$C_{10}$ aryl is preferably phenyl. Furthermore, when R6 is optionally substituted heteroaryl, the heteroaryl is preferably pyridyl. Examples of the substituent of optionally substituted C6-C10 aryl or the substituent of optionally substituted heteroaryl include C1-C4 alkyl, C1-C4 haloalkyl, C1-C4 alkoxy, C1-C4 haloalkoxy, C1-C6 alkenyloxy, halogen, C3-C8 cycloalkyl, —NRpRq (wherein Rp and Rq are independently hydrogen or C1-C4 alkyl), —CONRrRs (wherein Rr and Rs are independently selected from the group consisting of hydrogen, hydroxy, a protected hydroxy group, C1-C4 alkyl, and C1-C4 alkylsulfonyl), and cyclic boryl. More specific examples of these substituents include methyl, methoxy, chloro, fluoro, isopropyl, cyclopropyl, trifluoromethyl, methylaminocarbonyl, methylsulfonylamino, hydroxycarbamoyl (including those in which the hydroxy group is protected with a protecting group, such as (tetrahydro-2H-pyran-2-yl)oxycarbamoyl and methyl((tetrahydro-2H-pyran-2-yl)oxy)carbamoyl), pinacolatoboryl, neopentanediolatoboryl, catecolatoboryl, and allyloxy. The number of substituents of optionally substituted C6-C10 aryl or optionally substituted heteroaryl is not particularly limited, and, for example, having 0 to 3 substituents is preferred. When the number of substituents is two or more, examples of preferred substituent combinations include one $C_1$-$C_4$ haloalkyl and one or two halogens; two $C_1$-$C_4$ alkoxy groups, one $C_1$-$C_4$ alkoxy and one or two halogens; and one —CONR$_r$R$_s$ and one $C_1$-$C_4$ alkoxy. More specific examples of these substituent combinations include combinations such as trifluoromethyl and one or two fluorines; trifluoromethyl and one or two chlorines; one trifluoromethyl and one fluorine and one chlorine; two methoxy groups; methoxy and one or two fluorines; one methylaminocarbonyl and one methoxy; and one methylsulfonylamino and one methoxy.

Specific examples of R6 include the following groups. Here, "*" in the formulae means a point of bonding.

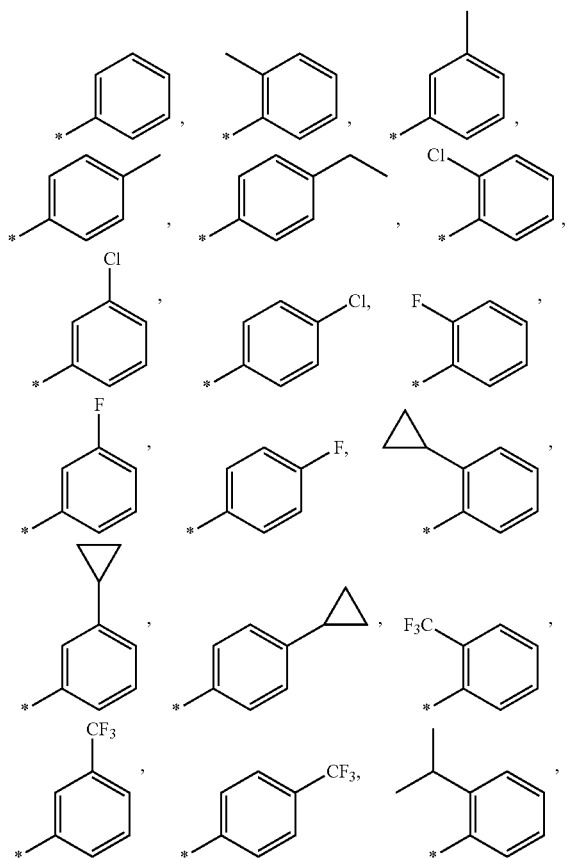

-continued

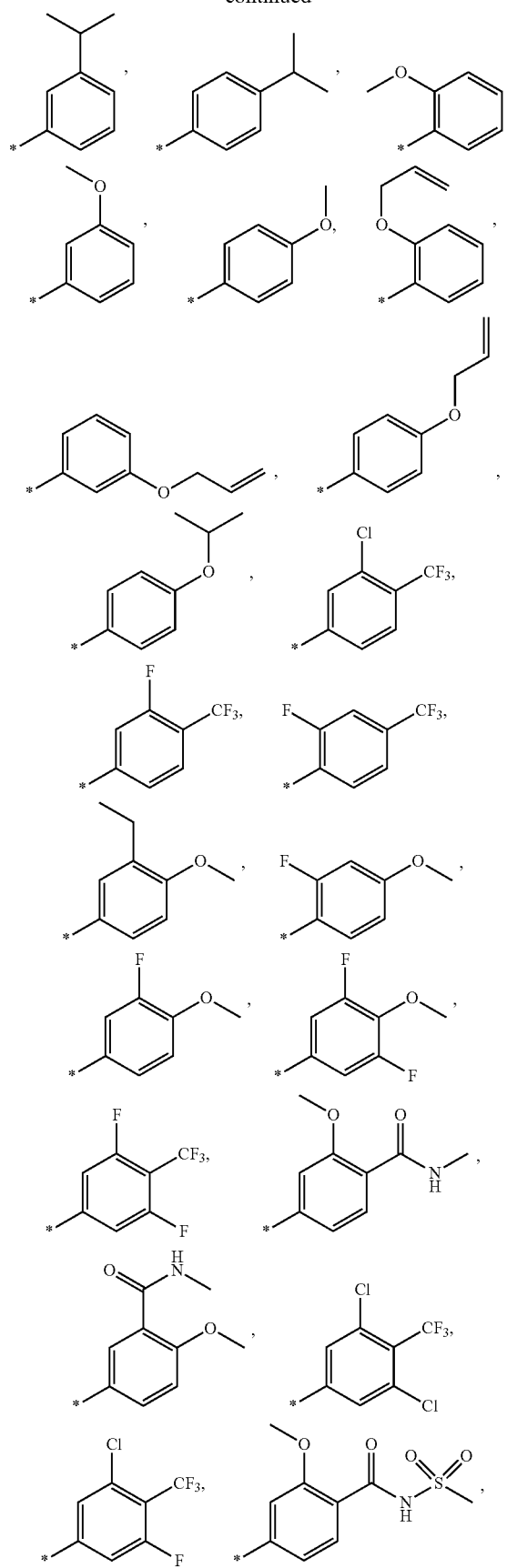

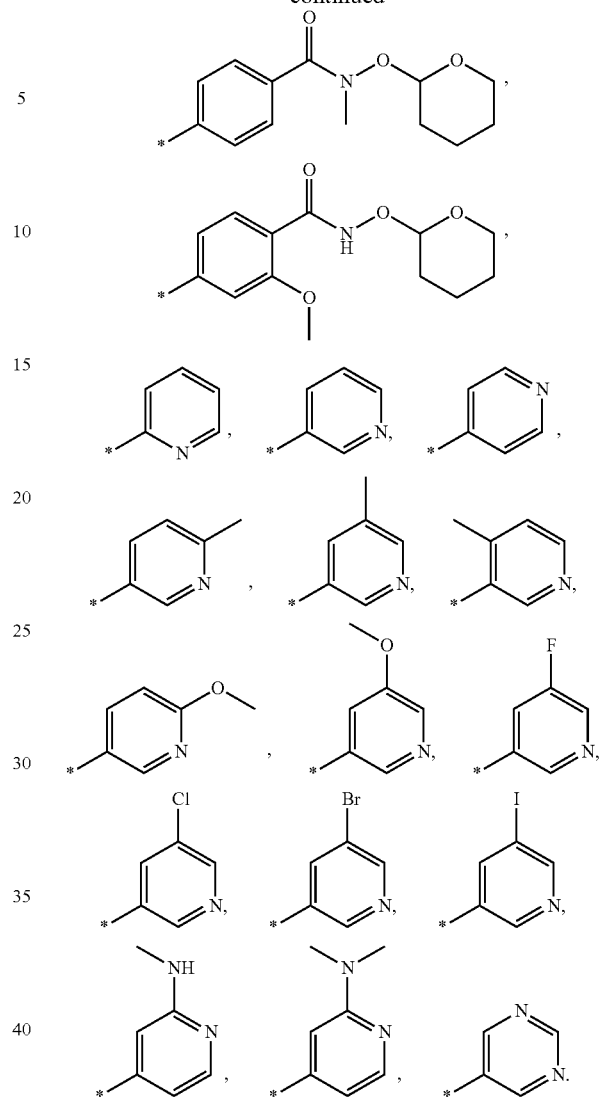

In Formula I, R₇ is hydrogen or $C_1$-$C_4$ alkyl, and is preferably hydrogen or methyl.

n in Formula I is 1 or 2.

$R_1$, $R_2$, $R_3$, $R_7$, and n in Formula II are the same as $R_1$, $R_2$, $R_3$, $R_7$, and n in Formula I, respectively.

$R_5$ in Formula II can be:

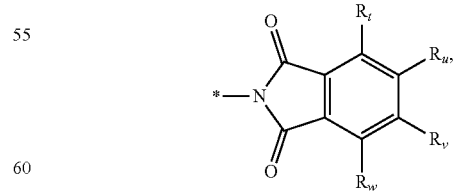

where "*" means a point of bonding, and $R_t$, $R_u$, $R_v$, and $R_w$ are independently hydrogen, halogen, or nitro. In this case, specific examples of $R_5$ include groups having the following structures:

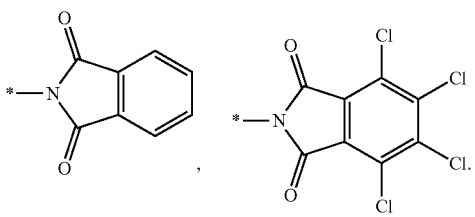

$R_5$ in Formula II can be:

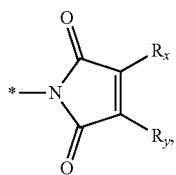

where "*" means a point of bonding, and $R_x$ and $R_y$ are independently hydrogen, $C_1$-$C_4$ alkyl, or optionally substituted phenyl. In this case, specific examples of $R_5$ include groups having the following structures:

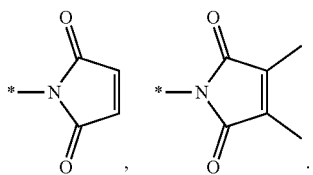

$R_5$ in Formula II can be:

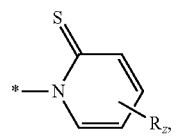

where "*" means a point of bonding, and $R_z$ is hydrogen, $C_1$-$C_4$ alkyl, or halogen. In this case, specific examples of $R_5$ include a group having the following structure:

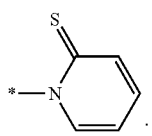

$R_5$ in Formula II can be:

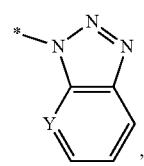

where "*" means a point of bonding, and Y is CH or N. In this case, specific examples of $R_5$ include groups having the following structures:

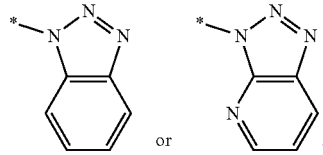

As for "$R_6$—X" used in this step, $R_6$ is optionally substituted $C_6$-$C_{10}$ aryl or optionally substituted heteroaryl, and X is halogen, OTf, or OMs. As for $R_6$, $R_6$ that is a group the same as $R_6$ in Formula I can be used. X is preferably iodine, bromine, or OTf.

More specific examples of $R_6$—X include bromobenzene, 1-bromo-2-methylbenzene, 1-bromo-3-methylbenzene, 1-bromo-4-methylbenzene, 1-bromo-4-ethylbenzene, 1-bromo-2-chlorobenzene, 1-bromo-3-chlorobenzene, 1-bromo-4-chlorobenzene, 1-bromo-2-fluorobenzene, 1-bromo-3-fluorobenzene, 1-bromo-4-fluorobenzene, 1-bromo-2-cyclopropylbenzene, 1-bromo-3-cyclopropylbenzene, 1-bromo-4-cyclopropylbenzene, 1-bromo-2-(trifluoromethyl)benzene, 1-bromo-3-(trifluoromethyl)benzene, 1-bromo-4-(trifluoromethyl)benzene, 1-bromo-2-isopropylbenzene, 1-bromo-3-isopropylbenzene, 1-bromo-4-isopropylbenzene, 1-bromo-2-methoxybenzene, 1-bromo-3-methoxybenzene, 1-bromo-4-methoxybenzene, 1-(allyloxy)-2-bromobenzene, 1-(allyloxy)-3-bromobenzene, 1-(allyloxy)-4-bromobenzene, 1-bromo-4-isopropoxybenzene, 4-bromo-2-chloro-1-(trifluoromethyl)benzene, 4-bromo-2-fluoro-1-(trifluoromethyl)benzene, 1-bromo-2-fluoro-4-(trifluoromethyl)benzene, 4-bromo-1,2-dimethoxybenzene, 1-bromo-2-fluoro-4-methoxybenzene, 4-bromo-2-fluoro-1-methoxybenzene, 5-bromo-1,3-difluoro-2-methoxybenzene, 5-bromo-1,3-difluoro-2-(trifluoromethyl)benzene, 4-bromo-2-methoxy-N-methylbenzamide, 5-bromo-2-methoxy-N-methylbenzamide, 5-bromo-1,3-dichloro-2-(trifluoromethyl)benzene, 5-bromo-1-chloro-3-fluoro-2-(trifluoromethyl)benzene, 4-bromo-2-methoxy-N-(methylsulfonyl)benzamide, 4-bromo-N-methyl-N-((tetrahydro-2H-pyran-2-yl)oxy)benzamide, 4-bromo-2-methoxy-N-((tetrahydro-2H-pyran-2-yl)oxy)benzamide, 2-bromopyridine, 3-bromopyridine, 4-bromopyridine, 5-bromo-2-methylpyridine, 3-bromo-5-methylpyridine, 3-bromo-4-methylpyridine, 5-bromo-2-methoxypyridine, 3-bromo-5-methoxypyridine, 3-bromo-5-fluoropyridine, 3-bromo-5-chloropyridine, 3,5-dibromopyridine, 4-bromo-N-methylpyridin-2-amine, 4-bromo-N,N-dimethylpyridin-2-amine, 5-bromopyrimidine, iodobenzene, 1-iodo-2-methylbenzene, 1-iodo-3-methylbenzene, 1-iodo-4-methylbenzene, 1-ethyl-4-iodobenzene, 1-chloro-2-iodobenzene, 1-chloro-3-iodobenzene, 1-chloro-4-iodobenzene, 1-fluoro-2-iodobenzene, 1-fluoro-3-iodobenzene, 1-fluoro-4-iodobenzene, 1-cyclopropyl-2-iodobenzene, 1-cyclopropyl-3-iodobenzene, 1-cyclopropyl-4-iodobenzene, 1-iodo-2-(trifluoromethyl)benzene, 1-iodo-3-(trifluoromethyl)benzene, 1-iodo-4-(trifluoromethyl)benzene, 1-iodo-2-isopropylbenzene, 1-iodo-3-isopropylbenzene, 1-iodo-4-isopropylbenzene, 1-iodo-2-methoxybenzene, 1-iodo-3-methoxybenzene, 1-iodo-4-methoxybenzene, 1-(allyloxy)-2-iodo-benzene, 1-(allyloxy)-3-iodo-benzene, 1-(allyloxy)-4-iodo-benzene, 1-iodo-4-isopropoxybenzene, 2-chloro-4-iodo-1-(trifluoromethyl)benzene, 2-fluoro-4-iodo-1-(trifluoromethyl)benzene, 2-fluoro-1-iodo-4-(trifluoromethyl)benzene, 4-iodo-1,2-dimethoxybenzene, 2-fluoro-1-iodo-4-methoxybenzene, 2-fluoro-4-iodo-1-methoxybenzene, 1,3-difluoro-5-iodo-2-methoxybenzene, 1,3-difluoro-5-iodo-2-(trifluoromethyl) benzene, 4-iodo-2-methoxy-N-methylbenzamide, 5-iodo-2-methoxy-N-methylbenzamide, 1,3-dichloro-5-iodo-2-(trifluoromethyl)benzene, 1-chloro-3-fluoro-5-iodo-2-(trifluoromethyl)benzene, 4-iodo-2-methoxy-N-(methylsulfonyl)benzamide, 4-iodo-N-methyl-N-((tetrahydro-2H-pyran-2-yl)oxy)benzamide, 4-iodo-2-methoxy-N-((tetrahydro-2H-pyran-2-yl)oxy)benzamide, 2-iodopyridine, 3-iodopyridine, 4-iodopyridine, 5-iodo-2-methylpyridine, 3-iodo-5-methylpyridine, 3-iodo-4-methylpyridine, 5-iodo-2-methoxypyridine, 3-iodo-5-methoxypyridine, 3-fluoro-5-iodopyridine, 3-chloro-5-iodopyridine, 3-bromo-5-iodopyridine, 3,5-diiodopyridine, 4-iodo-N-methylpyridin-2-amine, 4-iodo-N,N-dimethylpyridin-2-amine, 5-iodopyrimidine, phenyl trifluoromethanesulfonate, o-tolyl trifluoromethanesulfonate, m-tolyl trifluoromethanesulfonate, p-tolyl trifluoromethanesulfonate, 4-ethylphenyl trifluoromethanesulfonate, 2-chlorophenyl trifluoromethanesulfonate, 3-chlorophenyl trifluoromethanesulfonate, 4-chlorophenyl trifluoromethanesulfonate, 2-fluorophenyl trifluoromethanesulfonate, 3-fluorophenyl trifluoromethanesulfonate, 4-fluorophenyl trifluoromethanesulfonate, 2-cyclopropylphenyl trifluoromethanesulfonate, 3-cyclopropylphenyl trifluoromethanesulfonate, 4-cyclopropylphenyl trifluoromethanesulfonate, 2-(trifluoromethyl)phenyl trifluoromethanesulfonate, 3-(trifluoromethyl)phenyl trifluoromethanesulfonate, 4-(trifluoromethyl)phenyl trifluoromethanesulfonate, 2-isopropylphenyl trifluoromethanesulfonate, 3-isopropylphenyl trifluoromethanesulfonate, 4-isopropylphenyl trifluoromethanesulfonate, 2-methoxyphenyl trifluoromethanesulfonate, 3-methoxyphenyl trifluoromethanesulfonate, 4-methoxyphenyl trifluoromethanesulfonate, 2-(allyloxy)phenyl trifluoromethanesulfonate, 3-(allyloxy)phenyl trifluoromethanesulfonate, 4-(allyloxy)phenyl trifluoromethanesulfonate, 4-isopropoxyphenyl trifluoromethanesulfonate, 3-chloro-4-(trifluoromethyl)phenyl trifluoromethanesulfonate, 3-fluoro-4-(trifluoromethyl)phenyl trifluoromethanesulfonate, 2-fluoro-4-(trifluoromethyl)phenyl trifluoromethanesulfonate, 3,4-dimethoxyphenyl trifluoromethanesulfonate, 2-fluoro-4-methoxyphenyl trifluoromethanesulfonate, 3-fluoro-4-methoxyphenyl trifluoromethanesulfonate, 3,5-difluoro-4-methoxyphenyl trifluoromethanesulfonate, 3,5-difluoro-4-(trifluoromethyl)phenyl trifluoromethanesulfonate, 3-methoxy-4-(methylcarbamoyl)phenyl trifluoromethanesulfonate, 4-methoxy-3-(methylcarbamoyl) phenyl trifluoromethanesulfonate, 3,5-dichloro-4-(trifluoromethyl)phenyl trifluoromethanesulfonate, 3-chloro-5-fluoro-4-(trifluoromethyl)phenyl trifluoromethanesulfonate, 3-methoxy-4-((methylsulfonyl)carbamoyl)phenyl trifluoromethanesulfonate, 4-(methyl((tetrahydro-2H-pyran-2-yl)oxy)carbamoyl)phenyl trifluoromethanesulfonate, 3-methoxy-4-(((tetrahydro-2H-pyran-2-yl)oxy)carbamoyl) phenyl trifluoromethanesulfonate, pyridin-2-yl trifluoromethanesulfonate, pyridin-3-yl trifluoromethanesulfonate, pyridin-4-yl trifluoromethanesulfonate, 6-methylpyridin-3-yl trifluoromethanesulfonate, 5-methylpyridin-3-yl trifluoromethanesulfonate, 4-methylpyridin-3-yl trifluoromethanesulfonate, 6-methoxypyridin-3-yl trifluoromethanesulfonate, 5-methoxypyridin-3-yl trifluoromethanesulfonate, 5-fluoropyridin-3-yl trifluoromethanesulfonate, 5-chloropyridin-3-yl trifluoromethanesulfonate, 5-bromopyridin-3-yl trifluoromethanesulfonate, 2-(methylamino)pyridin-4-yl trifluoromethanesulfonate, 2-(dimethylamino)pyridin-4-yl trifluoromethanesulfonate, and pyrimidin-5-yl trifluoromethanesulfonate.

In this step, $R_6$—X can be used in an equal amount or an excessive amount relative to the compound represented by Formula II. Specifically, for example, 1 equivalent to 10 equivalents and preferably 1 equivalent to 5 equivalents of $R_6$—X can be used relative to the compound represented by Formula II.

The catalyst used in this step is:
(a) a metal;
(b) formed by mixing a metal and a possible ligand compound therefor;
(c) a complex of a metal and a ligand therefor; or
(d) formed by further mixing, with the complex of a metal and a ligand therefor, a possible ligand compound for the metal.

In each of cases (a) to (d) above, the metal used includes nickel, chromium, iron, copper, palladium, or a salt of these metals, or is a solvate of nickel, chromium, iron, copper, palladium, or a salt of these metals. Specific examples of such metals include nickel, bis(1,5-cyclooctadiene)nickel (0), $NiBr_2$, $NiI_2$, $NiCl_2$, $NiF_2$, $Ni(OAc)_2$, $Ni(acac)_2$, $Ni(OTf)_2$, $NiCO_3$, $Ni(NO_3)_2$, $NiSO_4$, $(NH_4)_2Ni(SO_4)_2$, allyl (cyclopentadienyl)nickel(II), bis(cyclopentadienyl)nickel, bis(cyclooctadienyl)nickel, or a solvate thereof formed with water, with methoxyethyl ether, with diglyme, or with ethylene glycol dimethyl ether.

When the catalyst is formed by mixing a metal and a possible ligand compound therefor, the possible ligand compound is represented by, for example, the following Formulae B to G.

Formula B:

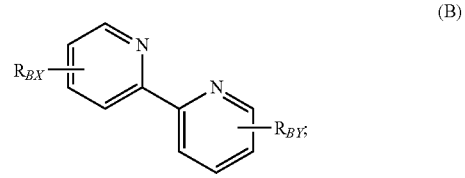

(B)

Formula C:

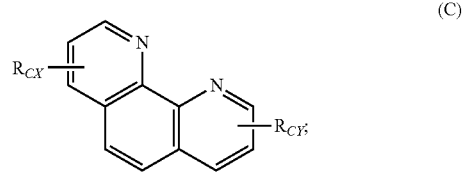

(C)

Formula D:

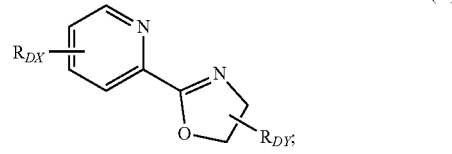

(D)

Formula E:

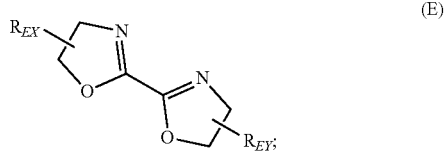

(E)

-continued

Formula F:

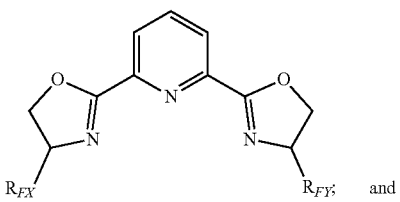

(F)

and

Formula G:

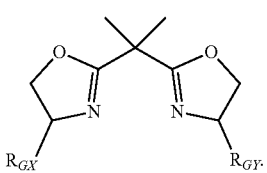

(G)

In Formula B:

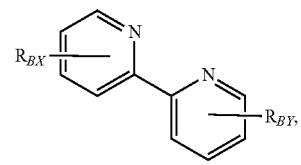

(B)

$R_{BX}$ and $R_{BY}$ are independently selected from hydrogen, $C_1$-$C_4$ alkyl, $C_1$-$C_4$ alkoxy, heterocyclyl, and $C_6$-$C_{10}$ aryl. Specific examples of the compound represented by Formula B include 2,2'-bipyridine, 6-methyl-2,2'-bipyridine, 4,4'-dimethyl-2,2'-bipyridine, 5,5'-dimethyl-2,2'-bipyridine, 4,4'-di-tert-butyl-2,2'-bipyridine, 4,4'-dimethoxy-2,2'-bipyridine, 4,4'-diphenyl-2,2'-bipyridine, 6,6'-bis(4,5-dihydrooxazol-2-yl)-2,2'-bipyridine, 6,6'-bis(4-phenyl-4,5-dihydrooxazol-2-yl)-2,2'-bipyridine, 6,6'-bis(4-isopropyl-4,5-dihydrooxazol-2-yl)-2,2'-bipyridine, and 6,6'-bis(4-(tert-butyl)-4,5-dihydrooxazol-2-yl)-2,2'-bipyridine.

In Formula C:

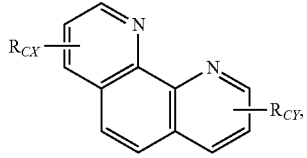

(C)

$R_{CX}$ and $R_{CY}$ are independently selected from hydrogen, $C_1$-$C_4$ alkyl, $C_6$-$C_{10}$ aryl, and heteroaryl. Specific examples of the compound represented by Formula C include 1,10-phenanthroline, 5-methyl-1,10-phenanthroline, 2,9-dimethyl-1,10-phenanthroline, 5,6-dimethyl-1,10-phenanthroline, and 4,7-dimethoxy-1,10-phenanthroline.

In Formula D:

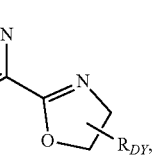

(D)

$R_{DX}$ and $R_{DY}$ are independently selected from hydrogen, $C_1$-$C_4$ alkyl, $C_1$-$C_4$ haloalkyl, and $C_6$-$C_{10}$ aryl. Specific examples of the compound represented by Formula D include 2-(pyridin-2-yl)-4,5-dihydrooxazole, 4-isopropyl-2-(pyridin-2-yl)-4,5-dihydrooxazole, 4-(tert-butyl)-2-(pyridin-2-yl)-4,5-dihydrooxazole, 4-isopropyl-2-(6-methylpyridin-2-yl)-4,5-dihydrooxazole, 4-(tert-butyl)-2-(6-methylpyridin-2-yl)-4,5-dihydrooxazole, 4-(tert-butyl)-2-(5-(trifluoromethyl)pyridin-2-yl)-4,5-dihydrooxazole, 4-(tert-butyl)-2-(5-(trifluoromethyl)pyridin-2-yl)-4,5-dihydrooxazole, and 4-phenyl-2-(pyridin-2-yl)-4,5-dihydrooxazole.

In Formula E:

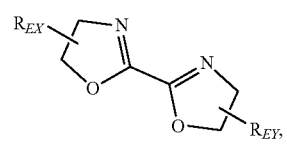

(E)

$R_{EX}$ and $R_{EY}$ are independently selected from hydrogen, $C_1$-$C_4$ alkyl, $C_6$-$C_{10}$ aryl$C_1$-$C_6$ alkyl, and $C_6$-$C_{10}$ aryl. Specific examples of the compound represented by Formula E include 4,4',5,5'-tetrahydro-2,2'-bioxazole, 4,4'-dimethyl-4,4',5,5'-tetrahydro-2,2'-bioxazole, 4,4'-diisopropyl-4,4',5,5'-tetrahydro-2,2'-bioxazole, 4,4'-di-tert-butyl-4,4',5,5'-tetrahydro-2,2'-bioxazole, 4,4'-diphenyl-4,4',5,5'-tetrahydro-2,2'-bioxazole, and 4,4'-dibenzyl-4,4',5,5'-tetrahydro-2,2'-bioxazole.

In Formula F:

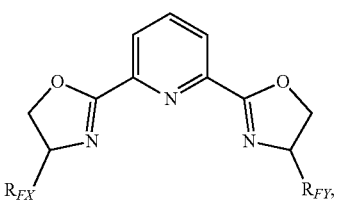

(F)

$R_{FX}$ and $R_{FY}$ are independently selected from hydrogen, $C_1$-$C_4$ alkyl, and $C_6$-$C_{10}$ aryl. Specific examples of the compound represented by Formula F include 2,6-bis(4,5-dihydrooxazol-2-yl)pyridine, 2,6-bis(4-isopropyl-4,5-dihydrooxazol-2-yl)pyridine, 2,6-bis(4-(tert-butyl)-4,5-dihydrooxazol-2-yl)pyridine, and 2,6-bis(4-phenyl-2-oxazolin-2-yl)pyridine.

In Formula G:

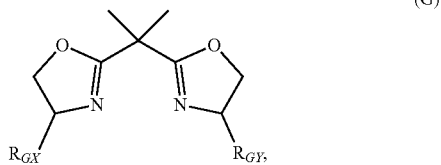

$R_{GX}$ and $R_{GY}$ are independently selected from hydrogen, $C_1$-$C_4$ alkyl, $C_6$-$C_{10}$ aryl$C_1$-$C_6$ alkyl, and $C_6$-$C_{10}$ aryl. Specific examples of the compound represented by Formula G include 2,2'-(propan-2,2-diyl)bis(4,5-dihydrooxazole), 2,2'-(propan-2,2-diyl)bis(4-isopropyl-4,5-dihydrooxazole), 2,2'-(propan-2,2-diyl)bis(4-(tert-butyl)-4,5-dihydrooxazole), 2,2'-(propan-2,2-diyl)bis(4-benzyl-4,5-dihydrooxazole), and 2,2'-(propan-2,2-diyl)bis(4-phenyl-4,5-dihydrooxazole).

When the catalyst is a complex of a metal and ligand therefor, specific examples of the complex of the metal and ligand therefor include tetrakis(triphenylphosphine)nickel(0), bis(triphenylphosphine)nickel(II) dichloride, bis(tricyclohexylphosphine)nickel(II) dichloride, dibromobis(triphenylphosphine)nickel(II), bis[(2-dimethylamino)phenyl]aminenickel(II) chloride, cis-[2,2'-bis(diphenylphosphino)-1,1'-binaphthyl](2-methylphenyl)nickel(II) chloride, and [1,2-bis(diphenylphosphino)ethane]dichloronickel(II).

When the catalyst is formed by further mixing, with the complex of a metal and a ligand therefor, a possible ligand compound for the metal, specific examples of the complex of a metal and a ligand therefor include tetrakis(triphenylphosphine)nickel(0), bis(triphenylphosphine)nickel(II) dichloride, cis-[2,2'-bis(diphenylphosphino)-1,1'-binaphthyl](2-methylphenyl)nickel(II) chloride, and [1,2-bis(diphenylphosphino)ethane]dichloronickel(II). Specific examples of the possible ligand compound include 2,2'-bipyridine, 6-methyl-2,2'-bipyridine, 4,4'-dimethyl-2,2'-bipyridine, 5,5'-dimethyl-2,2'-bipyridine, 4,4'-di-tert-butyl-2,2'-bipyridine, 4,4'-dimethoxy-2,2'-bipyridine, 4,4'-diphenyl-2,2'-bipyridine, 6,6'-bis(4,5-dihydrooxazol-2-yl)-2,2'-bipyridine, 6,6'-bis(4-phenyl-4,5-dihydrooxazol-2-yl)-2,2'-bipyridine, 6,6'-bis(4-isopropyl-4,5-dihydrooxazol-2-yl)-2,2'-bipyridine, and 6,6'-bis(4-(tert-butyl)-4,5-dihydrooxazol-2-yl)-2,2'-bipyridine.

The reducing agent used in this step can be a material that acts to lessen the positive charge of the catalyst used in this step. Examples of such reducing agents include metals having a greater ionization tendency than the metals contained in the catalyst. Specific examples of such metals include zinc, manganese, iron, and magnesium, and among these, zinc and manganese are preferred, and zinc is particularly preferred.

In an embodiment, when a nickel-containing catalyst is used, metals having a greater ionization tendency than nickel, such as zinc, iron, and magnesium, can be used as reducing agents.

The reducing agent can be used in an amount of 1 mol to 10 mol equivalents, preferably 1 mol to 5 mol equivalents, and more preferably 1 mol to 3 mol equivalents relative to the compound represented by Formula II.

The additive used in this step can be a material capable of efficiently converting the compound represented by Formula II, which is the starting material of this step, into the compound represented by Formula I, which is the target material, e.g., capable of shortening the time required for conversion of the starting material into the target material, compared with the case where the additive is not used. Specific examples of such additives include silyl compounds and 1,2-dibromoethane. Specific examples of silyl compounds include compounds represented by Formula A:

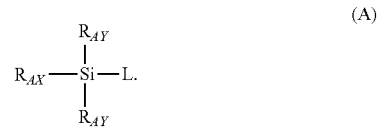

$R_{AX}$ and $R_{AY}$ in the Formula are independently selected from the group consisting of $C_1$-$C_4$ alkyl, $C_1$-$C_4$ alkoxy, and phenyl. More specific examples of $R_{AX}$ and $R_{AY}$ include methyl, ethyl, isopropyl, t-butyl, methoxy, ethoxy, isopropoxy, and phenyl.

L is selected from the group consisting of —Cl, —Br, —I, and —OTf.

More specific examples of the compound represented by Formula A include TMSCl, TMSBr, TMSI, TMSOTf, TBDMSCl, TESCl, TIPSCl, TBDPSCl, and chlorotriethoxysilane, and among these, TMSCl, TMSBr, TESCl, and TIPSCl are preferred.

The additive can be used in an amount of 1 mol % to 500 mol %, preferably 10 mol % to 500 mol %, and more preferably 25 mol % to 500 mol %, relative to the compound represented by Formula II.

By adding the additive in this step, the rate of conversion from the compound represented by Formula II into the compound represented by Formula I can be greatly improved compared with the case where the additive is not used. For example, the reaction can be caused to efficiently proceed at a high conversion rate irrespective of the mode of stirring such as stirring using stirring blade(s) or stirring using a stir bar(s).

The solvent used in this step can be, for example, an aprotic solvent such as an amide solvent or a urea solvent. Specific examples of such solvents include DMF, DMA, NMP, DMI, and DMPU.

The reaction of this step can be carried out at a temperature from −20° C. to around the boiling point of the solvent. The reaction can be carried out at a reaction temperature of preferably −10° C. to 110° C., −10° C. to 90° C., and more preferably −10° C. to 70° C.

The reaction of this step can be carried out for a reaction time of 10 minutes to 1 week. The reaction can be carried out for a reaction time of preferably 10 minutes to 6 hours, and more preferably 0.5 hours to 4 hours.

In this step, the order of mixing the compound represented by Formula II, the salt of the compound, or the solvate of the compound or the salt, the reducing agent, the additive, and $R_6$—X is not particularly limited; however, the mixing is performed, for example, by the following: (a) the compound represented by Formula II, the salt of the compound, or the solvate of the compound or the salt, the reducing agent, and $R_6$—X are mixed in the presence of the solvent and the catalyst, and then the additive is mixed therewith; (b) the reducing agent and the additive are mixed in the presence of the solvent and the catalyst, and then the compound represented by Formula II, the salt of the compound, or the solvate of the compound or the salt and $R_6$—X are mixed therewith; or (c) the reducing agent is mixed with the solvent and the catalyst, and then the compound represented by Formula II, the salt of the compound, or the solvate of the compound or the salt, R$_6$—X, and the additive are mixed therewith.

More specific embodiments of (a) mentioned above include, for example, adding a solution obtained by dissolving the catalyst in the solvent dropwise to a solution obtained by dissolving the compound represented by Formula II, the salt of the compound, or the solvate of the compound or the salt, the reducing agent, and R$_6$—X in the solvent, and then adding the additive thereto; or adding a solution obtained by dissolving the catalyst in the solvent dropwise to a solution obtained by dissolving the compound represented by Formula II, the salt of the compound, or the solvate of the compound or the salt and R$_6$—X in the solvent, and then after adding the reducing agent thereto, adding the additive thereto.

A more specific embodiment of (b) mentioned above includes, for example, adding the reducing agent and the additive to a solution obtained by dissolving the catalyst in the solvent, and then adding thereto a solution obtained by dissolving the compound represented by Formula II, the salt of the compound, or the solvate of the compound or the salt and R$_6$—X in the solvent dropwise.

A more specific embodiment of (c) mentioned above includes, for example, adding the reducing agent to a solution obtained by dissolving the catalyst in the solvent, and then adding thereto a solution obtained by dissolving the compound represented by Formula II, the salt of the compound, or the solvate of the compound or the salt, R$_6$—X, and the additive in the solvent.

When an optically active compound represented by Formula II is used in this step, the steric configuration thereof is maintained, and an optically active compound represented by Formula I can be obtained.

Methods of Producing Compound Represented by Formula II

The compound represented by Formula II, which is the starting material of the above step, can be synthesized using various methods known in the art.

In an embodiment, when R$_2$ is hydrogen, the compound represented by Formula II of the present invention can be synthesized, for example, according to the following scheme. In the scheme, R$_1$, R$_3$, R$_5$, R$_7$, and n are the same as R$_1$, R$_3$, R$_5$, R$_7$, and n of Formula II, respectively.

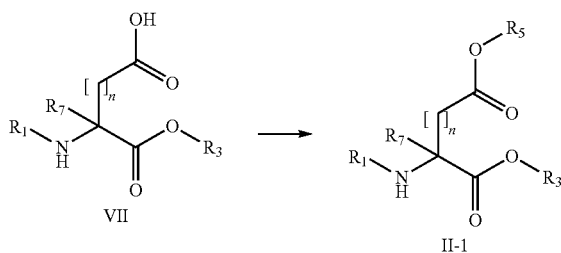

This step can be carried out by mixing an alcohol (R$_5$—OH) and a carboxylic acid with a dehydrative condensation agent such as a carbodiimide compound to condense the alcohol and the carboxylic acid following the method of Albert et al. (Synthesis, 1987, 7, 635-637) or the like.

In another embodiment, when R$_2$ is hydrogen, the compound represented by Formula II of the present invention can be synthesized, for example, according to the following scheme. In the scheme, R$_1$, R$_3$, R$_5$, R$_7$, and n are the same as R$_1$, R$_3$, R$_5$, R$_7$, and n of Formula II, respectively, and R$_{10}$ and R$_{11}$ are independently hydrogen, C$_1$-C$_4$ alkyl or C$_6$-C$_{10}$ aryl, or R$_{10}$ and R$_{11}$ together form oxo (=O).

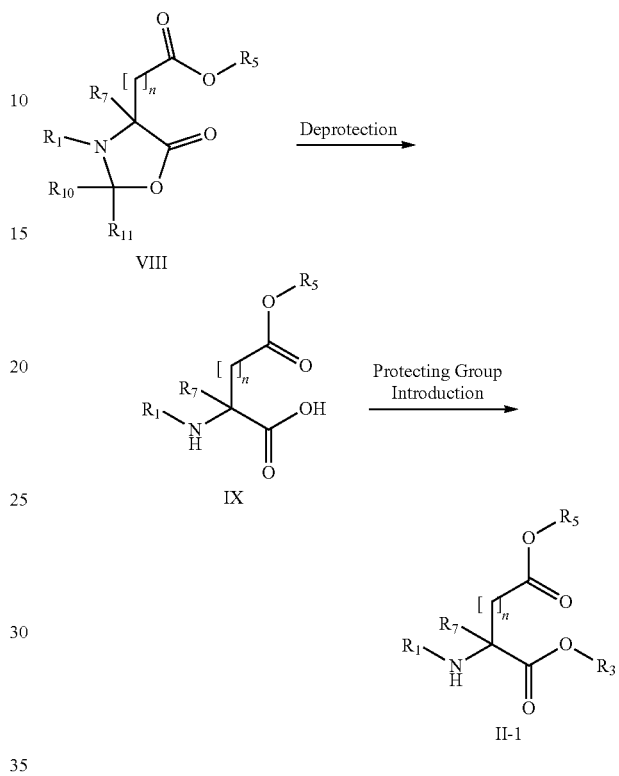

The steps of attaching/detaching the protecting group can be carried out following the methods described in Greene's, "Protective Groups in Organic Synthesis" (5th edition, John Wiley & Sons 2014).

In another embodiment, the compound represented by Formula II of the present invention in which R$_2$ is C$_1$-C$_6$ alkyl can be synthesized, for example, according to the following scheme. In the scheme, R$_1$, R$_3$, R$_5$, R$_7$, and n are the same as R$_1$, R$_3$, R$_5$, R$_7$, and n of Formula II, respectively, R$_4$ is a protecting group for a carboxyl group, and "Alk" is C$_1$-C$_6$ alkyl.

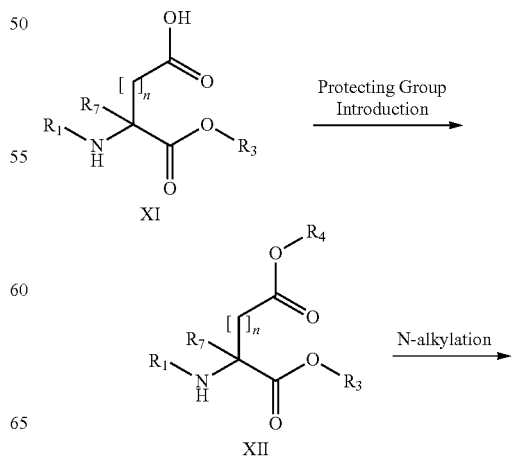

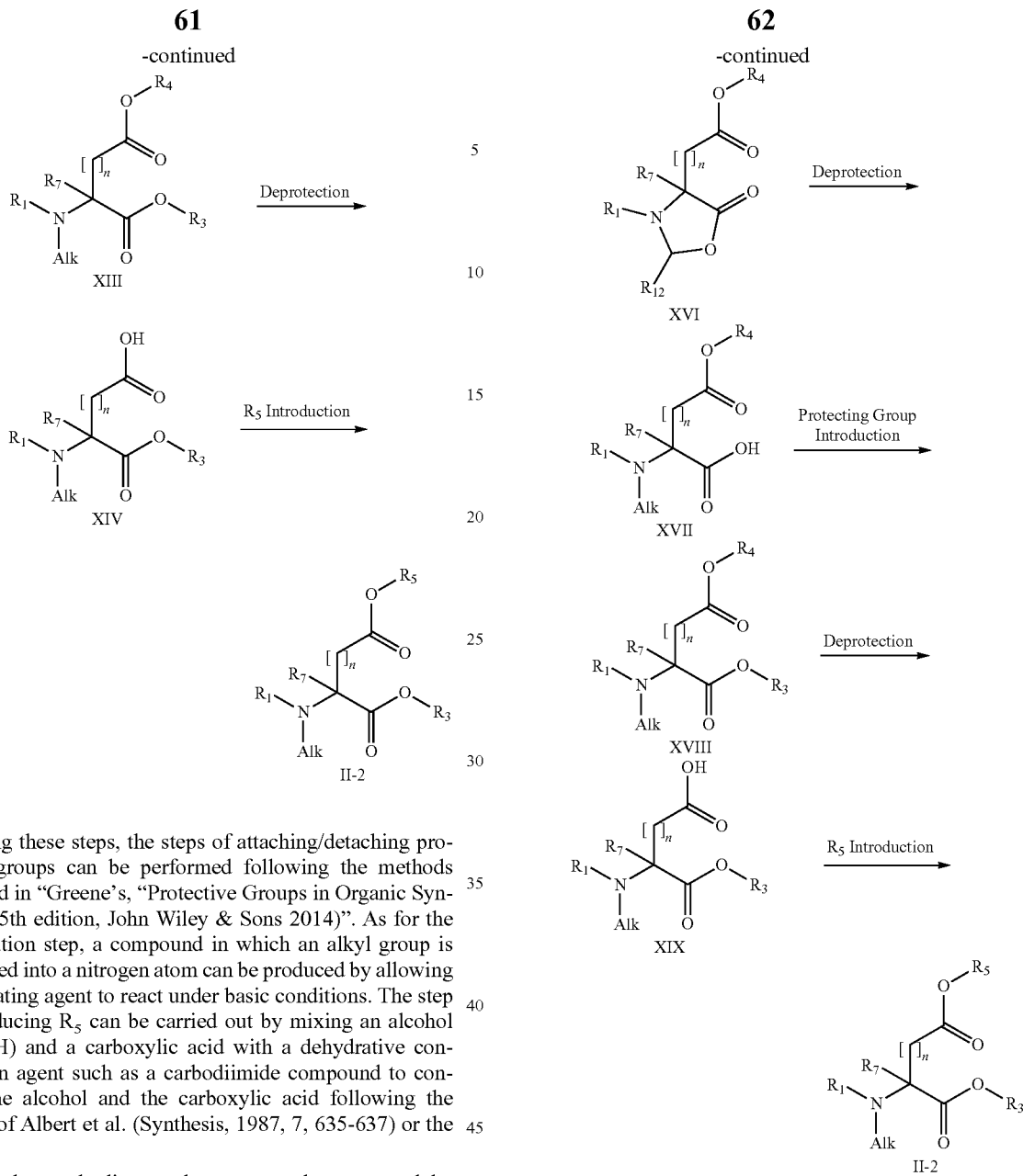

Among these steps, the steps of attaching/detaching protecting groups can be performed following the methods described in "Greene's, "Protective Groups in Organic Synthesis" (5th edition, John Wiley & Sons 2014)". As for the N-alkylation step, a compound in which an alkyl group is introduced into a nitrogen atom can be produced by allowing an alkylating agent to react under basic conditions. The step of introducing $R_5$ can be carried out by mixing an alcohol ($R_5$—OH) and a carboxylic acid with a dehydrative condensation agent such as a carbodiimide compound to condense the alcohol and the carboxylic acid following the method of Albert et al. (Synthesis, 1987, 7, 635-637) or the like.

In another embodiment, the compound represented by Formula II of the present invention in which $R_2$ is $C_1$-$C_6$ alkyl can be synthesized, for example, according to the following scheme. In the scheme, $R_1$, $R_3$, $R_5$, $R_7$, and n are the same as $R_1$, $R_3$, $R_5$, $R_7$, and n of Formula II mentioned above, respectively, $R_4$ is a protecting group for a carboxyl group, "Alk" is $C_1$-$C_6$ alkyl, and $R_{12}$ is hydrogen or $C_1$-$C_5$ alkyl.

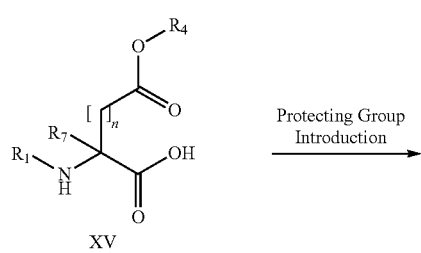

Among these steps, the steps of attaching/detaching protecting groups can be carried out following the methods described in "Greene's, "Protective Groups in Organic Synthesis" (5th edition, John Wiley & Sons 2014)". The N-alkylation step involving deprotection can also be carried out following the method of Freidinger et al. (J. Org. Chem., 1983, 48, 77-81) or the method of Buba et al. (Eur. J. Org. Chem., 2013, 4509-4513). The step of introducing $R_5$ can be carried out by mixing an alcohol ($R_5$—OH) and a carboxylic acid with a dehydrative condensation agent such as a carbodiimide compound to condense the alcohol and the carboxylic acid following the method of Albert et al. (Synthesis, 1987, 7, 635-637) or the like.

In another embodiment, when $R_2$ and $R_3$ together form —($CR_8R_9$)—, the compound represented by Formula IIA of the present invention can be synthesized according to the following scheme. In the scheme, $R_1$, $R_5$, $R_7$, $R_8$, $R_9$, and n are the same as $R_1$, $R_5$, $R_7$, $R_8$, $R_9$, and n of Formula IIA mentioned above, respectively, and $R_4$ is a protecting group for a carboxyl group.

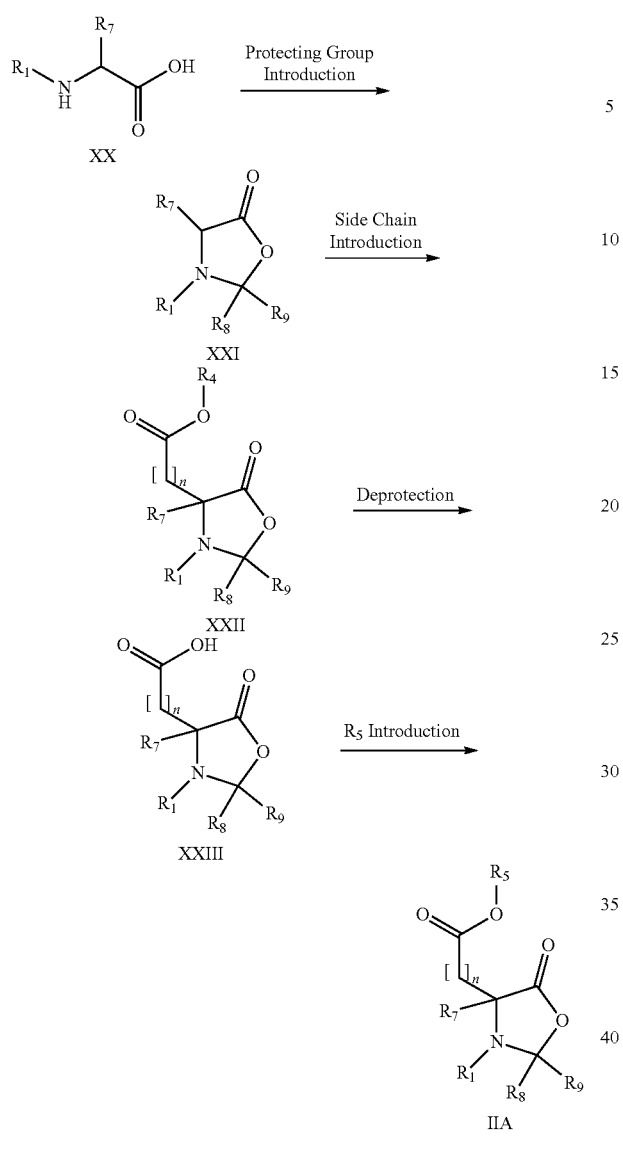

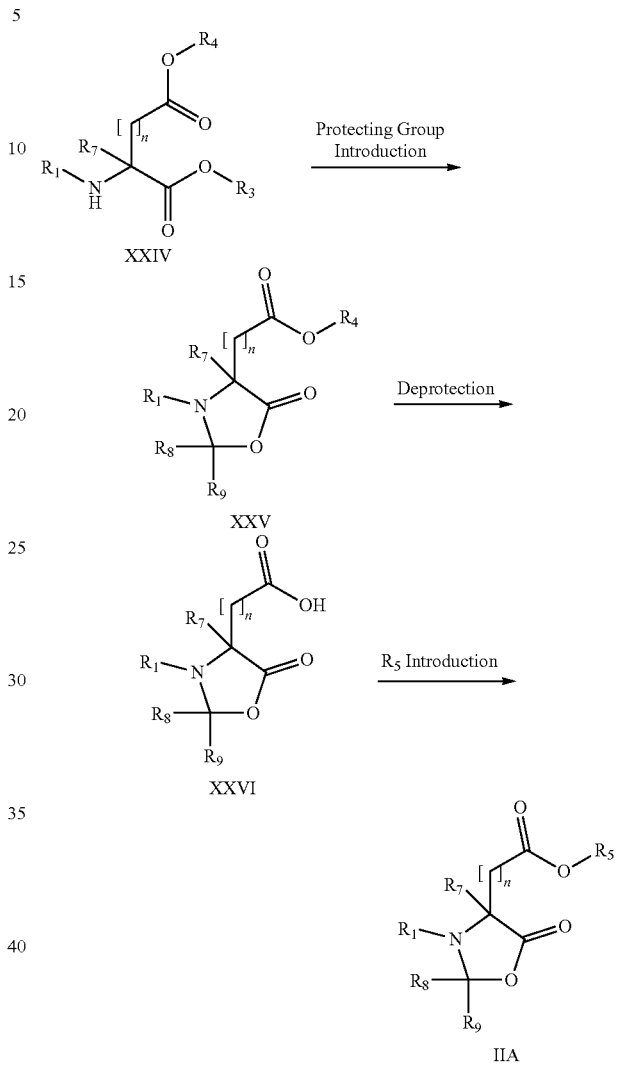

$R_9$, and n are the same as $R_1$, $R_5$, $R_7$, $R_8$, $R_9$, and n of Formula IIA mentioned above, respectively, and $R_4$ is a protecting group for a carboxyl group.

Among these reactions, the step of introducing a protecting group can be carried out by the method of dehydrative condensation with an aldehyde compound in the presence of an acid catalyst following the method of Freidinger et al. (J. Org. Chem., 1983, 48, 77-81) or the like, or the method described in "Greene's, "Protective Groups in Organic Synthesis" (5th Edition, John Wiley & Sons 2014)". The deprotection step can be carried out following the method described in "Greene's, "Protective Groups in Organic Synthesis" (5th edition, John Wiley & Sons 2014)". The step of introducing a side chain can be carried out following the method of Long et al. (J. Med. Chem., 2008, 51, 6371-6380) or the like. The step of introducing $R_5$ can be carried out by mixing an alcohol ($R_5$—OH) and a carboxylic acid with a dehydrative condensation agent such as a carbodiimide compound to condense the alcohol and the carboxylic acid following the method of Albert et al. (Synthesis, 1987, 7, 635-637) or the like.

In another embodiment, when $R_2$ and $R_3$ together form —($CR_8R_9$)—, the compound represented by Formula IIA of the present invention can be synthesized according to the following scheme. In the following scheme, $R_1$, $R_5$, $R_7$, $R_8$, Among these reactions, the step of introducing a protecting group can be carried out by the method of dehydrative condensation with an aldehyde compound in the presence of an acid catalyst following the method of Freidinger et al. (J. Org. Chem., 1983, 48, 77-81) or the like, or the method described in "Greene's, "Protective Groups in Organic Synthesis" (5th Edition, John Wiley & Sons 2014)". The deprotection step can be carried out following the method described in "Greene's, "Protective Groups in Organic Synthesis" (5th edition, John Wiley & Sons 2014)". The step of introducing $R_5$ can be carried out by condensing an alcohol and a carboxylic acid following the method of Albert et al. (Synthesis, 1987, 7, 635-637) or the like.

Modification of Compound Represented by Formula I

Starting from the compound represented by Formula I, the salt of the compound, or the solvate of the compound or the salt produced according to the method described above, the present invention enables preparation of further various amino acid analogs, salts of the analogs, or solvates of the analogs or the salts.

In an embodiment, when $R_3$ of the compound represented by Formula I is a protecting group for a carboxyl group, the compound represented by Formula III, the salt of the compound, or the solvate of the compound or the salt can be produced by using the compound represented by Formula I, the salt of the compound, or the solvate of the compound or the salt as a starting material, and removing the protecting group.

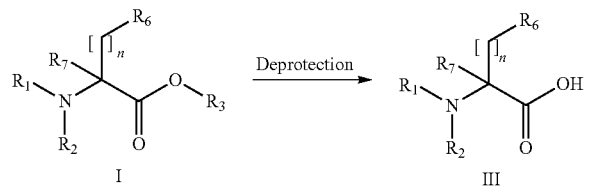

The deprotection step can be carried out following the method described in "Greene's, "Protective Groups in Organic Synthesis" (5th edition, John Wiley & Sons 2014)".

In an embodiment, when $R_1$ of the compound represented by Formula I, the salt of the compound, or the solvate of the compound or the salt is a protecting group for an amino group, and $R_3$ is a protecting group for a carboxyl group, the compound represented by Formula V can be produced by simultaneously removing these protecting groups to produce the compound represented by Formula IV, and further introducing a protecting group $R_{1'}$ to the amino group, as shown in the following scheme.

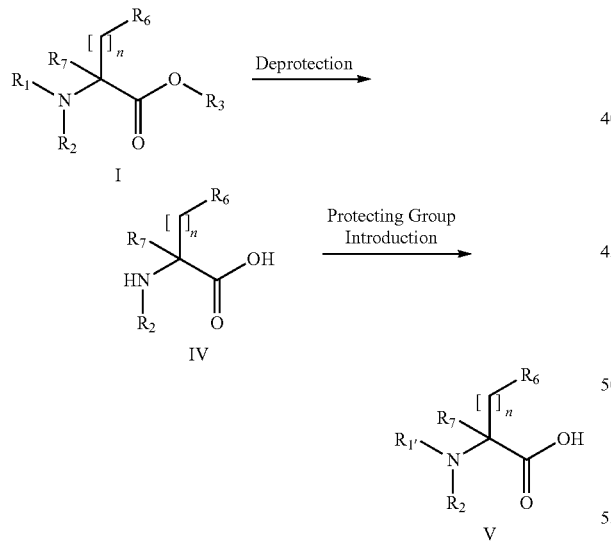

The steps of attaching/detaching these protecting groups can be carried out following the methods described in "Greene's, "Protective Groups in Organic Synthesis" (5th edition, John Wiley & Sons 2014)".

In an embodiment, when $R_2$ and $R_3$ of the compound represented by Formula I together form $—(CR_8R_9)—$ and thus the compound represented by Formula I is represented by Formula IA, the compound represented by Formula VI, the salt of the compound, or the solvate of the compound or the salt can be produced by using the compound represented by Formula IA, the salt of the compound, or the solvate of the compound or the salt as a starting material, and opening the oxazolidinone ring by a deprotection reaction.

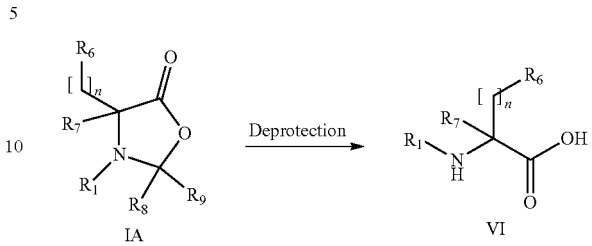

The above deprotection step can be carried out following the method described in "Greene's, "Protective Groups in Organic Synthesis" (5th edition, John Wiley & Sons 2014)".

In an embodiment, the present invention enables production of N-alkyl amino acid using the compound represented by Formula IA as a starting material, as shown in the following scheme.

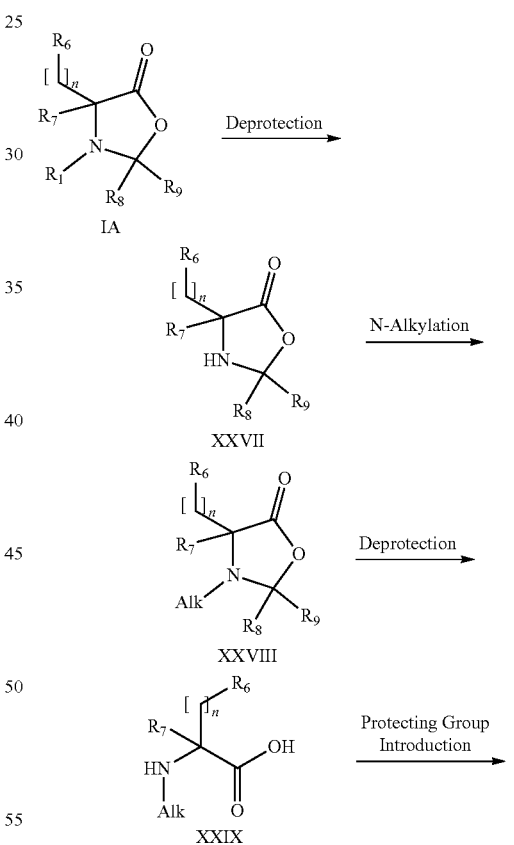

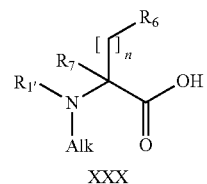

Among these steps, the steps of attaching/detaching protecting groups can be carried out following the methods described in "Greene's, "Protective Groups in Organic Synthesis" (5th edition, John Wiley & Sons 2014)". A compound in which an alkyl group is introduced into a nitrogen atom can be produced by allowing an alkylating agent to act under basic conditions following the method of Seebach et al. (Helv. Chim. Acta, 1987, 70, 237-261) or the like.

The present invention also relates to the amino acid derivatives represented by Formula I, and amino acid derivatives of the respective Formulae mentioned above obtained by modifying the amino acid derivatives.

In an embodiment, such amino acid derivatives preferably include those having the following combinations of groups in the compound of Formula (I):

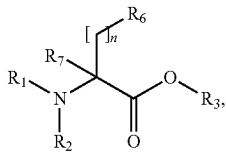

(a) $R_1$ is hydrogen, Boc, Fmoc, Cbz, Alloc or Teoc, $R_2$ is hydrogen or methyl, $R_3$ is hydrogen, methyl, t-butyl or benzyl, $R_6$ is 3-chloro-4-(trifluoromethyl)phenyl, $R_7$ is hydrogen, and n is 1 or 2;

(b) $R_1$ is hydrogen, Boc, Fmoc, Cbz, Alloc or Teoc, $R_2$ is ethyl, $R_3$ is hydrogen, methyl, t-butyl or benzyl, $R_6$ is 4-methylphenyl, $R_7$ is hydrogen, and n is 1;

(c) $R_1$ is hydrogen, Boc, Fmoc, Cbz, Alloc or Teoc, $R_2$ is hydrogen or methyl, $R_3$ is hydrogen, methyl or t-butyl, $R_6$ is 3,5-difluoro-4-(trifluoromethyl)phenyl, $R_7$ is hydrogen, and n is 1 or 2;

(d) $R_1$ is hydrogen, Boc, Fmoc, Cbz, Alloc or Teoc, $R_2$ is hydrogen or methyl, $R_3$ is hydrogen, methyl or t-butyl, $R_6$ is 3-methoxy-4-(methylcarbamoyl)phenyl, $R_7$ is hydrogen, and n is 1 or 2;

(e) $R_1$ is hydrogen, Boc, Fmoc, Cbz, Alloc or Teoc, $R_2$ is hydrogen or methyl, $R_3$ is hydrogen, methyl or t-butyl, and $R_6$ is 4-methoxy-3-(methylcarbamoyl)phenyl, $R_7$ is hydrogen, and n is 1 or 2;

(f) $R_1$ is hydrogen, Boc, Fmoc, Cbz, Alloc or Teoc, $R_2$ is hydrogen or methyl, $R_3$ is hydrogen, methyl or t-butyl, $R_6$ is 3-methoxy-4-((methylsulfonyl)carbamoyl)phenyl, $R_7$ is hydrogen, and n is 1 or 2;

(g) $R_1$ is hydrogen, Boc, Fmoc, Cbz, Alloc or Teoc, $R_2$ is hydrogen or methyl, $R_3$ is hydrogen, methyl or t-butyl, $R_6$ is 4-(methyl((tetrahydro-2H-pyran-2-yl)oxy)carbamoyl)phenyl, $R_7$ is hydrogen, and n is 1 or 2;

(h) $R_1$ is hydrogen, Boc, Fmoc, Cbz, Alloc or Teoc, $R_2$ is hydrogen or methyl, $R_3$ is hydrogen, methyl or t-butyl, $R_6$ is 3-methoxy-4-(((tetrahydro-2H-pyran-2-yl)oxy)carbamoyl)phenyl, $R_7$ is hydrogen, and n is 1 or 2; or (i) $R_1$ is hydrogen, Boc, Fmoc, Cbz, Alloc or Teoc, $R_2$ is hydrogen or methyl, $R_3$ is hydrogen, methyl or t-butyl, $R_6$ is 6-methoxypyridin-3-yl, $R_7$ is hydrogen, and n is 1 or 2.

The amino acid derivatives of the present invention include more preferably an amino acid derivative represented by Formula (1):

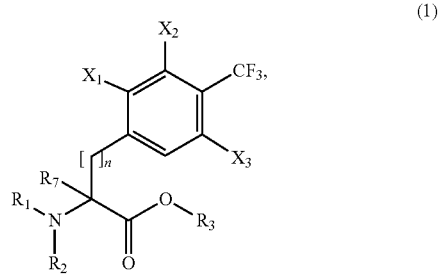

wherein
$R_1$ is hydrogen or a protecting group for an amino group selected from the group consisting of Boc, Fmoc, Cbz, Alloc and Teoc;
$R_2$ is hydrogen or methyl;
$R_3$ is hydrogen or a protecting group for a carboxyl group selected from the group consisting of methyl, t-butyl and benzyl;
$R_7$ is hydrogen;
n is 1 or 2; and
$X_1$, $X_2$, and $X_3$ are independently hydrogen or halogen;
provided that
when $X_1$ is halogen, $X_2$ and $X_3$ are hydrogen; and
when $X_1$ is hydrogen, both $X_2$ and $X_3$ are halogen, or one of $X_2$ and $X_3$ is halogen.

In Formula (1), when $X_1$ is halogen, the halogen is preferably F or Cl.

In Formula (1), when both $X_2$ and $X_3$ are halogen, the type of halogen may be the same or different. $X_2$ and $X_3$ are preferably $X_2$=F and $X_3$=F; $X_2$=F and $X_3$=Cl; or $X_2$=Cl and $X_3$=Cl.

In Formula (1), when one of $X_2$ and $X_3$ is halogen, the halogen is preferably F or Cl.

Specific examples of the amino acid derivative of Formula (1) include the following compounds, salts of the compounds, and solvates of the compounds or the salts:

(C-001) 2-(((benzyloxy)carbonyl)amino)-4-(3,5-difluoro-4-(trifluoromethyl)phenyl)butanoic acid, (C-002) methyl 2-(((benzyloxy)carbonyl)amino)-4-(3,5-difluoro-4-(trifluoromethyl)phenyl)butanoate, (C-003) tert-butyl 2-(((benzyloxy)carbonyl)amino)-4-(3,5-difluoro-4-(trifluoromethyl)phenyl)butanoate, (C-004) benzyl 2-(((benzyloxy)carbonyl)amino)-4-(3,5-difluoro-4-(trifluoromethyl)phenyl)butanoate, (C-005) 2-((((9H-fluoren-9-yl)methoxy)carbonyl)amino)-4-(3,5-difluoro-4-(trifluoromethyl)phenyl)butanoic acid, (C-006) methyl 2-((((9H-fluoren-9-yl)methoxy)carbonyl)amino)-4-(3,5-difluoro-4-(trifluoromethyl)phenyl)butanoate, (C-007) tert-butyl 2-((((9H-fluoren-9-yl)methoxy)carbonyl)amino)-4-(3,5-difluoro-4-(trifluoromethyl)phenyl)butanoate, (C-008) benzyl 2-((((9H-fluoren-9-yl)methoxy)carbonyl)amino)-4-(3,5-difluoro-4-(trifluoromethyl)phenyl)butanoate, (C-009) 2-((tert-butoxycarbonyl)amino)-4-(3,5-difluoro-4-(trifluoromethyl)phenyl)butanoic acid, (C-010) methyl 2-((tert-butoxycarbonyl)amino)-4-(3,5-difluoro-4-(trifluoromethyl)phenyl)butanoate, (C-011) tert-butyl 2-((tert-butoxycarbonyl)amino)-4-(3,5-difluoro-4-(trifluoromethyl)phenyl)butanoate,
(C-012) benzyl 2-((tert-butoxycarbonyl)amino)-4-(3,5-difluoro-4-(trifluoromethyl)phenyl)butanoate,
(C-013) 2-(((allyloxy)carbonyl)amino)-4-(3,5-difluoro-4-(trifluoromethyl)phenyl)butanoic acid,
(C-014) methyl 2-(((allyloxy)carbonyl)amino)-4-(3,5-difluoro-4-(trifluoromethyl)phenyl)butanoate,
(C-015) tert-butyl 2-(((allyloxy)carbonyl)amino)-4-(3,5-difluoro-4-(trifluoromethyl)phenyl)butanoate,
(C-016) benzyl 2-(((allyloxy)carbonyl)amino)-4-(3,5-difluoro-4-(trifluoromethyl)phenyl)butanoate,
(C-017) 4-(3,5-difluoro-4-(trifluoromethyl)phenyl)-2-(((2-(trimethylsilyl)ethoxy)carbonyl)amino)butanoic acid,
(C-018) methyl 4-(3,5-difluoro-4-(trifluoromethyl)phenyl)-2-(((2-(trimethylsilyl)ethoxy)carbonyl)amino)butanoate,
(C-019) tert-butyl 4-(3,5-difluoro-4-(trifluoromethyl)phenyl)-2-(((2-(trimethylsilyl)ethoxy)carbonyl)amino)butanoate,
(C-020) benzyl 4-(3,5-difluoro-4-(trifluoromethyl)phenyl)-2-(((2-(trimethylsilyl)ethoxy)carbonyl)amino)butanoate,
(C-021) 2-(((benzyloxy)carbonyl)(methyl)amino)-4-(3,5-difluoro-4-(trifluoromethyl)phenyl)butanoic acid,
(C-022) methyl 2-(((benzyloxy)carbonyl)(methyl)amino)-4-(3,5-difluoro-4-(trifluoromethyl)phenyl)butanoate,
(C-023) tert-butyl 2-(((benzyloxy)carbonyl)(methyl)amino)-4-(3,5-difluoro-4-(trifluoromethyl)phenyl)butanoate,
(C-024) benzyl 2-(((benzyloxy)carbonyl)(methyl)amino)-4-(3,5-difluoro-4-(trifluoromethyl)phenyl)butanoate,
(C-025) 2-((((9H-fluoren-9-yl)methoxy)carbonyl)(methyl)amino)-4-(3,5-difluoro-4-(trifluoromethyl)phenyl)butanoic acid,
(C-026) methyl 2-((((9H-fluoren-9-yl)methoxy)carbonyl)(methyl)amino)-4-(3,5-difluoro-4-(trifluoromethyl)phenyl)butanoate,
(C-027) tert-butyl 2-((((9H-fluoren-9-yl)methoxy)carbonyl)(methyl)amino)-4-(3,5-difluoro-4-(trifluoromethyl)phenyl)butanoate,
(C-028) benzyl 2-((((9H-fluoren-9-yl)methoxy)carbonyl)(methyl)amino)-4-(3,5-difluoro-4-(trifluoromethyl)phenyl)butanoate,
(C-029) 2-((tert-butoxycarbonyl)(methyl)amino)-4-(3,5-difluoro-4-(trifluoromethyl)phenyl)butanoic acid,
(C-030) methyl 2-((tert-butoxycarbonyl)(methyl)amino)-4-(3,5-difluoro-4-(trifluoromethyl)phenyl)butanoate,
(C-031) tert-butyl 2-((tert-butoxycarbonyl)(methyl)amino)-4-(3,5-difluoro-4-(trifluoromethyl)phenyl)butanoate,
(C-032) benzyl 2-((tert-butoxycarbonyl)(methyl)amino)-4-(3,5-difluoro-4-(trifluoromethyl)phenyl)butanoate,
(C-033) 2-(((allyloxy)carbonyl)(methyl)amino)-4-(3,5-difluoro-4-(trifluoromethyl)phenyl)butanoic acid,
(C-034) methyl 2-(((allyloxy)carbonyl)(methyl)amino)-4-(3,5-difluoro-4-(trifluoromethyl)phenyl)butanoate,
(C-035) tert-butyl 2-(((allyloxy)carbonyl)(methyl)amino)-4-(3,5-difluoro-4-(trifluoromethyl)phenyl)butanoate,
(C-036) benzyl 2-(((allyloxy)carbonyl)(methyl)amino)-4-(3,5-difluoro-4-(trifluoromethyl)phenyl)butanoate,
(C-037) 4-(3,5-difluoro-4-(trifluoromethyl)phenyl)-2-(methyl(((2-(trimethylsilyl)ethoxy)carbonyl)amino)butanoic acid,
(C-038) methyl 4-(3,5-difluoro-4-(trifluoromethyl)phenyl)-2-(methyl((2-(trimethylsilyl)ethoxy)carbonyl)amino)butanoate,
(C-039) tert-butyl 4-(3,5-difluoro-4-(trifluoromethyl)phenyl)-2-(methyl((2-(trimethylsilyl)ethoxy)carbonyl)amino)butanoate,
(C-040) benzyl 4-(3,5-difluoro-4-(trifluoromethyl)phenyl)-2-(methyl((2-(trimethylsilyl)ethoxy)carbonyl)amino)butanoate,
(C-041) 2-(((benzyloxy)carbonyl)amino)-3-(3,5-difluoro-4-(trifluoromethyl)phenyl)propanoic acid,
(C-042) methyl 2-(((benzyloxy)carbonyl)amino)-3-(3,5-difluoro-4-(trifluoromethyl)phenyl)propanoate,
(C-043) tert-butyl 2-(((benzyloxy)carbonyl)amino)-3-(3,5-difluoro-4-(trifluoromethyl)phenyl)propanoate,
(C-044) benzyl 2-(((benzyloxy)carbonyl)amino)-3-(3,5-difluoro-4-(trifluoromethyl)phenyl)propanoate,
(C-045) 2-((((9H-fluoren-9-yl)methoxy)carbonyl)amino)-3-(3,5-difluoro-4-(trifluoromethyl)phenyl)propanoic acid,
(C-046) methyl 2-((((9H-fluoren-9-yl)methoxy)carbonyl)amino)-3-(3,5-difluoro-4-(trifluoromethyl)phenyl)propanoate,
(C-047) tert-butyl 2-((((9H-fluoren-9-yl)methoxy)carbonyl)amino)-3-(3,5-difluoro-4-(trifluoromethyl)phenyl)propanoate,
(C-048) benzyl 2-((((9H-fluoren-9-yl)methoxy)carbonyl)amino)-3-(3,5-difluoro-4-(trifluoromethyl)phenyl)propanoate,
(C-049) 2-((tert-butoxycarbonyl)amino)-3-(3,5-difluoro-4-(trifluoromethyl)phenyl)propanoic acid,
(C-050) methyl 2-((tert-butoxycarbonyl)amino)-3-(3,5-difluoro-4-(trifluoromethyl)phenyl)propanoate,
(C-051) tert-butyl 2-((tert-butoxycarbonyl)amino)-3-(3,5-difluoro-4-(trifluoromethyl)phenyl)propanoate,
(C-052) benzyl 2-((tert-butoxycarbonyl)amino)-3-(3,5-difluoro-4-(trifluoromethyl)phenyl)propanoate,
(C-053) 2-(((allyloxy)carbonyl)amino)-3-(3,5-difluoro-4-(trifluoromethyl)phenyl)propanoic acid,
(C-054) methyl 2-(((allyloxy)carbonyl)amino)-3-(3,5-difluoro-4-(trifluoromethyl)phenyl)propanoate,
(C-055) tert-butyl 2-(((allyloxy)carbonyl)amino)-3-(3,5-difluoro-4-(trifluoromethyl)phenyl)propanoate,
(C-056) benzyl 2-(((allyloxy)carbonyl)amino)-3-(3,5-difluoro-4-(trifluoromethyl)phenyl)propanoate,
(C-057) 3-(3,5-difluoro-4-(trifluoromethyl)phenyl)-2-(((2-(trimethylsilyl)ethoxy)carbonyl)amino)propanoic acid,
(C-058) methyl 3-(3,5-difluoro-4-(trifluoromethyl)phenyl)-2-(((2-(trimethylsilyl)ethoxy)carbonyl)amino)propanoate,
(C-059) tert-butyl 3-(3,5-difluoro-4-(trifluoromethyl)phenyl)-2-(((2-(trimethylsilyl)ethoxy)carbonyl)amino)propanoate,
(C-060) benzyl 3-(3,5-difluoro-4-(trifluoromethyl)phenyl)-2-(((2-(trimethylsilyl)ethoxy)carbonyl)amino)propanoate,
(C-061) 2-(((benzyloxy)carbonyl)(methyl)amino)-3-(3,5-difluoro-4-(trifluoromethyl)phenyl)propanoic acid,
(C-062) methyl 2-(((benzyloxy)carbonyl)(methyl)amino)-3-(3,5-difluoro-4-(trifluoromethyl)phenyl)propanoate,
(C-063) tert-butyl 2-(((benzyloxy)carbonyl)(methyl)amino)-3-(3,5-difluoro-4-(trifluoromethyl)phenyl)propanoate,
(C-064) benzyl 2-(((benzyloxy)carbonyl)(methyl)amino)-3-(3,5-difluoro-4-(trifluoromethyl)phenyl)propanoate, (C-065) 2-((((9H-fluoren-9-yl)methoxy)carbonyl)(methyl)amino)-3-(3,5-difluoro-4-(trifluoromethyl)phenyl)propanoic acid,
(C-066) methyl 2-((((9H-fluoren-9-yl)methoxy)carbonyl)(methyl)amino)-3-(3,5-difluoro-4-(trifluoromethyl)phenyl)propanoate,
(C-067) tert-butyl 2-((((9H-fluoren-9-yl)methoxy)carbonyl)(methyl)amino)-3-(3,5-difluoro-4-(trifluoromethyl)phenyl)propanoate,
(C-068) benzyl 2-((((9H-fluoren-9-yl)methoxy)carbonyl)(methyl)amino)-3-(3,5-difluoro-4-(trifluoromethyl)phenyl)propanoate,
(C-069) 2-((tert-butoxycarbonyl)(methyl)amino)-3-(3,5-difluoro-4-(trifluoromethyl)phenyl)propanoic acid,
(C-070) methyl 2-((tert-butoxycarbonyl)(methyl)amino)-3-(3,5-difluoro-4-(trifluoromethyl)phenyl)propanoate,
(C-071) tert-butyl 2-((tert-butoxycarbonyl)(methyl)amino)-3-(3,5-difluoro-4-(trifluoromethyl)phenyl)propanoate,
(C-072) benzyl 2-((tert-butoxycarbonyl)(methyl)amino)-3-(3,5-difluoro-4-(trifluoromethyl)phenyl)propanoate,
(C-073) 2-(((allyloxy)carbonyl)(methyl)amino)-3-(3,5-difluoro-4-(trifluoromethyl)phenyl)propanoic acid,
(C-074) methyl 2-(((allyloxy)carbonyl)(methyl)amino)-3-(3,5-difluoro-4-(trifluoromethyl)phenyl)propanoate,
(C-075) tert-butyl 2-(((allyloxy)carbonyl)(methyl)amino)-3-(3,5-difluoro-4-(trifluoromethyl)phenyl)propanoate,
(C-076) benzyl 2-(((allyloxy)carbonyl)(methyl)amino)-3-(3,5-difluoro-4-(trifluoromethyl)phenyl)propanoate,
(C-077) 3-(3,5-difluoro-4-(trifluoromethyl)phenyl)-2-(methyl((2-(trimethylsilyl)ethoxy)carbonyl)amino)propanoic acid,
(C-078) methyl 3-(3,5-difluoro-4-(trifluoromethyl)phenyl)-2-(methyl((2-(trimethylsilyl)ethoxy)carbonyl)amino)propanoate,
(C-079) tert-butyl 3-(3,5-difluoro-4-(trifluoromethyl)phenyl)-2-(methyl((2-(trimethylsilyl)ethoxy)carbonyl)amino)propanoate, and
(C-080) benzyl 3-(3,5-difluoro-4-(trifluoromethyl)phenyl)-2-(methyl((2-(trimethylsilyl)ethoxy)carbonyl)amino)propanoate.

In another embodiment, specific examples of the amino acid derivative of the present invention include compounds provided in the following tables, salts of the compounds, and solvates of the compounds or the salts.

$R_1$, $R_2$, $R_3$, $R_6$, $R_7$, and n in the tables mean $R_1$, $R_2$, $R_3$, $R_6$, $R_7$, and n in the following formula, respectively. Furthermore, * indicates a point of bonding.

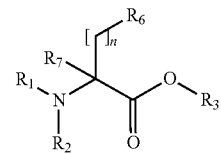

TABLE

| Compound ID | $R_1$ | $R_2$ | n | $R_3$ | $R_6$ | $R_7$ | Compound Name |
|---|---|---|---|---|---|---|---|
| 1-1 | Boc | H | 2 | Bn | 3-chloro-4-(trifluoromethyl)phenyl | H | Benzyl 2-((tert-butoxycarbonyl)amino)-4-(3-chloro-4-(trifluoromethyl)phenyl)butanoate |
| 1-2 | Boc | H | 2 | tBu | 3-chloro-4-(trifluoromethyl)phenyl | H | tert-Butyl 2-((tert-butoxycarbonyl)amino)-4-(3-chloro-4-(trifluoromethyl)phenyl)butanoate |
| 1-3 | Fmoc | H | 2 | Bn | 3-chloro-4-(trifluoromethyl)phenyl | H | Benzyl 2-((((9H-fluoren-9-yl)methoxy)carbonyl)amino)-4-(3-chloro-4-(trifluoromethyl)phenyl)butanoate |
| 1-4 | Fmoc | H | 2 | tBu | 3-chloro-4-(trifluoromethyl)phenyl | H | tert-Butyl 2-((((9H-fluoren-9-yl)methoxy)carbonyl)amino)-4-(3-chloro-4-(trifluoromethyl)phenyl)butanoate |
| 1-5 | Cbz | H | 2 | Bn | 3-chloro-4-(trifluoromethyl)phenyl | H | Benzyl 2-(((benzyloxy)carbonyl)amino)-4-(3-chloro-4-(trifluoromethyl)phenyl)butanoate |

TABLE-continued

| Compound ID | R₁ | R₂ | n | R₃ | R₆ | R₇ | Compound Name |
|---|---|---|---|---|---|---|---|
| 1-6 | Cbz | H | 2 | tBu | 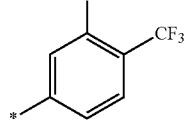 | H | tert-Butyl 2-(((benzyloxy)carbonyl)amino)-4-(3-chloro-4-(trifluoromethyl)phenyl)butanoate |
| 1-7 | Boc | Me | 2 | Bn | 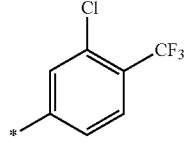 [SMILES: *c1ccc(C(F)(F)F)c(Cl)c1] | H | Benzyl 2-((tert-butoxycarbonyl)(methyl)amino)-4-(3-chloro-4-(trifluoromethyl)phenyl)butanoate |
| 1-8 | Boc | Me | 2 | tBu | 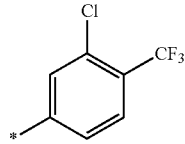 [SMILES: *c1ccc(C(F)(F)F)c(Cl)c1] | H | tert-Butyl 2-((tert-butoxycarbonyl)(methyl)amino)-4-(3-chloro-4-(trifluoromethyl)phenyl)butanoate |
| 1-9 | Fmoc | Me | 2 | Bn | 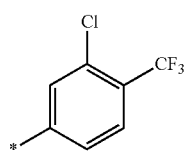 [SMILES: *c1ccc(C(F)(F)F)c(Cl)c1] | H | Benzyl 2-((((9H-fluoren-9-yl)methoxy)carbonyl)(methyl)amino)-4-(3-chloro-4-(trifluoromethyl)phenyl)butanoate |
| 1-10 | Fmoc | Me | 2 | tBu | 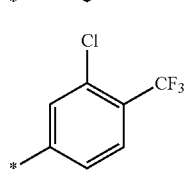 | H | tert-Butyl 2-((((9H-fluoren-9-yl)methoxy)carbonyl)(methyl)amino)-4-(3-chloro-4-(trifluoromethyl)phenyl)butanoate |
| 1-11 | Cbz | Me | 2 | Bn | 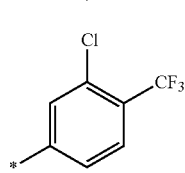 | H | Benzyl 2-(((benzyloxy)carbonyl)(methyl)amino)-4-(3-chloro-4-(trifluoromethyl)phenyl)butanoate |
| 1-12 | Cbz | Me | 2 | tBu | 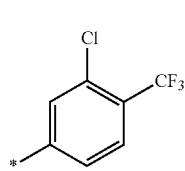 [SMILES: *c1ccc(C(F)(F)F)c(Cl)c1] | H | tert-Butyl 2-(((benzyloxy)carbonyl)(methyl)amino)-4-(3-chloro-4-(trifluoromethyl)phenyl)butanoate |
| 1-13 | Boc | H | 2 | H | 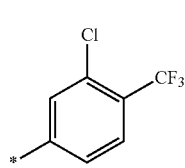 [SMILES: *c1ccc(C(F)(F)F)c(Cl)c1] | H | 2-((tert-Butoxycarbonyl)amino)-4-(3-chloro-4-(trifluoromethyl)phenyl)butanoic acid |
| 1-14 | Fmoc | H | 2 | H | 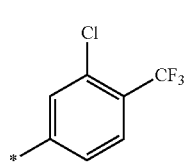 [SMILES: *c1ccc(C(F)(F)F)c(Cl)c1] | H | 2-((((9H-Fluoren-9-yl)methoxy)carbonyl)amino)-4-(3-chloro-4-(trifluoromethyl)phenyl)butanoic acid |
| 1-15 | Cbz | H | 2 | H | 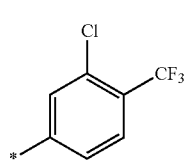 [SMILES: *c1ccc(C(F)(F)F)c(Cl)c1] | H | 2-(((Benzyloxy)carbonyl)amino)-4-(3-chloro-4-(trifluoromethyl)phenyl)butanoic acid |

TABLE-continued

| Compound ID | R₁ | R₂ | n | R₃ | R₆ | R₇ | Compound Name |
|---|---|---|---|---|---|---|---|
| 1-16 | Boc | Me | 2 | H | 3-Cl, 4-CF₃ phenyl | H | 2-((tert-Butoxycarbonyl)(methyl)amino)-4-(3-chloro-4-(trifluoromethyl)phenyl)butanoic acid |
| 1-17 | Fmoc | Me | 2 | H | 3-Cl, 4-CF₃ phenyl | H | 2-((((9H-Fluoren-9-yl)methoxy)carbonyl)(methyl)amino)-4-(3-chloro-4-(trifluoromethyl)phenyl)butanoic acid |
| 1-18 | Cbz | Me | 2 | H | 3-Cl, 4-CF₃ phenyl | H | 2-(((Benzyloxy)carbonyl)(methyl)amino)-4-(3-chloro-4-(trifluoromethyl)phenyl)butanoic acid |
| 1-19 | H | H | 2 | H | 3-Cl, 4-CF₃ phenyl | H | 2-Amino-4-(3-chloro-4-(trifluoromethyl)phenyl)butanoic acid |
| 1-20 | H | Me | 2 | H | 3-Cl, 4-CF₃ phenyl | H | 4-(3-Chloro-4-(trifluoromethyl)phenyl)-2-(methylamino)butanoic acid |
| 1-21 | Boc | H | 1 | Bn | 3-Cl, 4-CF₃ phenyl | H | Benzyl 2-((tert-butoxycarbonyl)amino)-3-(3-chloro-4-(trifluoromethyl)phenyl)propanoate |
| 1-22 | Boc | H | 1 | tBu | 3-Cl, 4-CF₃ phenyl | H | tert-Butyl 2-((tert-butoxycarbonyl)amino)-3-(3-chloro-4-(trifluoromethyl)phenyl)propanoate |
| 1-23 | Fmoc | H | 1 | Bn | 3-Cl, 4-CF₃ phenyl | H | Benzyl 2-((((9H-fluoren-9-yl)methoxy)carbonyl)amino)-3-(3-chloro-4-(trifluoromethyl)phenyl)propanoate |
| 1-24 | Fmoc | H | 1 | tBu | 3-Cl, 4-CF₃ phenyl | H | tert-Butyl 2-((((9H-fluoren-9-yl)methoxy)carbonyl)amino)-3-(3-chloro-4-(trifluoromethyl)phenyl)propanoate |

TABLE-continued

| Compound ID | R₁ | R₂ | n | R₃ | R₆ | R₇ | Compound Name |
|---|---|---|---|---|---|---|---|
| 1-25 | Cbz | H | 1 | Bn | 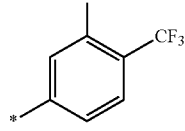 | H | Benzyl 2-(((benzyloxy)carbonyl)amino)-3-(3-chloro-4-(trifluoromethyl)phenyl)propanoate |
| 1-26 | Cbz | H | 1 | tBu | 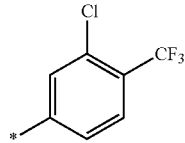 [SMILES: *c1ccc(C(F)(F)F)c(Cl)c1] | H | tert-Butyl 2-(((benzyloxy)carbonyl)amino)-3-(3-chloro-4-(trifluoromethyl)phenyl)propanoate |
| 1-27 | Boc | Me | 1 | Bn | 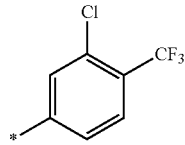 [SMILES: *c1ccc(C(F)(F)F)c(Cl)c1] | H | Benzyl 2-((tert-butoxycarbonyl)(methyl)amino)-3-(3-chloro-4-(trifluoromethyl)phenyl)propanoate |
| 1-28 | Boc | Me | 1 | tBu | 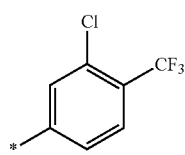 [SMILES: *c1ccc(C(F)(F)F)c(Cl)c1] | H | tert-Butyl 2-((tert-butoxycarbonyl)(methyl)amino)-3-(3-chloro-4-(trifluoromethyl)phenyl)propanoate |
| 1-29 | Fmoc | Me | 1 | Bn | 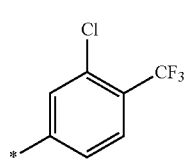 [SMILES: *c1ccc(C(F)(F)F)c(Cl)c1] | H | Benzyl 2-((((9H-fluoren-9-yl)methoxy)carbonyl)(methyl)amino)-3-(3-chloro-4-(trifluoromethyl)phenyl)propanoate |
| 1-30 | Fmoc | Me | 1 | tBu | 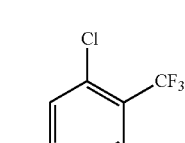 | H | tert-Butyl 2-((((9H-fluoren-9-yl)methoxy)carbonyl)(methyl)amino)-3-(3-chloro-4-(trifluoromethyl)phenyl)propanoate |
| 1-31 | Cbz | Me | 1 | Bn | 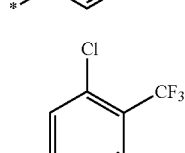 | H | Benzyl 2-(((benzyloxy)carbonyl)(methyl)amino)-3-(3-chloro-4-(trifluoromethyl)phenyl)propanoate |
| 1-32 | Cbz | Me | 1 | tBu | 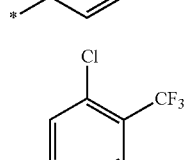 | H | tert-Butyl 2-(((benzyloxy)carbonyl)(methyl)amino)-3-(3-chloro-4-(trifluoromethyl)phenyl)propanoate |
| 1-33 | Boc | H | 1 | H | 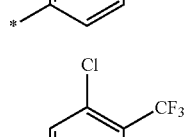 | H | 2-((tert-Butoxycarbonyl)amino)-3-(3-chloro-4-(trifluoromethyl)phenyl)propanoic acid |
| 1-34 | Fmoc | H | 1 | H | 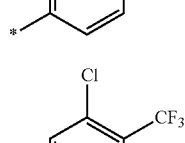 | H | 2-((((9H-Fluoren-9-yl)methoxy)carbonyl)amino)-3-(3-chloro-4-(trifluoromethyl)phenyl)propanoic acid |

TABLE-continued

| Compound ID | R₁ | R₂ | n | R₃ | R₆ | R₇ | Compound Name |
|---|---|---|---|---|---|---|---|
| 1-35 | Cbz | H | 1 | H | 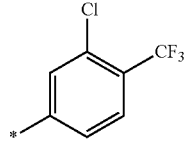 [SMILES: *c1ccc(C(F)(F)F)c(Cl)c1] | H | 2-(((Benzyloxy)carbonyl)amino)-3-(3-chloro-4-(trifluoromethyl)phenyl) propanoic acid |
| 1-36 | Boc | Me | 1 | H | 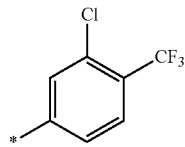 [SMILES: *c1ccc(C(F)(F)F)c(Cl)c1] | H | 2-((tert-Butoxycarbonyl)(methyl)amino)-3-(3-chloro-4-(trifluoromethyl)phenyl) propanoic acid |
| 1-37 | Fmoc | Me | 1 | H | 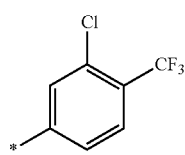 [SMILES: *c1ccc(C(F)(F)F)c(Cl)c1] | H | 2-((((9H-Fluoren-9-yl)methoxy)carbonyl)(methyl)amino)-3-(3-chloro-4-(trifluoromethyl)phenyl)propanoic acid |
| 1-38 | Cbz | Me | 1 | H | 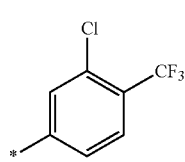 [SMILES: *c1ccc(C(F)(F)F)c(Cl)c1] | H | 2-(((Benzyloxy)carbonyl)(methyl)amino)-3-(3-chloro-4-(trifluoromethyl)phenyl)propanoic acid |
| 1-39 | H | H | 1 | H | 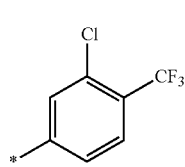 [SMILES: *c1ccc(C(F)(F)F)c(Cl)c1] | H | 2-Amino-3-(3-chloro-4-(trifluoromethyl)phenyl)propanoic acid |
| 1-40 | H | Me | 1 | H | 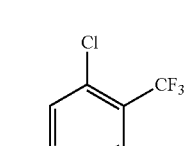 | H | 3-(3-Chloro-4-(trifluoromethyl)phenyl)-2-(methylamino)propanoic acid |

TABLE 2

| Compound ID | R₁ | R₂ | n | R₃ | R₆ | R₇ | Compound Name |
|---|---|---|---|---|---|---|---|
| 2-1 | Fmoc | H | 2 | tBu | 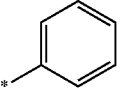 | H | tert-Butyl 2-((((9H-fluoren-9-yl)methoxy)carbonyl)amino)-4-phenylbutanoate |
| 2-2 | Fmoc | H | 2 | tBu | 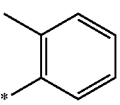 [SMILES: *c1ccccc1C] | H | tert-Butyl 2-((((9H-fluoren-9-yl)methoxy)carbonyl)amino)-4-(o-tolyl)butanoate |
| 2-3 | Fmoc | H | 2 | tBu | 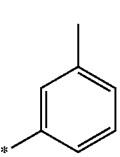 [SMILES: *c1cccc(C)c1] | H | tert-Butyl 2-((((9H-fluoren-9-yl)methoxy)carbonyl)amino)-4-(m-tolyl)butanoate |

TABLE 2-continued

| Compound ID | R₁ | R₂ | n | R₃ | R₆ | R₇ | Compound Name |
|---|---|---|---|---|---|---|---|
| 2-4 | Fmoc | H | 2 | tBu | 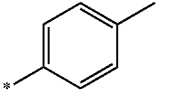 [SMILES: *c1ccc(C)cc1] | H | tert-Butyl 2-((((9H-fluoren-9-yl)methoxy)carbonyl)amino)-4-(p-tolyl)butanoate |
| 2-5 | Fmoc | H | 2 | tBu | 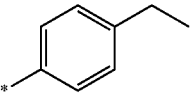 [SMILES: *c1ccc(CC)cc1] | H | tert-Butyl 2-((((9H-fluoren-9-yl)methoxy)carbonyl)amino)-4-(4-ethylphenyl)butanoate |
| 2-6 | Fmoc | H | 2 | tBu | 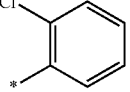 | H | tert-Butyl 2-((((9H-fluoren-9-yl)methoxy)carbonyl)amino)-4-(2-chlorophenyl)butanoate |
| 2-7 | Fmoc | H | 2 | tBu | 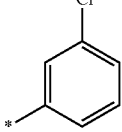 | H | tert-Butyl 2-((((9H-fluoren-9-yl)methoxy)carbonyl)amino)-4-(3-chlorophenyl)butanoate |
| 2-8 | Fmoc | H | 2 | tBu | 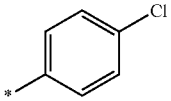 [SMILES: *c1ccc(Cl)cc1] | H | tert-Butyl 2-((((9H-fluoren-9-yl)methoxy)carbonyl)amino)-4-(4-chlorophenyl)butanoate |
| 2-9 | Fmoc | H | 2 | tBu | 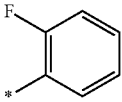 | H | tert-Butyl 2-((((9H-fluoren-9-yl)methoxy)carbonyl)amino)-4-(2-fluorophenyl)butanoate |
| 2-10 | Fmoc | H | 2 | tBu | 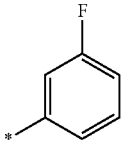 [SMILES: *c1cccc(F)c1] | H | tert-Butyl 2-((((9H-fluoren-9-yl)methoxy)carbonyl)amino)-4-(3-fluorophenyl)butanoate |
| 2-11 | Fmoc | H | 2 | tBu | 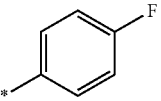 | H | tert-Butyl 2-((((9H-fluoren-9-yl)methoxy)carbonyl)amino)-4-(4-fluorophenyl)butanoate |
| 2-12 | Fmoc | H | 2 | tBu | 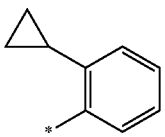 | H | tert-Butyl 2-((((9H-fluoren-9-yl)methoxy)carbonyl)amino)-4-(2-cyclopropylphenyl)butanoate |
| 2-13 | Fmoc | H | 2 | tBu | 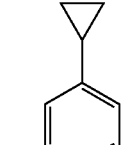 | H | tert-Butyl 2-((((9H-fluoren-9-yl)methoxy)carbonyl)amino)-4-(3-cyclopropylphenyl)butanoate |
| 2-14 | Fmoc | H | 2 | tBu | 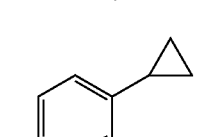 | H | tert-Butyl 2-((((9H-fluoren-9-yl)methoxy)carbonyl)amino)-4-(4-cyclopropylphenyl)butanoate |

TABLE 2-continued

| Compound ID | R₁ | R₂ | n | R₃ | R₆ | R₇ | Compound Name |
|---|---|---|---|---|---|---|---|
| 2-15 | Fmoc | H | 2 | tBu | 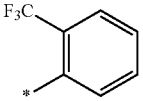 | H | tert-Butyl 2-((((9H-fluoren-9-yl)methoxy)carbonyl)amino)-4-(2-(trifluoromethyl)phenyl)butanoate |
| 2-16 | Fmoc | H | 2 | tBu | 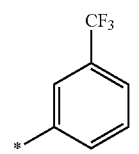 | H | tert-Butyl 2-((((9H-fluoren-9-yl)methoxy)carbonyl)amino)-4-(3-(trifluoromethyl)phenyl)butanoate |
| 2-17 | Fmoc | H | 2 | tBu | 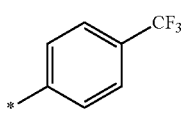 | H | tert-Butyl 2-((((9H-fluoren-9-yl)methoxy)carbonyl)amino)-4-(4-(trifluoromethyl)phenyl)butanoate |
| 2-18 | Fmoc | H | 2 | tBu | 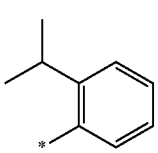 | H | tert-Butyl 2-((((9H-fluoren-9-yl)methoxy)carbonyl)amino)-4-(2-isopropylphenyl)butanoate |
| 2-19 | Fmoc | H | 2 | tBu | 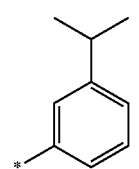 | H | tert-Butyl 2-((((9H-fluoren-9-yl)methoxy)carbonyl)amino)-4-(3-isopropylphenyl)butanoate |
| 2-20 | Fmoc | H | 2 | tBu | 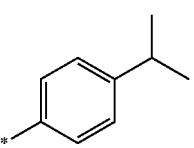 | H | tert-Butyl 2-((((9H-fluoren-9-yl)methoxy)carbonyl)amino)-4-(4-isopropylphenyl)butanoate |
| 2-21 | Fmoc | H | 2 | tBu | 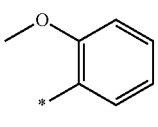 | H | tert-Butyl 2-((((9H-fluoren-9-yl)methoxy)carbonyl)amino)-4-(2-methoxyphenyl)butanoate |
| 2-22 | Fmoc | H | 2 | tBu | 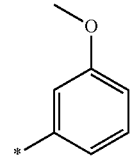 | H | tert-Butyl 2-((((9H-fluoren-9-yl)methoxy)carbonyl)amino)-4-(3-methoxyphenyl)butanoate |
| 2-23 | Fmoc | H | 2 | tBu | 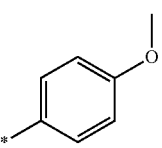 | H | tert-Butyl 2-((((9H-fluoren-9-yl)methoxy)carbonyl)amino)-4-(4-methoxyphenyl)butanoate |
| 2-24 | Fmoc | H | 2 | tBu | 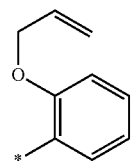 | H | tert-Butyl 2-((((9H-fluoren-9-yl)methoxy)carbonyl)amino)-4-(2-(allyloxy)phenyl)butanoate |

TABLE 2-continued

| Compound ID | R₁ | R₂ | n | R₃ | R₆ | R₇ | Compound Name |
|---|---|---|---|---|---|---|---|
| 2-25 | Fmoc | H | 2 | tBu | 3-(allyloxy)phenyl | H | tert-Butyl 2-((((9H-fluoren-9-yl)methoxy)carbonyl)amino)-4-(3-(allyloxy)phenyl)butanoate |
| 2-26 | Fmoc | H | 2 | tBu | 4-(allyloxy)phenyl | H | tert-Butyl 2-((((9H-fluoren-9-yl)methoxy)carbonyl)amino)-4-(4-(allyloxy)phenyl)butanoate |
| 2-27 | Fmoc | H | 2 | tBu | 4-isopropoxyphenyl | H | tert-Butyl 2-((((9H-fluoren-9-yl)methoxy)carbonyl)amino)-4-(4-isopropoxyphenyl)butanoate |
| 2-28 | Fmoc | H | 2 | tBu | 3-fluoro-4-(trifluoromethyl)phenyl | H | tert-Butyl 2-((((9H-fluoren-9-yl)methoxy)carbonyl)amino)-4-(3-fluoro-4-(trifluoromethyl)phenyl)butanoate |
| 2-29 | Fmoc | H | 2 | tBu | 2-fluoro-4-(trifluoromethyl)phenyl | H | tert-Butyl 2-((((9H-fluoren-9-yl)methoxy)carbonyl)amino)-4-(2-fluoro-4-(trifluoromethyl)phenyl)butanoate |
| 2-30 | Fmoc | H | 2 | tBu | 3,4-dimethoxyphenyl | H | tert-Butyl 2-((((9H-fluoren-9-yl)methoxy)carbonyl)amino)-4-(3,4-dimethoxyphenyl)butanoate |
| 2-31 | Fmoc | H | 2 | tBu | 2-fluoro-4-methoxyphenyl | H | tert-Butyl 2-((((9H-fluoren-9-yl)methoxy)carbonyl)amino)-4-(2-fluoro-4-methoxyphenyl)butanoate |
| 2-32 | Fmoc | H | 2 | tBu | 3-fluoro-4-methoxyphenyl | H | tert-Butyl 2-((((9H-fluoren-9-yl)methoxy)carbonyl)amino)-4-(3-fluoro-4-methoxyphenyl)butanoate |
| 2-33 | Fmoc | H | 2 | tBu | 3,5-difluoro-4-methoxyphenyl | H | tert-Butyl 2-((((9H-fluoren-9-yl)methoxy)carbonyl)amino)-4-(3,5-difluoro-4-methoxyphenyl)butanoate |
| 2-34 | Fmoc | H | 2 | tBu | 3,5-difluoro-4-(trifluoromethyl)phenyl | H | tert-Butyl 2-((((9H-fluoren-9-yl)methoxy)carbonyl)amino)-4-(3,5-difluoro-4-(trifluoromethyl)phenyl)butanoate |

TABLE 2-continued

| Compound ID | R₁ | R₂ | n | R₃ | R₆ | R₇ | Compound Name |
|---|---|---|---|---|---|---|---|
| 2-35 | Fmoc | H | 2 | tBu | (2-methoxy-4-substituted-N-methylbenzamide) | H | tert-Butyl 2-(((((9H-fluoren-9-yl)methoxy)carbonyl)amino)-4-(3-methoxy-4-(methylcarbamoyl)phenyl)butanoate |
| 2-36 | Fmoc | H | 2 | tBu | (4-methoxy-3-substituted-N-methylbenzamide) | H | tert-Butyl 2-(((((9H-fluoren-9-yl)methoxy)carbonyl)amino)-4-(4-methoxy-3-(methylcarbamoyl)phenyl)butanoate |
| 2-37 | Fmoc | H | 2 | tBu | (2-methoxy-4-substituted-N-(methylsulfonyl)benzamide) | H | tert-Butyl 2-(((((9H-fluoren-9-yl)methoxy)carbonyl)amino)-4-(3-methoxy-4-((methylsulfonyl)carbamoyl)phenyl)butanoate |
| 2-38 | Fmoc | H | 2 | tBu | (4-substituted-N-methyl-N-((tetrahydro-2H-pyran-2-yl)oxy)benzamide) | H | tert-Butyl 2-(((((9H-fluoren-9-yl)methoxy)carbonyl)amino)-4-(4-(methyl((tetrahydro-2H-pyran-2-yl)oxy)carbamoyl)phenyl)butanoate |
| 2-39 | Fmoc | H | 2 | tBu | (2-methoxy-4-substituted-N-((tetrahydro-2H-pyran-2-yl)oxy)benzamide) | H | tert-Butyl 2-(((((9H-fluoren-9-yl)methoxy)carbonyl)amino)-4-(3-methoxy-4-(((tetrahydro-2H-pyran-2-yl)oxy)carbamoyl)phenyl)butanoate |
| 2-40 | Fmoc | H | 2 | tBu | (pyridin-2-yl) | H | tert-Butyl 2-(((((9H-fluoren-9-yl)methoxy)carbonyl)amino)-4-(pyridin-2-yl)butanoate |
| 2-41 | Fmoc | H | 2 | tBu | (pyridin-3-yl) | H | tert-Butyl 2-(((((9H-fluoren-9-yl)methoxy)carbonyl)amino)-4-(pyridin-3-yl)butanoate |
| 2-42 | Fmoc | H | 2 | tBu | (pyridin-4-yl) | H | tert-Butyl 2-(((((9H-fluoren-9-yl)methoxy)carbonyl)amino)-4-(pyridin-4-yl)butanoate |
| 2-43 | Fmoc | H | 2 | tBu | (6-methylpyridin-3-yl) | H | tert-Butyl 2-(((((9H-fluoren-9-yl)methoxy)carbonyl)amino)-4-(6-methylpyridin-3-yl)butanoate |
| 2-44 | Fmoc | H | 2 | tBu | (5-methylpyridin-3-yl) | H | tert-Butyl 2-(((((9H-fluoren-9-yl)methoxy)carbonyl)amino)-4-(5-methylpyridin-3-yl)butanoate |

TABLE 2-continued

| Compound ID | R₁ | R₂ | n | R₃ | R₆ | R₇ | Compound Name |
|---|---|---|---|---|---|---|---|
| 2-45 | Fmoc | H | 2 | tBu | 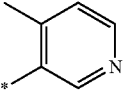 | H | tert-Butyl 2-((((9H-fluoren-9-yl)methoxy)carbonyl)amino)-4-(4-methylpyridin-3-yl)butanoate |
| 2-46 | Fmoc | H | 2 | tBu | 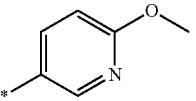 | H | tert-Butyl 2-((((9H-fluoren-9-yl)methoxy)carbonyl)amino)-4-(6-methoxypyridin-3-yl)butanoate |
| 2-47 | Fmoc | H | 2 | tBu | 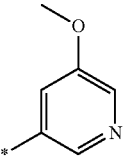 | H | tert-Butyl 2-((((9H-fluoren-9-yl)methoxy)carbonyl)amino)-4-(5-methoxypyridin-3-yl)butanoate |
| 2-48 | Fmoc | H | 2 | tBu | 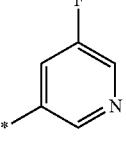 | H | tert-Butyl 2-((((9H-fluoren-9-yl)methoxy)carbonyl)amino)-4-(5-fluoropyridin-3-yl)butanoate |
| 2-49 | Fmoc | H | 2 | tBu | 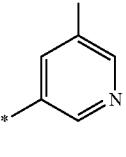 | H | tert-Butyl 2-((((9H-fluoren-9-yl)methoxy)carbonyl)amino)-4-(5-chloropyridin-3-yl)butanoate |
| 2-50 | Fmoc | H | 2 | tBu | 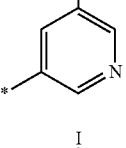 | H | tert-Butyl 2-((((9H-fluoren-9-yl)methoxy)carbonyl)amino)-4-(5-bromopyridin-3-yl)butanoate |
| 2-51 | Fmoc | H | 2 | tBu | 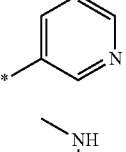 | H | tert-Butyl 2-((((9H-fluoren-9-yl)methoxy)carbonyl)amino)-4-(5-iodopyridin-3-yl)butanoate |
| 2-52 | Fmoc | H | 2 | tBu | 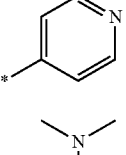 | H | tert-Butyl 2-((((9H-fluoren-9-yl)methoxy)carbonyl)amino)-4-(2-(methylamino)pyridin-4-yl)butanoate |
| 2-53 | Fmoc | H | 2 | tBu | 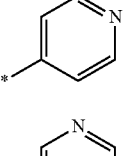 | H | tert-Butyl 2-((((9H-fluoren-9-yl)methoxy)carbonyl)amino)-4-(2-(dimethylamino)pyridin-4-yl)butanoate |
| 2-54 | Fmoc | H | 2 | tBu | 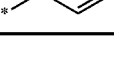 | H | tert-Butyl 2-((((9H-fluoren-9-yl)methoxy)carbonyl)amino)-4-(pyrimidin-5-yl)butanoate |

TABLE 3

| Compound ID | R₁ | R₂ | n | R₃ | R₆ | R₇ | Compound Name |
|---|---|---|---|---|---|---|---|
| 3-1 | Fmoc | Me | 2 | tBu | 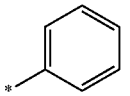 | H | tert-Butyl 2-((((9H-fluoren-9-yl)methoxy)carbonyl)(methyl)amino)-4-phenylbutanoate |
| 3-2 | Fmoc | Me | 2 | tBu | 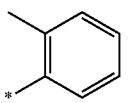 | H | tert-Butyl 2-((((9H-fluoren-9-yl)methoxy)carbonyl)(methyl)amino)-4-(o-tolyl)butanoate |
| 3-3 | Fmoc | Me | 2 | tBu | 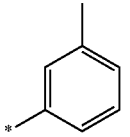 | H | tert-Butyl 2-((((9H-fluoren-9-yl)methoxy)carbonyl)(methyl)amino)-4-(m-tolyl)butanoate |
| 3-4 | Fmoc | Me | 2 | tBu | 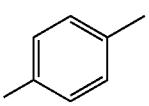 | H | tert-Butyl 2-((((9H-fluoren-9-yl)methoxy)carbonyl)(methyl)amino)-4-(p-tolyl)butanoate |
| 3-5 | Fmoc | Me | 2 | tBu | 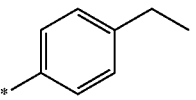 | H | tert-Butyl 2-((((9H-fluoren-9-yl)methoxy)carbonyl)(methyl)amino)-4-(4-ethylphenyl)butanoate |
| 3-6 | Fmoc | Me | 2 | tBu | 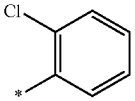 | H | tert-Butyl 2-((((9H-fluoren-9-yl)methoxy)carbonyl)(methyl)amino)-4-(2-chlorophenyl)butanoate |
| 3-7 | Fmoc | Me | 2 | tBu | 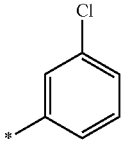 | H | tert-Butyl 2-((((9H-fluoren-9-yl)methoxy)carbonyl)(methyl)amino)-4-(3-chlorophenyl)butanoate |
| 3-8 | Fmoc | Me | 2 | tBu | 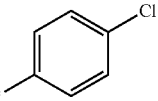 | H | tert-Butyl 2-((((9H-fluoren-9-yl)methoxy)carbonyl)(methyl)amino)-4-(4-chlorophenyl)butanoate |
| 3-9 | Fmoc | Me | 2 | tBu | 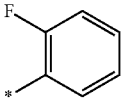 | H | tert-Butyl 2-((((9H-fluoren-9-yl)methoxy)carbonyl)(methyl)amino)-4-(2-fluorophenyl)butanoate |
| 3-10 | Fmoc | Me | 2 | tBu | 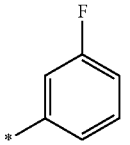 | H | tert-Butyl 2-((((9H-fluoren-9-yl)methoxy)carbonyl)(methyl)amino)-4-(3-fluorophenyl)butanoate |
| 3-11 | Fmoc | Me | 2 | tBu | 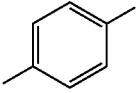 | H | tert-Butyl 2-((((9H-fluoren-9-yl)methoxy)carbonyl)(methyl)amino)-4-(4-fluorophenyl)butanoate |
| 3-12 | Fmoc | Me | 2 | tBu | 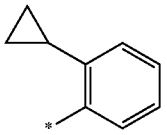 [SMILES: *c1ccccc1C1CC1] | H | tert-Butyl 2-((((9H-fluoren-9-yl)methoxy)carbonyl)(methyl)amino)-4-(2-cyclopropylphenyl)butanoate |

TABLE 3-continued

| Compound ID | R₁ | R₂ | n | R₃ | R₆ | R₇ | Compound Name |
|---|---|---|---|---|---|---|---|
| 3-13 | Fmoc | Me | 2 | tBu | 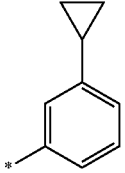 [SMILES: *c1cccc(C2CC2)c1] | H | tert-Butyl 2-((((9H-fluoren-9-yl)methoxy)carbonyl)(methyl)amino)-4-(3-cyclopropylphenyl)butanoate |
| 3-14 | Fmoc | Me | 2 | tBu | 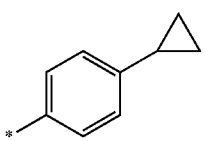 | H | tert-Butyl 2-((((9H-fluoren-9-yl)methoxy)carbonyl)(methyl)amino)-4-(4-cyclopropylphenyl)butanoate |
| 3-15 | Fmoc | Me | 2 | tBu | 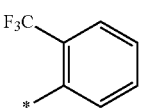 [SMILES: *c1ccccc1C(F)(F)F] | H | tert-Butyl 2-((((9H-fluoren-9-yl)methoxy)carbonyl)(methyl)amino)-4-(2-(trifluoromethyl)phenyl)butanoate |
| 3-16 | Fmoc | Me | 2 | tBu | 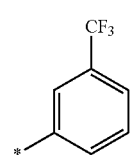 [SMILES: *c1cccc(C(F)(F)F)c1] | H | tert-Butyl 2-((((9H-fluoren-9-yl)methoxy)carbonyl)(methyl)amino)-4-(3-(trifluoromethyl)phenyl)butanoate |
| 3-17 | Fmoc | Me | 2 | tBu | 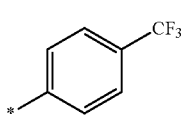 [SMILES: *c1ccc(C(F)(F)F)cc1] | H | tert-Butyl 2-((((9H-fluoren-9-yl)methoxy)carbonyl)(methyl)amino)-4-(4-(trifluoromethyl)phenyl)butanoate |
| 3-18 | Fmoc | Me | 2 | tBu | 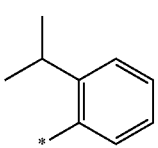 [SMILES: *c1ccccc1C(C)C] | H | tert-Butyl 2-((((9H-fluoren-9-yl)methoxy)carbonyl)(methyl)amino)-4-(2-isopropylphenyl)butanoate |
| 3-19 | Fmoc | Me | 2 | tBu | 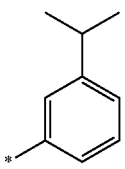 [SMILES: *c1cccc(C(C)C)c1] | H | tert-Butyl 2-((((9H-fluoren-9-yl)methoxy)carbonyl)(methyl)amino)-4-(3-isopropylphenyl)butanoate |
| 3-20 | Fmoc | Me | 2 | tBu | 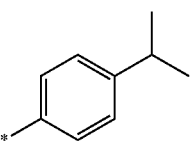 [SMILES: *c1ccc(C(C)C)cc1] | H | tert-Butyl 2-((((9H-fluoren-9-yl)methoxy)carbonyl)(methyl)amino)-4-(4-isopropylphenyl)butanoate |
| 3-21 | Fmoc | Me | 2 | tBu | 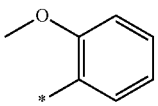 [SMILES: *c1ccccc1OC] | H | tert-Butyl 2-((((9H-fluoren-9-yl)methoxy)carbonyl)(methyl)amino)-4-(2-methoxyphenyl)butanoate |
| 3-22 | Fmoc | Me | 2 | tBu | 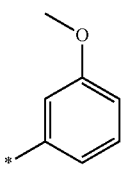 [SMILES: *c1cccc(OC)c1] | H | tert-Butyl 2-((((9H-fluoren-9-yl)methoxy)carbonyl)(methyl)amino)-4-(3-methoxyphenyl)butanoate |

TABLE 3-continued

| Compound ID | R₁ | R₂ | n | R₃ | R₆ | R₇ | Compound Name |
|---|---|---|---|---|---|---|---|
| 3-23 | Fmoc | Me | 2 | tBu | 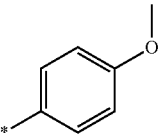 | H | tert-Butyl 2-((((9H-fluoren-9-yl)methoxy)carbonyl)(methyl)amino)-4-(4-methoxyphenyl)butanoate |
| 3-24 | Fmoc | Me | 2 | tBu | 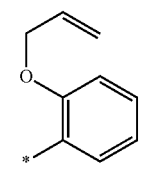 [SMILES: *c1ccccc1OCC=C] | H | tert-Butyl 2-((((9H-fluoren-9-yl)methoxy)carbonyl)(methyl)amino)-4-(2-(allyloxy)phenyl)butanoate |
| 3-25 | Fmoc | Me | 2 | tBu | 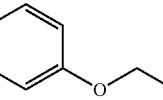 | H | tert-Butyl 2-((((9H-fluoren-9-yl)methoxy)carbonyl)(methyl)amino)-4-(3-(allyloxy)phenyl)butanoate |
| 3-26 | Fmoc | Me | 2 | tBu | 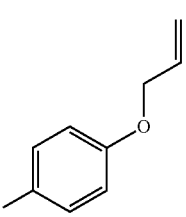 | H | tert-Butyl 2-((((9H-fluoren-9-yl)methoxy)carbonyl)(methyl)amino)-4-(4-(allyloxy)phenyl)butanoate |
| 3-27 | Fmoc | Me | 2 | tBu | 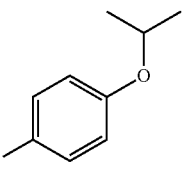 | H | tert-Butyl 2-((((9H-fluoren-9-yl)methoxy)carbonyl)(methyl)amino)-4-(4-isopropoxyphenyl)butanoate |
| 3-28 | Fmoc | Me | 2 | tBu | 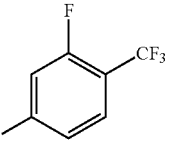 | H | tert-Butyl 2-((((9H-fluoren-9-yl)methoxy)carbonyl)(methyl)amino)-4-(3-fluoro-4-(trifluoromethyl)phenyl)butanoate |
| 3-29 | Fmoc | Me | 2 | tBu | 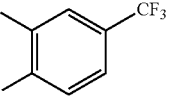 | H | tert-Butyl 2-((((9H-fluoren-9-yl)methoxy)carbonyl)(methyl)amino)-4-(2-fluoro-4-(trifluoromethyl)phenyl)butanoate |
| 3-30 | Fmoc | Me | 2 | tBu | 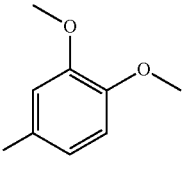 | H | tert-Butyl 2-((((9H-fluoren-9-yl)methoxy)carbonyl)(methyl)amino)-4-(3,4-dimethoxyphenyl)butanoate |
| 3-31 | Fmoc | Me | 2 | tBu | 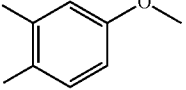 | H | tert-Butyl 2-((((9H-fluoren-9-yl)methoxy)carbonyl)(methyl)amino)-4-(2-fluoro-4-methoxyphenyl)butanoate |
| 3-32 | Fmoc | Me | 2 | tBu | 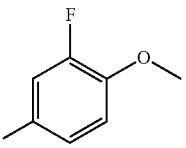 | H | tert-Butyl 2-((((9H-fluoren-9-yl)methoxy)carbonyl)(methyl)amino)-4-(3-fluoro-4-methoxyphenyl)butanoate |

TABLE 3-continued

| Compound ID | R₁ | R₂ | n | R₃ | R₆ | R₇ | Compound Name |
|---|---|---|---|---|---|---|---|
| 3-33 | Fmoc | Me | 2 | tBu | 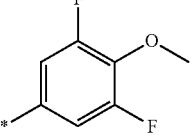 | H | tert-Butyl 2-((((9H-fluoren-9-yl)methoxy)carbonyl)(methyl)amino)-4-(3,5-difluoro-4-methoxyphenyl)butanoate |
| 3-34 | Fmoc | Me | 2 | tBu | 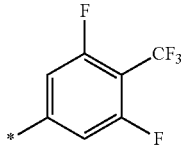 [SMILES: *c1cc(F)c(C(F)(F)F)c(F)c1] | H | tert-Butyl 2-((((9H-fluoren-9-yl)methoxy)carbonyl)(methyl)amino)-4-(3,5-difluoro-4-(trifluoromethyl)phenyl)butanoate |
| 3-35 | Fmoc | Me | 2 | tBu | 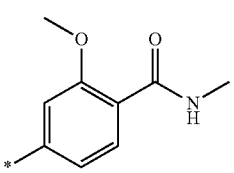 [SMILES: *c1ccc(C(=O)NC)c(OC)c1] | H | tert-Butyl 2-((((9H-fluoren-9-yl)methoxy)carbonyl)(methyl)amino)-4-(3-methoxy-4-(methylcarbamoyl)phenyl)butanoate |
| 3-36 | Fmoc | Me | 2 | tBu | 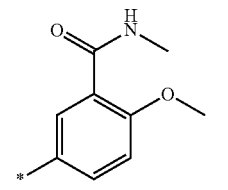 [SMILES: *c1ccc(OC)c(C(=O)NC)c1] | H | tert-Butyl 2-((((9H-fluoren-9-yl)methoxy)carbonyl)(methyl)amino)-4-(4-methoxy-3-(methylcarbamoyl)phenyl)butanoate |
| 3-37 | Fmoc | Me | 2 | tBu | 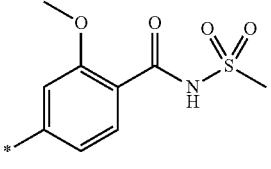 [SMILES: *c1ccc(C(=O)NS(C)(=O)=O)c(OC)c1] | H | tert-Butyl 2-((((9H-fluoren-9-yl)methoxy)carbonyl)(methyl)amino)-4-(3-methoxy-4-((methylsulfonyl)carbamoyl)phenyl)butanoate |
| 3-38 | Fmoc | Me | 2 | tBu | 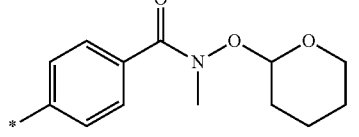 | H | tert-Butyl 2-((((9H-fluoren-9-yl)methoxy)carbonyl)(methyl)amino)-4-(4-(methyl((tetrahydro-2H-pyran-2-yl)oxy)carbamoyl)phenyl)butanoate |
| 3-39 | Fmoc | Me | 2 | tBu | 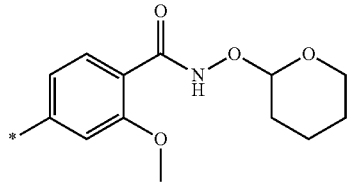 | H | tert-Butyl 2-((((9H-fluoren-9-yl)methoxy)carbonyl)(methyl)amino)-4-(3-methoxy-4-(((tetrahydro-2H-pyran-2-yl)oxy)carbamoyl)phenyl)butanoate |
| 3-40 | Fmoc | Me | 2 | tBu | 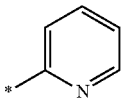 | H | tert-Butyl 2-((((9H-fluoren-9-yl)methoxy)carbonyl)(methyl)amino)-4-(pyridin-2-yl)butanoate |
| 3-41 | Fmoc | Me | 2 | tBu | 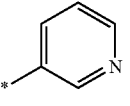 [SMILES: *c1cccnc1] | H | tert-Butyl 2-((((9H-fluoren-9-yl)methoxy)carbonyl)(methyl)amino)-4-(pyridin-3-yl)butanoate |
| 3-42 | Fmoc | Me | 2 | tBu | 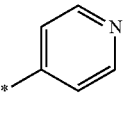 [SMILES: *c1ccncc1] | H | tert-Butyl 2-((((9H-fluoren-9-yl)methoxy)carbonyl)(methyl)amino)-4-(pyridin-4-yl)butanoate |

TABLE 3-continued

| Compound ID | R₁ | R₂ | n | R₃ | R₆ | R₇ | Compound Name |
|---|---|---|---|---|---|---|---|
| 3-43 | Fmoc | Me | 2 | tBu | 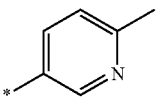 | H | tert-Butyl 2-((((9H-fluoren-9-yl)methoxy)carbonyl)(methyl)amino)-4-(6-methylpyridin-3-yl)butanoate |
| 3-44 | Fmoc | Me | 2 | tBu | 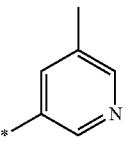 [SMILES: *c1cncc(C)c1] | H | tert-Butyl 2-((((9H-fluoren-9-yl)methoxy)carbonyl)(methyl)amino)-4-(5-methylpyridin-3-yl)butanoate |
| 3-45 | Fmoc | Me | 2 | tBu | 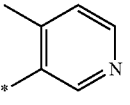 | H | tert-Butyl 2-((((9H-fluoren-9-yl)methoxy)carbonyl)(methyl)amino)-4-(4-methylpyridin-3-yl)butanoate |
| 3-46 | Fmoc | Me | 2 | tBu | 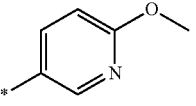 | H | tert-Butyl 2-((((9H-fluoren-9-yl)methoxy)carbonyl)(methyl)amino)-4-(6-methoxypyridin-3-yl)butanoate |
| 3-47 | Fmoc | Me | 2 | tBu | 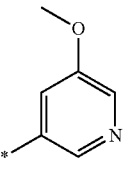 [SMILES: *c1cncc(OC)c1] | H | tert-Butyl 2-((((9H-fluoren-9-yl)methoxy)carbonyl)(methyl)amino)-4-(5-methoxypyridin-3-yl)butanoate |
| 3-48 | Fmoc | Me | 2 | tBu | 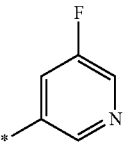 [SMILES: *c1cncc(F)c1] | H | tert-Butyl 2-((((9H-fluoren-9-yl)methoxy)carbonyl)(methyl)amino)-4-(5-fluoropyridin-3-yl)butanoate |
| 3-49 | Fmoc | Me | 2 | tBu | 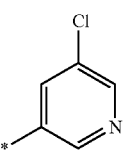 | H | tert-Butyl 2-((((9H-fluoren-9-yl)methoxy)carbonyl)(methyl)amino)-4-(5-chloropyridin-3-yl)butanoate |
| 3-50 | Fmoc | Me | 2 | tBu | 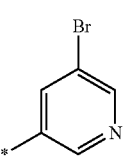 | H | tert-Butyl 2-((((9H-fluoren-9-yl)methoxy)carbonyl)(methyl)amino)-4-(5-bromopyridin-3-yl)butanoate |
| 3-51 | Fmoc | Me | 2 | tBu | 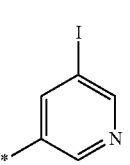 [SMILES: *c1cncc(I)c1] | H | tert-Butyl 2-((((9H-fluoren-9-yl)methoxy)carbonyl)(methyl)amino)-4-(5-iodopyridin-3-yl)butanoate |
| 3-52 | Fmoc | Me | 2 | tBu | 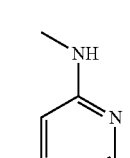 | H | tert-Butyl 2-((((9H-fluoren-9-yl)methoxy)carbonyl)(methyl)amino)-4-(2-(methylamino)pyridin-4-yl)butanoate |

TABLE 3-continued

| Compound ID | R₁ | R₂ | n | R₃ | R₆ | R₇ | Compound Name |
|---|---|---|---|---|---|---|---|
| 3-53 | Fmoc | Me | 2 | tBu | 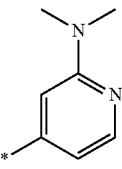 [SMILES: *c1ccnc(N(C)C)c1] | H | tert-Butyl 2-((((9H-fluoren-9-yl)methoxy)carbonyl)(methyl)amino)-4-(2-(dimethylamino)pyridin-4-yl)butanoate |
| 3-54 | Fmoc | Me | 2 | tBu | 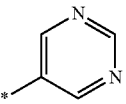 [SMILES: *c1cncnc1] | H | tert-Butyl 2-((((9H-fluoren-9-yl)methoxy)carbonyl)(methyl)amino)-4-(pyrimidin-5-yl)butanoate |

TABLE 4

| Compound ID | R₁ | R₂ | n | R₃ | R₆ | R₇ | Compound Name |
|---|---|---|---|---|---|---|---|
| 4-1 | Fmoc | H | 1 | tBu | 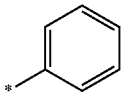 | H | tert-Butyl (((9H-fluoren-9-yl)methoxy)carbonyl)phenylalaninate |
| 4-2 | Fmoc | H | 1 | tBu | 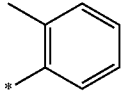 | H | tert-Butyl 2-((((9H-fluoren-9-yl)methoxy)carbonyl)amino)-3-(o-tolyl)propanoate |
| 4-3 | Fmoc | H | 1 | tBu | 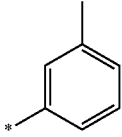 [SMILES: *c1cccc(C)c1] | H | tert-Butyl 2-((((9H-fluoren-9-yl)methoxy)carbonyl)amino)-3-(m-tolyl)propanoate |
| 4-4 | Fmoc | H | 1 | tBu | 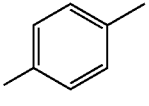 | H | tert-Butyl 2-((((9H-fluoren-9-yl)methoxy)carbonyl)amino)-3-(p-tolyl)propanoate |
| 4-5 | Fmoc | H | 1 | tBu | 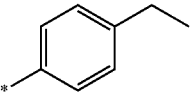 [SMILES: *c1ccc(CC)cc1] | H | tert-Butyl 2-((((9H-fluoren-9-yl)methoxy)carbonyl)amino)-3-(4-ethylphenyl)propanoate |
| 4-6 | Fmoc | H | 1 | tBu | 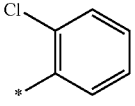 | H | tert-Butyl 2-((((9H-fluoren-9-yl)methoxy)carbonyl)amino)-3-(2-chlorophenyl)propanoate |
| 4-7 | Fmoc | H | 1 | tBu | 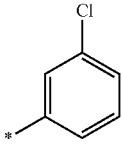 [SMILES: *c1cccc(Cl)c1] | H | tert-Butyl 2-((((9H-fluoren-9-yl)methoxy)carbonyl)amino)-3-(3-chlorophenyl)propanoate |
| 4-8 | Fmoc | H | 1 | tBu | 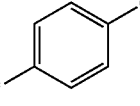 | H | tert-Butyl 2-((((9H-fluoren-9-yl)methoxy)carbonyl)amino)-3-(4-chlorophenyl)propanoate |
| 4-9 | Fmoc | H | 1 | tBu | 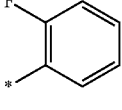 | H | tert-Butyl 2-((((9H-fluoren-9-yl)methoxy)carbonyl)amino)-3-(2-fluorophenyl)propanoate |

TABLE 4-continued

| Compound ID | R₁ | R₂ | n | R₃ | R₆ | R₇ | Compound Name |
|---|---|---|---|---|---|---|---|
| 4-10 | Fmoc | H | 1 | tBu | 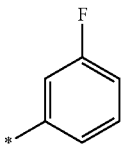 [SMILES: *c1cccc(F)c1] | H | tert-Butyl 2-((((9H-fluoren-9-yl)methoxy)carbonyl)amino)-3-(3-fluorophenyl)propanoate |
| 4-11 | Fmoc | H | 1 | tBu | 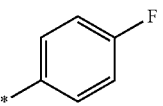 | H | tert-Butyl 2-((((9H-fluoren-9-yl)methoxy)carbonyl)amino)-3-(4-fluorophenyl)propanoate |
| 4-12 | Fmoc | H | 1 | tBu | 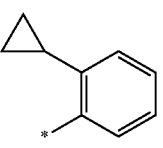 [SMILES: *c1ccccc1C1CC1] | H | tert-Butyl 2-((((9H-fluoren-9-yl)methoxy)carbonyl)amino)-3-(2-cyclopropylphenyl)propanoate |
| 4-13 | Fmoc | H | 1 | tBu | 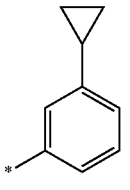 [SMILES: *c1cccc(C2CC2)c1] | H | tert-Butyl 2-((((9H-fluoren-9-yl)methoxy)carbonyl)amino)-3-(3-cyclopropylphenyl)propanoate |
| 4-14 | Fmoc | H | 1 | tBu | 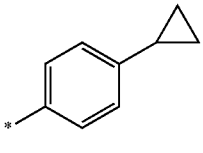 [SMILES: *c1ccc(C2CC2)cc1] | H | tert-Butyl 2-((((9H-fluoren-9-yl)methoxy)carbonyl)amino)-3-(4-cyclopropylphenyl)propanoate |
| 4-15 | Fmoc | H | 1 | tBu | 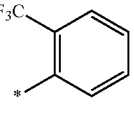 | H | tert-Butyl 2-((((9H-fluoren-9-yl)methoxy)carbonyl)amino)-3-(2-(trifluoromethyl)phenyl)propanoate |
| 4-16 | Fmoc | H | 1 | tBu | 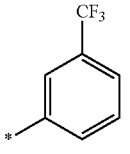 [SMILES: *c1cccc(C(F)(F)F)c1] | H | tert-Butyl 2-((((9H-fluoren-9-yl)methoxy)carbonyl)amino)-3-(3-(trifluoromethyl)phenyl)propanoate |
| 4-17 | Fmoc | H | 1 | tBu | 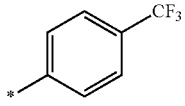 | H | tert-Butyl 2-((((9H-fluoren-9-yl)methoxy)carbonyl)amino)-3-(4-(trifluoromethyl)phenyl)propanoate |
| 4-18 | Fmoc | H | 1 | tBu | 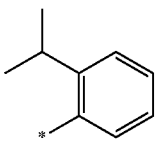 [SMILES: *c1ccccc1C(C)C] | H | tert-Butyl 2-((((9H-fluoren-9-yl)methoxy)carbonyl)amino)-3-(2-isopropylphenyl)propanoate |
| 4-19 | Fmoc | H | 1 | tBu | 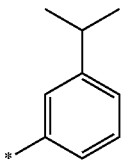 [SMILES: *c1cccc(C(C)C)c1] | H | tert-Butyl 2-((((9H-fluoren-9-yl)methoxy)carbonyl)amino)-3-(3-isopropylphenyl)propanoate |

TABLE 4-continued

| Compound ID | $R_1$ | $R_2$ | n | $R_3$ | $R_6$ | $R_7$ | Compound Name |
|---|---|---|---|---|---|---|---|
| 4-20 | Fmoc | H | 1 | tBu | 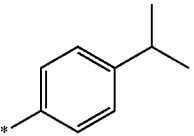 [SMILES: *c1ccc(C(C)C)cc1] | H | tert-Butyl 2-((((9H-fluoren-9-yl)methoxy)carbonyl)amino)-3-(4-isopropylphenyl)propanoate |
| 4-21 | Fmoc | H | 1 | tBu | 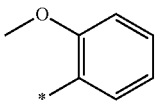 | H | tert-Butyl 2-((((9H-fluoren-9-yl)methoxy)carbonyl)amino)-3-(2-methoxyphenyl)propanoate |
| 4-22 | Fmoc | H | 1 | tBu | 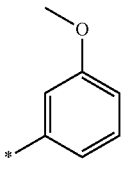 [SMILES: *c1cccc(OC)c1] | H | tert-Butyl 2-((((9H-fluoren-9-yl)methoxy)carbonyl)amino)-3-(3-methoxyphenyl)propanoate |
| 4-23 | Fmoc | H | 1 | tBu | 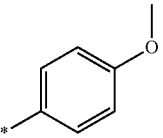 | H | tert-Butyl 2-((((9H-fluoren-9-yl)methoxy)carbonyl)amino)-3-(4-methoxyphenyl)propanoate |
| 4-24 | Fmoc | H | 1 | tBu | 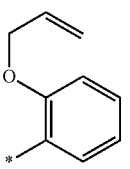 [SMILES: *c1ccccc1OCC=C] | H | tert-Butyl 2-((((9H-fluoren-9-yl)methoxy)carbonyl)amino)-3-(2-(allyloxy)phenyl)propanoate |
| 4-25 | Fmoc | H | 1 | tBu | 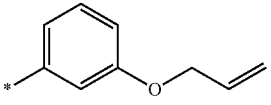 | H | tert-Butyl 2-((((9H-fluoren-9-yl)methoxy)carbonyl)amino)-3-(3-(allyloxy)phenyl)propanoate |
| 4-26 | Fmoc | H | 1 | tBu | 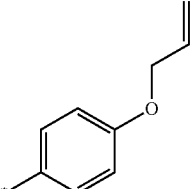 | H | tert-Butyl 2-((((9H-fluoren-9-yl)methoxy)carbonyl)amino)-3-(4-(allyloxy)phenyl)propanoate |
| 4-27 | Fmoc | H | 1 | tBu | 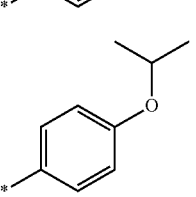 | H | tert-Butyl 2-((((9H-fluoren-9-yl)methoxy)carbonyl)amino)-3-(4-isopropoxyphenyl)propanoate |
| 4-28 | Fmoc | H | 1 | tBu | 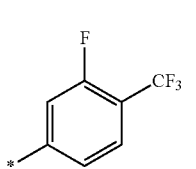 [SMILES: *c1ccc(C(F)(F)F)c(F)c1] | H | tert-Butyl 2-((((9H-fluoren-9-yl)methoxy)carbonyl)amino)-3-(3-fluoro-4-(trifluoromethyl)phenyl)propanoate |
| 4-29 | Fmoc | H | 1 | tBu | 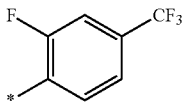 | H | tert-Butyl 2-((((9H-fluoren-9-yl)methoxy)carbonyl)amino)-3-(2-fluoro-4-(trifluoromethyl)phenyl)propanoate |

TABLE 4-continued

| Compound ID | R₁ | R₂ | n | R₃ | R₆ | R₇ | Compound Name |
|---|---|---|---|---|---|---|---|
| 4-30 | Fmoc | H | 1 | tBu | 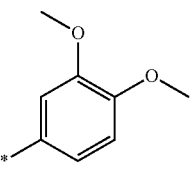 [SMILES: *c1ccc(OC)c(OC)c1] | H | tert-Butyl 2-((((9H-fluoren-9-yl)methoxy)carbonyl)amino)-3-(3,4-dimethoxyphenyl)propanoate |
| 4-31 | Fmoc | H | 1 | tBu | 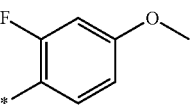 | H | tert-Butyl 2-((((9H-fluoren-9-yl)methoxy)carbonyl)amino)-3-(2-fluoro-4-methoxyphenyl)propanoate |
| 4-32 | Fmoc | H | 1 | tBu | 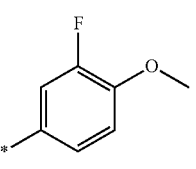 [SMILES: *c1ccc(OC)c(F)c1] | H | tert-Butyl 2-((((9H-fluoren-9-yl)methoxy)carbonyl)amino)-3-(3-fluoro-4-methoxyphenyl)propanoate |
| 4-33 | Fmoc | H | 1 | tBu | 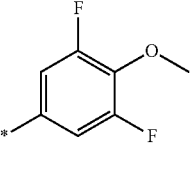 [SMILES: *c1cc(F)c(OC)c(F)c1] | H | tert-Butyl 2-((((9H-fluoren-9-yl)methoxy)carbonyl)amino)-3-(3,5-difluoro-4-methoxyphenyl)propanoate |
| 4-34 | Fmoc | H | 1 | tBu | 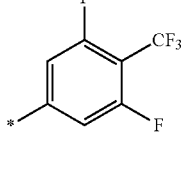 | H | tert-Butyl 2-((((9H-fluoren-9-yl)methoxy)carbonyl)amino)-3-(3,5-difluoro-4-(trifluoromethyl)phenyl)propanoate |
| 4-35 | Fmoc | H | 1 | tBu | 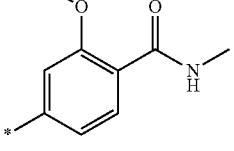 | H | tert-Butyl 2-((((9H-fluoren-9-yl)methoxy)carbonyl)amino)-3-(3-methoxy-4-(methylcarbamoyl)phenyl)propanoate |
| 4-36 | Fmoc | H | 1 | tBu | 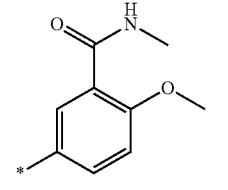 [SMILES: *c1ccc(OC)c(C(=O)NC)c1] | H | tert-Butyl 2-((((9H-fluoren-9-yl)methoxy)carbonyl)amino)-3-(4-methoxy-3-(methylcarbamoyl)phenyl)propanoate |
| 4-37 | Fmoc | H | 1 | tBu | 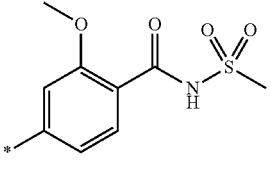 [SMILES: *c1ccc(C(=O)NS(C)(=O)=O)c(OC)c1] | H | tert-Butyl 2-((((9H-fluoren-9-yl)methoxy)carbonyl)amino)-3-(3-methoxy-4-((methylsulfonyl)carbamoyl)phenyl)propanoate |
| 4-38 | Fmoc | H | 1 | tBu | 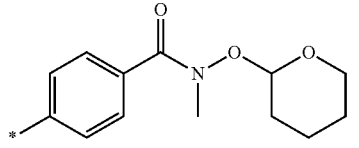 [SMILES: *c1ccc(C(=O)N(C)OC2CCCCO2)cc1] | H | tert-Butyl 2-((((9H-fluoren-9-yl)methoxy)carbonyl)amino)-3-(4-(methyl((tetrahydro-2H-pyran-2-yl)oxy)carbamoyl)phenyl)propanoate |

TABLE 4-continued

| Compound ID | R₁ | R₂ | n | R₃ | R₆ | R₇ | Compound Name |
|---|---|---|---|---|---|---|---|
| 4-39 | Fmoc | H | 1 | tBu | 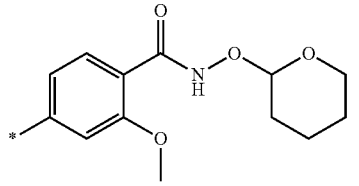 | H | tert-Butyl 2-((((9H-fluoren-9-yl)methoxy)carbonyl)amino)-3-(3-methoxy-4-((((tetrahydro-2H-pyran-2-yl)oxy)carbamoyl)phenyl)propanoate |
| 4-40 | Fmoc | H | 1 | tBu | 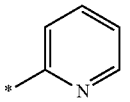 [SMILES: *c1ccccn1] | H | tert-Butyl 2-((((9H-fluoren-9-yl)methoxy)carbonyl)amino)-3-(pyridin-2-yl)propanoate |
| 4-41 | Fmoc | H | 1 | tBu | 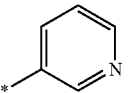 [SMILES: *c1cccnc1] | H | tert-Butyl 2-((((9H-fluoren-9-yl)methoxy)carbonyl)amino)-3-(pyridin-3-yl)propanoate |
| 4-42 | Fmoc | H | 1 | tBu | 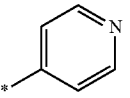 [SMILES: *c1ccncc1] | H | tert-Butyl 2-((((9H-fluoren-9-yl)methoxy)carbonyl)amino)-3-(pyridin-4-yl)propanoate |
| 4-43 | Fmoc | H | 1 | tBu | 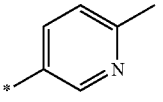 | H | tert-Butyl 2-((((9H-fluoren-9-yl)methoxy)carbonyl)amino)-3-(6-methylpyridin-3-yl)propanoate |
| 4-44 | Fmoc | H | 1 | tBu | 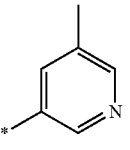 [SMILES: *c1cncc(C)c1] | H | tert-Butyl 2-((((9H-fluoren-9-yl)methoxy)carbonyl)amino)-3-(5-methylpyridin-3-yl)propanoate |
| 4-45 | Fmoc | H | 1 | tBu | 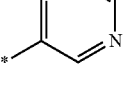 | H | tert-Butyl 2-((((9H-fluoren-9-yl)methoxy)carbonyl)amino)-3-(4-methylpyridin-3-yl)propanoate |
| 4-46 | Fmoc | H | 1 | tBu | 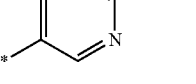 | H | tert-Butyl 2-((((9H-fluoren-9-yl)methoxy)carbonyl)amino)-3-(6-methoxypyridin-3-yl)propanoate |
| 4-47 | Fmoc | H | 1 | tBu | 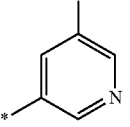 | H | tert-Butyl 2-((((9H-fluoren-9-yl)methoxy)carbonyl)amino)-3-(5-methoxypyridin-3-yl)propanoate |
| 4-48 | Fmoc | H | 1 | tBu | 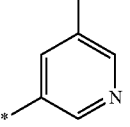 | H | tert-Butyl 2-((((9H-fluoren-9-yl)methoxy)carbonyl)amino)-3-(5-fluoropyridin-3-yl)propanoate |
| 4-49 | Fmoc | H | 1 | tBu | 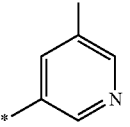 | H | tert-Butyl 2-((((9H-fluoren-9-yl)methoxy)carbonyl)amino)-3-(5-chloropyridin-3-yl)propanoate |

TABLE 4-continued

| Compound ID | R₁ | R₂ | n | R₃ | R₆ | R₇ | Compound Name |
|---|---|---|---|---|---|---|---|
| 4-50 | Fmoc | H | 1 | tBu | 5-bromopyridin-3-yl | H | tert-Butyl 2-((((9H-fluoren-9-yl)methoxy)carbonyl)amino)-3-(5-bromopyridin-3-yl)propanoate |
| 4-51 | Fmoc | H | 1 | tBu | 5-iodopyridin-3-yl | H | tert-Butyl 2-((((9H-fluoren-9-yl)methoxy)carbonyl)amino)-3-(5-iodopyridin-3-yl)propanoate |
| 4-52 | Fmoc | H | 1 | tBu | 2-(methylamino)pyridin-4-yl | H | tert-Butyl 2-((((9H-fluoren-9-yl)methoxy)carbonyl)amino)-3-(2-(methylamino)pyridin-4-yl)propanoate |
| 4-53 | Fmoc | H | 1 | tBu | 2-(dimethylamino)pyridin-4-yl | H | tert-Butyl 2-((((9H-fluoren-9-yl)methoxy)carbonyl)amino)-3-(2-(dimethylamino)pyridin-4-yl)propanoate |
| 4-54 | Fmoc | H | 1 | tBu | pyrimidin-5-yl | H | tert-Butyl 2-((((9H-fluoren-9-yl)methoxy)carbonyl)amino)-3-(pyrimidin-5-yl)propanoate |

TABLE 5

| Compound ID | R₁ | R₂ | n | R₃ | R₆ | R₇ | Compound Name |
|---|---|---|---|---|---|---|---|
| 5-1 | Fmoc | Me | 1 | tBu | phenyl | H | tert-Butyl N-methyl(((9H-fluoren-9-yl)methoxy)carbonyl)phenylalaninate |
| 5-2 | Fmoc | Me | 1 | tBu | o-tolyl | H | tert-Butyl 2-((((9H-fluoren-9-yl)methoxy)carbonyl)(methyl)amino)-3-(o-tolyl)propanoate |
| 5-3 | Fmoc | Me | 1 | tBu | m-tolyl | H | tert-Butyl 2-((((9H-fluoren-9-yl)methoxy)carbonyl)(methyl)amino)-3-(m-tolyl)propanoate |
| 5-4 | Fmoc | Me | 1 | tBu | p-tolyl | H | tert-Butyl 2-((((9H-fluoren-9-yl)methoxy)carbonyl)(methyl)amino)-3-(p-tolyl)propanoate |
| 5-5 | Fmoc | Me | 1 | tBu | 4-ethylphenyl | H | tert-Butyl 2-((((9H-fluoren-9-yl)methoxy)carbonyl)(methyl)amino)-3-(4-ethylphenyl)propanoate |

TABLE 5-continued

| Compound ID | R₁ | R₂ | n | R₃ | R₆ | R₇ | Compound Name |
|---|---|---|---|---|---|---|---|
| 5-6 | Fmoc | Me | 1 | tBu | 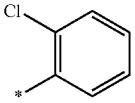 | H | tert-Butyl 2-((((9H-fluoren-9-yl)methoxy)carbonyl)(methyl)amino)-3-(2-chlorophenyl)propanoate |
| 5-7 | Fmoc | Me | 1 | tBu | 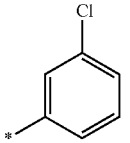 | H | tert-Butyl 2-((((9H-fluoren-9-yl)methoxy)carbonyl)(methyl)amino)-3-(3-chlorophenyl)propanoate |
| 5-8 | Fmoc | Me | 1 | tBu | 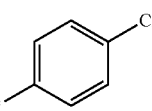 | H | tert-Butyl 2-((((9H-fluoren-9-yl)methoxy)carbonyl)(methyl)amino)-3-(4-chlorophenyl)propanoate |
| 5-9 | Fmoc | Me | 1 | tBu | 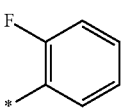 | H | tert-Butyl 2-((((9H-fluoren-9-yl)methoxy)carbonyl)(methyl)amino)-3-(2-fluorophenyl)propanoate |
| 5-10 | Fmoc | Me | 1 | tBu | 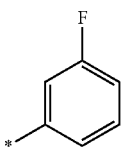 | H | tert-Butyl 2-((((9H-fluoren-9-yl)methoxy)carbonyl)(methyl)amino)-3-(3-ftuorophenyl)propanoate |
| 5-11 | Fmoc | Me | 1 | tBu | 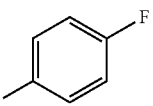 | H | tert-Butyl 2-((((9H-fluoren-9-yl)methoxy)carbonyl)(methyl)amino)-3-(4-fluorophenyl)propanoate |
| 5-12 | Fmoc | Me | 1 | tBu | 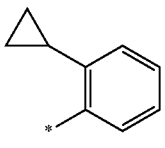 | H | tert-Butyl 2-((((9H-fluoren-9-yl)methoxy)carbonyl)(methyl)amino)-3-(2-cyclopropylphenyl)propanoate |
| 5-13 | Fmoc | Me | 1 | tBu | 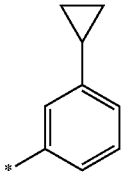 | H | tert-Butyl 2-((((9H-fluoren-9-yl)methoxy)carbonyl)(methyl)amino)-3-(3-cyclopropylphenyl)propanoate |
| 5-14 | Fmoc | Me | 1 | tBu | 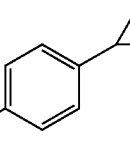 | H | tert-Butyl 2-((((9H-fluoren-9-yl)methoxy)carbonyl)(methyl)amino)-3-(4-cyclopropylphenyl)propanoate |
| 5-15 | Fmoc | Me | 1 | tBu | 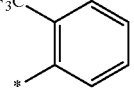 | H | tert-Butyl 2-((((9H-fluoren-9-yl)methoxy)carbonyl)(methyl)amino)-3-(2-(trifluoromethyl)phenyl)propanoate |
| 5-16 | Fmoc | Me | 1 | tBu | 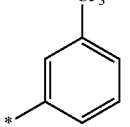 | H | tert-Butyl 2-((((9H-fluoren-9-yl)methoxy)carbonyl)(methyl)amino)-3-(3-(trifluoromethyl)phenyl)propanoate |

TABLE 5-continued

| Compound ID | R₁ | R₂ | n | R₃ | R₆ | R₇ | Compound Name |
|---|---|---|---|---|---|---|---|
| 5-17 | Fmoc | Me | 1 | tBu | 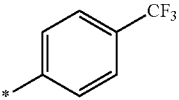 | H | tert-Butyl 2-((((9H-fluoren-9-yl)methoxy)carbonyl)(methyl)amino)-3-(4-(trifluoromethyl)phenyl)propanoate |
| 5-18 | Fmoc | Me | 1 | tBu | 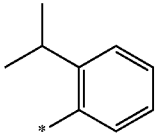 | H | tert-Butyl 2-((((9H-fluoren-9-yl)methoxy)carbonyl)(methyl)amino)-3-(2-isopropylphenyl)propanoate |
| 5-19 | Fmoc | Me | 1 | tBu | 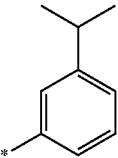 | H | tert-Butyl 2-((((9H-fluoren-9-yl)methoxy)carbonyl)(methyl)amino)-3-(3-isopropylphenyl)propanoate |
| 5-20 | Fmoc | Me | 1 | tBu | 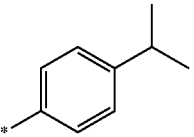 | H | tert-Butyl 2-((((9H-fluoren-9-yl)methoxy)carbonyl)(methyl)amino)-3-(4-isopropylphenyl)propanoate |
| 5-21 | Fmoc | Me | 1 | tBu | 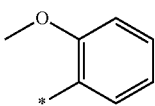 | H | tert-Butyl 2-((((9H-fluoren-9-yl)methoxy)carbonyl)(methyl)amino)-3-(2-methoxyphenyl)propanoate |
| 5-22 | Fmoc | Me | 1 | tBu | 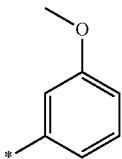 | H | tert-Butyl 2-((((9H-fluoren-9-yl)methoxy)carbonyl)(methyl)amino)-3-(3-methoxyphenyl)propanoate |
| 5-23 | Fmoc | Me | 1 | tBu | 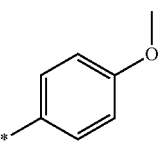 | H | tert-Butyl 2-((((9H-fluoren-9-yl)methoxy)carbonyl)(methyl)amino)-3-(4-methoxyphenyl)propanoate |
| 5-24 | Fmoc | Me | 1 | tBu | 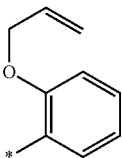 | H | tert-Butyl 2-((((9H-fluoren-9-yl)methoxy)carbonyl)(methyl)amino)-3-(2-(allyloxy)phenyl)propanoate |
| 5-25 | Fmoc | Me | 1 | tBu | 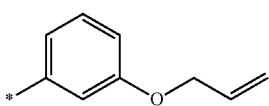 | H | tert-Butyl 2-((((9H-fluoren-9-yl)methoxy)carbonyl)(methyl)amino)-3-(3-(allyloxy)phenyl)propanoate |
| 5-26 | Fmoc | Me | 1 | tBu | 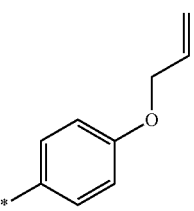 | H | tert-Butyl 2-((((9H-fluoren-9-yl)methoxy)carbonyl)(methyl)amino)-3-(4-(allyloxy)phenyl)propanoate |

TABLE 5-continued

| Compound ID | R₁ | R₂ | n | R₃ | R₆ | R₇ | Compound Name |
|---|---|---|---|---|---|---|---|
| 5-27 | Fmoc | Me | 1 | tBu | (4-isopropoxyphenyl) | H | tert-Butyl 2-((((9H-fluoren-9-yl)methoxy)carbonyl)(methyl)amino)-3-(4-isopropoxyphenyl)propanoate |
| 5-28 | Fmoc | Me | 1 | tBu | (2-fluoro-4-(trifluoromethyl)phenyl)* Note: actually 3-fluoro-4-(trifluoromethyl)phenyl | H | tert-Butyl 2-((((9H-fluoren-9-yl)methoxy)carbonyl)(methyl)amino)-3-(3-fluoro-4-(trifluoromethyl)phenyl)propanoate |
| 5-29 | Fmoc | Me | 1 | tBu | (2-fluoro-4-(trifluoromethyl)phenyl) | H | tert-Butyl 2-((((9H-fluoren-9-yl)methoxy)carbonyl)(methyl)amino)-3-(2-fluoro-4-(trifluoromethyl)phenyl)propanoate |
| 5-30 | Fmoc | Me | 1 | tBu | (3,4-dimethoxyphenyl) | H | tert-Butyl 2-((((9H-fluoren-9-yl)methoxy)carbonyl)(methyl)amino)-3-(3,4-dimethoxyphenyl)propanoate |
| 5-31 | Fmoc | Me | 1 | tBu | (2-fluoro-4-methoxyphenyl) | H | tert-Butyl 2-((((9H-fluoren-9-yl)methoxy)carbonyl)(methyl)amino)-3-(2-fluoro-4-methoxyphenyl)propanoate |
| 5-32 | Fmoc | Me | 1 | tBu | (3-fluoro-4-methoxyphenyl) | H | tert-Butyl 2-((((9H-fluoren-9-yl)methoxy)carbonyl)(methyl)amino)-3-(3-fluoro-4-methoxyphenyl)propanoate |
| 5-33 | Fmoc | Me | 1 | tBu | (3,5-difluoro-4-methoxyphenyl) | H | tert-Butyl 2-((((9H-fluoren-9-yl)methoxy)carbonyl)(methyl)amino)-3-(3,5-difluoro-4-methoxyphenyl)propanoate |
| 5-34 | Fmoc | Me | 1 | tBu | (3,5-difluoro-4-(trifluoromethyl)phenyl) | H | tert-Butyl 2-((((9H-fluoren-9-yl)methoxy)carbonyl)(methyl)amino)-3-(3,5-difluoro-4-(trifluoromethyl)phenyl)propanoate |
| 5-35 | Fmoc | Me | 1 | tBu | (3-methoxy-4-(methylcarbamoyl)phenyl) | H | tert-Butyl 2-((((9H-fluoren-9-yl)methoxy)carbonyl)(methyl)amino)-3-(3-methoxy-4-(methylcarbamoyl)phenyl)propanoate |
| 5-36 | Fmoc | Me | 1 | tBu | (4-methoxy-3-(methylcarbamoyl)phenyl) | H | tert-Butyl 2-((((9H-fluoren-9-yl)methoxy)carbonyl)(methyl)amino)-3-(4-methoxy-3-(methylcarbamoyl)phenyl)propanoate |

TABLE 5-continued

| Compound ID | R₁ | R₂ | n | R₃ | R₆ | R₇ | Compound Name |
|---|---|---|---|---|---|---|---|
| 5-37 | Fmoc | Me | 1 | tBu | 2-methoxy-4-(N-(methylsulfonyl)carbamoyl)phenyl group | H | tert-Butyl 2-((((9H-fluoren-9-yl)methoxy)carbonyl)(methyl)amino)-3-(3-methoxy-4-((methylsulfonyl)carbamoyl)phenyl)propanoate |
| 5-38 | Fmoc | Me | 1 | tBu | 4-(methyl((tetrahydro-2H-pyran-2-yl)oxy)carbamoyl)phenyl group | H | tert-Butyl 2-((((9H-fluoren-9-yl)methoxy)carbonyl)(methyl)amino)-3-(4-(methyl((tetrahydro-2H-pyran-2-yl)oxy)carbamoyl)phenyl)propanoate |
| 5-39 | Fmoc | Me | 1 | tBu | 3-methoxy-4-(((tetrahydro-2H-pyran-2-yl)oxy)carbamoyl)phenyl group | H | tert-Butyl 2-((((9H-fluoren-9-yl)methoxy)carbonyl)(methyl)amino)-3-(3-methoxy-4-(((tetrahydro-2H-pyran-2-yl)oxy)carbamoyl)phenyl)propanoate |
| 5-40 | Fmoc | Me | 1 | tBu | pyridin-2-yl | H | tert-Butyl 2-((((9H-fluoren-9-yl)methoxy)carbonyl)(methyl)amino)-3-(pyridin-2-yl)propanoate |
| 5-41 | Fmoc | Me | 1 | tBu | pyridin-3-yl | H | tert-Butyl 2-((((9H-fluoren-9-yl)methoxy)carbonyl)(methyl)amino)-3-(pyridin-3-yl)propanoate |
| 5-42 | Fmoc | Me | 1 | tBu | pyridin-4-yl | H | tert-Butyl 2-((((9H-fluoren-9-yl)methoxy)carbonyl)(methyl)amino)-3-(pyridin-4-yl)propanoate |
| 5-43 | Fmoc | Me | 1 | tBu | 6-methylpyridin-3-yl | H | tert-Butyl 2-((((9H-fluoren-9-yl)methoxy)carbonyl)(methyl)amino)-3-(6-methylpyridin-3-yl)propanoate |
| 5-44 | Fmoc | Me | 1 | tBu | 5-methylpyridin-3-yl | H | tert-Butyl 2-((((9H-fluoren-9-yl)methoxy)carbonyl)(methyl)amino)-3-(5-methylpyridin-3-yl)propanoate |
| 5-45 | Fmoc | Me | 1 | tBu | 4-methylpyridin-3-yl | H | tert-Butyl 2-((((9H-fluoren-9-yl)methoxy)carbonyl)(methyl)amino)-3-(4-methylpyridin-3-yl)propanoate |
| 5-46 | Fmoc | Me | 1 | tBu | 6-methoxypyridin-3-yl | H | tert-Butyl 2-((((9H-fluoren-9-yl)methoxy)carbonyl)(methyl)amino)-3-(6-methoxypyridin-3-yl)propanoate |
| 5-47 | Fmoc | Me | 1 | tBu | 5-methoxypyridin-3-yl | H | tert-Butyl 2-((((9H-fluoren-9-yl)methoxy)carbonyl)(methyl)amino)-3-(5-methoxypyridin-3-yl)propanoate |

TABLE 5-continued

| Compound ID | R₁ | R₂ | n | R₃ | R₆ | R₇ | Compound Name |
|---|---|---|---|---|---|---|---|
| 5-48 | Fmoc | Me | 1 | tBu | 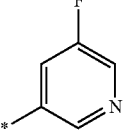 | H | tert-Butyl 2-((((9H-fluoren-9-yl)methoxy)carbonyl)(methyl)amino)-3-(5-fluoropyridin-3-yl)propanoate |
| 5-49 | Fmoc | Me | 1 | tBu | 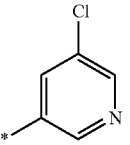 [SMILES: *c1cncc(Cl)c1] | H | tert-Butyl 2-((((9H-fluoren-9-yl)methoxy)carbonyl)(methyl)amino)-3-(5-chloropyridin-3-yl)propanoate |
| 5-50 | Fmoc | Me | 1 | tBu | 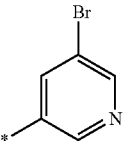 | H | tert-Butyl 2-((((9H-fluoren-9-yl)methoxy)carbonyl)(methyl)amino)-3-(5-bromopyridin-3-yl)propanoate |
| 5-51 | Fmoc | Me | 1 | tBu | 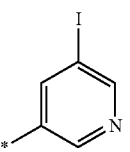 [SMILES: *c1cncc(I)c1] | H | tert-Butyl 2-((((9H-fluoren-9-yl)methoxy)carbonyl)(methyl)amino)-3-(5-iodopyridin-3-yl)propanoate |
| 5-52 | Fmoc | Me | 1 | tBu | 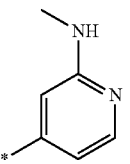 [SMILES: *c1ccnc(NC)c1] | H | tert-Butyl 2-((((9H-fluoren-9-yl)methoxy)carbonyl)(methyl)amino)-3-(2-(methylamino)pyridin-4-yl)propanoate |
| 5-53 | Fmoc | Me | 1 | tBu | 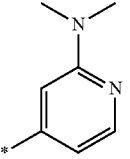 [SMILES: *c1ccnc(N(C)C)c1] | H | tert-Butyl 2-((((9H-fluoren-9-yl)methoxy)carbonyl)(methyl)amino)-3-(2-(dimethylamino)pyridin-4-yl)propanoate |
| 5-54 | Fmoc | Me | 1 | tBu | 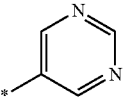 [SMILES: *c1cncnc1] | H | tert-Butyl 2-((((9H-fluoren-9-yl)methoxy)carbonyl)(methyl)amino)-3-(pyrimidin-5-yl)propanoate |

TABLE 6

| Compound ID | R₁ | R₂ | n | R₃ | R₆ | R₇ | Compound Name |
|---|---|---|---|---|---|---|---|
| 6-1 | Fmoc | H | 2 | H | 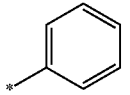 [SMILES: *c1ccccc1] | H | 2-((((9H-Fluoren-9-yl)methoxy)carbonyl)amino)-4-phenylbutanoic acid |
| 6-2 | Fmoc | H | 2 | H | 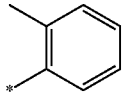 [SMILES: *c1ccccc1C] | H | 2-((((9H-Fluoren-9-yl)methoxy)carbonyl)amino)-4-(o-tolyl)butanoic acid |

TABLE 6-continued

| Compound ID | R₁ | R₂ | n | R₃ | R₆ | R₇ | Compound Name |
|---|---|---|---|---|---|---|---|
| 6-3 | Fmoc | H | 2 | H | 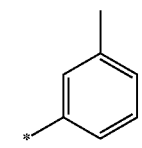 [SMILES: *c1cccc(C)c1] | H | 2-((((9H-Fluoren-9-yl)methoxy)carbonyl)amino)-4-(m-tolyl)butanoic acid |
| 6-4 | Fmoc | H | 2 | H | 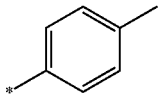 | H | 2-((((9H-Fluoren-9-yl)methoxy)carbonyl)amino)-4-(p-tolyl)butanoic acid |
| 6-5 | Fmoc | H | 2 | H | 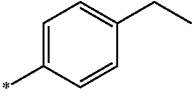 [SMILES: *c1ccc(CC)cc1] | H | 2-((((9H-Fluoren-9-yl)methoxy)carbonyl)amino)-4-(4-ethylphenyl)butanoic acid |
| 6-6 | Fmoc | H | 2 | H | 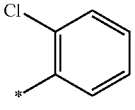 | H | 2-((((9H-Fluoren-9-yl)methoxy)carbonyl)amino)-4-(2-chlorophenyl)butanoic acid |
| 6-7 | Fmoc | H | 2 | H | 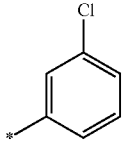 [SMILES: *c1cccc(Cl)c1] | H | 2-((((9H-Fluoren-9-yl)methoxy)carbonyl)amino)-4-(3-chlorophenyl)butanoic acid |
| 6-8 | Fmoc | H | 2 | H | 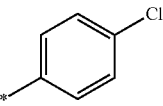 [SMILES: *c1ccc(Cl)cc1] | H | 2-((((9H-Fluoren-9-yl)methoxy)carbonyl)amino)-4-(4-chlorophenyl)butanoic acid |
| 6-9 | Fmoc | H | 2 | H | 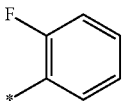 | H | 2-((((9H-Fluoren-9-yl)methoxy)carbonyl)amino)-4-(2-fluorophenyl)butanoic acid |
| 6-10 | Fmoc | H | 2 | H | 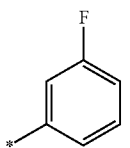 [SMILES: *c1cccc(F)c1] | H | 2-((((9H-Fluoren-9-yl)methoxy)carbonyl)amino)-4-(3-fluorophenyl)butanoic acid |
| 6-11 | Fmoc | H | 2 | H | 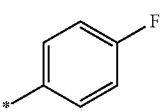 [SMILES: *c1ccc(F)cc1] | H | 2-((((9H-Fluoren-9-yl)methoxy)carbonyl)amino)-4-(4-fluorophenyl)butanoic acid |
| 6-12 | Fmoc | H | 2 | H | 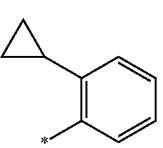 [SMILES: *c1ccccc1C1CC1] | H | 2-((((9H-Fluoren-9-yl)methoxy)carbonyl)amino)-4-(2-cyclopropylphenyl)butanoic acid |
| 6-13 | Fmoc | H | 2 | H | 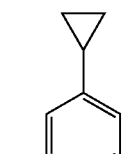 | H | 2-((((9H-Fluoren-9-yl)methoxy)carbonyl)amino)-4-(3-cyclopropylphenyl)butanoic acid |

TABLE 6-continued

| Compound ID | R₁ | R₂ | n | R₃ | R₆ | R₇ | Compound Name |
|---|---|---|---|---|---|---|---|
| 6-14 | Fmoc | H | 2 | H | 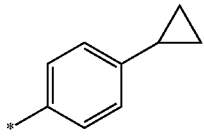 [SMILES: *c1ccc(C2CC2)cc1] | H | 2-((((9H-Fluoren-9-yl)methoxy)carbonyl)amino)-4-(4-cyclopropylphenyl)butanoic acid |
| 6-15 | Fmoc | H | 2 | H | 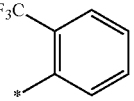 | H | 2-((((9H-Fluoren-9-yl)methoxy)carbonyl)amino)-4-(2-(trifluoromethyl)phenyl)butanoic acid |
| 6-16 | Fmoc | H | 2 | H | 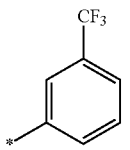 | H | 2-((((9H-Fluoren-9-yl)methoxy)carbonyl)amino)-4-(3-(trifluoromethyl)phenyl)butanoic acid |
| 6-17 | Fmoc | H | 2 | H | 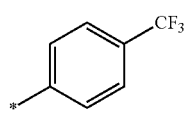 [SMILES: *c1ccc(C(F)(F)F)cc1] | H | 2-((((9H-Fluoren-9-yl)methoxy)carbonyl)amino)-4-(4-(trifluoromethyl)phenyl)butanoic acid |
| 6-18 | Fmoc | H | 2 | H | 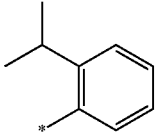 [SMILES: *c1ccccc1C(C)C] | H | 2-((((9H-Fluoren-9-yl)methoxy)carbonyl)amino)-4-(2-isopropylphenyl)butanoic acid |
| 6-19 | Fmoc | H | 2 | H | 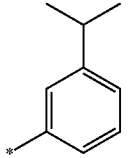 | H | 2-((((9H-Fluoren-9-yl)methoxy)carbonyl)amino)-4-(3-isopropylphenyl)butanoic acid |
| 6-20 | Fmoc | H | 2 | H | 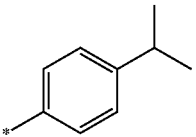 [SMILES: *c1ccc(C(C)C)cc1] | H | 2-((((9H-Fluoren-9-yl)methoxy)carbonyl)amino)-4-(4-isopropylphenyl)butanoic acid |
| 6-21 | Fmoc | H | 2 | H | 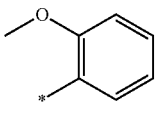 | H | 2-((((9H-Fluoren-9-yl)methoxy)carbonyl)amino)-4-(2-methoxyphenyl)butanoic acid |
| 6-22 | Fmoc | H | 2 | H | 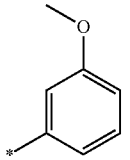 [SMILES: *c1cccc(OC)c1] | H | 2-((((9H-Fluoren-9-yl)methoxy)carbonyl)amino)-4-(3-methoxyphenyl)butanoic acid |
| 6-23 | Fmoc | H | 2 | H | 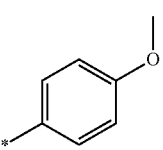 [SMILES: *c1ccc(OC)cc1] | H | 2-((((9H-Fluoren-9-yl)methoxy)carbonyl)amino)-4-(4-methoxyphenyl)butanoic acid |

TABLE 6-continued

| Compound ID | R₁ | R₂ | n | R₃ | R₆ | R₇ | Compound Name |
|---|---|---|---|---|---|---|---|
| 6-24 | Fmoc | H | 2 | H | 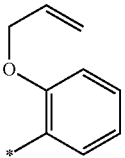 [SMILES: *c1ccccc1OCC=C] | H | 2-((((9H-Fluoren-9-yl)methoxy)carbonyl)amino)-4-(2-(allyloxy)phenyl)butanoic acid |
| 6-25 | Fmoc | H | 2 | H | 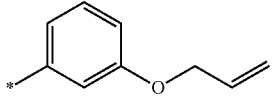 [SMILES: *c1cccc(OCC=C)c1] | H | 2-((((9H-Fluoren-9-yl)methoxy)carbonyl)amino)-4-(3-(allyloxy)phenyl)butanoic acid |
| 6-26 | Fmoc | H | 2 | H | 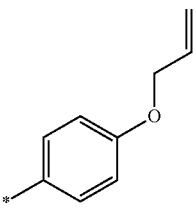 | H | 2-((((9H-Fluoren-9-yl)methoxy)carbonyl)amino)-4-(4-(allyloxy)phenyl)butanoic acid |
| 6-27 | Fmoc | H | 2 | H | 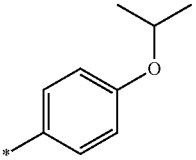 [SMILES: *c1ccc(OC(C)C)cc1] | H | 2-((((9H-Fluoren-9-yl)methoxy)carbonyl)amino)-4-(4-isopropoxyphenyl)butanoic acid |
| 6-28 | Fmoc | H | 2 | H | 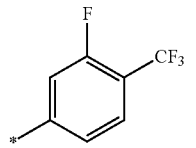 | H | 2-((((9H-Fluoren-9-yl)methoxy)carbonyl)amino)-4-(3-fluoro-4-(trifluoromethyl)phenyl)butanoic acid |
| 6-29 | Fmoc | H | 2 | H | 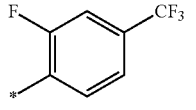 | H | 2-((((9H-Fluroen-9-yl)methoxy)carbonyl)amino)-4-(2-fluoro-4-(trifluoromethyl)phenyl)butanoic acid |
| 6-30 | Fmoc | H | 2 | H | 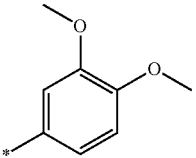 | H | 2-((((9H-Fluoren-9-yl)methoxy)carbonyl)amino)-4-(3,4-dimethoxyphenyl)butanoic acid |
| 6-31 | Fmoc | H | 2 | H | 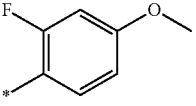 [SMILES: *c1ccc(OC)cc1F] | H | 2-((((9H-Fluoren-9-yl)methoxy)carbonyl)amino)-4-(2-fluoro-4-methoxyphenyl)butanoic acid |
| 6-32 | Fmoc | H | 2 | H | 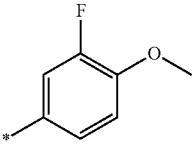 [SMILES: *c1ccc(OC)c(F)c1] | H | 2-((((9H-Fluoren-9-yl)methoxy)carbonyl)amino)-4-(3-fluoro-4-methoxyphenyl)butanoic acid |

TABLE 6-continued

| Compound ID | R₁ | R₂ | n | R₃ | R₆ | R₇ | Compound Name |
|---|---|---|---|---|---|---|---|
| 6-33 | Fmoc | H | 2 | H | 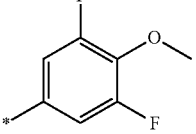 | H | 2-((((9H-Fluoren-9-yl)methoxy)carbonyl)amino)-4-(3,5-difluoro-4-methoxyphenyl)butanoic acid |
| 6-34 | Fmoc | H | 2 | H | 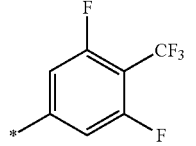 | H | 2-((((9H-Fluoren-9-yl)methoxy)carbonyl)amino)-4-(3,5-difluoro-4-(trifluoromethyl)phenyl)butanoic acid |
| 6-35 | Fmoc | H | 2 | H | 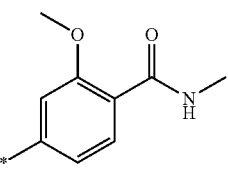 [SMILES: *c1ccc(C(=O)NC)c(OC)c1] | H | 2-((((9H-Fluoren-9-yl)methoxy)carbonyl)amino)-4-(3-methoxy-4-(methylcarbamoyl)phenyl)butanoic acid |
| 6-36 | Fmoc | H | 2 | H | 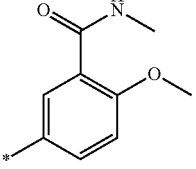 | H | 2-((((9H-Fluoren-9-yl)methoxy)carbonyl)amino)-4-(4-methoxy-3-(methylcarbamoyl)phenyl)butanoic acid |
| 6-37 | Fmoc | H | 2 | H | 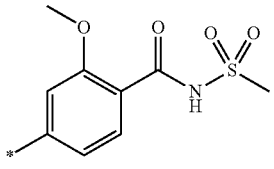 [SMILES: *c1ccc(C(=O)NS(C)(=O)=O)c(OC)c1] | H | 2-((((9H-Fluoren-9-yl)methoxy)carbonyl)amino)-4-(3-methoxy-4-((methylsulfonyl)carbamoyl)phenyl)butanoic acid |
| 6-38 | Fmoc | H | 2 | H | 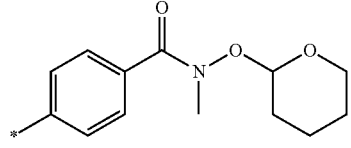 [SMILES: *c1ccc(C(=O)N(C)OC2CCCCO2)cc1] | H | 2-((((9H-Fluoren-9-yl)methoxy)carbonyl)amino)-4-(4-(methyl((tetrahydro-2H-pyran-2-yl)oxy)carbamoyl)phenyl)butanoic acid |
| 6-39 | Fmoc | H | 2 | H | 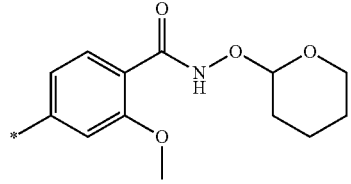 | H | 2-((((9H-Fluoren-9-yl)methoxy)carbonyl)amino)-4-(3-methoxy-4-(((tetrahydro-2H-pyran-2-yl)oxy)carbamoyl)phenyl)butanoic acid |
| 6-40 | Fmoc | H | 2 | H | 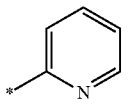 | H | 2-((((9H-Fluoren-9-yl)methoxy)carbonyl)amino)-4-(pyridin-2-yl)butanoic acid |
| 6-41 | Fmoc | H | 2 | H | 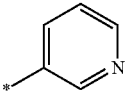 | H | 2-((((9H-Fluoren-9-yl)methoxy)carbonyl)amino)-4-(pyridin-3-yl)butanoic acid |
| 6-42 | Fmoc | H | 2 | H | 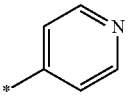 | H | 2-((((9H-Fluoren-9-yl)methoxy)carbonyl)amino)-4-(pyridin-4-yl)butanoic acid |

TABLE 6-continued

| Compound ID | R₁ | R₂ | n | R₃ | R₆ | R₇ | Compound Name |
|---|---|---|---|---|---|---|---|
| 6-43 | Fmoc | H | 2 | H | 6-methylpyridin-3-yl | H | 2-((((9H-Fluoren-9-yl)methoxy)carbonyl)amino)-4-(6-methylpyridin-3-yl)butanoic acid |
| 6-44 | Fmoc | H | 2 | H | 5-methylpyridin-3-yl | H | 2-((((9H-Fluoren-9-yl)methoxy)carbonyl)amino)-4-(5-methylpyridin-3-yl)butanoic acid |
| 6-45 | Fmoc | H | 2 | H | 4-methylpyridin-3-yl | H | 2-((((9H-Fluoren-9-yl)methoxy)carbonyl)amino)-4-(4-methylpyridin-3-yl)butanoic acid |
| 6-46 | Fmoc | H | 2 | H | 6-methoxypyridin-3-yl | H | 2-((((9H-Fluoren-9-yl)methoxy)carbonyl)amino)-4-(6-methoxypyridin-3-yl)butanoic acid |
| 6-47 | Fmoc | H | 2 | H | 5-methoxypyridin-3-yl | H | 2-((((9H-Fluoren-9-yl)methoxy)carbonyl)amino)-4-(5-methoxypyridin-3-yl)butanoic acid |
| 6-48 | Fmoc | H | 2 | H | 5-fluoropyridin-3-yl | H | 2-((((9H-Fluoren-9-yl)methoxy)carbonyl)amino)-4-(5-fluoropyridin-3-yl)butanoic acid |
| 6-49 | Fmoc | H | 2 | H | 5-chloropyridin-3-yl | H | 2-((((9H-Fluoren-9-yl)methoxy)carbonyl)amino)-4-(5-chloropyridin-3-yl)butanoic acid |
| 6-50 | Fmoc | H | 2 | H | 5-bromopyridin-3-yl | H | 2-((((9H-Fluoren-9-yl)methoxy)carbonyl)amino)-4-(5-bromopyridin-3-yl)butanoic acid |
| 6-51 | Fmoc | H | 2 | H | 5-iodopyridin-3-yl | H | 2-((((9H-Fluoren-9-yl)methoxy)carbonyl)amino)-4-(5-iodopyridin-3-yl)butanoic acid |
| 6-52 | Fmoc | H | 2 | H | 2-(methylamino)pyridin-4-yl | H | 2-((((9H-Fluoren-9-yl)methoxy)carbonyl)amino)-4-(2-(methylamino)pyridin-4-yl)butanoic acid |

TABLE 6-continued

| Compound ID | R₁ | R₂ | n | R₃ | R₆ | R₇ | Compound Name |
|---|---|---|---|---|---|---|---|
| 6-53 | Fmoc | H | 2 | H | 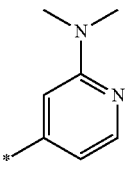 | H | 2-((((9H-Fluoren-9-yl)methoxy)carbonyl) amino)-4-(2-(dimethylamino)pyridin-4-yl) butanoic acid |
| 6-54 | Fmoc | H | 2 | H | 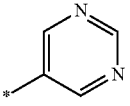 | H | 2-((((9H-Fluoren-9-yl)methoxy)carbonyl) amino)-4-(pyrimidin-5-yl)butanoic acid |

TABLE 7

| Compound ID | R₁ | R₂ | n | R₃ | R₆ | R₇ | Compound Name |
|---|---|---|---|---|---|---|---|
| 7-1 | Fmoc | Me | 2 | H | 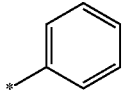 | H | 2-((((9H-Fluoren-9-yl)methoxy)carbonyl) (methy)amino)-4-phenylbutanoic acid |
| 7-2 | Fmoc | Me | 2 | H | 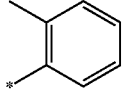 | H | 2-((((9H-Fluoren-9-yl)methoxy)carbonyl) (methyl)amino)-4-(o-tolyl)butanoic acid |
| 7-3 | Fmoc | Me | 2 | H | 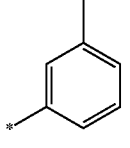 | H | 2-((((9H-Fluoren-9-yl)methoxy)carbonyl) (methyl)amino)-4-(m-tolyl)butanoic acid |
| 7-4 | Fmoc | Me | 2 | H | 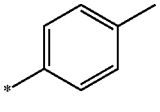 | H | 2-((((9H-Fluoren-9-yl)methoxy)carbonyl) (methyl)amino)-4-(p-tolyl)butanoic acid |
| 7-5 | Fmoc | Me | 2 | H | 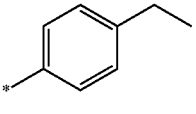 | H | 2-((((9H-Fluoren-9-yl)methoxy)carbonyl) (methyl)amino)-4-(4-ethylphenyl)butanoic acid |
| 7-6 | Fmoc | Me | 2 | H | 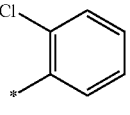 | H | 2-((((9H-Fluoren-9-yl)methoxy)carbonyl) (methyl)amino)-4-(2-chlorophenyl) butanoic acid |
| 7-7 | Fmoc | Me | 2 | H | 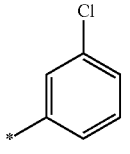 | H | 2-((((9H-Fluoren-9-yl)methoxy)carbonyl) (methyl)amino)-4-(3-chlorophenyl) butanoic acid |
| 7-8 | Fmoc | Me | 2 | H | 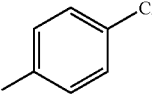 | H | 2-((((9H-Fluoren-9-yl)methoxy)carbonyl) (methyl)amino)-4-(4-chlorophenyl) butanoic acid |

TABLE 7-continued

| Compound ID | R₁ | R₂ | n | R₃ | R₆ | R₇ | Compound Name |
|---|---|---|---|---|---|---|---|
| 7-9 | Fmoc | Me | 2 | H | 2-fluorophenyl | H | 2-((((9H-Fluoren-9-yl)methoxy)carbonyl)(methyl)amino)-4-(2-flurophenyl)butanoic acid |
| 7-10 | Fmoc | Me | 2 | H | 3-fluorophenyl | H | 2-((((9H-Fluoren-9-yl)methoxy)carbonyl)(methyl)amino)-4-(3-fluorophenyl)butanoic acid |
| 7-11 | Fmoc | Me | 2 | H | 4-fluorophenyl | H | 2-((((9H-Fluoren-9-yl)methoxy)carbonyl)(methyl)amino)-4-(4-fluorophenyl)butanoic acid |
| 7-12 | Fmoc | Me | 2 | H | 2-cyclopropylphenyl | H | 2-((((9H-Fluoren-9-yl)methoxy)carbonyl)(methyl)amino)-4-(2-cyclopropylphenyl)butanoic acid |
| 7-13 | Fmoc | Me | 2 | H | 3-cyclopropylphenyl | H | 2-((((9H-Fluoren-9-yl)methoxy)carbonyl)(methyl)amino)-4-(3-cyclopropylphenyl)butanoic acid |
| 7-14 | Fmoc | Me | 2 | H | 4-cyclopropylphenyl | H | 2-((((9H-Fluoren-9-yl)methoxy)carbonyl)(methyl)amino)-4-(4-cyclopropylphenyl)butanoic acid |
| 7-15 | Fmoc | Me | 2 | H | 2-(trifluoromethyl)phenyl | H | 2-((((9H-Fluoren-9-yl)methoxy)carbonyl)(methyl)amino)-4-(2-(trifluoromethyl)phenyl)butanoic acid |
| 7-16 | Fmoc | Me | 2 | H | 3-(trifluoromethyl)phenyl | H | 2-((((9H-Fluoren-9-yl)methoxy)carbonyl)(methyl)amino)-4-(3-(trifluoromethyl)phenyl)butanoic acid |
| 7-17 | Fmoc | Me | 2 | H | 4-(trifluoromethyl)phenyl | H | 2-((((9H-Fluoren-9-yl)methoxy)carbonyl)(methyl)amino)-4-(4-(trifluoromethyl)phenyl)butanoic acid |
| 7-18 | Fmoc | Me | 2 | H | 2-isopropylphenyl | H | 2-((((9H-Fluoren-9-yl)methoxy)carbonyl)(methyl)amino)-4-(2-isopropylphenyl)butanoic acid |

TABLE 7-continued

| Compound ID | R₁ | R₂ | n | R₃ | R₆ | R₇ | Compound Name |
|---|---|---|---|---|---|---|---|
| 7-19 | Fmoc | Me | 2 | H | 3-isopropylphenyl | H | 2-((((9H-Fluoren-9-yl)methoxy)carbonyl)(methyl)amino)-4-(3-isopropylphenyl)butanoic acid |
| 7-20 | Fmoc | Me | 2 | H | 4-isopropylphenyl | H | 2-((((9H-Fluoren-9-yl)methoxy)carbonyl)(methyl)amino)-4-(4-isopropylphenyl)butanoic acid |
| 7-21 | Fmoc | Me | 2 | H | 2-methoxyphenyl | H | 2-((((9H-Fluoren-9-yl)methoxy)carbonyl)(methyl)amino)-4-(2-methoxyphenyl)butanoic acid |
| 7-22 | Fmoc | Me | 2 | H | 3-methoxyphenyl | H | 2-((((9H-Fluoren-9-yl)methoxy)carbonyl)(methyl)amino)-4-(3-methoxyphenyl)butanoic acid |
| 7-23 | Fmoc | Me | 2 | H | 4-methoxyphenyl | H | 2-((((9H-Fluoren-9-yl)methoxy)carbonyl)(methyl)amino)-4-(4-methoxypehnyl)butanoic acid |
| 7-24 | Fmoc | Me | 2 | H | 2-(allyloxy)phenyl | H | 2-((((9H-Fluoren-9-yl)methoxy)carbonyl)(methyl)amino)-4-(2-(allyloxy)phenyl)butanoic acid |
| 7-25 | Fmoc | Me | 2 | H | 3-(allyloxy)phenyl | H | 2-((((9H-Fluoren-9-yl)methoxy)carbonyl)(methyl)amino)-4-(3-(allyloxy)phenyl)butanoic acid |
| 7-26 | Fmoc | Me | 2 | H | 4-(allyloxy)phenyl | H | 2-((((9H-Fluoren-9-yl)methoxy)carbonyl)(methyl)amino)-4-(4-(allyloxy)phenyl)butanoic acid |
| 7-27 | Fmoc | Me | 2 | H | 4-isopropoxyphenyl | H | 2-((((9H-Fluoren-9-yl)methoxy)carbonyl)(methyl)amino)-4-(4-isopropoxyphenyl)butanoic acid |

TABLE 7-continued

| Compound ID | R₁ | R₂ | n | R₃ | R₆ | R₇ | Compound Name |
|---|---|---|---|---|---|---|---|
| 7-28 | Fmoc | Me | 2 | H | 3-fluoro-4-(trifluoromethyl)phenyl | H | 2-((((9H-Fluoren-9-yl)methoxy)carbonyl)(methyl)amino)-4-(3-fluoro-4-(trifluoromethyl)phenyl)butanoic acid |
| 7-29 | Fmoc | Me | 2 | H | 2-fluoro-4-(trifluoromethyl)phenyl | H | 2-((((9H-Fluoren-9-yl)methoxy)carbonyl)(methyl)amino)-4-(2-fluoro-4-(trifluoromethyl)phenyl)butanoic acid |
| 7-30 | Fmoc | Me | 2 | H | 3,4-dimethoxyphenyl | H | 2-((((9H-Fluoren-9-yl)methoxy)carbonyl)(methyl)amino)-4-(3,4-dimethoxyphenyl)butanoic acid |
| 7-31 | Fmoc | Me | 2 | H | 2-fluoro-4-methoxyphenyl | H | 2-((((9H-Fluoren-9-yl)methoxy)carbonyl)(methyl)amino)-4-(2-fluoro-4-methoxypehnyl)butanoic acid |
| 7-32 | Fmoc | Me | 2 | H | 3-fluoro-4-methoxyphenyl | H | 2-((((9H-Fluoren-9-yl)methoxy)carbonyl)(methyl)amino)-4-(3-fluoro-4-methoxyphenyl)butanoic acid |
| 7-33 | Fmoc | Me | 2 | H | 3,5-difluoro-4-methoxyphenyl | H | 2-((((9H-Fluoren-9-yl)methoxy)carbonyl)(methyl)amino)-4-(3,5-difluoro-4-methoxyphenyl)butanoic acid |
| 7-34 | Fmoc | Me | 2 | H | 3,5-difluoro-4-(trifluoromethyl)phenyl | H | 2-((((9H-Fluoren-9-yl)methoxy)carbonyl)(methyl)amino)-4-(3,5-difluoro-4-(trifluoromethyl)phenyl)butanoic acid |
| 7-35 | Fmoc | Me | 2 | H | 3-methoxy-4-(methylcarbamoyl)phenyl | H | 2-((((9H-Fluoren-9-yl)methoxy)carbonyl)(methyl)amino)-4-(3-methoxy-4-(methylcarbamoyl)phenyl)butanoic acid |
| 7-36 | Fmoc | Me | 2 | H | 4-methoxy-3-(methylcarbamoyl)phenyl | H | 2-((((9H-Fluoren-9-yl)methoxy)carbonyl)(methyl)amino)-4-(4-methoxy-3-(methylcarbamoyl)phenyl)butanoic acid |

TABLE 7-continued

| Compound ID | R₁ | R₂ | n | R₃ | R₆ | R₇ | Compound Name |
|---|---|---|---|---|---|---|---|
| 7-37 | Fmoc | Me | 2 | H | (2-methoxy-4-substituted phenyl)-C(O)-NH-S(O)₂-Me | H | 2-((((9H-Fluoren-9-yl)methoxy)carbonyl)(methyl)amino)-4-(3-methoxy-4-((methylsulfonyl)carbamoyl)phenyl)butanoic acid |
| 7-38 | Fmoc | Me | 2 | H | 4-substituted phenyl-C(O)-N(Me)-O-(tetrahydro-2H-pyran-2-yl) | H | 2-((((9H-Fluoren-9-yl)methoxy)carbonyl)(methyl)amino)-4-(4-(methyl((tetrahydro-2H-pyran-2-yl)oxy)carbamoyl)phenyl)butanoic acid |
| 7-39 | Fmoc | Me | 2 | H | (2-methoxy-4-substituted phenyl)-C(O)-NH-O-(tetrahydro-2H-pyran-2-yl) | H | 2-((((9H-Fluoren-9-yl)methoxy)carbonyl)(methyl)amino)-4-(3-methoxy-4-(((((tetrahydro-2H-pyran-2-yl)oxy)carbamoyl)phenyl)butanoic acid |
| 7-40 | Fmoc | Me | 2 | H | pyridin-2-yl | H | 2-((((9H-Fluoren-9-yl)methoxy)carbonyl)(methyl)amino)-4-(pyridin-2-yl)butanoic acid |
| 7-41 | Fmoc | Me | 2 | H | pyridin-3-yl | H | 2-((((9H-Fluoren-9-yl)methoxy)carbonyl)(methyl)amino)-4-(pyridin-3-yl)butanoic acid |
| 7-42 | Fmoc | Me | 2 | H | pyridin-4-yl | H | 2-((((9H-Fluoren-9-yl)methoxy)carbonyl)(methyl)amino)-4-(pyridin-4-yl)butanoic acid |
| 7-43 | Fmoc | Me | 2 | H | 6-methylpyridin-3-yl | H | 2-((((9H-Fluoren-9-yl)methoxy)carbonyl)(methyl)amino)-4-(6-methylpyridin-3-yl)butanoic acid |
| 7-44 | Fmoc | Me | 2 | H | 5-methylpyridin-3-yl | H | 2-((((9H-Fluoren-9-yl)methoxy)carbonyl)(methyl)amino)-4-(5-methylpyridin-3-yl)butanoic acid |
| 7-45 | Fmoc | Me | 2 | H | 4-methylpyridin-3-yl | H | 2-((((9H-Fluoren-9-yl)methoxy)carbonyl)(methyl)amino)-4-(4-methylpyridin-3-yl)butanoic acid |
| 7-46 | Fmoc | Me | 2 | H | 6-methoxypyridin-3-yl | H | 2-((((9H-Fluoren-9-yl)methoxy)carbonyl)(methyl)amino)-4-(6-methoxypyridin-3-yl)butanoic acid |

TABLE 7-continued

| Compound ID | R₁ | R₂ | n | R₃ | R₆ | R₇ | Compound Name |
|---|---|---|---|---|---|---|---|
| 7-47 | Fmoc | Me | 2 | H | 5-methoxypyridin-3-yl (*-position 3) | H | 2-((((9H-Fluoren-9-yl)methoxy)carbonyl)(methyl)amino)-4-(5-methoxypyridin-3-yl)butanoic acid |
| 7-48 | Fmoc | Me | 2 | H | 5-fluoropyridin-3-yl | H | 2-((((9H-Fluoren-9-yl)methoxy)carbonyl)(methyl)amino)-4-(5-fluoropyridin-3-yl)butanoic acid |
| 7-49 | Fmoc | Me | 2 | H | 5-chloropyridin-3-yl | H | 2-((((9H-fluoren-9-yl)methoxy)carbonyl)(methyl)amino)-4-(5-chloropyridin-3-yl)butanoic acid |
| 7-50 | Fmoc | Me | 2 | H | 5-bromopyridin-3-yl | H | 2-((((9H-Fluoren-9-yl)methoxy)carbonyl)(methyl)amino)-4-(5-bromopyridin-3-yl)butanoic acid |
| 7-51 | Fmoc | Me | 2 | H | 5-iodopyridin-3-yl | H | 2-((((9H-Fluoren-9-yl)methoxy)carbonyl)(methyl)amino)-4-(5-iodopyridin-3-yl)butanoic acid |
| 7-52 | Fmoc | Me | 2 | H | 2-(methylamino)pyridin-4-yl | H | 2-((((9H-Fluoren-9-yl)methoxy)carbonyl)(methyl)amino)-4-(2-(methylamino)pyridin-4-yl)butanoic acid |
| 7-53 | Fmoc | Me | 2 | H | 2-(dimethylamino)pyridin-4-yl | H | 2-((((9H-Fluoren-9-yl)methoxy)carbonyl)(methyl)amino)-4-(2-(dimethylamino)pyridin-4-yl)butanoic acid |
| 7-54 | Fmoc | Me | 2 | H | pyrimidin-5-yl | H | 2-((((9H-Fluoren-9-yl)methoxy)carbonyl)(methyl)amino)-4-(pyrimidin-5-yl)butanoic acid |

TABLE 8

| Compound ID | R₁ | R₂ | n | R₃ | R₆ | R₇ | Compound Name |
|---|---|---|---|---|---|---|---|
| 8-1 | Fmoc | H | 1 | H | 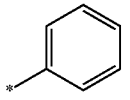 | H | (((9H-Fluoren-9-yl)methoxy)carbonyl)phenylalanine |
| 8-2 | Fmoc | H | 1 | H | 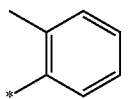 | H | 2-((((9H-Fluoren-9-yl)methoxy)carbonyl)amino)-3-(o-tolyl)propanoic acid |
| 8-3 | Fmoc | H | 1 | H | 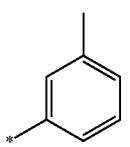 | H | 2-((((9H-Fluoren-9-yl)methoxy)carbonyl)amino)-3-(m-tolyl)propanoic acid |
| 8-4 | Fmoc | H | 1 | H | 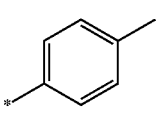 | H | 2-((((9H-Fluoren-9-yl)methoxy)carbonyl)amino)-3-(p-tolyl)propanoic acid |
| 8-5 | Fmoc | H | 1 | H | 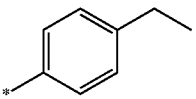 | H | 2-((((9H-Fluoren-9-yl)methoxy)carbonyl)amino)-3-(4-ethylphenyl)propanoic acid |
| 8-6 | Fmoc | H | 1 | H | 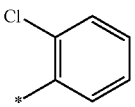 | H | 2-((((9H-Fluoren-9-yl)methoxy)carbonyl)amino)-3-(2-chlorophenyl)propanoic acid |
| 8-7 | Fmoc | H | 1 | H | 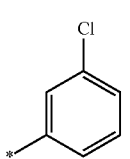 | H | 2-((((9H-Fluoren-9-yl)methoxy)carbonyl)amino)-3-(3-chlorophenyl)propanoic acid |
| 8-8 | Fmoc | H | 1 | H | 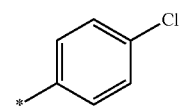 | H | 2-((((9H-Fluoren-9-yl)methoxy)carbonyl)amino)-3-(4-chlorophenyl)propanoic acid |
| 8-9 | Fmoc | H | 1 | H | 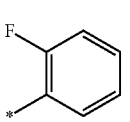 | H | 2-((((9H-Fluoren-9-yl)methoxy)carbonyl)amino)-3-(2-fluorophenyl)propanoic acid |
| 8-10 | Fmoc | H | 1 | H | 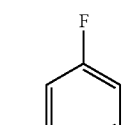 | H | 2-((((9H-Fluoren-9-yl)methoxy)carbonyl)amino)-3-(3-fluorophenyl)propanoic acid |
| 8-11 | Fmoc | H | 1 | H | 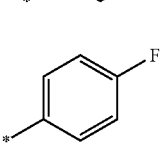 | H | 2-((((9H-Fluoren-9-yl)methoxy)carbonyl)amino)-3-(4-fluorophenyl)propanoic acid |

TABLE 8-continued

| Compound ID | R₁ | R₂ | n | R₃ | R₆ | R₇ | Compound Name |
|---|---|---|---|---|---|---|---|
| 8-12 | Fmoc | H | 1 | H | 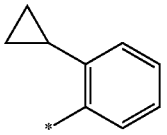 | H | 2-((((9H-Fluoren-9-yl)methoxy)carbonyl)amino)-3-(2-cyclopropylphenyl)propanoic acid |
| 8-13 | Fmoc | H | 1 | H | 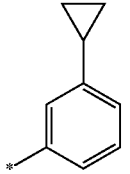 | H | 2-((((9H-Fluoren-9-yl)methoxy)carbonyl)amino)-3-(3-cyclopropylphenyl)propanoic acid |
| 8-14 | Fmoc | H | 1 | H | 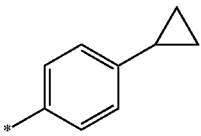 | H | 2-((((9H-Fluoren-9-yl)methoxy)carbonyl)amino)-3-(4-cyclopropylphenyl)propanoic acid |
| 8-15 | Fmoc | H | 1 | H | 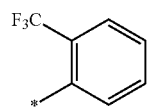 | H | 2-((((9H-Fluoren-9-yl)methoxy)carbonyl)amino)-3-(2-(trifluoromethyl)phenyl)propanoic acid |
| 8-16 | Fmoc | H | 1 | H | 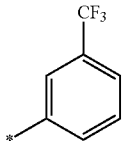 | H | 2-((((9H-Fluoren-9-yl)methoxy)carbonyl)amino)-3-(3-(trifluoromethyl)phenyl)propanoic acid |
| 8-17 | Fmoc | H | 1 | H | 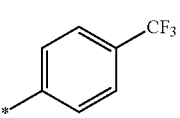 | H | 2-((((9H-Fluoren-9-yl)methoxy)carbonyl)amino)-3-(4-(trifluoromethyl)phenyl)propanoic acid |
| 8-18 | Fmoc | H | 1 | H | 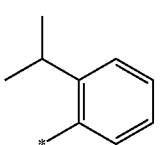 | H | 2-((((9H-Fluoren-9-yl)methoxy)carbonyl)amino)-3-(2-isopropylphenyl)propanoic acid |
| 8-19 | Fmoc | H | 1 | H | 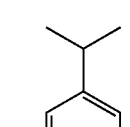 | H | 2-((((9H-Fluoren-9-yl)methoxy)carbonyl)amino)-3-(3-isopropylphenyl)propanoic acid |
| 8-20 | Fmoc | H | 1 | H | 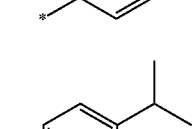 | H | 2-((((9H-Fluoren-9-yl)methoxy)carbonyl)amino)-3-(4-isopropylphenyl)propanoic acid |
| 8-21 | Fmoc | H | 1 | H | 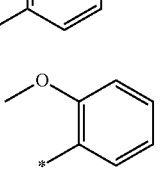 | H | 2-((((9H-Fluoren-9-yl)methoxy)carbonyl)amino)-3-(2-methoxyphenyl)propanoic acid |

TABLE 8-continued

| Compound ID | R₁ | R₂ | n | R₃ | R₆ | R₇ | Compound Name |
|---|---|---|---|---|---|---|---|
| 8-22 | Fmoc | H | 1 | H | 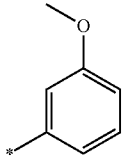 | H | 2-((((9H-Fluoren-9-yl)methoxy)carbonyl)amino)-3-(3-methoxyphenyl)propanoic acid |
| 8-23 | Fmoc | H | 1 | H | 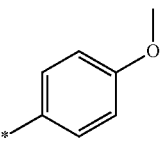 | H | 2-((((9H-Fluoren-9-yl)methoxy)carbonyl)amino)-3-(4-methoxyphenyl)propanoic acid |
| 8-24 | Fmoc | H | 1 | H | 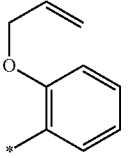 | H | 2-((((9H-Fluoren-9-yl)methoxy)carbonyl)amino)-3-(2-(allyloxy)phenyl)propanoic acid |
| 8-25 | Fmoc | H | 1 | H | 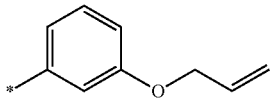 | H | 2-((((9H-Fluoren-9-yl)methoxy)carbonyl)amino)-3-(3-(allyloxy)phenyl)propanoic acid |
| 8-26 | Fmoc | H | 1 | H | 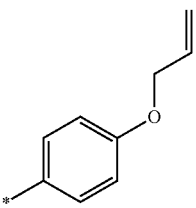 | H | 2-((((9H-Fluoren-9-yl)methoxy)carbonyl)amino)-3-(4-(allyloxy)pehnyl)propanoic acid |
| 8-27 | Fmoc | H | 1 | H | 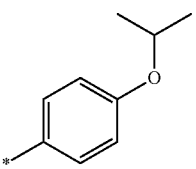 | H | 2-((((9H-Fluoren-9-yl)methoxy)carbonyl)amino)-3-(4-isopropoxyphenyl)propanoic acid |
| 8-28 | Fmoc | H | 1 | H | 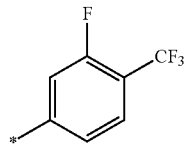 | H | 2-((((9H-Fluoren-9-yl)methoxy)carbonyl)amino)-3-(3-fluoro-4-(trifluoromethyl)phenyl)propanoic acid |
| 8-29 | Fmoc | H | 1 | H | 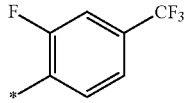 | H | 2-((((9H-Fluoren-9-yl)methoxy)carbonyl)amino)-3-(2-fluoro-4-(trifluoromethyl)phenyl)propanoic acid |
| 8-30 | Fmoc | H | 1 | H | 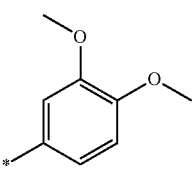 | H | 2-((((9H-Fluoren-9-yl)methoxy)carbonyl)amino)-3-(3,4-dimethoxyphenyl)propanoic acid |

TABLE 8-continued

| Compound ID | R₁ | R₂ | n | R₃ | R₆ | R₇ | Compound Name |
|---|---|---|---|---|---|---|---|
| 8-31 | Fmoc | H | 1 | H | 2-fluoro-4-methoxyphenyl group | H | 2-((((9H-Fluoren-9-yl)methoxy)carbonyl)amino)-3-(2-fluoro-4-methoxyphenyl)propanoic acid |
| 8-32 | Fmoc | H | 1 | H | 3-fluoro-4-methoxyphenyl group | H | 2-((((9H-Fluoren-9-yl)methoxy)carbonyl)amino)-3-(3-fluoro-4-methoxyphenyl)propanoic acid |
| 8-33 | Fmoc | H | 1 | H | 3,5-difluoro-4-methoxyphenyl group | H | 2-((((9H-Fluoren-9-yl)methoxy)carbonyl)amino)-3-(3,5-difluoro-4-methoxyphenyl)propanoic acid |
| 8-34 | Fmoc | H | 1 | H | 3,5-difluoro-4-(trifluoromethyl)phenyl group | H | 2-((((9H-Fluoren-9-yl)methoxy)carbonyl)amino)-3-(3,5-difluoro-4-(trifluoromethyl)phenyl)propanoic acid |
| 8-35 | Fmoc | H | 1 | H | 3-methoxy-4-(methylcarbamoyl)phenyl group | H | 2-((((9H-Fluoren-9-yl)methoxy)carbonyl)amino)-3-(3-methoxy-4-(methylcarbamoyl)phenyl)propanoic acid |
| 8-36 | Fmoc | H | 1 | H | 4-methoxy-3-(methylcarbamoyl)phenyl group | H | 2-((((9H-Fluoren-9-yl)methoxy)carbonyl)amino)-3-(4-methoxy-3-(methylcarbamoyl)phenyl)propanoic acid |
| 8-37 | Fmoc | H | 1 | H | 3-methoxy-4-((methylsulfonyl)carbamoyl)phenyl group | H | 2-((((9H-Fluoren-9-yl)methoxy)carbonyl)amino)-3-(3-methoxy-4-((methylsulfonyl)carbamoyl)phenyl)propanoic acid |
| 8-38 | Fmoc | H | 1 | H | 4-(methyl((tetrahydro-2H-pyran-2-yl)oxy)carbamoyl)phenyl group | H | 2-((((9H-Fluoren-9-yl)methoxy)carbonyl)amino)-3-(4-(methyl((tetrahydro-2H-pyran-2-yl)oxy)carbamoyl)phenyl)proanoic acid |
| 8-39 | Fmoc | H | 1 | H | 3-methoxy-4-(((tetrahydro-2H-pyran-2-yl)oxy)carbamoyl)phenyl group | H | 2-((((9H-Fluoren-9-yl)methoxy)carbonyl)amino)-3-(3-methoxy-4-(((tetrahydro-2H-pyran-2-yl)oxy)carbamoyl)phenyl)propanoic acid |

TABLE 8-continued

| Compound ID | R₁ | R₂ | n | R₃ | R₆ | R₇ | Compound Name |
|---|---|---|---|---|---|---|---|
| 8-40 | Fmoc | H | 1 | H | 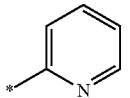 | H | 2-((((9H-Fluoren-9-yl)methoxy)carbonyl)amino)-3-(pyridin-2-yl)propanoic acid |
| 8-41 | Fmoc | H | 1 | H | 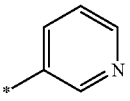 | H | 2-((((9H-Fluoren-9-yl)methoxy)carbonyl)amino)-3-(pyridin-3-yl)propanoic acid |
| 8-42 | Fmoc | H | 1 | H | 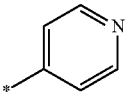 | H | 2-((((9H-Fluoren-9-yl)methoxy)carbonyl)amino)-3-(pyridin-4-yl)propanoic acid |
| 8-43 | Fmoc | H | 1 | H | 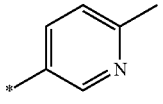 | H | 2-((((9H-Fluoren-9-yl)methoxy)carbonyl)amino)-3-(6-methylpyridin-3-yl)propanoic acid |
| 8-44 | Fmoc | H | 1 | H | 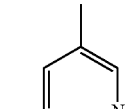 | H | 2-((((9H-Fluoren-9-yl)methoxy)carbonyl)amino)-3-(5-methylpyridin-3-yl)propanoic acid |
| 8-45 | Fmoc | H | 1 | H | 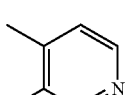 | H | 2-((((9H-Fluoren-9-yl)methoxy)carbonyl)amino)-3-(4-methylpyridin-3-yl)propanoic acid |
| 8-46 | Fmoc | H | 1 | H | 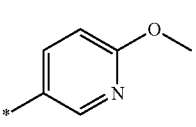 | H | 2-((((9H-Fluoren-9-yl)methoxy)carbonyl)amino)-3-(6-methoxypyridin-3-yl)propanoic acid |
| 8-47 | Fmoc | H | 1 | H | 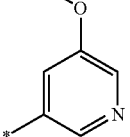 | H | 2-((((9H-Fluoren-9-yl)methoxy)carbonyl)amino)-3-(5-methoxypyridin-3-yl)propanoic acid |
| 8-48 | Fmoc | H | 1 | H | 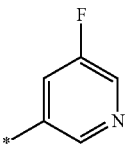 | H | 2-((((9H-Fluoren-9-yl)methoxy)carbonyl)amino)-3-(5-fluoropyridin-3-yl)propanoic acid |
| 8-49 | Fmoc | H | 1 | H | 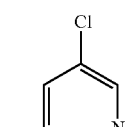 | H | 2-((((9H-Fluoren-9-yl)methoxy)carbonyl)amino)-3-(5-chloropyridin-3-yl)propanoic acid |
| 8-50 | Fmoc | H | 1 | H | 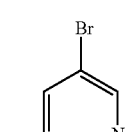 | H | 2-((((9H-Fluoren-9-yl)methoxy)carbonyl)amino)-3-(5-bromopyridin-3-yl)propanoic acid |

TABLE 8-continued

| Compound ID | R₁ | R₂ | n | R₃ | R₆ | R₇ | Compound Name |
|---|---|---|---|---|---|---|---|
| 8-51 | Fmoc | H | 1 | H | 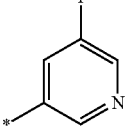 | H | 2-((((9H-Fluoren-9-yl)methoxy)carobnyl)amino)-3-(5-iodopyridin-3-yl)propanoic acid |
| 8-52 | Fmoc | H | 1 | H | 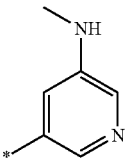 | H | 2-((((9H-Fluoren-9-yl)methoxy)carbonyl)amino)-3-(2-(methylamino)pyridin-4-yl)propanoic acid |
| 8-53 | Fmoc | H | 1 | H | 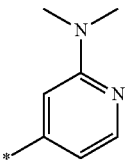 | H | 2-((((9H-Fluoren-9-yl)methoxy)carbonyl)amino)-3-(2-(dimethylamino)pyridin-4-yl)propanoic acid |
| 8-54 | Fmoc | H | 1 | H | 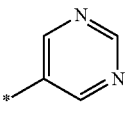 | H | 2-((((9H-Fluoren-9-yl)methoxy)carbonyl)amino)-3-(pyrimidin-5-yl)propanoic acid |

TABLE 9

| Compound ID | R₁ | R₂ | n | R₃ | R₆ | R₇ | Compound Name |
|---|---|---|---|---|---|---|---|
| 9-1 | Fmoc | Me | 1 | H | 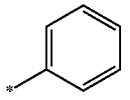 | H | N-(((9H-Fluoren-9-yl)methoxy)carbonyl)-N-methylphenylalanine |
| 9-2 | Fmoc | Me | 1 | H | 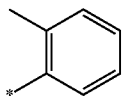 | H | 2-((((9H-Fluoren-9-yl)methoxy)carbonyl)(methyl)amino)-3-(o-tolyl)propanoic acid |
| 9-3 | Fmoc | Me | 1 | H | 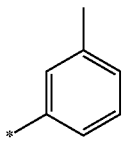 | H | 2-((((9H-Fluoren-9-yl)methoxy)carbonyl)(methyl)amino)-3-(m-tolyl)propanoic acid |
| 9-4 | Fmoc | Me | 1 | H | 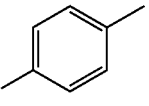 | H | 2-((((9H-Fluoren-9-yl)methoxy)carbonyl)(methyl)amino)-3-(p-tolyl)propanoic acid |
| 9-5 | Fmoc | Me | 1 | H | 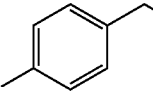 | H | 2-((((9H-Fluoren-9-yl)methoxy)carbonyl)(methyl)amino)-3-(4-ethylphenyl)propanoic acid |
| 9-6 | Fmoc | Me | 1 | H | 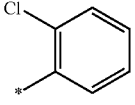 | H | 2-((((9H-Fluoren-9-yl)methoxy)carbonyl)(methyl)amino)-3-(2-chlorophenyl)propanoic acid |

TABLE 9-continued

| Compound ID | R₁ | R₂ | n | R₃ | R₆ | R₇ | Compound Name |
|---|---|---|---|---|---|---|---|
| 9-7 | Fmoc | Me | 1 | H | 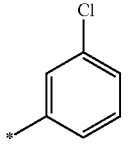 | H | 2-((((9H-Fluoren-9-yl)methoxy)carbonyl)(methyl)amino)-3-(3-chlorophenyl)propanoic acid |
| 9-8 | Fmoc | Me | 1 | H | 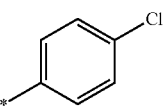 | H | 2-((((9H-Fluoren-9-yl)methoxy)carbonyl)(methyl)amino)-3-(4-chlorophenyl)propanoic acid |
| 9-9 | Fmoc | Me | 1 | H | 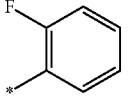 | H | 2-((((9H-Fluoren-9-yl)methoxy)carbonyl)(methyl)amino)-3-(2-fluorophenyl)propanoic acid |
| 9-10 | Fmoc | Me | 1 | H | 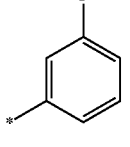 | H | 2-((((9H-Fluoren-9-yl)methoxy)carbonyl)(methyl)amino)-3-(3-fluorophenyl)propanoic acid |
| 9-11 | Fmoc | Me | 1 | H | 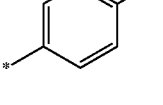 | H | 2-((((9H-Fluoren-9-yl)methoxy)carbonyl)(methyl)amino)-3-(4-fluorophenyl)propanoic acid |
| 9-12 | Fmoc | Me | 1 | H | 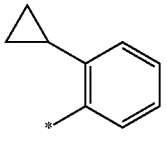 | H | 2-((((9H-Fluoren-9-yl)methoxy)carbonyl)(methyl)amino)-3-(2-cyclopropylphenyl)propanoic acid |
| 9-13 | Fmoc | Me | 1 | H | 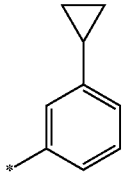 |  | 2-((((9H-Fluoren-9-yl)methoxy)carbonyl)(methyl)amino)-3-(3-cyclopropylphenyl)propanoic acid |
| 9-14 | Fmoc | Me | 1 | H | 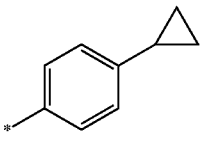 | H | 2-((((9H-Fluoren-9-yl)methoxy)carbonyl)(methyl)amino)-3-(4-cyclopropylphenyl)propanoic acid |
| 9-15 | Fmoc | Me | 1 | H | 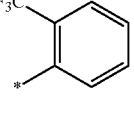 | H | 2-((((9H-Fluoren-9-yl)methoxy)carbonyl)(methyl)amino)-3-(2-(trifluoromethyl)phenyl)propanoic acid |
| 9-16 | Fmoc | Me | 1 | H | 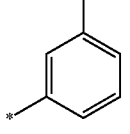 | H | 2-((((9H-Fluoren-9-yl)methoxy)carbonyl)(methyl)amino)-3-(3-(trifluoromethyl)phenyl)propanoic acid |

TABLE 9-continued

| Compound ID | R₁ | R₂ | n | R₃ | R₆ | R₇ | Compound Name |
|---|---|---|---|---|---|---|---|
| 9-17 | Fmoc | Me | 1 | H | 4-(trifluoromethyl)phenyl | H | 2-((((9H-Fluoren-9-yl)methoxy)carbonyl)(methyl)amino)-3-(4-(trifluoromethyl)phenyl)propanoic acid |
| 9-18 | Fmoc | Me | 1 | H | 2-isopropylphenyl | H | 2-((((9H-Fluoren-9-yl)methoxy)carbonyl)(methyl)amino)-3-(2-isopropylphenyl)propanoic acid |
| 9-19 | Fmoc | Me | 1 | H | 3-isopropylphenyl | H | 2-((((9H-Fluoren-9-yl)methoxy)carbonyl)(methyl)amino)-3-(3-isopropylphenyl)propanoic acid |
| 9-20 | Fmoc | Me | 1 | H | 4-isopropylphenyl | H | 2-((((9H-Fluoren-9-yl)methoxy)carbonyl)(methyl)amino)-3-(4-isopropylphenyl)propanoic acid |
| 9-21 | Fmoc | Me | 1 | H | 2-methoxyphenyl | H | 2-((((9H-Fluoren-9-yl)methoxy)carbonyl)(methyl)amino)-3-(2-methoxyphenyl)propanoic acid |
| 9-22 | Fmoc | Me | 1 | H | 3-methoxyphenyl | H | 2-((((9H-Fluoren-9-yl)methoxy)carbonyl)(methyl)amino)-3-(3-methoxyphenyl)propanoic acid |
| 9-23 | Fmoc | Me | 1 | H | 4-methoxyphenyl | H | 2-((((9H-Fluoren-9-yl)methoxy)carbonyl)(methyl)amino)-3-(4-methoxyphenyl)propanoic acid |
| 9-24 | Fmoc | Me | 1 | H | 2-(allyloxy)phenyl | H | 2-((((9H-Fluoren-9-yl)methoxy)carbonyl)(methyl)amino)-3-(2-(allyloxy)phenyl)propanoic acid |
| 9-25 | Fmoc | Me | 1 | H | 3-(allyloxy)phenyl | H | 2-((((9H-Fluoren-9-yl)methoxy)carbonyl)(methyl)amino)-3-(3-(allyloxy)phenyl)propanoic acid |

TABLE 9-continued

| Compound ID | R₁ | R₂ | n | R₃ | R₆ | R₇ | Compound Name |
|---|---|---|---|---|---|---|---|
| 9-26 | Fmoc | Me | 1 | H | 4-(allyloxy)phenyl | H | 2-((((9H-Fluoren-9-yl)methoxy)carbonyl)(methyl)amino)-3-(4-(allyloxy)phenyl)propanoic acid |
| 9-27 | Fmoc | Me | 1 | H | 4-isopropoxyphenyl | H | 2-((((9H-Fluoren-9-yl)methoxy)carbonyl)(methyl)amino)-3-(4-isopropoxyphenyl)propanoic acid |
| 9-28 | Fmoc | Me | 1 | H | 3-fluoro-4-(trifluoromethyl)phenyl | H | 2-((((9H-Fluoren-9-yl)methoxy)carbonyl)(methyl)amino)-3-(3-fluoro-4-(trifluoromethyl)phenyl)propanoic acid |
| 9-29 | Fmoc | Me | 1 | H | 2-fluoro-4-(trifluoromethyl)phenyl | H | 2-((((9H-Fluoren-9-yl)methoxy)carbonyl)(methyl)amino)-3-(2-fluoro-4-(trifluoromethyl)phenyl)propanoic acid |
| 9-30 | Fmoc | Me | 1 | H | 3,4-dimethoxyphenyl | H | 2-((((9H-Fluoren-9-yl)methoxy)carbonyl)(methyl)amino)-3-(3,4-dimethoxyphenyl)propanoic acid |
| 9-31 | Fmoc | Me | 1 | H | 2-fluoro-4-methoxyphenyl | H | 2-((((9H-Fluoren-9-yl)methoxy)carbonyl)(methyl)amino)-3-(2-fluoro-4-methoxyphenyl)propanoic acid |
| 9-32 | Fmoc | Me | 1 | H | 3-fluoro-4-methoxyphenyl | H | 2-((((9H-Fluoren-9-yl)methoxy)carbonyl)(methyl)amino)-3-(3-fluoro-4-methoxyphenyl)propanoic acid |
| 9-33 | Fmoc | Me | 1 | H | 3,5-difluoro-4-methoxyphenyl | H | 2-((((9H-Fluoren-9-yl)methoxy)carbonyl)(methyl)amino)-3-(3,5-difluoro-4-methoxyphenyl)propanoic acid |
| 9-34 | Fmoc | Me | 1 | H | 3,5-difluoro-4-(trifluoromethyl)phenyl | H | 2-((((9H-Fluoren-9-yl)methoxy)carbonyl)(methyl)amino)-3-(3,5-difluoro-4-(trifluoromethyl)phenyl)propanoic acid |

TABLE 9-continued

| Compound ID | R₁ | R₂ | n | R₃ | R₆ | R₇ | Compound Name |
|---|---|---|---|---|---|---|---|
| 9-35 | Fmoc | Me | 1 | H | | H | 2-((((9H-Fluoren-9-yl)methoxy)carbonyl)(methyl)amino)-3-(3-methoxy-4-(methylcarbamoyl)phenyl)propanoic acid |
| 9-36 | Fmoc | Me | 1 | H | | H | 2-((((9H-Fluoren-9-yl)methoxy)carbonyl)(methyl)amino)-3-(4-methoxy-3-(methylcarbamoyl)phenyl)propanoic acid |
| 9-37 | Fmoc | Me | 1 | H | | H | 2-((((9H-Fluoren-9-yl)methoxy)carbonyl)(methyl)amino)-3-(3-methoxy-4-((methylsulfonyl)carbamoyl)phenyl)propanoic acid |
| 9-38 | Fmoc | Me | 1 | H | | H | 2-((((9H-Fluoren-9-yl)methoxy)carbonyl)(methyl)amino)-3-(4-(methyl((tetrahydro-2H-pyran-4-yl)oxy)carbamoyl)phenyl)propanoic acid |
| 9-39 | Fmoc | Me | 1 | H | | H | 2-((((9H-Fluoren-9-yl)methoxy)carbonyl)(methyl)amino)-3-(3-methoxy-4-(((tetrahydro-2H-pyran-2-yl)oxy)carbamoyl)phenyl)propanoic acid |
| 9-40 | Fmoc | Me | 1 | H | | H | 2-((((9H-Fluoren-9-yl)methoxy)carbonyl)(methyl)amino)-3-(pyridin-2-yl)propanoic acid |
| 9-41 | Fmoc | Me | 1 | H | | H | 2-((((9H-Fluoren-9-yl)methoxy)carbonyl)(methyl)amino)-3-(pyridin-3-yl)propanoic acid |
| 9-42 | Fmoc | Me | 1 | H | | H | 2-((((9H-Fluoren-9-yl)methoxy)carbonyl)(methyl)amino)-3-(pyridin-4-yl)propanoic acid |
| 9-43 | Fmoc | Me | 1 | H | | H | 2-((((9H-Fluoren-9-yl)methoxy)carbonyl)(methyl)amino)-3-(6-methylpyridin-3-yl)propanoic acid |
| 9-44 | Fmoc | Me | 1 | H | | H | 2-((((9H-Fluoren-9-yl)methoxy)carbonyl)(methyl)amino)-3-(5-methylpyridin-3-yl)propanoic acid |

TABLE 9-continued

| Compound ID | R₁ | R₂ | n | R₃ | R₆ | R₇ | Compound Name |
|---|---|---|---|---|---|---|---|
| 9-45 | Fmoc | Me | 1 | H | 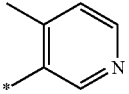 | H | 2-((((9H-Fluoren-9-yl)methoxy)carbonyl)(methyl)amino)-3-(4-methylpyridin-3-yl)propanoic acid |
| 9-46 | Fmoc | Me | 1 | H | 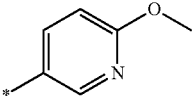 | H | 2-((((9H-Fluoren-9-yl)methoxy)carbonyl)(methyl)amino)-3-(6-methoxypyridin-3-yl)propanoic acid |
| 9-47 | Fmoc | Me | 1 | H | 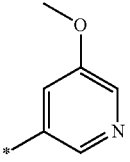 | H | 2-((((9H-Fluoren-9-yl)methoxy)carbonyl)(methyl)amino)-3-(5-methoxypyridin-3-yl)propanoic acid |
| 9-48 | Fmoc | Me | 1 | H | 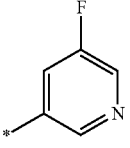 | H | 2-((((9H-Fluoren-9-yl)methoxy)carbonyl)(methyl)amino)-3-(5-fluoropyridin-3-yl)propanoic acid |
| 9-49 | Fmoc | Me | 1 | H | 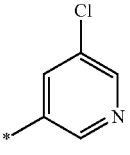 | H | 2-((((9H-Fluoren-9-yl)methoxy)carbonyl)(methyl)amino)-3-(5-chloropyridin-3-yl)propanoic acid |
| 9-50 | Fmoc | Me | 1 | H | 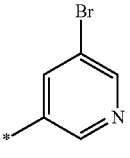 | H | 2-((((9H-Fluoren-9-yl)methoxy)carbonyl)(methyl)amino)-3-(5-bromopyridin-3-yl)propanoic acid |
| 9-51 | Fmoc | Me | 1 | H | 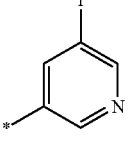 | H | 2-((((9H-Fluoren-9-yl)methoxy)carbonyl)(methyl)amino)-3-(5-iodopyridin-3-yl)propanoic acid |
| 9-52 | Fmoc | Me | 1 | H | 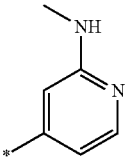 | H | 2-((((9H-Fluoren-9-yl)methoxy)carbonyl)(methyl)amino)-3-(2-(methylamino)pyridin-4-yl)propanoic acid |
| 9-53 | Fmoc | Me | 1 | H | 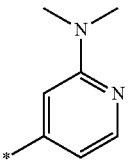 | H | 2-((((9H-Fluoren-9-yl)methoxy)carbonyl)(methyl)amino)-3-(2-(dimethylamino)pyridin-4-yl)propanoic acid |

TABLE 9-continued

| Compound ID | R₁ | R₂ | n | R₃ | R₆ | R₇ | Compound Name |
|---|---|---|---|---|---|---|---|
| 9-54 | Fmoc | Me | 1 | H | 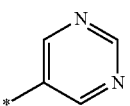 | H | 2-((((9H-Fluoren-9-yl)methoxy)carbonyl)(methyl)amino)-3-(pyrimidin-5-yl)propanoic acid |

TABLE 10

| Compound ID | R₁ | R₂ | n | R₃ | R₆ | R₇ | Compound Name |
|---|---|---|---|---|---|---|---|
| 10-1 | H | H | 2 | H | 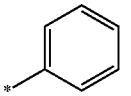 | H | 2-Amino-4-phenylbutanoic acid |
| 10-2 | H | H | 2 | H | 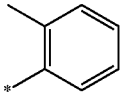 | H | 2-Amino-4-(o-tolyl)butanoic acid |
| 10-3 | H | H | 2 | H | 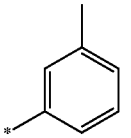 | H | 2-Amino-4-(m-tolyl)butanoic acid |
| 10-4 | H | H | 2 | H | 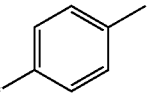 | H | 2-Amino-4-(p-tolyl)butanoic acid |
| 10-5 | H | H | 2 | H | 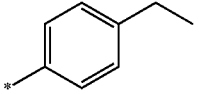 | H | 2-Amino-4-(4-ethylphenyl)butanoic acid |
| 10-6 | H | H | 2 | H | 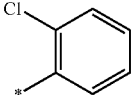 | H | 2-Amino-4-(2-chlorophenyl)butanoic acid |
| 10-7 | H | H | 2 | H | 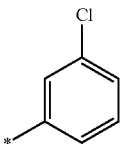 | H | 2-Amino-4-(3-chlorophenyl)butanoic acid |
| 10-8 | H | H | 2 | H | 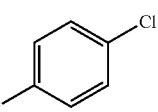 | H | 2-Amino-4-(4-chlorophenyl)butanoic acid |
| 10-9 | H | H | 2 | H | 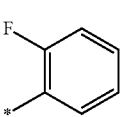 | H | 2-Amino-4-(2-fluorophenyl)butanoic acid |

TABLE 10-continued

| Compound ID | R₁ | R₂ | n | R₃ | R₆ | R₇ | Compound Name |
|---|---|---|---|---|---|---|---|
| 10-10 | H | H | 2 | H | 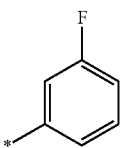 | H | 2-Amino-4-(3-fluorophenyl)butanoic acid |
| 10-11 | H | H | 2 | H | 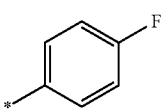 | H | 2-Amino-4-(4-fluorophenyl)butanoic acid |
| 10-12 | H | H | 2 | H | 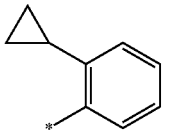 | H | 2-Amino-4-(2-cyclopropylphenyl)butanoic acid |
| 10-13 | H | H | 2 | H | 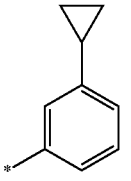 | H | 2-Amino-4-(3-cyclopropylphenyl)butanoic acid |
| 10-14 | H | H | 2 | H | 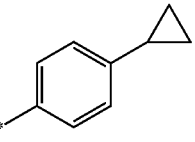 | H | 2-Amino-4-(4-cyclopropylphenyl)butanoic acid |
| 10-15 | H | H | 2 | H | 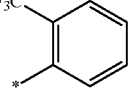 | H | 2-Amino-4-(2-(trifluoromethyl)phenyl)butanoic acid |
| 10-16 | H | H | 2 | H | 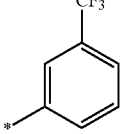 | H | 2-Amino-4-(3-(trifluoromethyl)phenyl)butanoic acid |
| 10-17 | H | H | 2 | H | 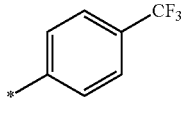 | H | 2-Amino-4-(4-(trifluoromethyl)phenyl)butanoic acid |
| 10-18 | H | H | 2 | H | 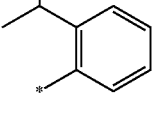 | H | 2-Amino-4-(2-isopropylphenyl)butanoic acid |
| 10-19 | H | H | 2 | H | 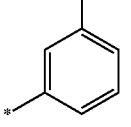 | H | 2-Amino-4-(3-isopropylphenyl)butanoic acid |

TABLE 10-continued

| Compound ID | R₁ | R₂ | n | R₃ | R₆ | R₇ | Compound Name |
|---|---|---|---|---|---|---|---|
| 10-20 | H | H | 2 | H | 4-isopropylphenyl | H | 2-Amino-4-(4-isopropylphenyl)butanoic acid |
| 10-21 | H | H | 2 | H | 2-methoxyphenyl | H | 2-Amino-4-(2-methoxypehnyl)butanoic acid |
| 10-22 | H | H | 2 | H | 3-methoxyphenyl | H | 2-Amino-4-(3-methoxyphenyl)butanoic acid |
| 10-23 | H | H | 2 | H | 4-methoxyphenyl | H | 2-Amino-4-(4-methoxyphenyl)butanoic acid |
| 10-24 | H | H | 2 | H | 2-(allyloxy)phenyl | H | 2-Amino-4-(2-(allyloxy)phenyl)butanoic acid |
| 10-25 | H | H | 2 | H | 3-(allyloxy)phenyl | H | 2-Amino-4-(3-(allyloxy)phenyl)butanoic acid |
| 10-26 | H | H | 2 | H | 4-(allyloxy)phenyl | H | 2-Amino-4-(4-(allyloxy)phenyl)butanoic acid |
| 10-27 | H | H | 2 | H | 4-isopropoxyphenyl | H | 2-Amino-4-(4-isopropoxyphenyl)butanoic acid |
| 10-28 | H | H | 2 | H | 3-fluoro-4-(trifluoromethyl)phenyl | H | 2-Amino-4-(3-fluoro-4-(trifluoromethyl-phenyl)butanoic acid |

TABLE 10-continued

| Compound ID | R₁ | R₂ | n | R₃ | R₆ | R₇ | Compound Name |
|---|---|---|---|---|---|---|---|
| 10-29 | H | H | 2 | H | 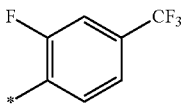 | H | 2-Amino-4-(2-fluoro-4-(trifluoromethyl)phenyl)butanoic acid |
| 10-30 | H | H | 2 | H | 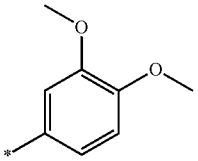 | H | 2-Amino-4-(3,4-dimethoxyphenyl)butanoic acid |
| 10-31 | H | H | 2 | H | 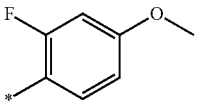 | H | 2-Amino-4-(2-fluoro-4-methoxyphenyl)butanoic acid |
| 10-32 | H | H | 2 | H | 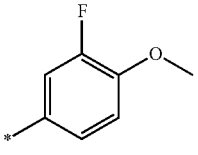 | H | 2-Amino-4-(3-fluoro-4-methoxyphenyl)butanoic acid |
| 10-33 | H | H | 2 | H | 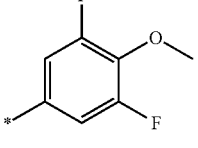 | H | 2-Amino-4-(3,5-difluoro-4-methoxyphenyl)butanoic acid |
| 10-34 | H | H | 2 | H | 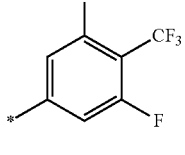 | H | 2-Amino-4-(3,5-difluoro-4-(trifluoromethyl)phenyl)butanoic acid |
| 10-35 | H | H | 2 | H | 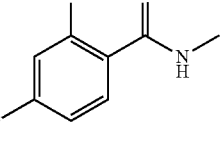 | H | 2-Amino-4-(3-methoxy-4-(methylcarbamoyl)phenyl)butanoic acid |
| 10-36 | H | H | 2 | H | 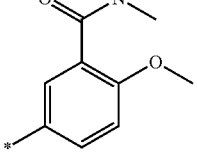 | H | 2-Amino-4-(4-methoxy-3-(methylcarbamoyl)phenyl)butanoic acid |
| 10-37 | H | H | 2 | H | 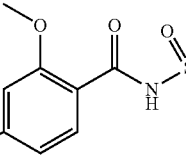 | H | 2-Amino-4-(3-methoxy-4-((methylsulfonyl)carbamoyl)phenyl)butanoic acid |

TABLE 10-continued

| Compound ID | R₁ | R₂ | n | R₃ | R₆ | R₇ | Compound Name |
|---|---|---|---|---|---|---|---|
| 10-38 | H | H | 2 | H | 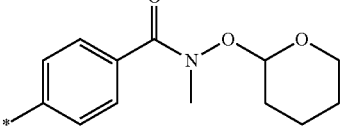 | H | 2-Amino-4-(4-(methyl((tetrahydro-2H-pyran-2-yl)oxy)carbamoyl)phenyl)butanoic acid |
| 10-39 | H | H | 2 | H | 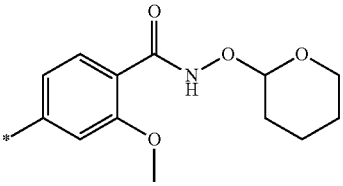 | H | 2-Amino-4-(3-methoxy-4-(((tetrahydro-2H-pyran-2-yl)oxy)carbamoyl)phenyl)butanoic acid |
| 10-40 | H | H | 2 | H | 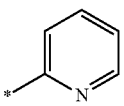 | H | 2-Amino-4-(pyridin-2-yl)butanoic acid |
| 10-41 | H | H | 2 | H | 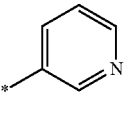 [SMILES: *c1cccnc1] | H | 2-Amino-4-(pyridin-3-yl)butanoic acid |
| 10-42 | H | H | 2 | H | 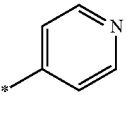 [SMILES: *c1ccncc1] | H | 2-Amino-4-(pyridin-4-yl)butanoic acid |
| 10-43 | H | H | 2 | H | 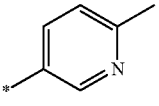 | H | 2-Amino-4-(6-methylpyridin-3-yl)butanoic acid |
| 10-44 | H | H | 2 | H | 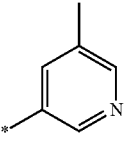 [SMILES: *c1cncc(C)c1] | H | 2-Amino-4-(5-methylpyridin-3-yl)butanoic acid |
| 10-45 | H | H | 2 | H | 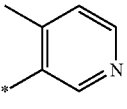 [SMILES: *c1cnccc1C] | H | 2-Amino-4-(4-methylpyridin-3-yl)butanoic acid |
| 10-46 | H | H | 2 | H | 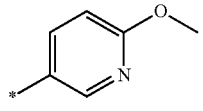 [SMILES: *c1ccc(OC)nc1] | H | 2-Amino-4-(6-methoxypyridin-3-yl)butanoic acid |
| 10-47 | H | H | 2 | H | 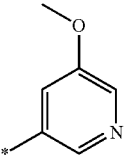 [SMILES: *c1cncc(OC)c1] | H | 2-Amino-4-(5-methoxypyridin-3-yl)butanoic acid |
| 10-48 | H | H | 2 | H | 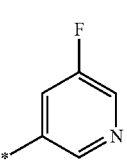 [SMILES: *c1cncc(F)c1] | H | 2-Amino-4-(5-fluoropyridin-3-yl)butanoic acid |

TABLE 10-continued

| Compound ID | R1 | R2 | n | R3 | R6 | R7 | Compound Name |
|---|---|---|---|---|---|---|---|
| 10-49 | H | H | 2 | H | 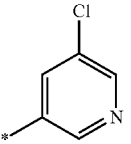 [SMILES: *c1cncc(Cl)c1] | H | 2-Amino-4-(5-chloropyridin-3-yl)butanoic acid |
| 10-50 | H | H | 2 | H | 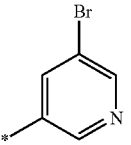 | H | 2-Amino-4-(5-bromopyridin-3-yl)butanoic acid |
| 10-51 | H | H | 2 | H | 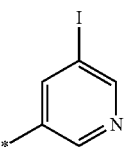 [SMILES: *c1cncc(I)c1] | H | 2-Amino-4-(5-iodopyridin-3-yl)butanoic acid |
| 10-52 | H | H | 2 | H | 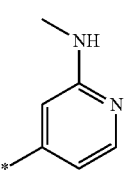 [SMILES: *c1ccnc(NC)c1] | H | 2-Amino-4-(2-(methylamino)pyridin-4-yl)butanoic acid |
| 10-53 | H | H | 2 | H | 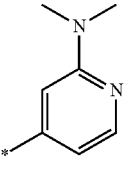 | H | 2-Amino-4-(2-(dimethylamino)pyridin-4-yl)butanoic acid |
| 10-54 | H | H | 2 | H | 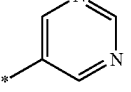 | H | 2-Amino-4-(pyrimidin-5-yl)butanoic acid |

TABLE 11

| Compound ID | R1 | R2 | n | R3 | R6 | R7 | Compound Name |
|---|---|---|---|---|---|---|---|
| 11-1 | H | Me | 2 | H | 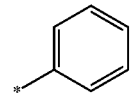 | H | 2-(Methylamino)-4-phenylbutanoic acid |
| 11-2 | H | Me | 2 | H | 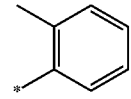 | H | 2-(Methylamino)-4-(o-tolyl)butanoic acid |
| 11-3 | H | Me | 2 | H | 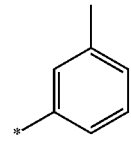 | H | 2-(Methylamino)-4-(m-tolyl)butanoic acid |

TABLE 11-continued

| Compound ID | R₁ | R₂ | n | R₃ | R₆ | R₇ | Compound Name |
|---|---|---|---|---|---|---|---|
| 11-4 | H | Me | 2 | H | 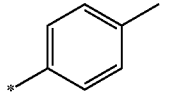 | H | 2-(Methylamino)-4-(p-tolyl)butanoic acid |
| 11-5 | H | Me | 2 | H | 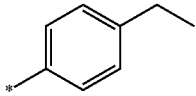 | H | 2-(Methylamino)-4-(4-ethylphenyl)butanoic acid |
| 11-6 | H | Me | 2 | H | 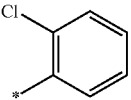 | H | 2-(Methylamino)-4-(2-chlorophenyl)butanoic acid |
| 11-7 | H | Me | 2 | H | 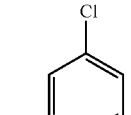 | H | 2-(Methylamino)-4-(3-chlorophenyl)butanoic acid |
| 11-8 | H | Me | 2 | H | 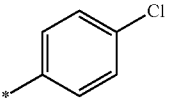 | H | 2-(Methylamino)-4-(4-chlorophenyl)butanoic acid |
| 11-9 | H | Me | 2 | H | 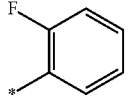 | H | 2-(Methylamino)-4-(2-fluorophenyl)butanoic acid |
| 11-10 | H | Me | 2 | H | 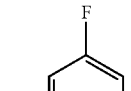 | H | 2-(Methylamino)-4-(3-fluorophenyl)butanoic acid |
| 11-11 | H | Me | 2 | H | 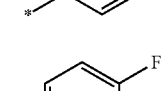 | H | 2-(Methylamino)-4-(4-fluorophenyl)butanoic acid |
| 11-12 | H | Me | 2 | H | 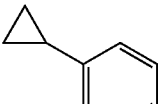 | H | 2-(Methylamino)-4-(2-cyclopropylphenyl)butanoic acid |
| 11-13 | H | Me | 2 | H | 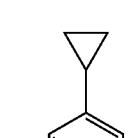 | H | 2-(Methylamino)-4-(3-cyclopropylphenyl)butanoic acid |
| 11-14 | H | Me | 2 | H | 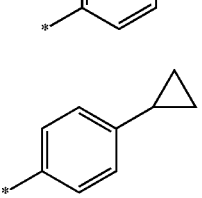 | H | 2-(Methylamino)-4-(4-cyclopropylphenyl)butanoic acid |

TABLE 11-continued

| Compound ID | R₁ | R₂ | n | R₃ | R₆ | R₇ | Compound Name |
|---|---|---|---|---|---|---|---|
| 11-15 | H | Me | 2 | H | 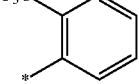 | H | 2-(Methylamino)-4-(2-(trifluoromethyl)phenyl)butanoic acid |
| 11-16 | H | Me | 2 | H | 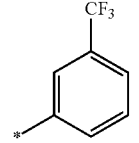 | H | 2-(Methylamino)-4-(3-(trifluoromethyl)phenyl)butanoic acid |
| 11-17 | H | Me | 2 | H | 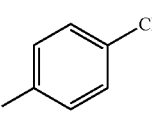 | H | 2-(Methylamino)-4-(4-(trifluoromethyl)phenyl)butanoic acid |
| 11-18 | H | Me | 2 | H | 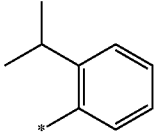 | H | 2-(Methylamino)-4-(2-isopropylphenyl)butanoic acid |
| 11-19 | H | Me | 2 | H | 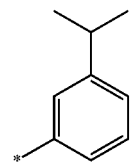 | H | 2-(Methylamino)-4-(3-isopropylphenyl)butanoic acid |
| 11-20 | H | Me | 2 | H | 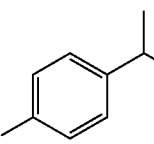 | H | 2-(Methylamino)-4-(4-isopropylphenyl)butanoic acid |
| 11-21 | H | Me | 2 | H | 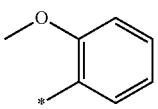 | H | 2-(Methylamino)-4-(2-methoxyphenyl)butanoic acid |
| 11-22 | H | Me | 2 | H | 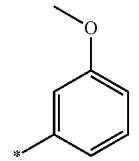 | H | 2-(Methylamino)-4-(3-methoxyphenyl)butanoic acid |
| 11-23 | H | Me | 2 | H | 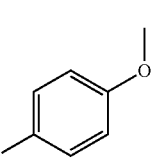 | H | 2-(Methylamino)-4-(4-methoxyphenyl)butanoic acid |
| 11-24 | H | Me | 2 | H | 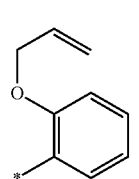 | H | 2-(Methylamino)-4-(2-(allyloxy)phenyl)butanoic acid |

TABLE 11-continued

| Compound ID | R₁ | R₂ | n | R₃ | R₆ | R₇ | Compound Name |
|---|---|---|---|---|---|---|---|
| 11-25 | H | Me | 2 | H | 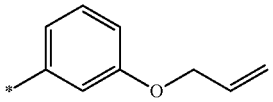 | H | 2-(Methylamino)-4-(3-(allyloxy)phenyl)butanoic acid |
| 11-26 | H | Me | 2 | H | 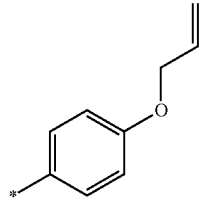 | H | 2-(Methylamino)-4-(4-(allyloxy)phenyl)butanoic acid |
| 11-27 | H | Me | 2 | H | 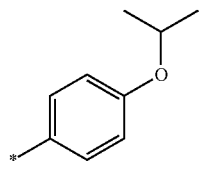 | H | 2-(Methylamino)-4-(4-isopropoxyphenyl)butanoic acid |
| 11-28 | H | Me | 2 | H | 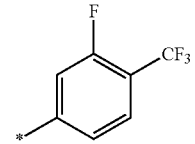 | H | 2-(Methylamino)-4-(3-fluoro-4-(trifluoromethyl)phenyl)butanoic acid |
| 11-29 | H | Me | 2 | H | 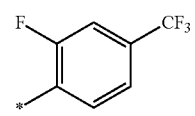 | H | 2-(Methylamino)-4-(2-fluoro-4-(trifluoromethyl)phenyl)butanoic acid |
| 11-30 | H | Me | 2 | H | 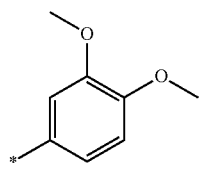 | H | 2-(Methylamino)-4-(3,4-dimethoxyphenyl)butanoic acid |
| 11-31 | H | Me | 2 | H | 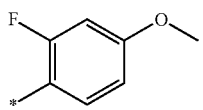 | H | 2-(Methylamino)-4-(2-fluoro-4-methoxyphenyl)butanoic acid |
| 11-32 | H | Me | 2 | H | 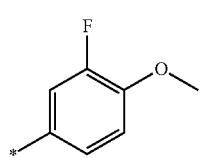 | H | 2-(Methylamino)-4-(3-fluoro-4-methoxyphenyl)butanoic acid |
| 11-33 | H | Me | 2 | H | 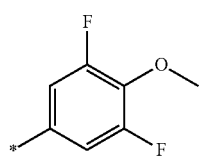 | H | 2-(Methylamino)-4-(3,5-difluoro-4-methoxyphenyl)butanoic acid |

TABLE 11-continued

| Compound ID | R₁ | R₂ | n | R₃ | R₆ | R₇ | Compound Name |
|---|---|---|---|---|---|---|---|
| 11-34 | H | Me | 2 | H | 3,5-difluoro-4-(trifluoromethyl)phenyl | H | 2-(Methylamino)-4-(3,5-difluoro-4-(trifluoromethyl)phenyl)butanoic acid |
| 11-35 | H | Me | 2 | H | 3-methoxy-4-(methylcarbamoyl)phenyl | H | 2-(Methylamino)-4-(3-methoxy-4-(methylcarbamoyl)phenyl)butanoic acid |
| 11-36 | H | Me | 2 | H | 4-methoxy-3-(methylcarbamoyl)phenyl | H | 2-(Methylamino)-4-(4-methoxy-3-(methylcarbamoyl)phenyl)butanoic acid |
| 11-37 | H | Me | 2 | H | 3-methoxy-4-((methylsulfonyl)carbamoyl)phenyl | H | 2-(Methylamino)-4-(3-methoxy-4-((methylsulfonyl)carbamoyl)phenyl)butanoic acid |
| 11-38 | H | Me | 2 | H | 4-(methyl((tetrahydro-2H-pyran-2-yl)oxy)carbamoyl)phenyl | H | 2-(Methylamino)-4-(4-(methyl((tetrahydro-2H-pyran-2-yl)oxy)carbamoyl)phenyl)butanoic acid |
| 11-39 | H | Me | 2 | H | 3-methoxy-4-((tetrahydro-2H-pyran-2-yl)oxy)carbamoyl)phenyl | H | 2-(Methylamino)-4-(3-methoxy-4-((tetrahydro-2H-pyran-2-yl)oxy)carbamoyl)phenyl)butanoic acid |
| 11-40 | H | Me | 2 | H | pyridin-2-yl | H | 2-(Methylamino)-4-(pyridin-2-yl)butanoic acid |
| 11-41 | H | Me | 2 | H | pyridin-3-yl | H | 2-(Methylamino)-4-(pyridin-3-yl)butanoic acid |
| 11-42 | H | Me | 2 | H | pyridin-4-yl | H | 2-(Methylamino)-4-(pyridin-4-yl)butanoic acid |
| 11-43 | H | Me | 2 | H | 6-methylpyridin-3-yl | H | 2-(Methylamino)-4-(6-methylpyridin-3-yl)butanoic acid |

TABLE 11-continued

| Compound ID | R₁ | R₂ | n | R₃ | R₆ | R₇ | Compound Name |
|---|---|---|---|---|---|---|---|
| 11-44 | H | Me | 2 | H | 5-methylpyridin-3-yl | H | 2-(Methylamino)-4-(5-methylpyridin-3-yl)butanoic acid |
| 11-45 | H | Me | 2 | H | 4-methylpyridin-3-yl | H | 2-(Methylamino)-4-(4-methylpyridin-3-yl)butanoic acid |
| 11-46 | H | Me | 2 | H | 6-methoxypyridin-3-yl | H | 2-(Methylamino)-4-(6-methoxypyridin-3-yl)butanoic acid |
| 11-47 | H | Me | 2 | H | 5-methoxypyridin-3-yl | H | 2-(Methylamino)-4-(5-methoxypyridin-3-yl)butanoic acid |
| 11-48 | H | Me | 2 | H | 5-fluoropyridin-3-yl | H | 2-(Methylamino)-4-(5-fluoropyridin-3-yl)butanoic acid |
| 11-49 | H | Me | 2 | H | 5-chloropyridin-3-yl | H | 2-(Methylamino)-4-(5-chloropyridin-3-yl)butanoic acid |
| 11-50 | H | Me | 2 | H | 5-bromopyridin-3-yl | H | 2-(Methylamino)-4-(5-bromopyridin-3-yl)butanoic acid |
| 11-51 | H | Me | 2 | H | 5-iodopyridin-3-yl | H | 2-(Methylamino)-4-(5-iodopyridin-3-yl)butanoic acid |
| 11-52 | H | Me | 2 | H | 2-(methylamino)pyridin-4-yl | H | 2-(Methylamino)-4-(2-(methylamino)pyridin-4-yl)butanoic acid |

TABLE 11-continued

| Compound ID | R₁ | R₂ | n | R₃ | R₆ | R₇ | Compound Name |
|---|---|---|---|---|---|---|---|
| 11-53 | H | Me | 2 | H | 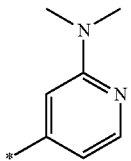 [SMILES: *c1ccnc(N(C)C)c1] | H | 2-(Methylamino)-4-(2-(dimethylamino)pyridin-4-yl)butanoic acid |
| 11-54 | H | Me | 2 | H | 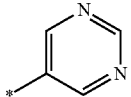 [SMILES: *c1cncnc1] | H | 2-(Methylamino)-4-(pyrimidin-5-yl)butanoic acid |

TABLE 12

| Compound ID | R₁ | R₂ | n | R₃ | R₆ | R₇ | Compound Name |
|---|---|---|---|---|---|---|---|
| 12-1 | H | H | 1 | H | 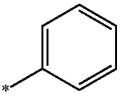 | H | Phenylalanine |
| 12-2 | H | H | 1 | H | 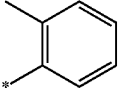 [SMILES: *c1ccccc1C] | H | 2-Amino-3-(o-tolyl)propanoic acid |
| 12-3 | H | H | 1 | H | 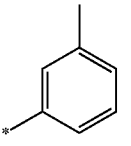 [SMILES: *c1cccc(C)c1] | H | 2-Amino-3-(m-tolyl)propanoic acid |
| 12-4 | H | H | 1 | H | 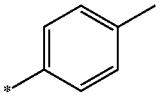 | H | 2-Amino-3-(p-tolyl)propanoic acid |
| 12-5 | H | H | 1 | H | 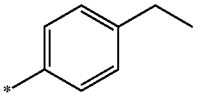 [SMILES: *c1ccc(CC)cc1] | H | 2-Amino-3-(4-ethylphenyl)propanoic acid |
| 12-6 | H | H | 1 | H | 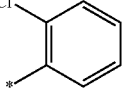 | H | 2-Amino-3-(2-chlorophenyl)propanoic acid |
| 12-7 | H | H | 1 | H | 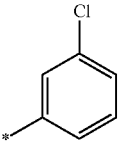 [SMILES: *c1cccc(Cl)c1] | H | 2-Amino-3-(3-chlorophenyl)propanoic acid |
| 12-8 | H | H | 1 | H | 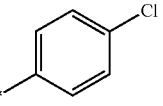 | H | 2-Amino-3-(4-chlorophenyl)propanoic acid |

TABLE 12-continued

| Compound ID | $R_1$ | $R_2$ | n | $R_3$ | $R_6$ | $R_7$ | Compound Name |
|---|---|---|---|---|---|---|---|
| 12-9 | H | H | 1 | H | 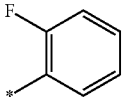 | H | 2-Amino-3-(2-fluorophenyl)propanoic acid |
| 12-10 | H | H | 1 | H | 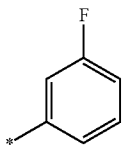 [SMILES: *c1cccc(F)c1] | H | 2-Amino-3-(3-fluorophenyl)propanoic acid |
| 12-11 | H | H | 1 | H | 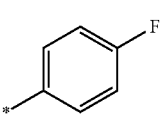 [SMILES: *c1ccc(F)cc1] | H | 2-Amino-3-(4-fluorophenyl)propanoic acid |
| 12-12 | H | H | 1 | H | 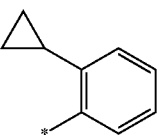 [SMILES: *c1ccccc1C1CC1] | H | 2-Amino-3-(2-cyclopropylphenyl)propanoic acid |
| 12-13 | H | H | 1 | H | 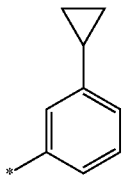 [SMILES: *c1cccc(C2CC2)c1] | H | 2-Amino-3-(3-cyclopropylphenyl)propanoic acid |
| 12-14 | H | H | 1 | H | 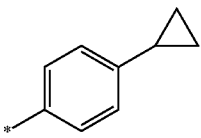 [SMILES: *c1ccc(C2CC2)cc1] | H | 2-Amino-3-(4-cyclopropylphenyl)propanoic acid |
| 12-15 | H | H | 1 | H | 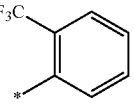 | H | 2-Amino-3-(2-(trifluoromethyl)phenyl)propanoic acid |
| 12-16 | H | H | 1 | H | 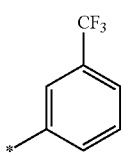 | H | 2-Amino-3-(3-(trifluoromethyl)phenyl)propanoic acid |
| 12-17 | H | H | 1 | H | 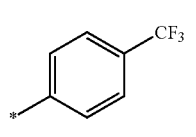 | H | 2-Amino-3-(4-(trifluoromethyl)phenyl)propanoic acid |
| 12-18 | H | H | 1 | H | 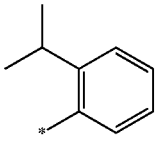 [SMILES: *c1ccccc1C(C)C] | H | 2-Amino-3-(2-isopropylphenyl)propanoic acid |

TABLE 12-continued

| Compound ID | R₁ | R₂ | n | R₃ | R₆ | R₇ | Compound Name |
|---|---|---|---|---|---|---|---|
| 12-19 | H | H | 1 | H | 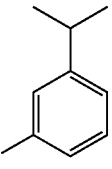 | H | 2-Amino-3-(3-isopropylphenyl)propanoic acid |
| 12-20 | H | H | 1 | H | 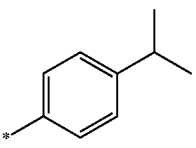 [SMILES: *c1ccc(C(C)C)cc1] | H | 2-Amino-3-(4-isopropylphenyl)propanoic acid |
| 12-21 | H | H | 1 | H | 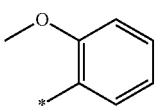 | H | 2-Amino-3-(2-methoxyphenyl)propanoic acid |
| 12-22 | H | H | 1 | H | 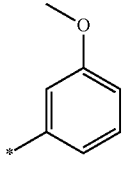 [SMILES: *c1cccc(OC)c1] | H | 2-Amino-3-(3-methoxyphenyl)propanoic acid |
| 12-23 | H | H | 1 | H | 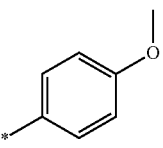 | H | 2-Amino-3-(4-methoxyphenyl)propanoic acid |
| 12-24 | H | H | 1 | H | 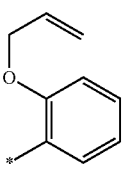 [SMILES: *c1ccccc1OCC=C] | H | 2-Amino-3-(2-(allyloxy)phenyl)propanoic acid |
| 12-25 | H | H | 1 | H | 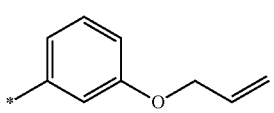 | H | 2-Amino-3-(3-(allyloxy)phenyl)propanoic acid |
| 12-26 | H | H | 1 | H | 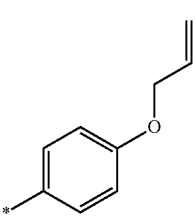 | H | 2-Amino-3-(4-(allyloxy)phenyl)propanoic acid |
| 12-27 | H | H | 1 | H | 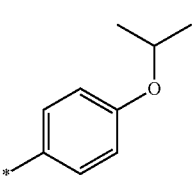 [SMILES: *c1ccc(OC(C)C)cc1] | H | 2-Amino-3-(4-isopropoxyphenyl)propanoic acid |

TABLE 12-continued

| Compound ID | R$_1$ | R$_2$ | n | R$_3$ | R$_6$ | R$_7$ | Compound Name |
|---|---|---|---|---|---|---|---|
| 12-28 | H | H | 1 | H | 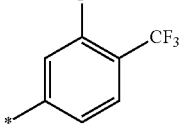 | H | 2-Amino-3-(3-fluoro-4-(trifluoromethyl)phenyl)propanoic acid |
| 12-29 | H | H | 1 | H | 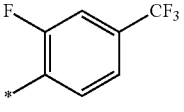 | H | 2-Amino-3-(2-fluoro-4-(trifluoromethyl)phenyl)propanoic acid |
| 12-30 | H | H | 1 | H | 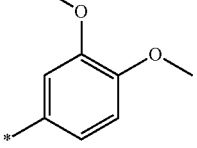 | H | 2-Amino-3-(3,4-dimethoxyphenyl)propanoic acid |
| 12-31 | H | H | 1 | H | 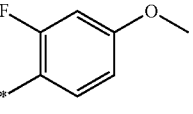 | H | 2-Amino-3-(2-fluoro-4-methoxyphenyl)propanoic acid |
| 12-32 | H | H | 1 | H | 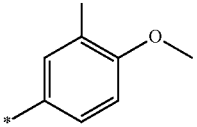 | H | 2-Amino-3-(3-fluoro-4-methoxyphenyl)propanoic acid |
| 12-33 | H | H | 1 | H | 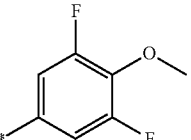 | H | 2-Amino-3-(3,5-difluoro-4-methoxyphenyl)propanoic acid |
| 12-34 | H | H | 1 | H | 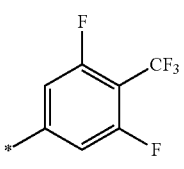 | H | 2-Amino-3-(3,5-difluoro-4-(trifluoromethyl)phenyl)propanoic acid |
| 12-35 | H | H | 1 | H | 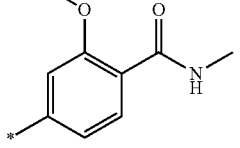 | H | 2-Amino-3-(3-methoxy-4-(methylcarbamoyl)phenyl)propanoic acid |
| 12-36 | H | H | 1 | H | 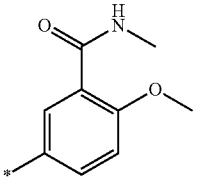 [SMILES: *c1ccc(OC)c(C(=O)NC)c1] | H | 2-Amino-3-(4-methoxy-3-(methylcarbamoyl)phenyl)propanoic acid |

TABLE 12-continued

| Compound ID | R₁ | R₂ | n | R₃ | R₆ | R₇ | Compound Name |
|---|---|---|---|---|---|---|---|
| 12-37 | H | H | 1 | H | (3-methoxy-4-((methylsulfonyl)carbamoyl)phenyl group) | H | 2-Amino-3-(3-methoxy-4-((methylsulfonyl)carbamoyl)phenyl) propanoic acid |
| 12-38 | H | H | 1 | H | (4-(methyl((tetrahydro-2H-pyran-2-yl)oxy)carbamoyl)phenyl group) | H | 2-Amino-3-(4-(methyl((tetrahydro-2H-pyran-2-yl)oxy)carbamoyl)phenyl) propanoic acid |
| 12-39 | H | H | 1 | H | (3-methoxy-4-(((tetrahydro-2H-pyran-2-yl)oxy)carbamoyl)phenyl group) | H | 2-Amino-3-(3-methoxy-4-(((tetrahydro-2H-pyran-2-yl)oxy carbamoyl)phenyl)propanoic acid |
| 12-40 | H | H | 1 | H | pyridin-2-yl | H | 2-Amino-3-(pyridin-2-yl)propanoic acid |
| 12-41 | H | H | 1 | H | pyridin-3-yl | H | 2-Amino-3-(pyridin-3-yl)propanoic acid |
| 12-42 | H | H | 1 | H | pyridin-4-yl | H | 2-Amino-3-(pyridin-4-yl)propanoic acid |
| 12-43 | H | H | 1 | H | 6-methylpyridin-3-yl | H | 2-Amino-3-(6-methylpyridin-3-yl) propanoic acid |
| 12-44 | H | H | 1 | H | 5-methylpyridin-3-yl | H | 2-Amino-3-(5-methylpyridin-3-yl) propanoic acid |
| 12-45 | H | H | 1 | H | 4-methylpyridin-3-yl | H | 2-Amino-3-(4-methylpyridin-3-yl) propanoic acid |
| 12-46 | H | H | 1 | H | 6-methoxypyridin-3-yl | H | 2-Amino-3-(6-methoxypyridin-3-yl) propanoic acid |
| 12-47 | H | H | 1 | H | 5-methoxypyridin-3-yl | H | 2-Amino-3-(5-methoxypyridin-3-yl) propanoic acid |

TABLE 12-continued

| Compound ID | R₁ | R₂ | n | R₃ | R₆ | R₇ | Compound Name |
|---|---|---|---|---|---|---|---|
| 12-48 | H | H | 1 | H | 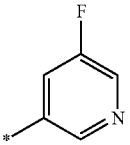 | H | 2-Amino-3-(5-fluoropyridin-3-yl)propanoic acid |
| 12-49 | H | H | 1 | H | 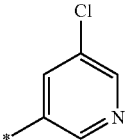 [SMILES: *c1cncc(Cl)c1] | H | 2-Amino-3-(5-chloropyridin-3-yl)propanoic acid |
| 12-50 | H | H | 1 | H | 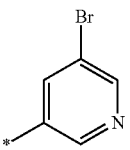 | H | 2-Amino-3-(5-bromopyridin-3-yl)propanoic acid |
| 12-51 | H | H | 1 | H | 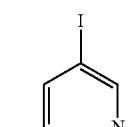 | H | 2-Amino-3-(5-iodopyridin-3-yl)propanoic acid |
| 12-52 | H | H | 1 | H | 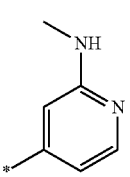 [SMILES: *c1ccnc(NC)c1] | H | 2-Amino-3-(2-(methylamino)pyridin-4-yl)propanoic acid |
| 12-53 | H | H | 1 | H | 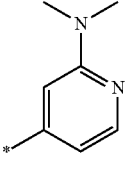 | H | 2-Amino-3-(2-(dimethylamino)pyridin-4-yl)propanoic acid |
| 12-54 | H | H | 1 | H | 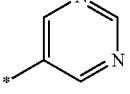 | H | 2-Amino-3-(pyrimidin-5-yl)propanoic acid |

TABLE 13

| Compound ID | R₁ | R₂ | n | R₃ | R₆ | R₇ | Compound Name |
|---|---|---|---|---|---|---|---|
| 13-1 | H | Me | 1 | H | 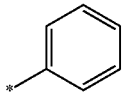 | H | Methylphenylalanine |
| 13-2 | H | Me | 1 | H | 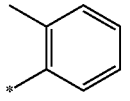 | H | 2-(Methylamino)-3-(o-tolyl)propanoic acid |

TABLE 13-continued

| Compound ID | R₁ | R₂ | n | R₃ | R₆ | R₇ | Compound Name |
|---|---|---|---|---|---|---|---|
| 13-3 | H | Me | 1 | H | 3-methylphenyl | H | 2-(Methylamino)-3-(m-tolyl)propanoic acid |
| 13-4 | H | Me | 1 | H | 4-methylphenyl | H | 2-(Methylamino)-3-(p-tolyl)propanoic acid |
| 13-5 | H | Me | 1 | H | 4-ethylphenyl | H | 2-(Methylamino)-3-(4-ethylphenyl)propanoic acid |
| 13-6 | H | Me | 1 | H | 2-chlorophenyl | H | 2-(Methylamino)-3-(2-chlorophenyl)propanoic acid |
| 13-7 | H | Me | 1 | H | 3-chlorophenyl | H | 2-(Methylamino)-3-(3-chlorophenyl)propanoic acid |
| 13-8 | H | Me | 1 | H | 4-chlorophenyl | H | 2-(Methylamino)-3-(4-chlorophenyl)propanoic acid |
| 13-9 | H | Me | 1 | H | 2-fluorophenyl | H | 2-(Methylamino)-3-(2-fluorophenyl)propanoic acid |
| 13-10 | H | Me | 1 | H | 3-fluorophenyl | H | 2-(Methylamino)-3-(3-fluorophenyl)propanoic acid |
| 13-11 | H | Me | 1 | H | 4-fluorophenyl | H | 2-(Methylamino)-3-(4-fluorophenyl)propanoic acid |
| 13-12 | H | Me | 1 | H | 2-cyclopropylphenyl | H | 2-(Methylamino)-3-(2-cyclopropylphenyl)propanoic acid |
| 13-13 | H | Me | 1 | H | 3-cyclopropylphenyl | H | 2-(Methylamino)-3-(3-cyclopropylphenyl)propanoic acid |

TABLE 13-continued

| Compound ID | R$_1$ | R$_2$ | n | R$_3$ | R$_6$ | R$_7$ | Compound Name |
|---|---|---|---|---|---|---|---|
| 13-14 | H | Me | 1 | H | 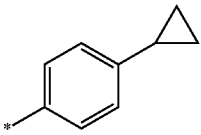 | H | 2-(Methylamino)-3-(4-cyclopropylphenyl)propanoic acid |
| 13-15 | H | Me | 1 | H | 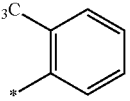 | H | 2-(Methylamino)-3-(2-(trifluoromethyl)phenyl)propanoic acid |
| 13-16 | H | Me | 1 | H | 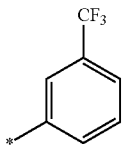 | H | 2-(Methylamino)-3-(3-(trifluoromethyl)phenyl)propanoic acid |
| 13-17 | H | Me | 1 | H | 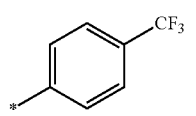 | H | 2-(Methylamino)-3-(4-(trifluoromethyl)phenyl)propanoic acid |
| 13-18 | H | Me | 1 | H | 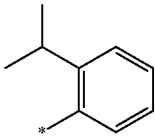 | H | 2-(Methylamino)-3-(2-isopropylphenyl)propanoic acid |
| 13-19 | H | Me | 1 | H | 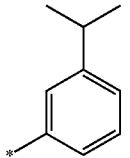 | H | 2-(Methylamino)-3-(3-isopropylphenyl)propanoic acid |
| 13-20 | H | Me | 1 | H | 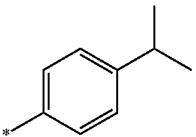 | H | 2-(Methylamino)-3-(4-isopropylphenyl)propanoic acid |
| 13-21 | H | Me | 1 | H | 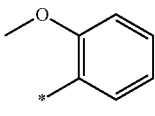 | H | 2-(Methylamino)-3-(2-methoxyphenyl)propanoic acid |
| 13-22 | H | Me | 1 | H | 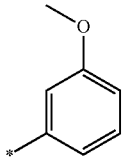 | H | 2-(Methylamino)-3-(3-methoxyphenyl)propanoic acid |
| 13-23 | H | Me | 1 | H | 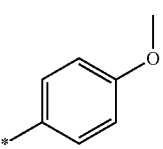 | H | 2-(Methylamino)-3-(4-methoxyphenyl)propanoic acid |

TABLE 13-continued

| Compound ID | R₁ | R₂ | n | R₃ | R₆ | R₇ | Compound Name |
|---|---|---|---|---|---|---|---|
| 13-24 | H | Me | 1 | H | (2-allyloxyphenyl) | H | 2-(Methylamino)-3-(2-(allyloxy)phenyl)propanoic acid |
| 13-25 | H | Me | 1 | H | (3-allyloxyphenyl) | H | 2-(Methylamino)-3-(3-(allyloxy)phenyl)propanoic acid |
| 13-26 | H | Me | 1 | H | (4-allyloxyphenyl) | H | 2-(Methylamino)-3-(4-(allyloxy)phenyl)propanoic acid |
| 13-27 | H | Me | 1 | H | (4-isopropoxyphenyl) | H | 2-(Methylamino)-3-(4-isopropoxyphenyl)propanoic acid |
| 13-28 | H | Me | 1 | H | (3-fluoro-4-CF₃-phenyl) | H | 2-(Methylamino)-3-(3-fluoro-4-(trifluoromethyl)phenyl)propanoic acid |
| 13-29 | H | Me | 1 | H | (2-fluoro-4-CF₃-phenyl) | H | 2-(Methylamino)-3-(2-fluoro-4-(trifluoromethyl)phenyl)propanoic acid |
| 13-30 | H | Me | 1 | H | (3,4-dimethoxyphenyl) | H | 2-(Methylamino)-3-(3,4-dimethoxyphenyl)propanoic acid |
| 13-31 | H | Me | 1 | H | (2-fluoro-4-methoxyphenyl) | H | 2-(Methylamino)-3-(2-fluoro-4-methoxyphenyl)propanoic acid |
| 13-32 | H | Me | 1 | H | (3-fluoro-4-methoxyphenyl) | H | 2-(Methylamino)-3-(3-fluoro-4-methoxyphenyl)propanoic acid |

TABLE 13-continued

| Compound ID | R₁ | R₂ | n | R₃ | R₆ | R₇ | Compound Name |
|---|---|---|---|---|---|---|---|
| 13-33 | H | Me | 1 | H | (3,5-difluoro-4-methoxyphenyl) | H | 2-(Methylamino)-3-(3,5-difluoro-4-methoxyphenyl)propanoic acid |
| 13-34 | H | Me | 1 | H | (3,5-difluoro-4-(trifluoromethyl)phenyl) | H | 2-(Methylamino)-3-(3,5-difluoro-4-(trifluoromethyl)phenyl)propanoic acid |
| 13-35 | H | Me | 1 | H | (2-methoxy-4-(methylcarbamoyl)phenyl) | H | 2-(Methylamino)-3-(3-methoxy-4-(methylcarbamoyl)phenyl)propanoic acid |
| 13-36 | H | Me | 1 | H | (4-methoxy-3-(methylcarbamoyl)phenyl) | H | 2-(Methylamino)-3-(4-methoxy-3-(methylcarbamoyl)phenyl)propanoic acid |
| 13-37 | H | Me | 1 | H | (3-methoxy-4-((methylsulfonyl)carbamoyl)phenyl) | H | 2-(Methylamino)-3-(3-methoxy-4-((methylsulfonyl)carbamoyl)phenyl)propanoic acid |
| 13-38 | H | Me | 1 | H | (4-(methyl((tetrahydro-2H-pyran-2-yl)oxy)carbamoyl)phenyl) | H | 2-(Methylamino)-3-(4-(methyl((tetrahydro-2H-pyran-2-yl)oxy)carbamoyl)phenyl)propanoic acid |
| 13-39 | H | Me | 1 | H | (3-methoxy-4-(((tetrahydro-2H-pyran-2-yl)oxy)carbamoyl)phenyl) | H | 2-(Methylamino)-3-(3-methoxy-4-(((tetrahydro-2H-pyran-2-yl)oxy)carbamoyl)phenyl)propanoic acid |
| 13-40 | H | Me | 1 | H | pyridin-2-yl | H | 2-(Methylamino)-3-(pyridin-2-yl)propanoic acid |
| 13-41 | H | Me | 1 | H | pyridin-3-yl | H | 2-(Methylamino)-3-(pyridin-3-yl)propanoic acid |

TABLE 13-continued

| Compound ID | R₁ | R₂ | n | R₃ | R₆ | R₇ | Compound Name |
|---|---|---|---|---|---|---|---|
| 13-42 | H | Me | 1 | H | 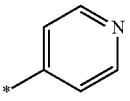 | H | 2-(Methylamino)-3-(pyridin-4-yl)propanoic acid |
| 13-43 | H | Me | 1 | H | 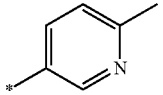 | H | 2-(Methylamino)-3-(6-methylpyridin-3-yl)propanoic acid |
| 13-44 | H | Me | 1 | H | 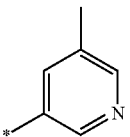 | H | 2-(Methylamino)-3-(5-methylpyridin-3-yl)propanoic acid |
| 13-45 | H | Me | 1 | H | 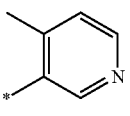 | H | 2-(Methylamino)-3-(4-methylpyridin-3-yl)propanoic acid |
| 13-46 | H | Me | 1 | H | 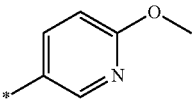 | H | 2-(Methylamino)-3-(6-methoxypyridin-3-yl)propanoic acid |
| 13-47 | H | Me | 1 | H | 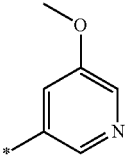 | H | y2-(Methylamino)-3-(5-methoxypyridin-3-yl)propanoic acid |
| 13-48 | H | Me | 1 | H | 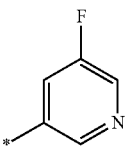 | H | 2-(Methylamino)-3-(5-fluoropyridin-3-yl)propanoic acid |
| 13-49 | H | Me | 1 | H | 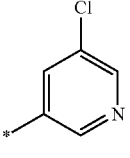 | H | 2-(Methylamino)-3-(5-chloropyridin-3-yl)propanoic acid |
| 13-50 | H | Me | 1 | H | 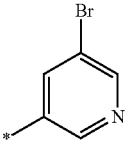 | H | 2-(Methylamino)-3-(5-bromopyridin-3-yl)propanoic acid |
| 13-51 | H | Me | 1 | H | 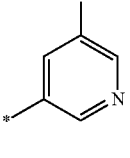 | H | 2-(Methylamino)-3-(5-iodopyridin-3-yl)propanoic acid |

TABLE 13-continued

| Compound ID | R₁ | R₂ | n | R₃ | R₆ | R₇ | Compound Name |
|---|---|---|---|---|---|---|---|
| 13-52 | H | Me | 1 | H | 3-(methylamino)pyridin-5-yl | H | 2-(Methylamino)-3-(2-(methylamino)pyridin-4-yl)propanoic acid |
| 13-53 | H | Me | 1 | H | 3-(dimethylamino)pyridin-5-yl | H | 2-(Methylamino)-3-(2-(dimethylamino)pyridin-4-yl)propanoic acid |
| 13-54 | H | Me | 1 | H | pyrimidin-5-yl | H | 2-(Methylamino)-3-(pyrimidin-5-yl)propanoic acid |

TABLE 14

| Compound ID | R₁ | R₂ | n | R₃ | R₆ | R₇ | Compound Name |
|---|---|---|---|---|---|---|---|
| 14-1 | Fmoc | Et | 1 | tBu | p-tolyl | H | tert-Butyl 2-((((9H-fluoren-9-yl)methoxy)carbonyl)(ethyl)amino)-3-(p-tolyl)propanoate |
| 14-2 | Fmoc | Et | 1 | Bn | p-tolyl | H | Benzyl 2-((((9H-fluoren-9-yl)methoxy)carbonyl)(ethyl)amino)-3-(p-tolyl)propanoate |
| 14-3 | Boc | Et | 1 | tBu | p-tolyl | H | tert-Butyl 2-((tert-butoxycarbonyl)(ethyl)amino)-3-(p-tolyl)propanoate |
| 14-4 | Boc | Et | 1 | Bn | p-tolyl | H | Benzyl 2-((tert-butoxycarbonyl)(ethyl)amino)-3-(p-tolyl)propanoate |
| 14-5 | Cbz | Et | 1 | tBu | p-tolyl | H | tert-Butyl 2-(((benzyloxy)carbonyl)(ethyl)amino)-3-(p-tolyl)propanoate |
| 14-6 | Cbz | Et | 1 | Bn | p-tolyl | H | Benzyl 2-(((benzyloxy)carbonyl)(ethyl)amino)-3-(p-tolyl)propanoate |
| 14-7 | Alloc | Et | 1 | tBu | p-tolyl | H | tert-Butyl 2-(((allyloxy)carbonyl)(ethyl)amino)-3-(p-tolyl)propanoate |

TABLE 14-continued

| Compound ID | $R_1$ | $R_2$ | n | $R_3$ | $R_6$ | $R_7$ | Compound Name |
|---|---|---|---|---|---|---|---|
| 14-8 | Alloc | Et | 1 | Bn | *-C6H4-CH3 (p-tolyl) | H | Benzyl 2-(((allyloxy)carbonyl)(ethyl)amino)-3-(p-tolyl)propanoate |
| 14-9 | Teoc | Et | 1 | tBu | *-C6H4-CH3 (p-tolyl) | H | tert-Butyl 2-(ethyl((2-(trimethylsilyl)ethoxy)carbonyl)amino)-3-(p-tolyl)propanoate |
| 14-10 | Teoc | Et | 1 | Bn | *-C6H4-CH3 (p-tolyl) | H | Benzyl 2-(ethyl((2-(trimethylsilyl)ethoxy)carbonyl)amino)-3-(p-tolyl)propanoate |
| 14-11 | Fmoc | Et | 1 | H | *-C6H4-CH3 (p-tolyl) | H | 2-((((9H-Fluoren-9-yl)methoxy)carbonyl)(ethyl)amino)-3-(p-tolyl)propanoic acid |
| 14-12 | Boc | Et | 1 | H | *-C6H4-CH3 (p-tolyl) | H | 2-((tert-Butoxycarbonyl)(ethyl)amino)-3-(p-tolyl)propanoic acid |
| 14-13 | Cbz | Et | 1 | H | *-C6H4-CH3 (p-tolyl) | H | 2-(((Benzyloxy)carbonyl)(ethyl)amino)-3-(p-tolyl)propanoic acid |
| 14-14 | Alloc | Et | 1 | H | *-C6H4-CH3 (p-tolyl) | H | 2-(((Allyloxy)carbonyl)(ethyl)amino)-3-(p-tolyl)propanoic acid |
| 14-15 | Teoc | Et | 1 | H | *-C6H4-CH3 (p-tolyl) | H | 2-(Ethyl((2-(trimethylsilyl)ethoxy)carbonyl)amino)-3-(p-tolyl)propionic acid |
| 14-16 | H | Et | 1 | H | *-C6H4-CH3 (p-tolyl) | H | 2-(Ethylamino)-3-(p-tolyl)propanoic acid |

Isolation/purification of the target compounds obtained through the above-described reaction steps can be carried out by applying ordinary chemical operations such as extraction, concentration, distillation, crystallization, filtration, recrystallization, and various types of chromatography.

The compound, the salt of the compound, or the solvate of the compound or the salt of the present invention includes all stereoisomers of the target compound obtained through the above-described reaction steps (such as enantiomers and diastereomers (including cis and trans geometric isomers)), racemates of the isomers, and other mixtures. For example, the compound of the present invention may have one or more asymmetric centers, and the present invention includes racemic mixtures, diastereomeric mixtures, and enantiomers of such a compound.

When the compound according to the present invention is obtained in a free form, the compound can be converted to the state of a salt of the compound or a hydrate or a solvate of the compound or the salt, which the compound may form, according to a conventional method.

When the compound according to the present invention is obtained as a salt, hydrate, or solvate of the compound, the compound can be converted to a free form thereof according to a conventional method.

All prior art documents cited in the present specification are incorporated herein by reference.

EXAMPLES

The present invention is further illustrated by the following Examples, but is not limited thereto.

As for the solvents used in the working of the present invention, exemplified by DMF, DMA, NMP, DMI, and DMPU, commercially available products were used without purification. In a reaction in which water was not added as a solvent, a commercially available dehydration solvent, super-dehydration solvent, anhydrous solvent, and the like were used without purification.

As for the reagents used in the working of the present invention, such as additives exemplified by silyl compounds or 1,2-dibromoethane, metals, possible ligand compounds, metal-ligand complexes, reducing agents, reagents used in the step of introducing a protecting group, and reagents used in the deprotection step, commercially available products were used without purification unless otherwise specifically described.

As for the starting materials of aromatic amino acid derivatives used in the working of the present invention, which are represented by phenylalanine derivatives and homophenylalanine derivatives, commercially available products were used without purification unless otherwise specifically described. Furthermore, such starting materials were produced by known methods as necessary, and used.

A $^1$H-NMR spectrum was measured using an AVANCE III HD 400 BBFO-SMART probe (manufactured by Bruker), the chemical shift of Me$_4$Si used as an internal standard material was set at 0 ppm, and a deuterium lock signal from a sample solvent was referred to. The chemical shift of the signal of an analyte compound was expressed as ppm. Abbreviations for signal splitting were s=singlet, brs=broad singlet, d=doublet, t=triplet, q=quartet, dd=double doublet, and m=multiplet, and the width of signal splitting was expressed as J value (Hz). The integrated value of a signal was calculated based on the ratio between the signal area intensities of respective signals.

[High performance liquid chromatography Condition 1]
Apparatus: manufactured by Shimadzu Corporation
  Column: Ascentis Express RP-Amide (3.0 mm I.D.×50 mm)
  Mobile Phase: water containing 0.05% trifluoroacetic acid (A) and acetonitrile containing 0.05% trifluoroacetic acid (B)
  Elution Method: Stepwise solvent gradient elution from 5% B to 95% B (5.0 min), maintained at 95% B (2.0 min)
  Flow Rate: 0.7 mL/min
  Column temperature: 30° C.

[High performance liquid chromatography Condition 2]
Apparatus: Waters Acquity UPLC/SQD
  Column: Ascentis Express C18 (2.1 mm I.D.×50 mm)
  Mobile Phase: water containing 0.1% formic acid (A) and acetonitrile containing 0.1% formic acid (B)
  Elution Method: stepwise solvent gradient elution from 5% B to 100% B (5.0 min), maintained at 100% B (2.0 min)
  Flow Rate: 1.0 mL/min

[High performance liquid chromatography Condition 3]
Apparatus: Waters Acquity UPLC/SQD
  Column: Ascentis Express C18 (2.1 mm I.D.×50 mm)
  Mobile Phase: 10 mM aqueous ammonium acetate solution (A) and 10 mM ammonium acetate solution in acetonitrile (B)
  Elution Method: stepwise solvent gradient elution from 5% B to 100% B (1.0 min), maintained at 100% B (0.4 min)
  Flow Rate: 1.0 mL/min

[High performance liquid chromatography Condition 4]
Apparatus: Waters Acquity UPLC/SQD
  Column: Ascentis Express C18 (2.1 mm I.D.×50 mm)
  Mobile Phase: water containing 0.1% formic acid (A) and acetonitrile containing 0.1% formic acid (B)
  Elution Method: stepwise solvent gradient elution from 5% B to 100% B (1.0 min), maintained at 100% B (0.4 min)
  Flow Rate: 1.0 mL/min

[High performance liquid chromatography Condition 5]
Apparatus: manufactured by Shimadzu Corporation
  Column: Ascentis Express C18 (3.0 mm I.D.×50 mm)
  Mobile Phase: water containing 0.05% trifluoroacetic acid (A) and acetonitrile containing 0.05% trifluoroacetic acid (B)
  Elution Method: stepwise solvent gradient elution from 5% B to 95% B (2.0 min), maintained at 95% B (0.7 min)
  Flow Rate: 1.0 mL/min

[High performance liquid chromatography Condition 6]
Apparatus: manufactured by Shimadzu Corporation
  Column: Ascentis Express C18 (3.0 mm I.D.×50 mm)
  Mobile Phase: water containing 0.05% trifluoroacetic acid (A) and acetonitrile containing 0.05% trifluoroacetic acid (B)
  Elution Method: stepwise solvent gradient elution from 5% B to 95% B (1.1 min), maintained at 95% B (0.5 min)
  Flow Rate: 1.0 mL/min

[Reference Example 1] The case where TMSCl was not used as additive, and stirring with stirring blade was performed Production of benzyl (S)-2-((tert-butoxycarbonyl)amino)-4-(3-chloro-4-(trifluoromethyl)phenyl)butanoate

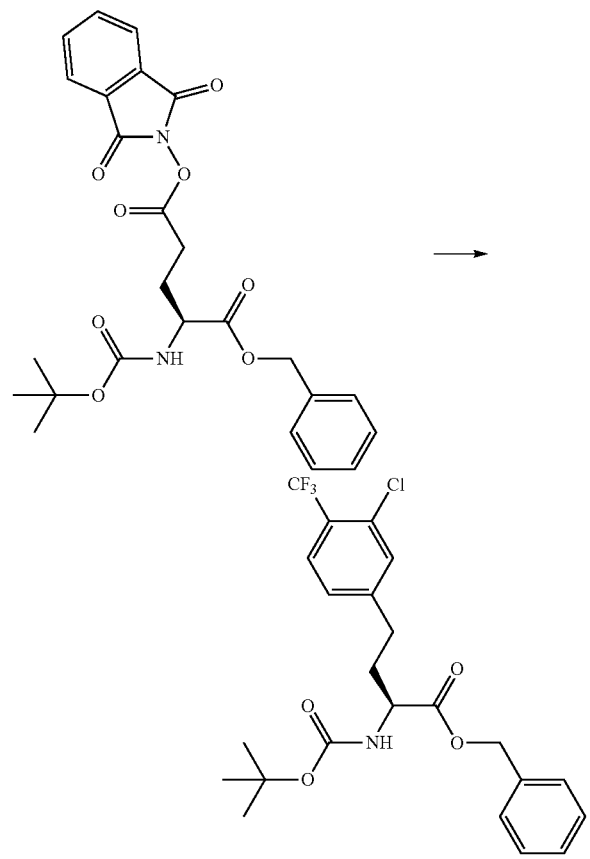

Nickel bromide trihydrate (0.12 g, 0.44 mmol) and 4,4'-di-tert-butyl-2,2'-bipyridine (0.12 g, 0.44 mmol) were dissolved in DMA (15 mL), and the mixture was purged with nitrogen and then stirred for 10 min to prepare a catalyst solution. Zinc powder (2.0 g, 31 mmol), 1-benzyl 5-(1,3-dioxoisoindolin-2-yl) (tert-butoxycarbonyl)-L-glutamate (3.0 g, 6.2 mmol), and DMA (15 mL) were added to a flask equipped with a stirring blade, 4-bromo-2-chloro-1-(trifluoromethyl)benzene (4.8 g, 19 mmol) was added, and then the mixture was purged with nitrogen. The prepared catalyst solution was added dropwise to the reaction solution under a nitrogen atmosphere, the solution was stirred at 25° C. for 2 h, and the reaction mixture was analyzed by HPLC. The UV intensity ratio of the raw material to the target compound was 92.5:7.5 (detection wavelength: 210 nm), and thus it was confirmed that 90% or more of the raw material remained.

Benzyl (S)-2-((tert-butoxycarbonyl)amino)-4-(3-chloro-4-(trifluoromethyl)phenyl)butanoate Retention time: raw material 2.7 min, Target compound 3.4 min (High performance liquid chromatography Condition 2)

ESI (LC/MS positive mode m/z 472 (M+H)$^+$) Example 1

The case where 5 mol % of TMSCl was used as additive, and stirring with stirring blade was performed Production of benzyl (S)-2-((tert-butoxycarbonyl)amino)-4-(3-chloro-4-(trifluoromethyl)phenyl)butanoate

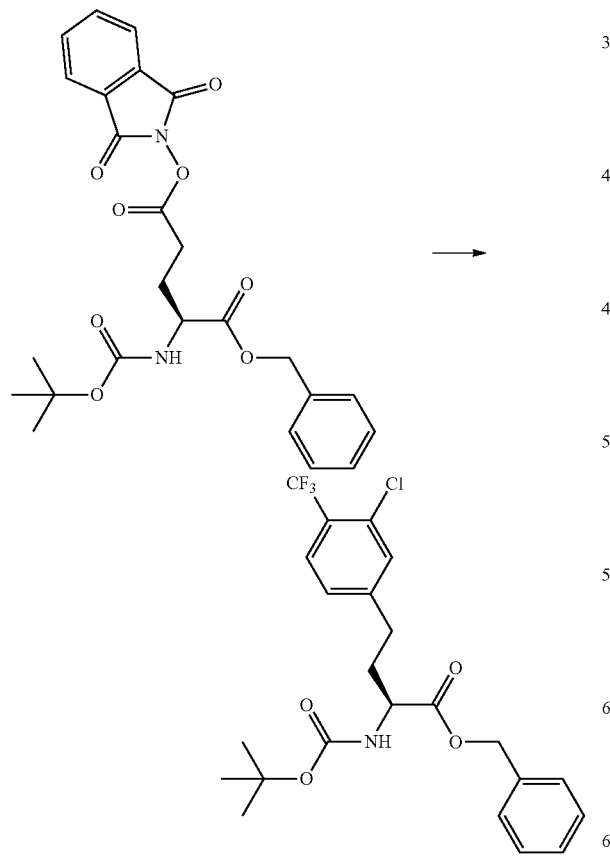

Nickel bromide trihydrate (0.20 g, 0.73 mmol) and 4,4'-di-tert-butyl-2,2'-bipyridine (0.20 g, 0.73 mmol) were dissolved in DMA (25 mL), and the mixture was purged with nitrogen and then stirred for 10 min to prepare a catalyst solution. Zinc powder (3.4 g, 52 mmol), 1-benzyl 5-(1,3-dioxoisoindolin-2-yl) (tert-butoxycarbonyl)-L-glutamate (5.0 g, 10 mmol), and DMA (25 mL) were added to a flask equipped with a stirring blade, 4-bromo-2-chloro-1-(trifluoromethyl)benzene (8.1 g, 31 mmol) was added, and then the mixture was purged with nitrogen. After the prepared catalyst solution was added dropwise to the reaction solution under a nitrogen atmosphere, TMSCl (56 mg, 0.52 mmol) was added. The solution was stirred at 25° C. for 2 h, and the reaction mixture was analyzed by HPLC. The UV intensity ratio of the raw material to the target compound was 67:33 (detection wavelength: 210 nm), and it was thus confirmed that, while the raw material remained, the production of the target compound significantly increased as compared with the case where TMSCl was not used (Reference Example 1).

Benzyl (S)-2-((tert-butoxycarbonyl)amino)-4-(3-chloro-4-(trifluoromethyl)phenyl)butanoate Retention time: Raw material 4.3 min, Target compound 5.0 min (High performance liquid chromatography Condition 1)

ESI (LC/MS positive mode m/z 472 (M+H)$^+$)

Example 2

The case where 50 mol % of TMSCl was used as additive, and stirring with stirring blade was performed Production of benzyl (S)-2-((tert-butoxycarbonyl)amino)-4-(3-chloro-4-(trifluoromethyl)phenyl)butanoate

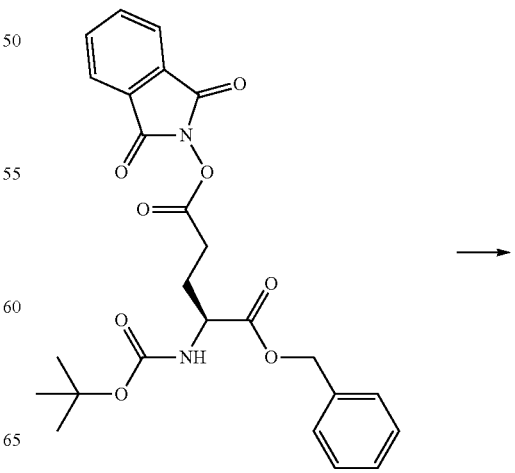

219
-continued

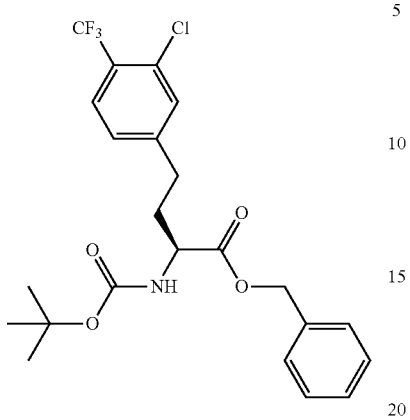

Nickel bromide trihydrate (39 mg, 0.15 mmol) and 4,4'-di-tert-butyl-2,2'-bipyridine (40 mg, 0.15 mmol) were dissolved in DMA (5.0 mL), and the mixture was purged with nitrogen and then stirred for 10 min to prepare a catalyst solution. Zinc powder (0.68 g, 10 mmol), 1-benzyl 5-(1,3-dioxoisoindolin-2-yl) (tert-butoxycarbonyl)-L-glutamate (1.0 g, 2.1 mmol), and DMA (5.0 mL) were added to a flask equipped with a stirring blade, 4-bromo-2-chloro-1-(trifluoromethyl)benzene (1.6 g, 6.2 mmol) was added, and then the mixture was purged with nitrogen. After the prepared catalyst solution was added dropwise to the reaction solution under a nitrogen atmosphere, TMSCl (0.11 g, 1.0 mmol) was added. The solution was stirred at 25° C. for 2 h, and the reaction mixture was analyzed by HPLC. The UV intensity ratio of the raw material to the target compound was 0:100 (detection wavelength: 210 nm), and it was thus confirmed that the raw material had completely disappeared, and that the target compound was the main product. The reaction solution was purified by chromatography to afford benzyl (S)-2-((tert-butoxycarbonyl)amino)-4-(3-chloro-4-(trifluoromethyl)phenyl)butanoate (0.79 g, yield 80%).

Benzyl (S)-2-((tert-butoxycarbonyl)amino)-4-(3-chloro-4-(trifluoromethyl)phenyl)butanoate Retention time: Raw Material 4.0 min, Target compound 4.7 min (High performance liquid chromatography Condition 1)

1H-NMR (DMSO-D6) δ:7.76 (1H, d, J=8.1 Hz), 7.55 (1H, s), 7.44 (0.8H, d, J=7.8 Hz), 7.36-7.34 (6H, m), 7.10 (0.2H, m), 5.15 (1H, d, J=12.5 Hz), 5.08 (1H, d, J=12.5 Hz), 3.98-3.96 (0.8H, m), 3.87 (0.2H, br s), 2.71 (2H, t, J=7.9 Hz), 2.01-1.87 (2H, m), 1.39 (8H, s), 1.27 (1H, s)

220
Example 3

The case where 52 mol % of TMSCl was used as additive, and stirring with stirring blade was performed Production of (S)-2-(((((9H-fluoren-9-yl)methoxy)carbonyl)amino)-4-(3-chloro-4-(trifluoromethyl)phenyl)butanoic Acid Nickel bromide trihydrate (0.20 g, 0.73 mmol) and 4,4'-di-tert-butyl-2,2'-bipyridine (0.20 g, 0.73 mmol) were dissolved in DMA (25 mL), and the mixture was purged with nitrogen and then stirred for 10 min to prepare a catalyst solution. Zinc powder (3.4 g, 52 mmol), 1-benzyl 5-(1,3-dioxoisoindolin-2-yl) (tert-butoxycarbonyl)-L-glutamate (5.0 g, 10 mmol), and DMA (25 mL) were added to a flask equipped with a stirring blade, 4-bromo-2-chloro-1-(trifluoromethyl)benzene (8.1 g, 31 mmol) was added, and then the mixture was purged with nitrogen. After the prepared catalyst solution was added dropwise to the reaction solution under a nitrogen atmosphere, TMSCl (0.56 g, 5.2 mmol) was added and the solution was stirred at 25° C. for 3 h. When the reaction mixture was analyzed by HPLC, it was confirmed that the raw material had completely disappeared, and that the target compound was the main product. Ethyl acetate (50 mL) and a 10% aqueous EDTA·2Na solution (50 mL) were added to the reaction solution, and the organic layer was washed with a 10% aqueous NaCl solution (50 mL). The resulting organic layer was concentrated under reduced pressure, toluene (25 mL) was added to prepare a solution, and the solution was divided into two portions. The solution was cooled to 0° C., TfOH (2.3 g) was added dropwise, the temperature was raised to 25° C., and then water (2.5 mL) was added. After the mixture was stirred for 45 min, 10 mL of water was added for separation. A 40% aqueous K$_3$PO$_4$ solution (2.0 mL) and acetonitrile (13 mL) were added to the aqueous layer. FmocOSu (1.8 g) was added, and a 40% aqueous K$_3$PO$_4$ solution (3.5 mL) was added. After the lower layer was discharged, 5N HCl (2.2 mL) was added, the precipitated solids were filtered, and the resulting solids were dried to afford (S)-2-((((9H-fluoren-9-yl)methoxy)carbonyl)amino)-4-(3-chloro-4-(trifluoromethyl)phenyl)butanoic acid (1.8 g, yield 68%) as white solids.

(S)-2-((((9H-fluoren-9-yl)methoxy)carbonyl)amino)-4-(3-chloro-4-(trifluoromethyl)phenyl)butanoic Acid Target compound retention time: 3.1 min (High performance liquid chromatography Condition 2)

1H-NMR (DMSO-D6) δ: 12.65 (1H, s), 7.90 (2H, d, J=7.5 Hz), 7.77-7.58 (5H, m), 7.44-7.32 (5H, m), 4.37-4.18 (3H, m), 3.91-3.88 (1H, m), 2.79-2.66 (2H, m), 2.07-1.86 (2H, m).

Example 4

Production of tert-butyl (S)-2-((((9H-fluoren-9-yl)methoxy)carbonyl)amino)-4-(4-fluorophenyl)butanoate

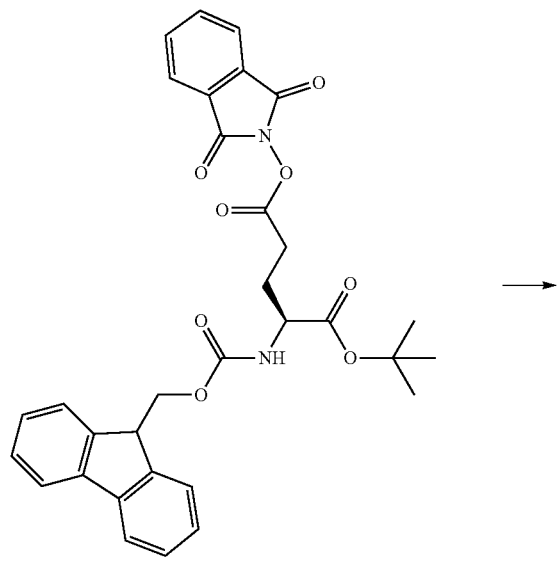

→

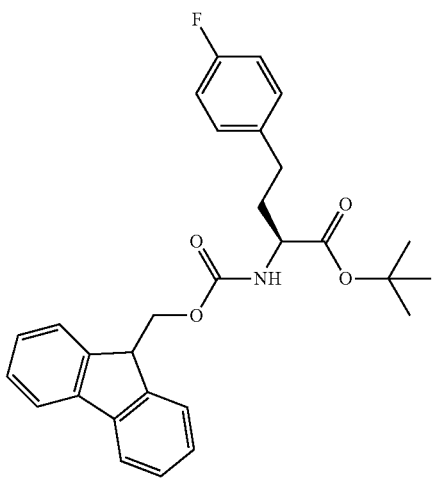

Nickel bromide trihydrate (4.0 mg, 0.015 mmol) and 4,4'-di-tert-butyl-2,2'-bipyridine (3.9 mg, 0.015 mmol) were dissolved in DMA (0.50 mL), and the mixture was purged with nitrogen and then stirred to prepare a catalyst solution. 1-(tert-Butyl) 5-(1,3-dioxoisoindolin-2-yl) (((9H-fluoren-9-yl)methoxy)carbonyl)-L-glutamate (0.12 g, 0.21 mmol) and 1-fluoro-4-iodobenzene (0.14 g, 0.62 mmol) were added to and dissolved in DMA (0.5 mL). The prepared catalyst solution was added dropwise thereto under a nitrogen atmosphere, zinc powder (68 mg, 1.0 mmol) and then TMSCl (11 mg, 0.1 mmol) were added, and the reaction vessel was shaken at 25° C. for 2 h. When the reaction mixture was analyzed by HPLC, it was confirmed that the raw material had completely disappeared, and that the target compound was the main product. The reaction solution was purified by chromatography to afford tert-butyl (S)-2-((((9H-fluoren-9-yl)methoxy)carbonyl)amino)-4-(4-fluorophenyl)butanoate (70 mg, yield 71%).

tert-Butyl (S)-2-((((9H-fluoren-9-yl)methoxy)carbonyl)amino)-4-(4-fluorophenyl)butanoate Target compound retention time: 1.1 min (High performance liquid chromatography Condition 3)

ESI (LC/MS positive mode m/z 498 (M+Na)$^+$)

Example 5

Production of tert-butyl (S)-2-((((9H-fluoren-9-yl)methoxy)carbonyl)amino)-4-(pyridin-3-yl)butanoate

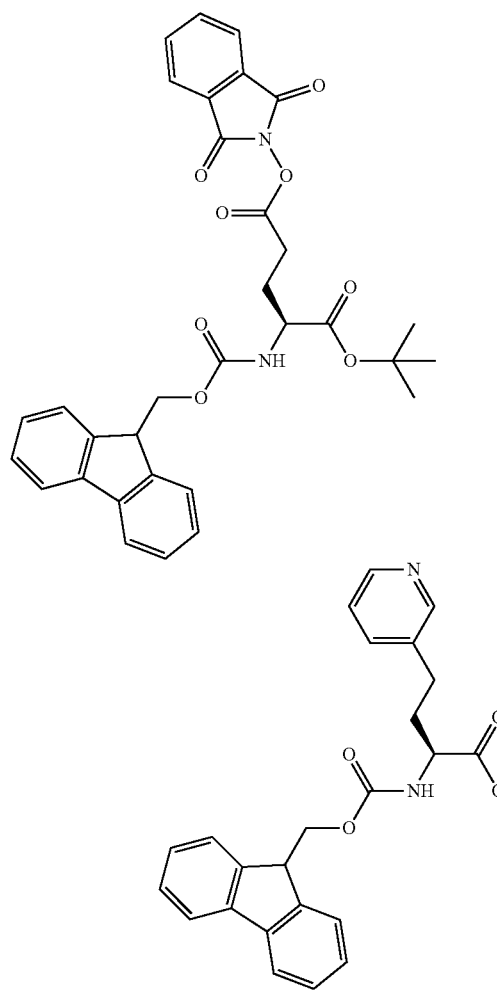

Nickel bromide trihydrate (0.14 g, 0.53 mmol) and 4,4'-di-tert-butyl-2,2'-bipyridine (0.14 g, 0.53 mmol) were dissolved in DMA (8.0 mL), and the mixture was purged with nitrogen and then stirred to prepare a catalyst solution. Zinc powder (0.57 g, 8.8 mmol), 5-(1,3-dioxoisoindolin-2-yl) 1-tert-butyl N-(((9H-fluoren-9-yl)methoxy)carbonyl)-L-glutamate (1.0 g, 1.8 mmol), and DMA (8.0 mL) were added to a flask, 3-iodopyridine (1.1 g, 5.3 mmol) was added, and then the mixture was purged with nitrogen. After the prepared catalyst solution was added dropwise to the reaction solution under a nitrogen atmosphere, TMSCl (95 mg, 0.88 mmol) and 1,2-dibromoethane (0.33 g, 1.8 mmol) were added, and the mixture was stirred at 25° C. for 3 h. When the reaction mixture was analyzed by HPLC, it was confirmed that the raw material had completely disappeared, and that the target compound was produced. The reaction solution was quenched with an aqueous EDTA·2Na solution, then the organic layer extracted with MTBE was washed with saline, then the organic layer was dried over sodium sulfate, the desiccant was filtered off, and then the filtrate was concentrated under reduced pressure. The resulting crude product was purified by chromatography to afford tert-butyl (S)-2-((((9H-fluoren-9-yl)methoxy)carbonyl)amino)-4-(pyridin-3-yl)butanoate (0.21 g, yield 26%).

tert-Butyl (S)-2-((((9H-fluoren-9-yl)methoxy)carbonyl)amino)-4-(pyridin-3-yl)butanoate Target compound retention time: 1.0 min (High performance liquid chromatography Condition 3)
ESI (LC/MS positive mode m/z 459 (M+H)$^+$)

Example 6

Production of tert-butyl (S)-2-((((9H-fluoren-9-yl)methoxy)carbonyl)amino)-4-(3,5-difluoro-4-(trifluoromethyl)phenyl)butanoate

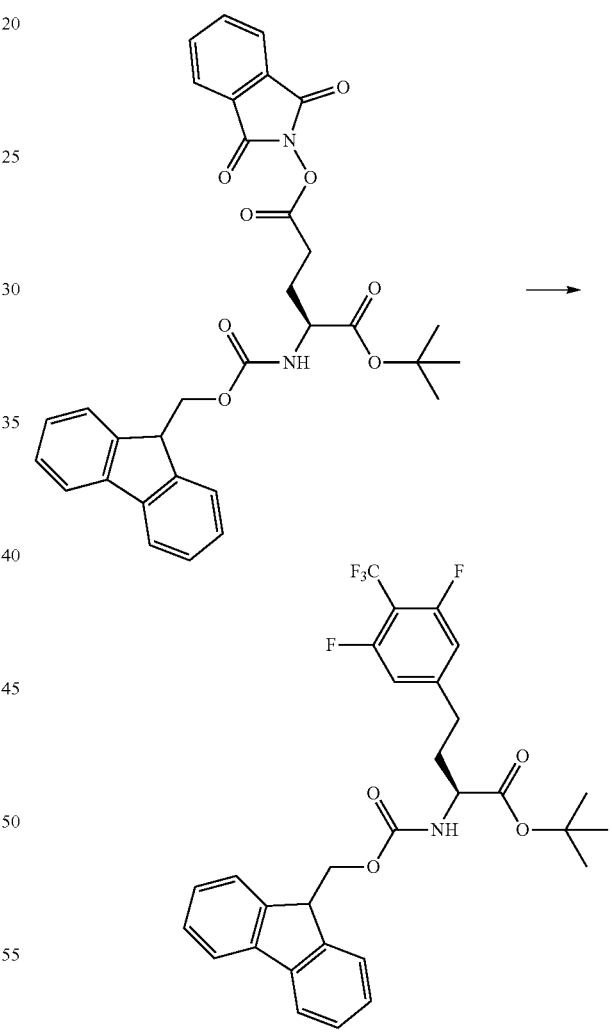

Nickel bromide trihydrate (2.9 g, 11 mmol) and 4,4'-di-tert-butyl-2,2'-bipyridine (2.8 g, 11 mmol) were dissolved in DMA (175 mL), and the mixture was purged with nitrogen and then stirred to prepare a catalyst solution. Zinc powder (11 g, 175 mmol), 5-(1,3-dioxoisoindolin-2-yl) 1-tert-butyl N-(((9H-fluoren-9-yl)methoxy)carbonyl)-L-glutamate (20 g, 35 mmol) and DMA (175 mL) were added to a flask, 5-bromo-1,3-difluoro-2-(trifluoromethyl)benzene (27 g, 105 mmol) was added, and then the mixture was purged with nitrogen. The prepared catalyst solution was added dropwise to the reaction solution under a nitrogen atmosphere, then TMSCl (1.9 g, 18 mmol) was added, and the mixture was stirred at 25° C. for 1 h. When the reaction mixture was analyzed by HPLC, it was confirmed that the raw material had completely disappeared, and that the target compound was the main product. The reaction solution was quenched with an aqueous EDTA·2Na solution, and then the mixture was extracted with MTBE. After the organic layer was washed with an aqueous sodium hydrogen carbonate solution and with an aqueous ammonium chloride solution, the organic layer was concentrated, and the resulting crude product was purified by recrystallization to afford tert-butyl (S)-2-((((9H-fluoren-9-yl)methoxy)carbonyl)amino)-4-(3,5-difluoro-4-(trifluoromethyl)phenyl)butanoate (15 g, yield 76%).

tert-Butyl (S)-2-((((9H-fluoren-9-yl)methoxy)carbonyl)amino)-4-(3,5-difluoro-4-(trifluoromethyl)phenyl)butanoate Target compound retention time: 1.3 min (High performance liquid chromatography Condition 4)

ESI (LC/MS positive mode m/z 562 (M+H)$^+$)

Example 7

Production of 5-allyl 1-(tert-butyl)N-(((9H-fluoren-9-yl)methoxy)carbonyl)-N-methyl-L-glutamate

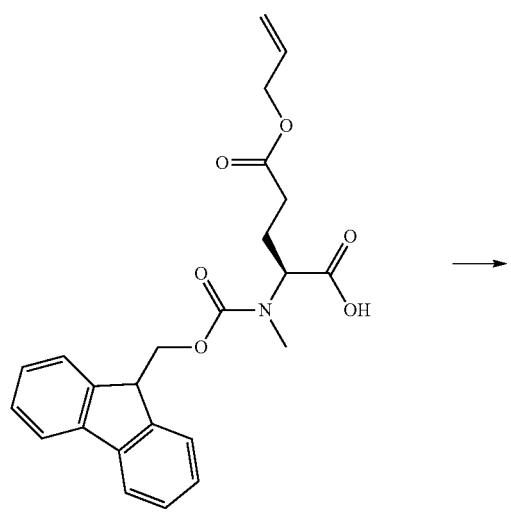

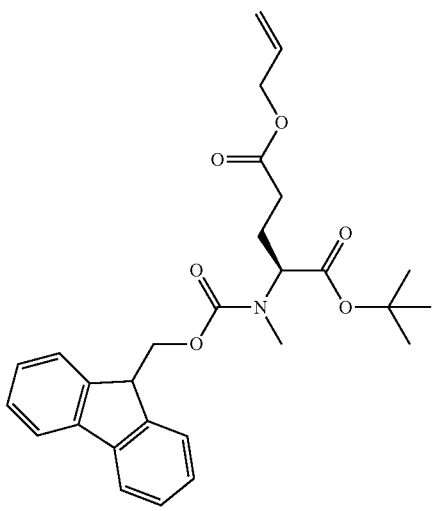

(S)-2-((((9H-Fluoren-9-yl)methoxy)carbonyl)(methyl)amino)-5-(allyloxy)-5-oxopentanoic acid (19 g, 46 mmol) was dissolved in dichloromethane (40 mL), and a solution of tert-butyl 2,2,2-trichloroacetimidate (22 g, 100 mmol) in cyclohexane (80 mL) was added dropwise. BF$_3$·OEt$_2$ (0.87 mL, 6.8 mmol) was added to the solution, and the mixture was stirred at 25° C. for 20 min. Sodium bicarbonate was added, the mixture was stirred, and then insoluble matter was removed by filtration. The filtrate was diluted with MTBE and washed with an aqueous Na$_2$CO$_3$ solution and with saline. The organic layer was concentrated to afford N-(((9H-fluoren-9-yl)methoxy)carbonyl)-N-methyl-L5-allyl 1-(tert-butyl)N-(((9H-fluoren-9-yl)methoxy)carbonyl)-N-methyl-L-glutamate (20 g, yield 91%).

5-Allyl 1-(tert-butyl)N-(((9H-fluoren-9-yl)methoxy)carbonyl)-N-methyl-L-glutamate Target compound retention time: 1.1 min (High performance liquid chromatography Condition 4)

ESI (LC/MS positive mode m/z 502 (M+Na)$^+$)

Example 8

Production of (S)-4-((((9H-fluoren-9-yl)methoxy)carbonyl)(methyl)amino)-5-(tert-butoxy)-5-oxopentanoic Acid

Example 9

Production of 1-(tert-butyl) 5-(1,3-dioxoisoindolin-2-yl)N-(((9H-fluoren-9-yl)methoxy)carbonyl)-N-methyl-L-glutamate

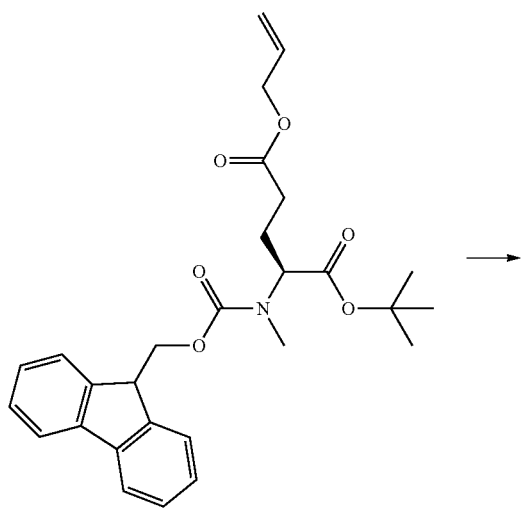

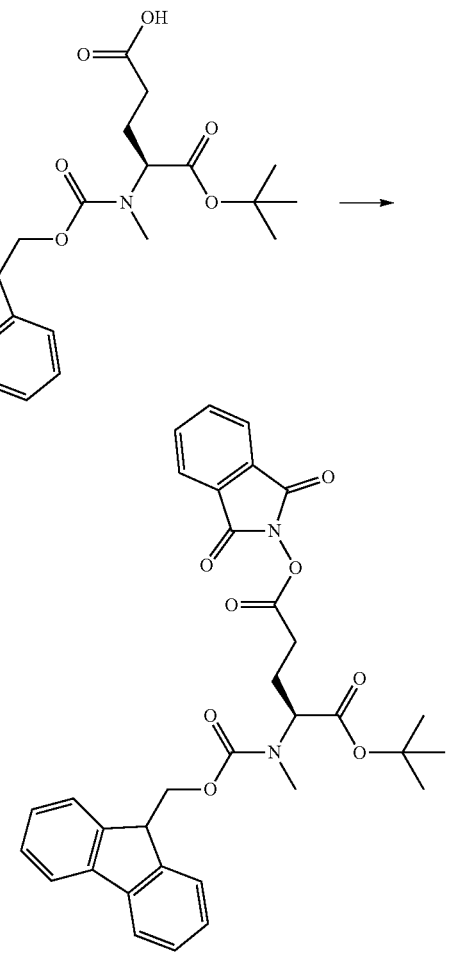

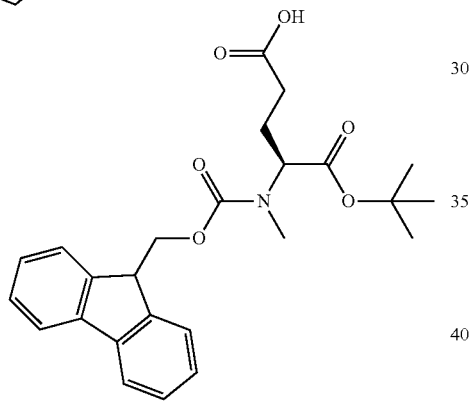

5-Allyl 1-(tert-butyl)N-(((9H-fluoren-9-yl)methoxy)carbonyl)-N-methyl-L-glutamate (22 g, 46 mmol) and tetrakistriphenylphosphine palladium (0.53 g, 0.46 mmol) were dissolved in dichloromethane (91 mL), and phenylsilane (3.4 g, 32 mmol) was added. After the mixture was stirred for 2 h, tetrakistriphenylphosphine palladium (0.53 g, 0.46 mmol) was added, and the reaction solution was stirred at 25° C. for 2.5 h. MTBE (500 mL) and an aqueous sodium carbonate solution were added to the reaction solution to separate the solution into two layers. $H_3PO_4$ (30 mL) was added to acidify the aqueous layer, and the target compound was extracted with MTBE (500 mL). The organic layer after being washed with saline was concentrated to afford (S)-4-((((9H-fluoren-9-yl)methoxy)carbonyl)(methyl)amino)-5-(tert-butoxy)-5-oxopentanoic acid (19 g, yield 97%).

(S)-4-((((9H-fluoren-9-yl)methoxy)carbonyl)(methyl)amino)-5-(tert-butoxy)-5-oxopentanoic Acid Target compound retention time: 0.88 min (High performance liquid chromatography Condition 4)
ESI (LC/MS positive mode m/z 440 (M+H)$^+$)

(S)-4-((((9H-Fluoren-9-yl)methoxy)carbonyl)(methyl)amino)-5-(tert-butoxy)-5-oxopentanoic acid (7.7 g, 47 mmol) and N-hydroxyphthalimide (19 g, 43 mmol) were dissolved in THF (130 mL), and a solution of N,N'-diisopropylcarbodiimide (8.1 g, 64 mmol) in THF (10 mL) was added dropwise. After the reaction solution was stirred at 25° C. for 1 h, toluene (40 mL) was added, and solids were removed by filtration. The filtrate was concentrated, MTBE (150 mL) was added to form a suspension, and the precipitate was removed by filtration. The filtrate was concentrated to afford 1-(tert-butyl) 5-(1,3-dioxoisoindolin-2-yl)N-(((9H-fluoren-9-yl)methoxy)carbonyl)-N-methyl-L-glutamate (26 g, yield 100%).

1-(tert-Butyl) 5-(1,3-dioxoisoindolin-2-yl)N-(((9H-fluoren-9-yl)methoxy)carbonyl)-N-methyl-L-glutamate Target compound retention time: 1.1 min (High performance liquid chromatography Condition 4)
ESI (LC/MS positive mode m/z 585 (M+H)$^+$)

Example 10

Production of tert-butyl (S)-2-((((9H-fluoren-9-yl)methoxy)carbonyl)(methyl)amino)-4-(pyridin-3-yl)butanoate

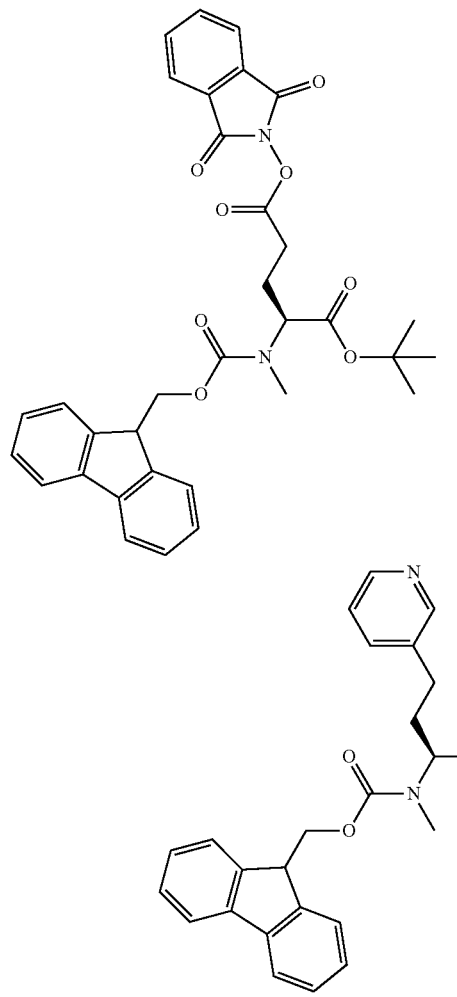

Nickel bromide trihydrate (4.0 mg, 0.015 mmol) and 4,4'-di-tert-butyl-2,2'-bipyridine (3.9 mg, 0.015 mmol) were dissolved in DMA (0.50 mL), and the mixture was purged with nitrogen and then stirred to prepare a catalyst solution. 1-(tert-Butyl) 5-(1,3-dioxoisoindolin-2-yl)N-(((9H-fluoren-9-yl)methoxy)carbonyl)-N-methyl-L-glutamate (0.12 g, 0.21 mmol) and 3-iodopyridine (0.13 g, 0.62 mmol) were added to and dissolved in DMA (0.5 mL). The prepared catalyst solution was added dropwise thereto under a nitrogen atmosphere, zinc powder (68 mg, 1.0 mmol) and then TMSCl (56 mg, 0.52 mmol) were added, and the reaction vessel was shaken at 25° C. for 20 h. When the reaction mixture was analyzed by HPLC, it was confirmed that the raw material had completely disappeared, and that the target compound was produced. The reaction solution was purified by chromatography to afford tert-butyl (S)-2-((((9H-fluoren-9-yl)methoxy)carbonyl)(methyl)amino)-4-(pyridin-3-yl)butanoate (20 mg, yield 20%).

tert-Butyl (S)-2-((((9H-fluoren-9-yl)methoxy)carbonyl)(methyl)amino)-4-(pyridin-3-yl)butanoate Target compound retention time: 1.1 min (High performance liquid chromatography Condition 3)
ESI (LC/MS positive mode m/z 473 (M+H)$^+$)

Example 11

Production of 1-(tert-butyl) 4-(1,3-dioxoisoindolin-2-yl) (((9H-fluoren-9-yl)methoxy)carbonyl)-L-aspartate

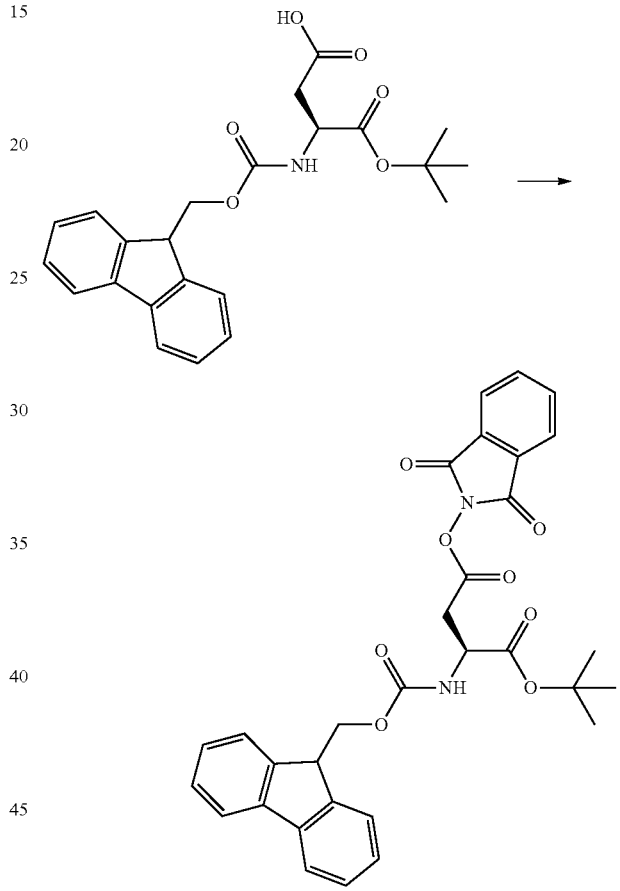

(S)-3-((((9H-Fluoren-9-yl)methoxy)carbonyl)amino)-4-(tert-butoxy)-4-oxobutanoic acid (2.0 g, 4.9 mmol) and N-hydroxyphthalimide (0.87 g, 5.4 mmol) were dissolved in THF (19 mL), and N,N'-diisopropylcarbodiimide (0.92 g, 7.3 mmol) was added dropwise. The reaction solution was stirred at 25° C. for 30 min, the solution was concentrated, toluene (20 mL) was added, and the solids were removed by filtration. The filtrate was concentrated, and purified by chromatography to afford 1-(tert-butyl) 4-(1,3-dioxoisoindolin-2-yl) (((9H-fluoren-9-yl)methoxy)carbonyl)-L-aspartate (2.7 g, yield 100%).

1-(tert-Butyl) 4-(1,3-dioxoisoindolin-2-yl) (((9H-fluoren-9-yl)methoxy)carbonyl)-L-aspartate Target compound retention time: 1.0 min (High performance liquid chromatography Condition 4)
ESI (LC/MS positive mode m/z 479 (M+Na)$^+$)

Example 12

Production of tert-butyl (S)-2-((((9H-fluoren-9-yl)methoxy)carbonyl)amino)-3-(3-methoxyphenyl)propanoate

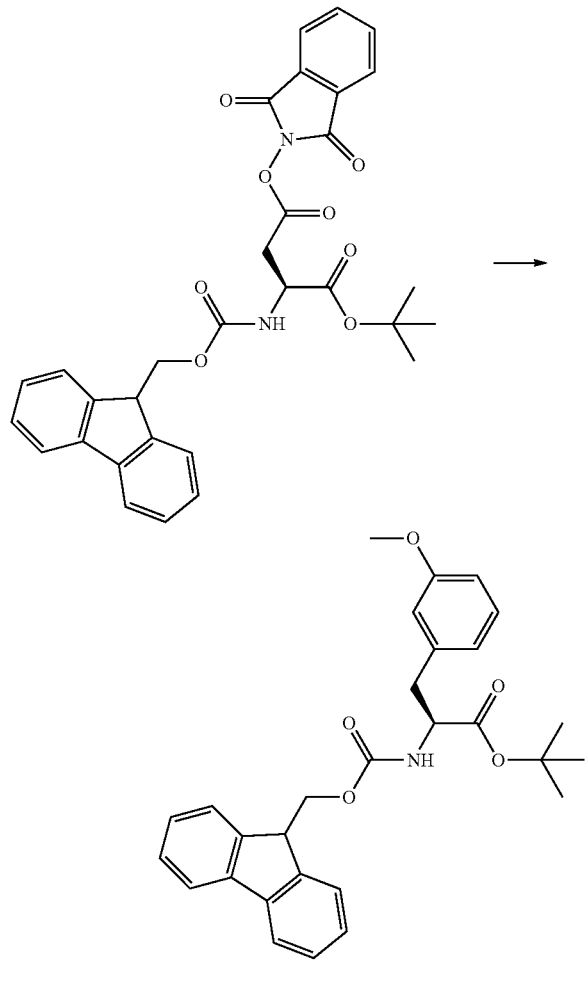

Nickel bromide trihydrate (4.0 mg, 0.015 mmol) and 4,4'-di-tert-butyl-2,2'-bipyridine (3.9 mg, 0.015 mmol) were dissolved in DMA (0.50 mL), and the mixture was purged with nitrogen and then stirred to prepare a catalyst solution. 1-(tert-Butyl) 4-(1,3-dioxoisoindolin-2-yl) (((9H-fluoren-9-yl)methoxy)carbonyl)-L-aspartate (0.12 g, 0.21 mmol) and 1-iodo-3-methoxybenzene (0.15 g, 0.62 mmol) were added to and dissolved in DMA (0.5 mL). The prepared catalyst solution was added dropwise thereto under a nitrogen atmosphere, zinc powder (68 mg, 1.0 mmol) and then TMSCl (11 mg, 0.10 mmol) were added, and the reaction vessel was shaken at 25° C. for 2 h. When the reaction mixture was analyzed by HPLC, it was confirmed that the raw material had completely disappeared, and that the target compound was the main product. The reaction solution was purified by chromatography to afford tert-butyl (S)-2-((((9H-fluoren-9-yl)methoxy)carbonyl)amino)-3-(3-methoxyphenyl)propanoate (70 mg, yield 71%).

tert-Butyl (S)-2-((((9H-fluoren-9-yl)methoxy)carbonyl)amino)-3-(3-methoxyphenyl)propanoate Target compound retention time: 1.1 min (High performance liquid chromatography Condition 3)
ESI (LC/MS positive mode m/z 496 (M+Na)$^+$)

Example 13

Production of 4-allyl 1-(tert-butyl)N-(((9H-fluoren-9-yl)methoxy)carbonyl)-N-methyl-L-aspartate

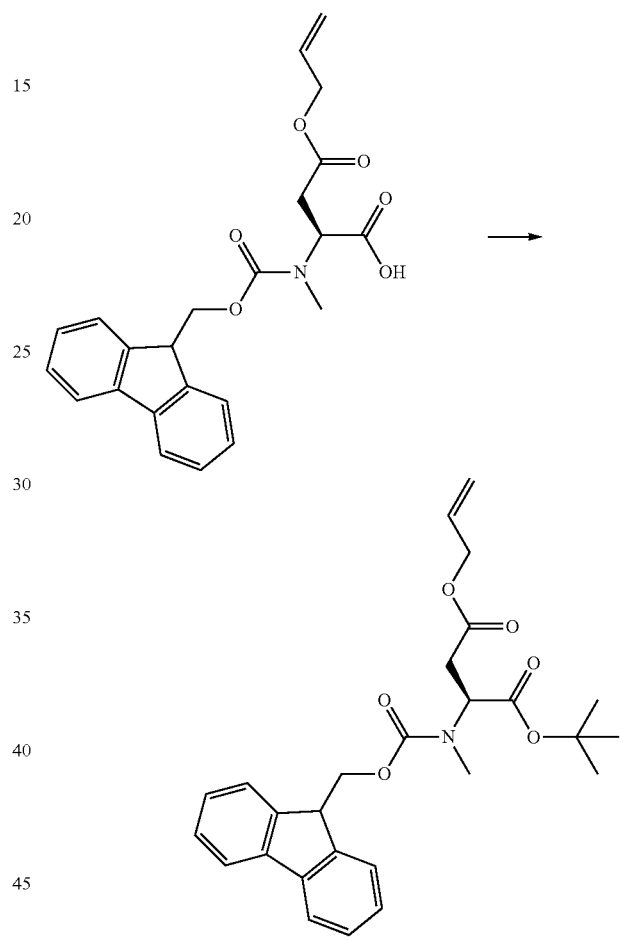

(S)-2-((((9H-Fluoren-9-yl)methoxy)carbonyl)(methyl)amino)-4-(allyloxy)-4-oxobutanoic acid (16 g, 39 mmol) was dissolved in dichloromethane (36 mL), and a solution of tert-butyl 2,2,2-trichloroacetimidate (14 g, 77 mmol) in cyclohexane (72 mL) was added dropwise. BF3·OEt2 (0.73 mL, 5.8 mmol) was added to the solution, and the mixture was stirred at 25° C. for 10 min. NaHCO$_3$ was added, the mixture was stirred, and then insoluble matter was removed by filtration. The filtrate was diluted with MTBE and washed with an aqueous Na$_2$CO$_3$ solution. The organic layer was concentrated, and purified by chromatography to afford 4-allyl 1-(tert-butyl)N-(((9H-fluoren-9-yl)methoxy)carbonyl)-N-methyl-L-aspartate (20 g, yield 95%).

4-Allyl 1-(tert-butyl)N-(((9H-fluoren-9-yl)methoxy)carbonyl)-N-methyl-L-aspartate Target compound retention time: 1.1 min (High performance liquid chromatography Condition 4)
ESI (LC/MS positive mode m/z 488 (M+Na)$^+$)

Example 14

Production of (S)-3-((((9H-fluoren-9-yl)methoxy)carbonyl)(methyl)amino)-4-(tert-butoxy)-4-oxobutanoic Acid

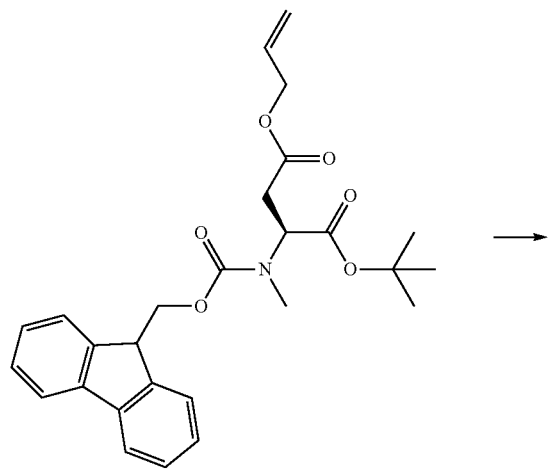

4-Allyl 1-(tert-butyl)N-(((9H-fluoren-9-yl)methoxy)carbonyl)-N-methyl-L-aspartate (14 g, 31 mmol) and tetrakistriphenylphosphine palladium (0.36 g, 0.31 mmol) were dissolved in dichloromethane (61 mL), and phenylsilane (2.3 g, 22 mmol) was added. After the reaction solution was stirred at 25° C. for 40 min, MTBE (500 mL) and an aqueous sodium carbonate solution were added to the reaction solution to separate the solution into two layers. $H_3PO_4$ (80 mL) was added to acidify the aqueous layer, and the target compound was extracted with MTBE (700 mL). The organic layer after being washed with saline was concentrated to afford (S)-3-((((9H-fluoren-9-yl)methoxy)carbonyl)(methyl)amino)-4-(tert-butoxy)-4-oxobutanoic acid (14 g, yield 100%).

(S)-3-((((9H-Fluoren-9-yl)methoxy)carbonyl)(methyl)amino)-4-(tert-butoxy)-4-oxobutanoic Acid Target compound retention time: 0.90 min (High performance liquid chromatography Condition 4)

ESI (LC/MS positive mode m/z 448 (M+Na)$^+$)

Example 15

Production of 1-(tert-butyl) 4-(1,3-dioxoisoindolin-2-yl)N-(((9H-fluoren-9-yl)methoxy)carbonyl)-N-methyl-L-aspartate

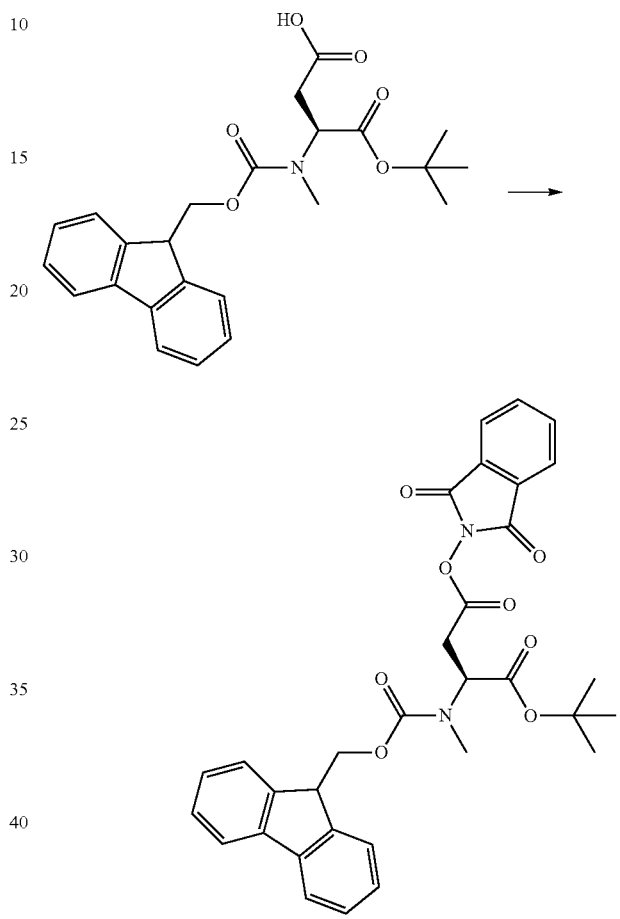

(S)-3-((((9H-Fluoren-9-yl)methoxy)carbonyl)(methyl)amino)-4-(tert-butoxy)-4-oxobutanoic acid (0.27 g, 0.6 mmol) and N-hydroxyphthalimide (0.12 g, 0.71 mmol) were dissolved in THF (2.6 mL), and N,N'-diisopropylcarbodiimide (0.12 g, 1.0 mmol) was added dropwise. After the reaction solution was stirred at 25° C. for 90 min, the solution was concentrated, toluene (2 mL) was added, and solids were removed by filtration. The filtrate was concentrated, and purified by chromatography to afford 1-(tert-butyl) 4-(1,3-dioxoisoindolin-2-yl)N-(((9H-fluoren-9-yl)methoxy)carbonyl)-N-methyl-L-aspartate (0.22 g, yield 59%).

1-(tert-Butyl) 4-(1,3-dioxoisoindolin-2-yl)N-(((9H-fluoren-9-yl)methoxy)carbonyl)-N-methyl-L-aspartate Target compound retention time: 1.1 min (High performance liquid chromatography Condition 4)

ESI (LC/MS positive mode m/z 593 (M+Na)$^+$)

Example 16

Production of tert-butyl (S)-2-((((9H-fluoren-9-yl)methoxy)carbonyl)(methyl)amino)-3-(pyrimidin-5-yl)propanoate

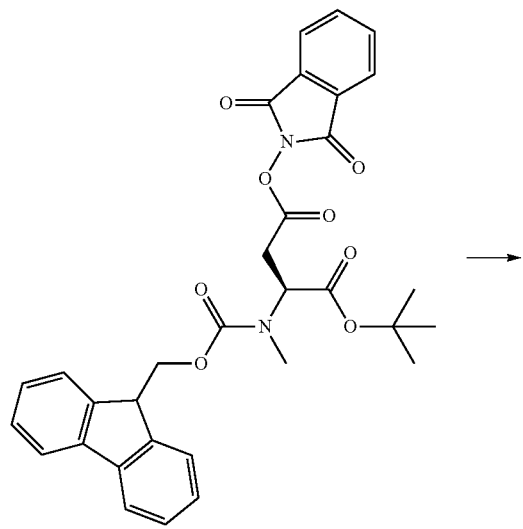

Nickel bromide trihydrate (4.0 mg, 0.015 mmol) and 4,4'-di-tert-butyl-2,2'-bipyridine (3.9 mg, 0.015 mmol) were dissolved in DMA (0.50 mL), and the mixture was purged with nitrogen and then stirred to prepare a catalyst solution. 1-(tert-Butyl) 4-(1,3-dioxoisoindolin-2-yl)N-(((9H-fluoren-9-yl)methoxy)carbonyl)-N-methyl-L-aspartate (0.12 g, 0.21 mmol) and 5-bromopyrimidine (99 mg, 0.62 mmol) were added to and dissolved in DMA (0.50 mL). The prepared catalyst solution was added dropwise to the reaction solution under a nitrogen atmosphere, zinc powder (68 mg, 1.0 mmol) and then TMSCl (34 mg, 0.31 mmol) were added, and the reaction vessel was shaken at 25° C. for 2 h. When the reaction mixture was analyzed by HPLC, it was confirmed that the raw material had completely disappeared, and that the target compound was produced. The reaction solution was purified by chromatography to afford tert-butyl (S)-2-((((9H-fluoren-9-yl)methoxy)carbonyl)(methyl)amino)-3-(pyrimidin-5-yl)propanoate (32 mg, yield 34%).

tert-Butyl (S)-2-((((9H-fluoren-9-yl)methoxy)carbonyl)(methyl)amino)-3-(pyrimidin-5-yl)propanoate Target compound retention time: 1.0 min (High performance liquid chromatography Condition 3)
ESI (LC/MS positive mode m/z 460 (M+H)$^+$)

Example 17

Production of tert-Butyl (S)-2-((((9H-fluoren-9-yl)methoxy)carbonyl)(methyl)amino)-3-(2-fluoro-4-(trifluoromethyl)phenyl)propanoate

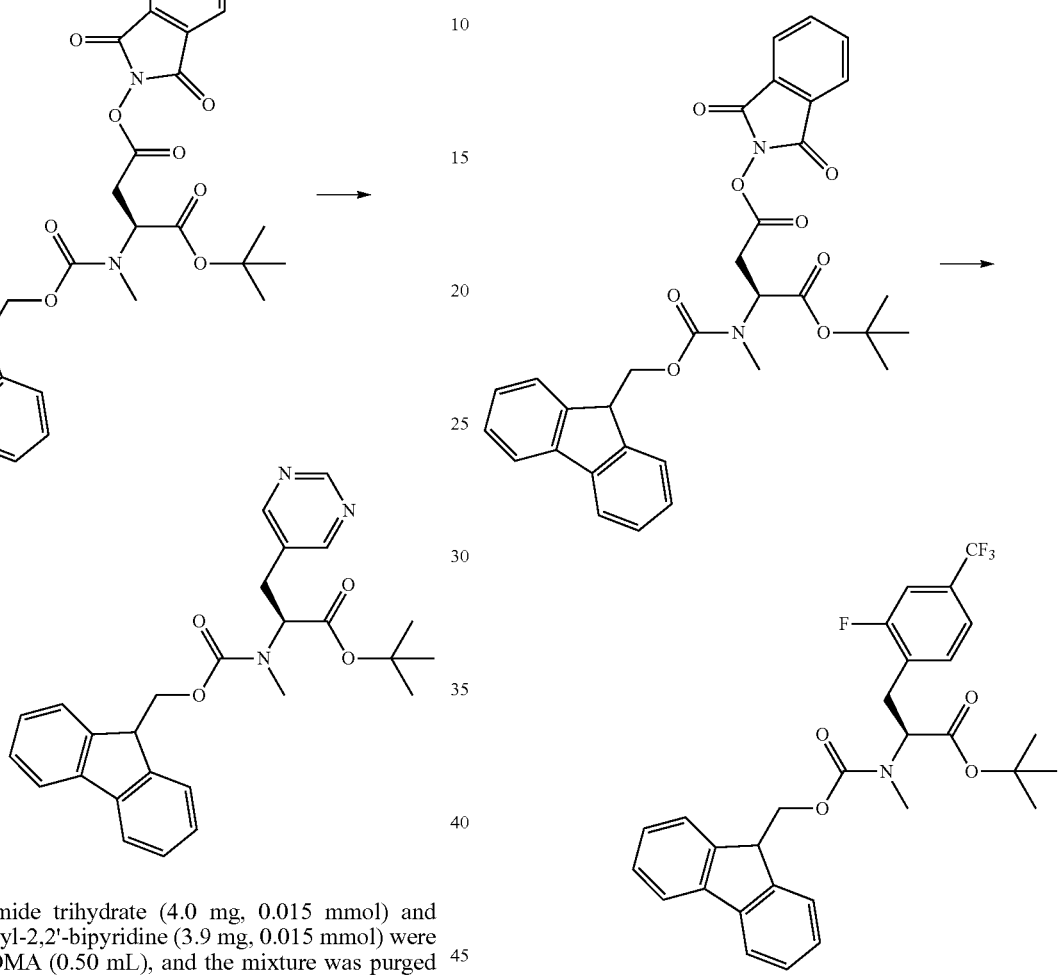

Nickel bromide trihydrate (0.21 g, 0.77 mmol) and 4,4'-di-tert-butyl-2,2'-bipyridine (0.25 g, 0.95 mmol) were dissolved in DMA (15 mL), and the mixture was purged with nitrogen and then stirred to prepare a catalyst solution. Zinc powder (1.0 g, 16 mmol), 1-(tert-butyl) 4-(1,3-dioxoisoindolin-2-yl)N-(((9H-fluoren-9-yl)methoxy)carbonyl)-N-methyl-L-aspartate (1.8 g, 3.2 mmol), and DMA (8.0 mL) were added to a flask, 1-bromo-2-fluoro-4-(trifluoromethyl)benzene (2.3 g, 9.5 mmol) was added, and then the mixture was purged with nitrogen. After the prepared catalyst solution was added dropwise to the reaction solution under a nitrogen atmosphere, TMSCl (0.17 g, 1.6 mmol) was added, and the mixture was stirred at 25° C. for 30 min. When the reaction mixture was analyzed by HPLC, it was confirmed that the raw material had completely disappeared, and that the target compound was the main product. The reaction solution was quenched with an aqueous EDTA·2Na solution, and then the mixture was extracted with MTBE. After the organic layer was washed with saline, the organic layer was concentrated and the resulting crude product was purified by chromatography to afford tert-butyl (S)-2-((((9H-fluoren-9-yl)methoxy)carbonyl)(methyl)amino)-3-(2-fluoro-4-(trifluoromethyl)phenyl)propanoate (0.93 g, yield 55%).

tert-Butyl (S)-2-((((9H-fluoren-9-yl)methoxy)carbonyl)(methyl)amino)-3-(2-fluoro-4-(trifluoromethyl)phenyl)propanoate Target compound retention time: 1.2 min (High performance liquid chromatography Condition 4)
ESI (LC/MS positive mode m/z 566 (M+Na)$^+$)

Example 18

Production of tert-butyl (S)-2-((((9H-fluoren-9-yl)methoxy)carbonyl)(methyl)amino)-3-(3-fluoro-4-(trifluoromethyl)phenyl)propanoate Nickel bromide trihydrate (0.21 g, 0.77 mmol) and 4,4'-di-tert-butyl-2,2'-bipyridine (0.25 g, 0.95 mmol) were dissolved in DMA (15 mL), and the mixture was purged with nitrogen and then stirred to prepare a catalyst solution. Zinc powder (1.0 g, 16 mmol), 1-(tert-butyl) 4-(1,3-dioxoisoindolin-2-yl)N-(((9H-fluoren-9-yl)methoxy)carbonyl)-N-methyl-L-aspartate (1.8 g, 3.2 mmol) and DMA (8.0 mL) were added to a flask, 4-bromo-2-fluoro-1-(trifluoromethyl)benzene (2.3 g, 9.5 mmol) was added, and then the mixture was purged with nitrogen. After the prepared catalyst solution was added dropwise to the reaction solution under a nitrogen atmosphere, TMSCl (0.17 g, 1.6 mmol) was added, and the mixture was stirred at 25° C. for 30 min. When the reaction mixture was analyzed by HPLC, it was confirmed that the raw material had completely disappeared, and that the target compound was the main product. The reaction solution was quenched with an aqueous EDTA·2Na solution, and then the mixture was extracted with MTBE. After the organic layer was washed with saline, the organic layer was concentrated, and the resulting crude product was purified by chromatography to afford tert-butyl (S)-2-((((9H-fluoren-9-yl)methoxy)carbonyl)(methyl)amino)-3-(3-fluoro-4-(trifluoromethyl)phenyl)propanoate (1.2 g, yield 68%).

tert-Butyl (S)-2-((((9H-fluoren-9-yl)methoxy)carbonyl)(methyl)amino)-3-(3-fluoro-4-(trifluoromethyl)phenyl)propanoate Target compound retention time: 1.1 min (High performance liquid chromatography Condition 4)
ESI (LC/MS positive mode m/z 566 (M+Na)$^+$)

Example 19

Production of tert-butyl (S)-2-((((9H-fluoren-9-yl)methoxy)carbonyl)(methyl)amino)-3-(2-fluoro-4-methoxyphenyl)propanoate

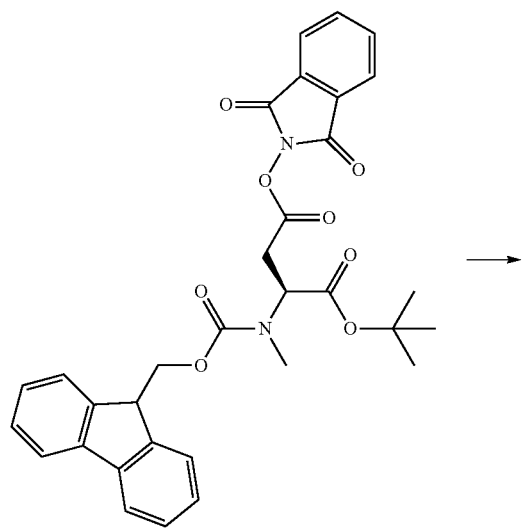

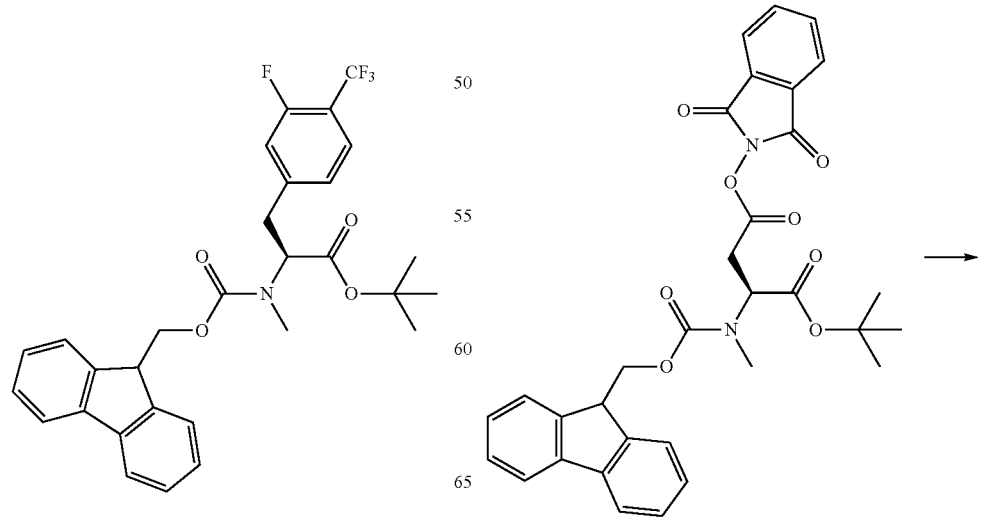

-continued

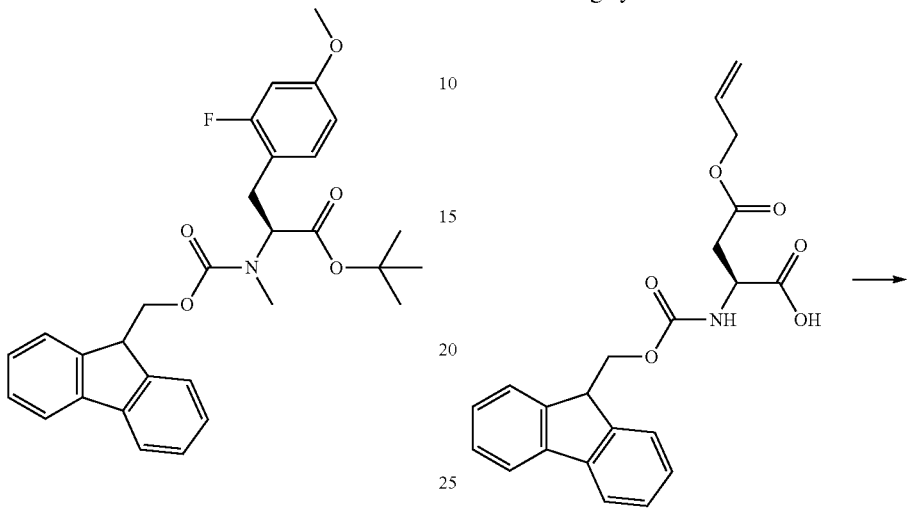

Nickel bromide trihydrate (0.37 g, 1.4 mmol) and 4,4'-di-tert-butyl-2,2'-bipyridine (0.45 g, 1.7 mmol) were dissolved in DMA (25 mL), and the mixture was purged with nitrogen and then stirred to prepare a catalyst solution. Zinc powder (1.8 g, 28 mmol), 1-(tert-butyl) 4-(1,3-dioxoisoindolin-2-yl)N-(((9H-fluoren-9-yl)methoxy)carbonyl)-N-methyl-L-aspartate (3.2 g, 5.6 mmol) and DMA (25 mL) were added to a flask, 1-bromo-2-fluoro-4-methoxybenzene (3.5 g, 17 mmol) was added, and then the mixture was purged with nitrogen. After the prepared catalyst solution was added dropwise under a nitrogen atmosphere, TMSCl (0.31 g, 2.8 mmol) was added, and the mixture was stirred at 25° C. for 30 min. When the reaction mixture was analyzed by HPLC, it was confirmed that the raw material had completely disappeared, and that the target compound was produced. The reaction solution was quenched with an aqueous EDTA·2Na solution, and then the mixture was extracted with MTBE. After the organic layer was washed with saline, the organic layer was concentrated, and the resulting crude product was purified by chromatography to afford tert-butyl (S)-2-((((9H-fluoren-9-yl)methoxy)carbonyl)(methyl)amino)-3-(2-fluoro-4-methoxyphenyl)propanoate (0.48 g, yield 17%).

tert-Butyl (S)-2-((((9H-fluoren-9-yl)methoxy)carbonyl)(methyl)amino)-3-(2-fluoro-4-methoxyphenyl)propanoate Target compound retention time: 1.1 min (High performance liquid chromatography Condition 4)

ESI (LC/MS positive mode m/z 506 (M+H)$^+$)

Production of (S)-2-((((9H-fluoren-9-yl)methoxy)carbonyl)(ethyl)amino)-3-(p-tolyl)propanoic Acid (S)-2-((((9H-Fluoren-9-yl)methoxy)carbonyl)(ethyl)amino)-3-(p-tolyl)propanoic acid was produced according to the following synthesis scheme.

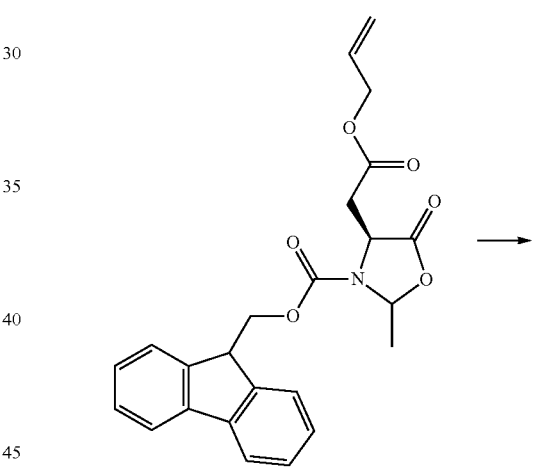

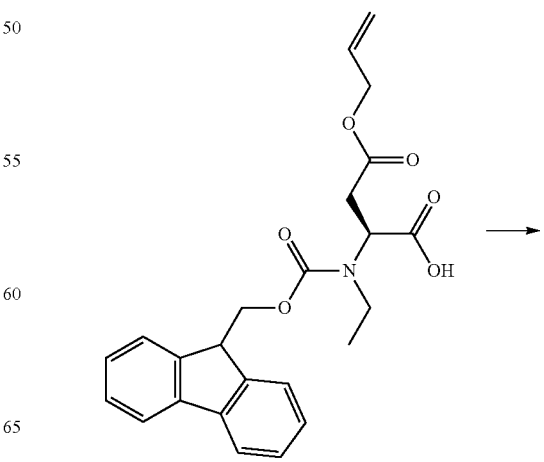

241
-continued
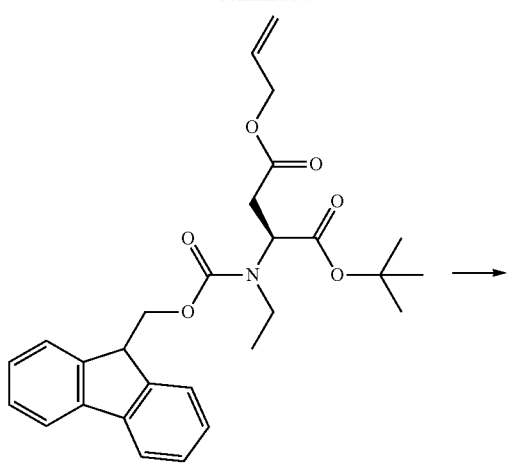
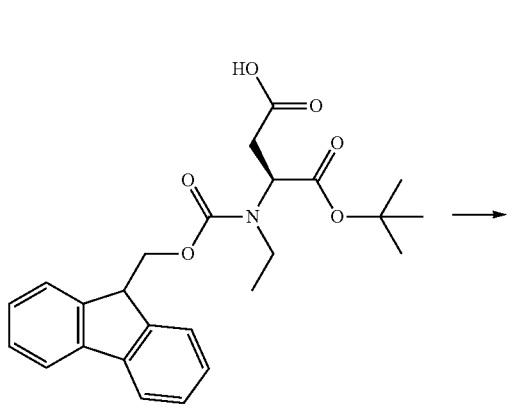
242
-continued
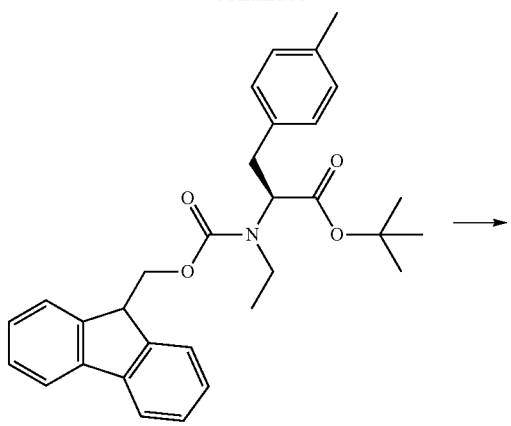
Example 20
Production of (9H-fluoren-9-yl)methyl (4S)-4-(2-(allyloxy)-2-oxoethyl)-2-methyl-5-oxooxazolidine-3-carboxylate
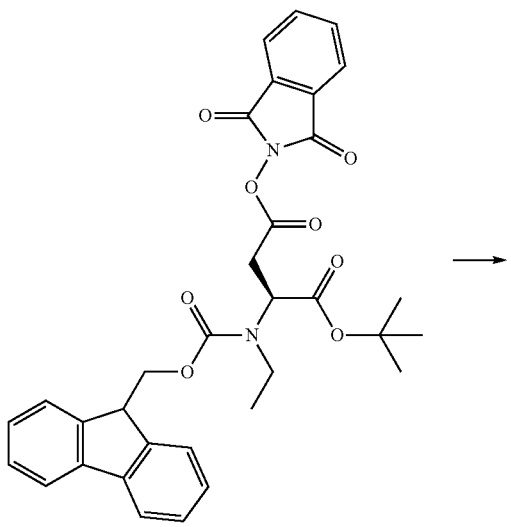
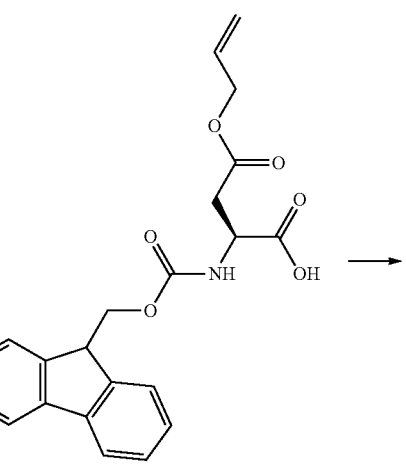

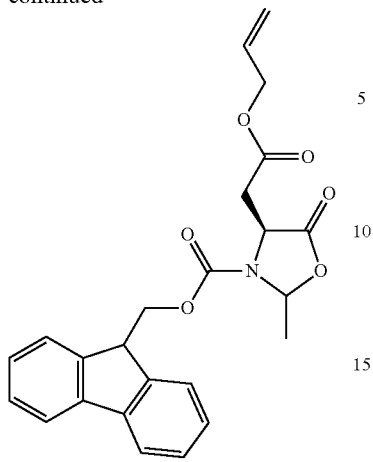

Trifluoracetic acid (29 g, 0.8 mol) as added at room temperature to a suspension of (S)-2-((((9H-fluoren-9-yl)methoxy)carbonyl)amino)-4-(allyloxy)-4-oxobutanoic acid (50 g, 0.13 mol), magnesium sulfate (55 g, 0.38 mol), and paraldehyde (25 g, 0.19 mol) in toluene (0.50 L). The mixture was stirred at 90° C. for 16 h, then cooled to room temperature, diluted with ethyl acetate, and washed with an aqueous sodium hydrogen carbonate solution. The organic layer was dried over sodium sulfate and concentrated under reduced pressure to afford (9H-fluoren-9-yl)methyl (4S)-4-(2-(allyloxy)-2-oxoethyl)-2-methyl-5-oxooxazolidine-3-carboxylate (45 g, yield 82%).

(9H-Fluoren-9-yl)methyl (4S)-4-(2-(allyloxy)-2-oxoethyl)-2-methyl-5-oxooxazolidine-3-carboxylate Target compound retention time: 1.4 min (High performance liquid chromatography Condition 6)
ESI (LC/MS positive mode m/z 422 (M+H)$^+$)

Example 21

Production of (S)-2-((((9H-fluoren-9-yl)methoxy)carbonyl)(ethyl)amino)-4-(allyloxy)-4-oxobutanoic Acid

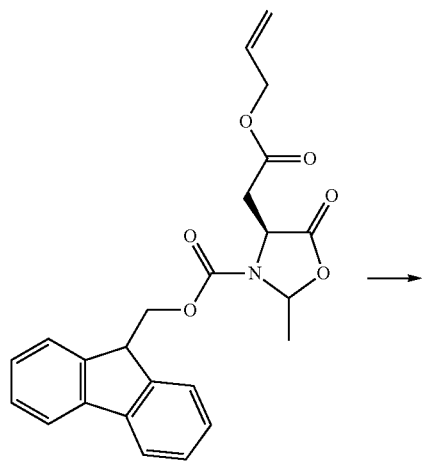

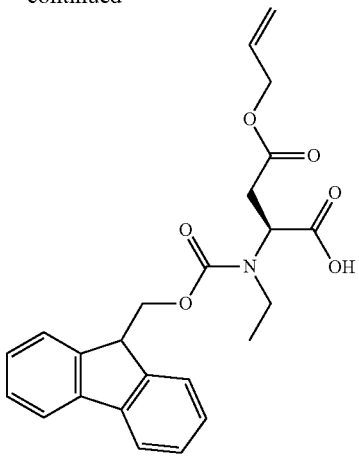

(9H-Fluoren-9-yl)methyl (4S)-4-(2-(allyloxy)-2-oxoethyl)-2-methyl-5-oxooxazolidine-3-carboxylate (46 g, 0.11 mol) and triethylsilane (38 g, 0.32 mol) were dissolved in dichloromethane (0.45 L), and trifluoroacetic acid (0.45 L) was added at 25° C. The solution was stirred at 25° C. for 48 h and then concentrated under reduced pressure. MTBE was added to the concentrated residue, followed by extraction with an aqueous sodium hydrogen carbonate solution into an aqueous layer, and the aqueous layer was washed with hexane three times. The aqueous layer was regulated to pH 2 with hydrochloric acid, and extracted with MTBE twice. The organic layer was dried over sodium sulfate and then concentrated under reduced pressure to afford (S)-2-((((9H-fluoren-9-yl)methoxy)carbonyl)(ethyl)amino)-4-(allyloxy)-4-oxobutanoic acid (33 g, yield 71%).

(S)-2-((((9H-Fluoren-9-yl)methoxy)carbonyl)(ethyl)amino)-4-(allyloxy)-4-oxobutanoic Acid Target compound retention time: 1.9 min (High performance liquid chromatography Condition 5)
ESI (LC/MS positive mode m/z 424 (M+H)$^+$)

Example 22

Production of 4-allyl 1-(tert-butyl)N-(((9H-fluoren-9-yl)methoxy)carbonyl)-N-ethyl-L-aspartate

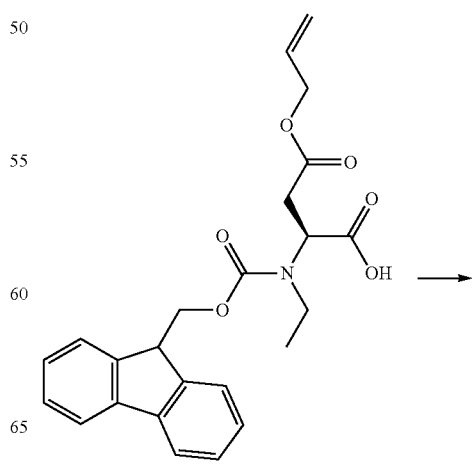

-continued

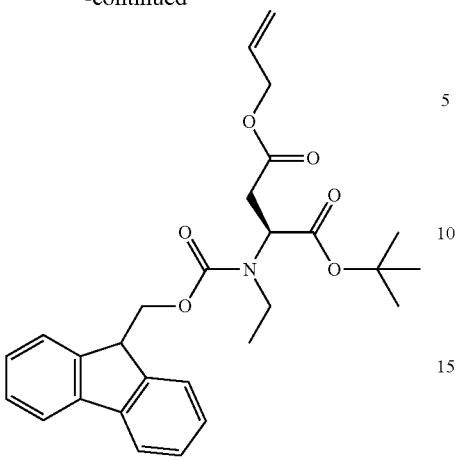

(S)-2-((((9H-Fluoren-9-yl)methoxy)carbonyl)(ethyl)amino)-4-(allyloxy)-4-oxobutanoic acid (5.0 g, 12 mmol) was dissolved in dichloromethane (10 mL), and a solution of tert-butyl 2,2,2-trichloroacetimidate (5.1 g, 24 mmol) in cyclohexane (20 mL) was added dropwise. $BF_3 \cdot OEt_2$ (17 mg, 0.12 mmol) was added to the solution, and the mixture was stirred at 25° C. for 16 h. Insoluble matter was removed by filtration, and the filtrate was concentrated, then diluted with MTBE, and washed with an aqueous sodium hydrogen carbonate solution. The organic layer was dried over sodium sulfate and concentrated to afford 4-allyl 1-(tert-butyl)N-(((9H-fluoren-9-yl)methoxy)carbonyl)-N-ethyl-L-aspartate (4.9 g, yield 85%).

4-Allyl 1-(tert-butyl)N-(((9H-fluoren-9-yl)methoxy)carbonyl)-N-ethyl-L-aspartate Target compound retention time: 1.6 min (High performance liquid chromatography Condition 6)
ESI (LC/MS positive mode m/z 480 (M+H)$^+$)

Example 23

Production of (S)-3-((((9H-fluoren-9-yl)methoxy)carbonyl)(ethyl)amino)-4-(tert-butoxy)-4-oxobutanoic Acid

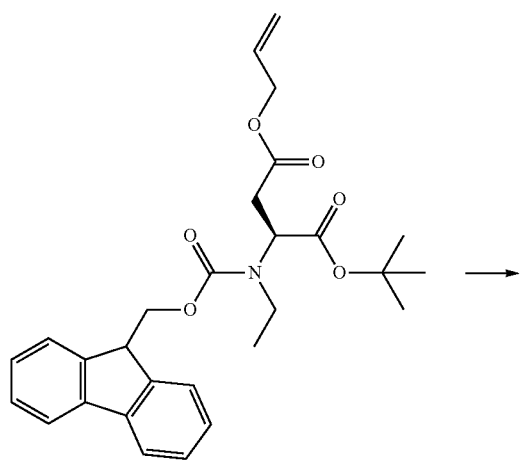

-continued

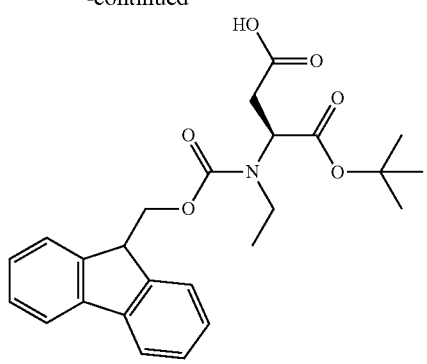

4-Allyl 1-(tert-butyl)N-(((9H-fluoren-9-yl)methoxy)carbonyl)-N-methyl-L-aspartate (4.9 g, 10 mmol) and tetrakistriphenylphosphine palladium (0.12 g, 0.10 mmol) were dissolved in dichloromethane (25 mL), and phenylsilane (0.77 g, 7.2 mmol) was added. The reaction solution was stirred at 25° C. for 16 h and then concentrated, and MTBE was added to dissolve the concentrate. The target compound was extracted with an aqueous sodium carbonate solution into an aqueous layer. The aqueous layer was acidified by adding phosphoric acid to the aqueous layer, and the target compound was extracted with MTBE three times. The organic layer was washed with saline and then dried over sodium sulfate, and the concentrate was purified by chromatography to afford (S)-3-((((9H-fluoren-9-yl)methoxy)carbonyl)(ethyl)amino)-4-(tert-butoxy)-4-oxobutanoic acid (2 g, yield 46%).

(S)-3-((((9H-Fluoren-9-yl)methoxy)carbonyl)(ethyl)amino)-4-(tert-butoxy)-4-oxobutanoic Acid Target compound retention time: 1.7 min (High performance liquid chromatography Condition 5)
ESI (LC/MS positive mode m/z 440 (M+H)$^+$)

Example 24

Production of 1-(tert-butyl) 4-(1,3-dioxoisoindolin-2-yl)N-(((9H-fluoren-9-yl)methoxy)carbonyl)-N-ethyl-L-aspartate

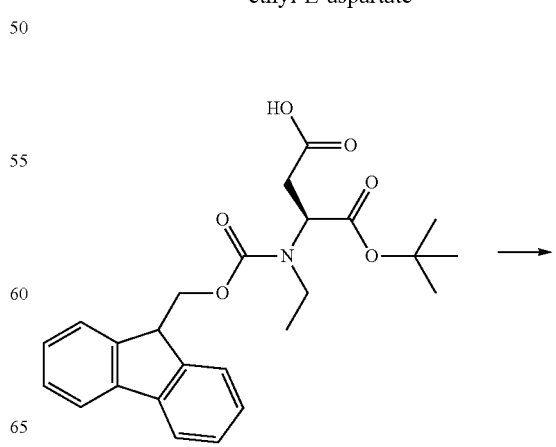

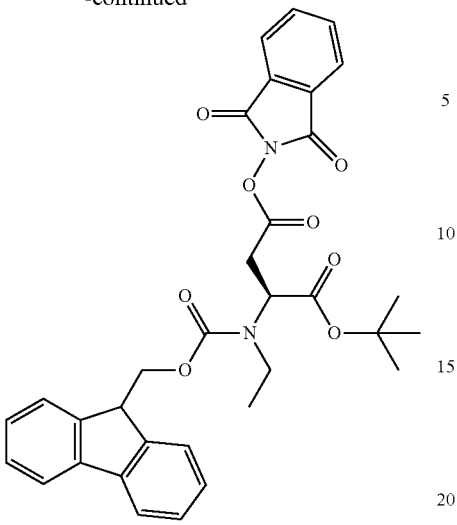

(S)-3-((((9H-Fluoren-9-yl)methoxy)carbonyl)(ethyl)amino)-4-(tert-butoxy)-4-oxobutanoic acid (0.65 g, 1.5 mmol) and N-hydroxyphthalimide (0.27 g, 1.6 mmol) were suspended in ethyl acetate (6.5 mL), and N,N'-diisopropylcarbodiimide (0.28 g, 2.2 mmol) was added dropwise. The reaction solution was stirred at 25° C. for 60 min, and solids were removed by filtration. The filtrate was concentrated, and purified by chromatography to afford 1-(tert-butyl) 4-(1,3-dioxoisoindolin-2-yl)N-(((9H-fluoren-9-yl)methoxy)carbonyl)-N-ethyl-L-aspartate (0.78 g, yield 90%).

1-(tert-Butyl) 4-(1,3-dioxoisoindolin-2-yl)N-(((9H-fluoren-9-yl)methoxy)carbonyl)-N-ethyl-L-aspartate Target compound retention time: 1.1 min (High performance liquid chromatography Condition 4)
ESI (LC/MS positive mode m/z 607 (M+Na)$^+$)

Example 25

Production of tert-butyl (S)-2-((((9H-fluoren-9-yl)methoxy)carbonyl)(ethyl)amino)-3-(p-tolyl)propanoate

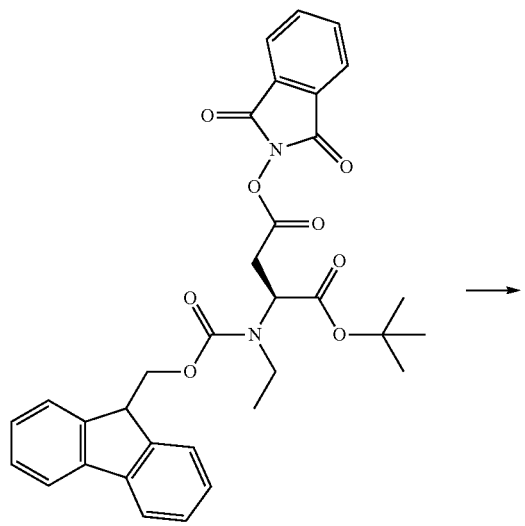

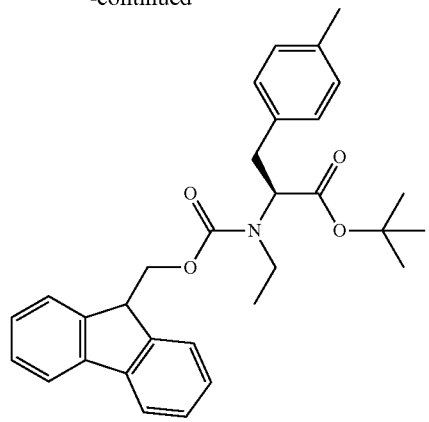

Nickel bromide trihydrate (4.0 mg, 0.015 mmol) and 4,4'-di-tert-butyl-2,2'-bipyridine (3.9 mg, 0.015 mmol) were dissolved in DMA (0.50 mL), and the mixture was purged with nitrogen and then stirred to prepare a catalyst solution. 1-(tert-Butyl) 4-(1,3-dioxoisoindolin-2-yl)N-(((9H-fluoren-9-yl)methoxy)carbonyl)-N-ethyl-L-aspartate (0.12 g, 0.21 mmol) and 1-iodo-4-methylbenzene (0.14 g, 0.62 mmol) were added to and dissolved in DMA (0.50 mL). The prepared catalyst solution was added dropwise to the reaction solution under a nitrogen atmosphere, zinc powder (68 mg, 1.0 mmol) and then TMSCl (11 mg, 0.10 mmol) were added, and the reaction vessel was shaken at 25° C. for 2 h. When the reaction mixture was analyzed by HPLC, it was confirmed that the raw material had completely disappeared, and that the target compound was produced. The reaction solution was purified by chromatography to afford tert-butyl (S)-2-((((9H-fluoren-9-yl)methoxy)carbonyl)(ethyl)amino)-3-(p-tolyl)propanoate (66 mg, yield 65%).

tert-Butyl (S)-2-((((9H-fluoren-9-yl)methoxy)carbonyl)(ethyl)amino)-3-(p-tolyl)propanoate Target compound retention time: 1.2 min (High performance liquid chromatography Condition 4)
ESI (LC/MS positive mode m/z 508 (M+Na)$^+$)

Example 26

Production of (S)-2-((((9H-fluoren-9-yl)methoxy)carbonyl)(ethyl)amino)-3-(p-tolyl)propanoic Acid

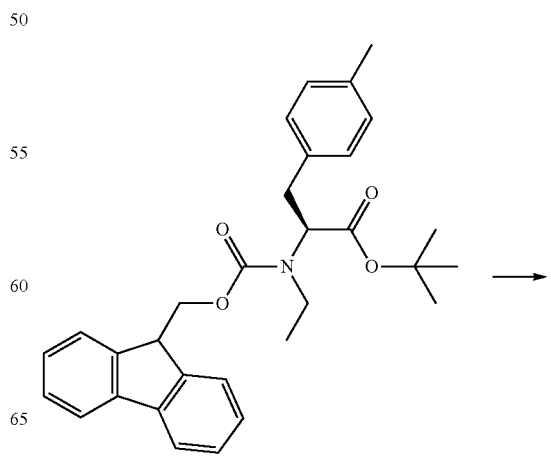

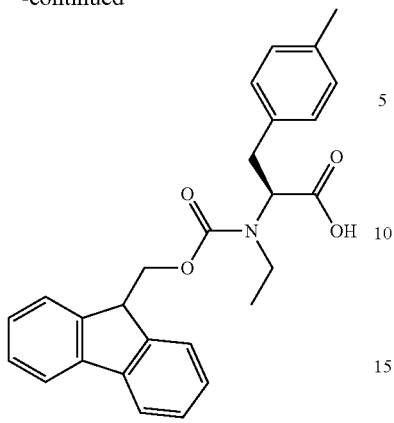

tert-Butyl (S)-2-((((9H-fluoren-9-yl)methoxy)carbonyl)(ethyl)amino)-3-(p-tolyl)propanoate (50 mg, 0.10 mmol) was dissolved in trifluoroethanol (0.50 mL), TMSCl (17 mg, 0.15 mmol) was added at room temperature, and the mixture was stirred for 2 h. The reaction solution was concentrated under reduced pressure, and the concentrate was purified by chromatography to afford (S)-2-((((9H-fluoren-9-yl)methoxy)carbonyl)(ethyl)amino)-3-(p-tolyl)propanoic acid (38 mg, yield 86%).

(S)-2-((((9H-Fluoren-9-yl)methoxy)carbonyl)(ethyl)amino)-3-(p-tolyl)propanoic Acid Target compound retention time: 0.95 min (High performance liquid chromatography Condition 4)

ESI (LC/MS positive mode m/z 430 (M+H)$^+$)

Example 27

Production of tert-butyl (S)-2-((((9H-fluoren-9-yl)methoxy)carbonyl)(methyl)amino)-3-(p-tolyl)propanoate

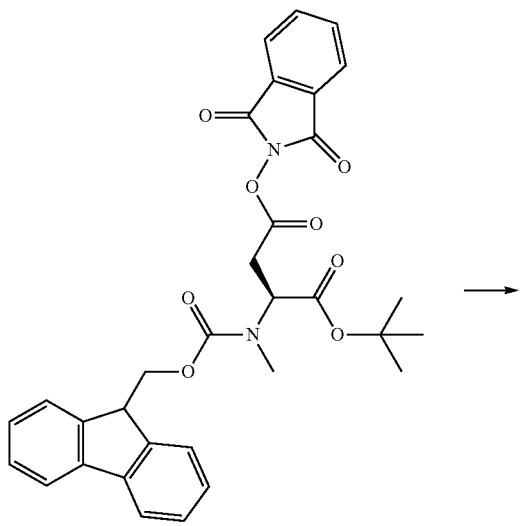

→

Nickel bromide trihydrate (3.8 mg, 0.014 mmol) and 4,4'-di-tert-butyl-2,2'-bipyridine (3.8 mg, 0.014 mmol) were dissolved in DMA (0.50 mL), and the mixture was purged with nitrogen and then stirred to prepare a catalyst solution. Zinc powder (65 mg, 1.0 mmol) and TMSCl (11 mg, 0.10 mmol) were added to the solution, and the mixture was shaken for 10 min. A solution of 1-(tert-butyl) 4-(1,3-dioxoisoindolin-2-yl)N-(((9H-fluoren-9-yl)methoxy)carbonyl)-N-methyl-L-aspartate (0.11 g, 0.20 mmol) and 1-iodo-4-methylbenzene (0.13 g, 0.60 mmol) in DMA (0.50 mL) was added dropwise to the catalyst solution under a nitrogen atmosphere, and the reaction vessel was shaken at 25° C. for 2 h. When the reaction mixture was analyzed by HPLC, it was confirmed that the raw material had completely disappeared, and that the target compound was produced. The reaction solution was purified by chromatography to afford tert-butyl (S)-2-((((9H-fluoren-9-yl)methoxy)carbonyl)(methyl)amino)-3-(p-tolyl)propanoate (56 mg, yield 59%).

tert-Butyl (S)-2-((((9H-fluoren-9-yl)methoxy)carbonyl)(methyl)amino)-3-(p-tolyl)propanoate Target compound retention time: 1.2 min (High performance liquid chromatography Condition 4)

ESI (LC/MS positive mode m/z 494 (M+Na)$^+$)

Example 28

Production of tert-butyl (S)-2-((((9H-fluoren-9-yl)methoxy)carbonyl)(methyl)amino)-4-(3-methoxyphenyl)butanoate

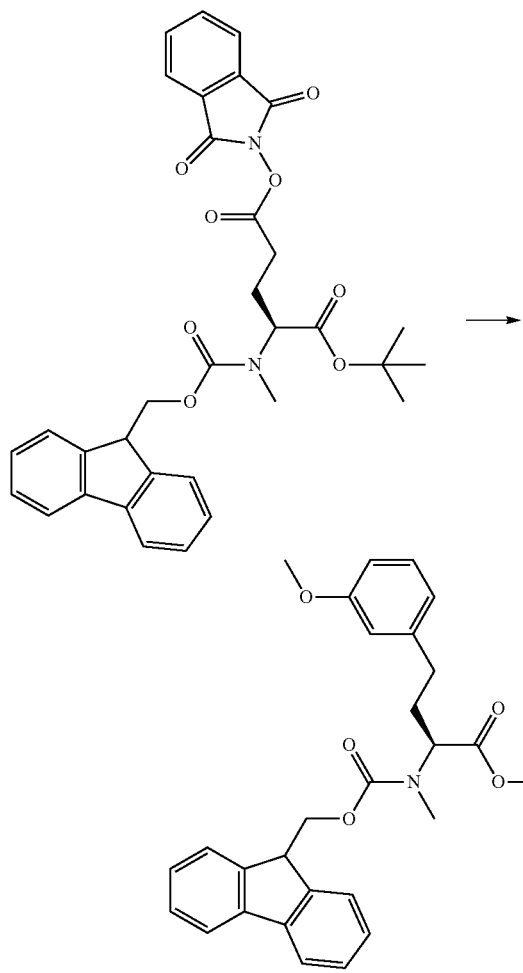

Nickel bromide trihydrate (3.8 mg, 0.014 mmol) and 4,4'-di-tert-butyl-2,2'-bipyridine (3.8 mg, 0.014 mmol) were dissolved in DMA (0.50 mL), the mixture was purged with nitrogen and then stirred, and zinc powder (65 mg, 1.0 mmol) was further added to the solution to prepare a catalyst solution. 1-(tert-Butyl) 5-(1,3-dioxoisoindolin-2-yl)N-(((9H-fluoren-9-yl) methoxy)carbonyl)-N-methyl-L-glutamate (0.12 g, 0.20 mmol) and 1-iodo-3-methoxybenzene (0.14 g, 0.60 mmol) were dissolved in DMA (0.50 mL), and then TMSCl (11 mg, 0.10 mmol) was added. The solution was added dropwise to the catalyst solution under a nitrogen atmosphere, and the reaction vessel was shaken at 25° C. for 2 h. When the reaction mixture was analyzed by HPLC, it was confirmed that the raw material had completely disappeared, and that the target compound was produced. The reaction solution was purified by chromatography to afford tert-butyl (S)-2-((((9H-fluoren-9-yl)methoxy)carbonyl)(methyl)amino)-4-(3-methoxyphenyl)butanoate (67 mg, yield 67%).

tert-Butyl (S)-2-((((9H-fluoren-9-yl)methoxy)carbonyl)(methyl)amino)-4-(3-methoxyphenyl)butanoate Target compound retention time: 1.1 min (High performance liquid chromatography Condition 4)

ESI (LC/MS positive mode m/z 524 (M+Na)$^+$)

Production of (S)-2-((((9H-fluoren-9-yl)methoxy)carbonyl)amino)-4-(4-methoxyphenyl)butanoic Acid (S)-2-((((9H-Fluoren-9-yl)methoxy)carbonyl)amino)-4-(4-methoxyphenyl)butanoic acid can be produced according to the following synthesis scheme including the step of reacting an N-hydroxyphthalimide ester with an aromatic bromide using the same conditions and method as in the above Examples to obtain an aromatic amino acid derivative.

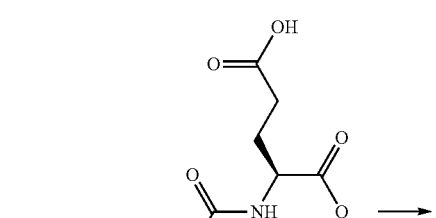

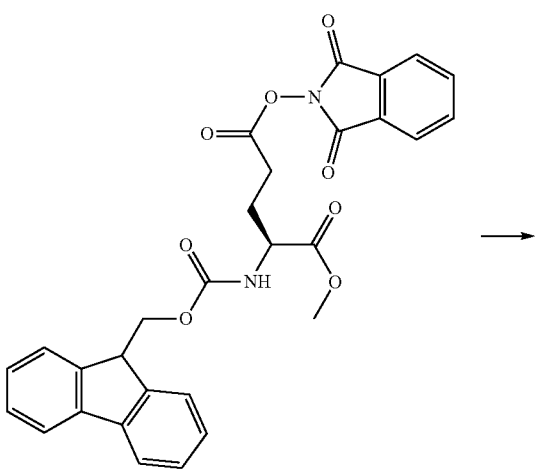

253

-continued

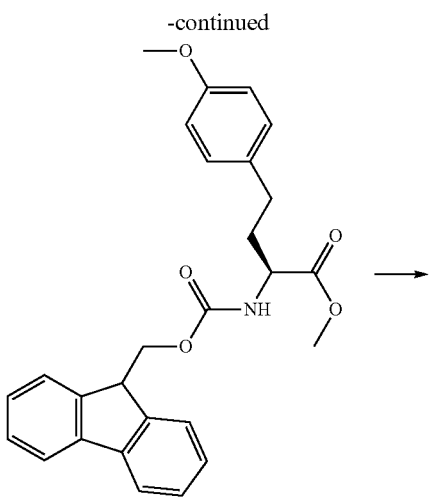

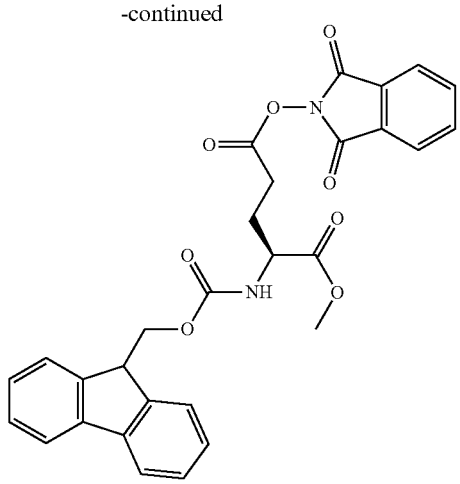

(S)-4-((((9H-Fluoren-9-yl)methoxy)carbonyl)amino)-5-(methoxy)-5-oxopentanoic acid (1.0 g, 2.6 mmol) and N-hydroxyphthalimide (0.47 g, 2.9 mmol) were suspended in ethyl acetate (10 mL), and N,N'-diisopropylcarbodiimide (0.61 mL, 3.9 mmol) was added dropwise. The reaction solution was stirred at 25° C. for 60 min, and solids were removed by filtration. The filtrate was concentrated, and purified by chromatography to afford 1-methyl 5-(1,3-dioxoisoindolin-2-yl) (((9H-fluoren-9-yl)methoxy)carbonyl)-L-glutamate (1.0 g, yield 73%).

1-Methyl 5-(1,3-dioxoisoindolin-2-yl) (((9H-fluoren-9-yl)methoxy)carbonyl)-L-glutamate Target compound retention time: 1.0 min (High performance liquid chromatography Condition 3)

ESI (LC/MS positive mode m/z 529 (M+H)$^+$)

Example 30

Production of methyl (S)-2-((((9H-fluoren-9-yl)methoxy)carbonyl)amino)-4-(4-methoxyphenyl)butanoate Example 29

Production of 1-methyl 5-(1,3-dioxoisoindolin-2-yl) (((9H-fluoren-9-yl)methoxy)carbonyl)-L-glutamate

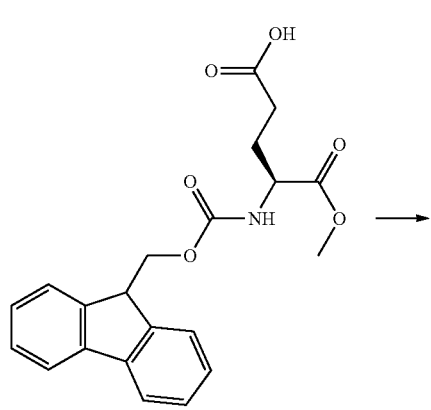

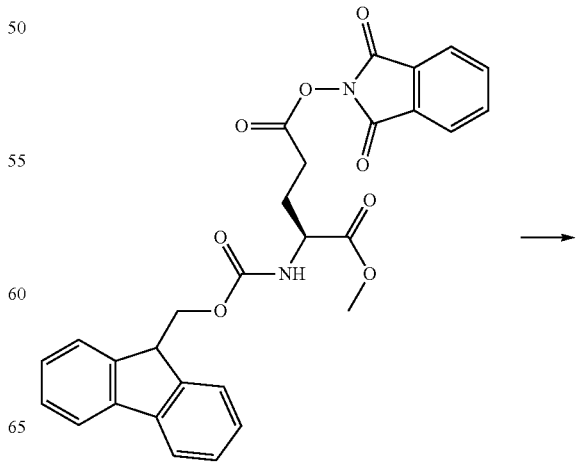

Example 31

Production of (S)-2-((((9H-fluoren-9-yl)methoxy)carbonyl)amino)-4-(4-methoxyphenyl)butanoic Acid

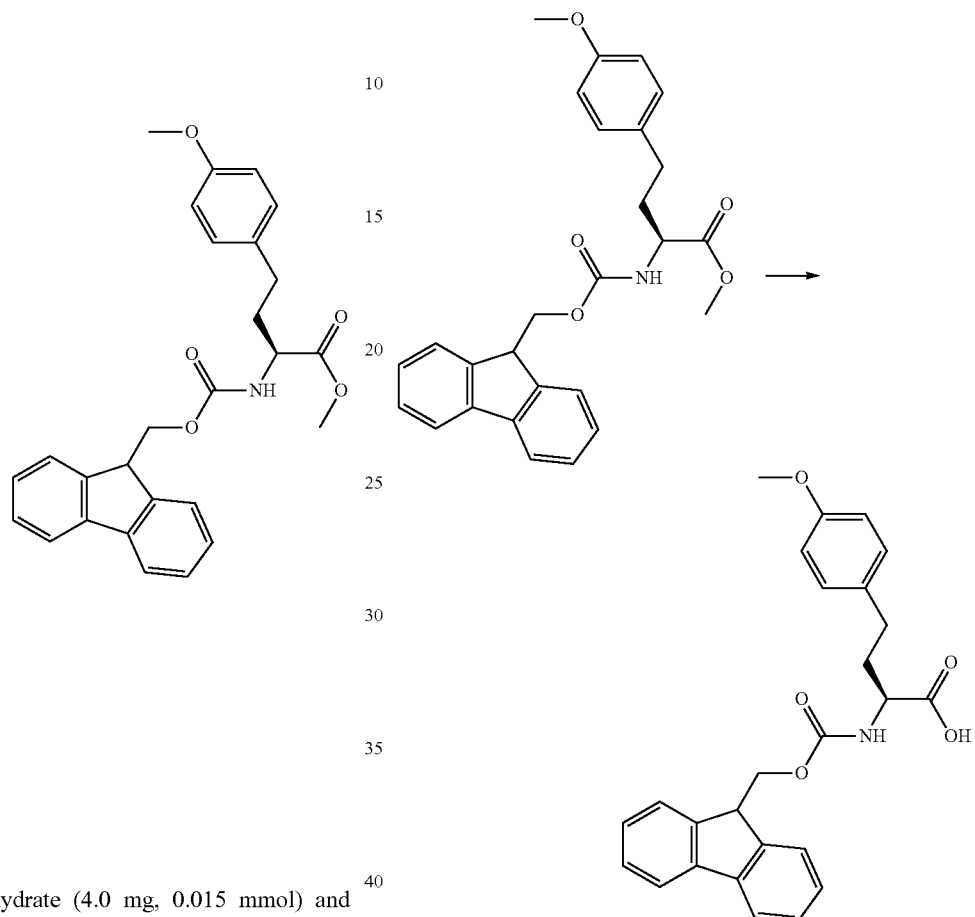

Nickel bromide trihydrate (4.0 mg, 0.015 mmol) and 4,4'-di-tert-butyl-2,2'-bipyridine (4.0 mg, 0.015 mmol) were dissolved in DMA (0.50 mL), and the mixture was purged with nitrogen and then stirred to prepare a catalyst solution. In another vessel, zinc powder (69 mg, 1.1 mmol), 1-methyl 5-(1,3-dioxoisoindolin-2-yl) (((9H-fluoren-9-yl)methoxy)carbonyl)-L-glutamate (0.11 g, 0.21 mmol) and 1-iodo-4-methoxybenzene (0.15 g, 0.63 mmol) were added to and dissolved in DMA (0.50 mL). The prepared catalyst solution was added dropwise to the reaction solution under a nitrogen atmosphere, then TMSCl (11 mg, 0.11 mmol) was added, and the reaction vessel was shaken at 25° C. for 1 h. When the reaction mixture was analyzed by HPLC, it was confirmed that the raw material had completely disappeared, and that the target compound was produced. The reaction solution was purified by chromatography to afford methyl (S)-2-((((9H-fluoren-9-yl)methoxy)carbonyl)amino)-4-(4-methoxyphenyl)butanoate (64 mg, yield 68%).

Methyl (S)-2-((((9H-fluoren-9-yl)methoxy)carbonyl)amino)-4-(4-methoxyphenyl)butanoate Target compound retention time: 0.9 min (High performance liquid chromatography Condition 4)
ESI (LC/MS positive mode m/z 446 (M+H)$^+$)

Water (0.49 mL) and 2-propanol (2.0 mL) were added to calcium chloride (0.19 g, 1.7 mmol) and lithium hydroxide hydrate (19 mg, 0.45 mmol), and the mixture was stirred at room temperature for 15 min. A solution of methyl (S)-2-((((9H-fluoren-9-yl)methoxy)carbonyl)amino)-4-(4-methoxyphenyl)butanoate (50 mg, 0.11 mmol) in THF (0.49 mL) was added dropwise at room temperature thereto, and the mixture was stirred for 20 h. Insoluble matter was removed by filtration, and solids were washed with THF. The filtrate was concentrated, and then purified by chromatography to afford (S)-2-((((9H-fluoren-9-yl)methoxy)carbonyl)amino)-4-(4-methoxyphenyl)butanoic acid (35 mg, 72%).

(S)-2-((((9H-Fluoren-9-yl)methoxy)carbonyl)amino)-4-(4-methoxyphenyl)butanoic Acid Target compound retention time: 0.8 min (High performance liquid chromatography Condition 4)
ESI (LC/MS positive mode m/z 432 (M+H)$^+$)

INDUSTRIAL APPLICABILITY

The present invention provides novel methods of producing optically active aromatic amino acid derivatives that are usable as a raw material of a pharmaceutical product. The use of the production method of the present invention enables efficient production and supply of an optically active aromatic amino acid derivative.

Isolation/purification of the target compounds obtained through the above-described reaction steps can be carried out by applying ordinary chemical operations such as extraction, concentration, distillation, crystallization, filtration, recrystallization, and various types of chromatography.

The compound, the salt of the compound, or the solvate of the compound or the salt of the present invention includes all stereoisomers of the target compound obtained through the above-described reaction steps (such as enantiomers and diastereomers (including cis and trans geometric isomers)), racemates of the isomers, and other mixtures. For example, the compound of the present invention may have one or more asymmetric centers, and the present invention includes racemic mixtures, diastereomeric mixtures, and enantiomers of such a compound.

When the compound according to the present invention is obtained in a free form, the compound can be converted to the state of a salt of the compound or a hydrate or a solvate of the compound or the salt, which the compound may form, according to a conventional method.

The invention claimed is:

1. A method of producing a compound represented by Formula I, a salt of the compound, or a solvate of the compound or the salt:

Formula I

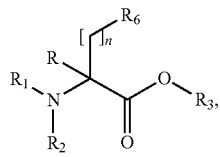

wherein $R_1$ is hydrogen or a protecting group for an amino group;

$R_2$ is hydrogen or $C_1$-$C_6$ alkyl, and $R_3$ is hydrogen or a protecting group for a carboxyl group, or $R_2$ and $R_3$ together form a divalent protecting group;

$R_6$ is optionally substituted $C_6$-$C_{10}$ aryl or optionally substituted heteroaryl;

$R_7$ is hydrogen or $C_1$-$C_4$ alkyl; and n is 1 or 2, the method comprising the step of mixing a compound represented by Formula II, a salt of the compound, or a solvate of the compound or the salt, with a reducing agent, an additive, and $R_6$—X, wherein $R_6$ is the same as $R_6$ of the compound represented by Formula I, and X is halogen, OTf, or OMs, in the presence of a solvent and a catalyst to obtain the compound represented by Formula I, the salt of the compound, or the solvate of the compound or the salt:

Formula II

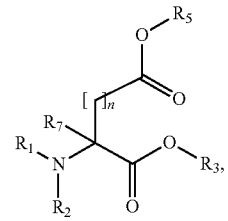

wherein $R_1$, $R_2$, $R_3$, $R_7$, and n are the same as $R_1$, $R_2$, $R_3$, $R_7$, and n of the compound represented by Formula I, respectively;

$R_5$ is

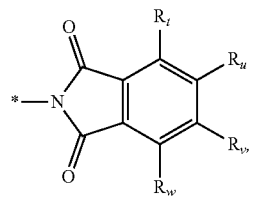

$R_t$, $R_u$, $R_v$, and $R_w$ are independently hydrogen, halogen, or nitro; and

* indicates a point of bonding wherein the additive is (1) a silyl compound represented by Formula A:

wherein $R_{AX}$ and $R_{AY}$ are independently selected from the group consisting of $C_1$-$C_4$ alkyl, $C_1$-$C_4$ alkoxy, and phenyl; and L is selected from the group consisting of —Cl, —Br, —I, and —OTf, or (2) 1,2-dibromoethane.

2. The method of claim 1, wherein $R_1$ is a protecting group for an amino group, and the protecting group for an amino group is selected from the group consisting of Fmoc, Boc, Alloc, Cbz, Teoc, and trifluoroacetyl.

3. The method of claim 1, wherein $R_3$ is a protecting group for a carboxyl group, and the protecting group for a carboxyl group is selected from the group consisting of methyl, ethyl, t-Bu, benzyl, trityl, cumyl, methoxytrityl, and 2-(trimethylsilyl)ethyl.

4. The method of claim 1, wherein
R₂ and R₃ together form a divalent protecting group, the divalent protecting group is —(CR₈R₉)—, and Formula I is represented by Formula IA:

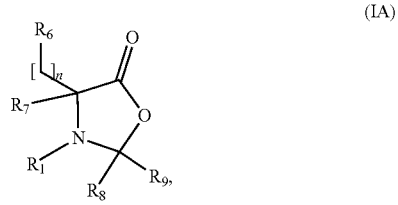
(IA)

wherein
R₁, R₆, R₇, and n are the same as R₁, R₆, R₇, and n of the compound represented by Formula I, respectively; and R₈ and R₉ are independently hydrogen, $C_1$-$C_4$ alkyl or $C_6$-$C_{10}$ aryl, or R₈ and R₉ together form oxo (=O).

5. The method of claim 1, wherein the additive is selected from the group consisting of TMSCl, TMSBr, TMSI, TMSOTf, TBDMSCl, TESCl, TIPSCl, TBDPSCl, and chlorotriethoxysilane.

6. The method of claim 1 wherein R₅ is:

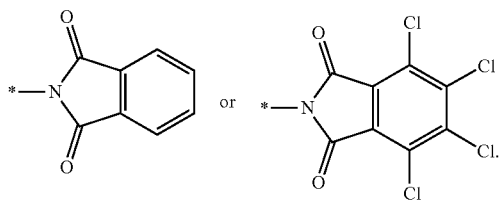 [SMILES: *N1C(=O)c2ccccc2C1=O ; *N1C(=O)c2c(Cl)c(Cl)c(Cl)c(Cl)c2C1=O]

7. The method of claim 1, wherein X is iodine or bromine, and R₆ is optionally substituted phenyl or optionally substituted pyridyl.

8. The method of claim 7, wherein the optionally substituted phenyl or the optionally substituted pyridyl is substituted with 0 to 3 substituents independently selected from the group consisting of $C_1$-$C_4$ alkyl, $C_1$-$C_4$ haloalkyl, $C_1$-$C_4$ alkoxy, $C_1$-$C_4$ haloalkoxy, $C_2$-$C_6$ alkenyloxy, halogen, $C_3$-$C_8$ cycloalkyl, —NR$_p$R$_q$, wherein R$_p$ and R$_q$ are independently hydrogen or $C_1$-$C_4$ alkyl, —CONR$_r$R$_s$, wherein R$_r$ and R$_s$ are independently selected from the group consisting of hydrogen, hydroxy, protected hydroxy, $C_1$-$C_4$ alkyl, and $C_1$-$C_4$ alkylsulfonyl, and cyclic boryl.

9. The method of claim 1, wherein the catalyst is:
(a) a metal;
(b) formed by mixing a metal and a ligand compound therefor;
(c) a complex of a metal and a ligand therefor; or
(d) formed by further mixing, with the complex of a metal and a ligand therefor, a ligand compound for the metal, and
wherein the metal is nickel, chromium, iron, copper, palladium or a salt of these metals, or is a solvate of nickel, chromium, iron, copper, palladium or a salt of these metals.

10. The method of claim 9, wherein the metal is selected from the group consisting of NiBr₂, NiI₂, NiCl₂, NiF₂, Ni(OAc)₂, Ni(acac)₂, Ni(OTf)₂, NiCO₃, Ni(NO₃)₂, NiSO₄, (NH₄)₂Ni(SO₄)₂, allyl(cyclopentadienyl)nickel(II), bis(cyclopentadienyl)nickel, and bis(cyclooctadienyl)nickel, or is a solvate of these metals.

11. The method of claim 9, wherein the ligand compound is selected from:
(i) a compound represented by Formula B:

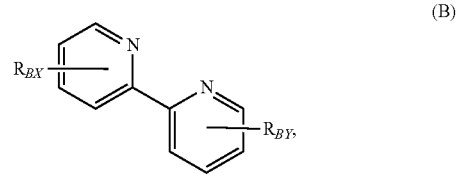
(B)

wherein R$_{BX}$ and R$_{BY}$ are independently selected from hydrogen, $C_1$-$C_4$ alkyl, $C_1$-$C_4$ alkoxy, heterocyclyl, and $C_6$-$C_{10}$ aryl;

(ii) a compound represented by Formula C:

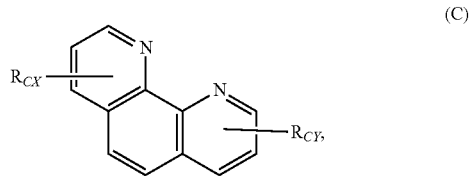
(C)

wherein R$_{CX}$ and R$_{CY}$ are independently selected from hydrogen, $C_1$-$C_4$ alkyl, $C_6$-$C_{10}$ aryl, and heteroaryl;

(iii) a compound represented by Formula D:

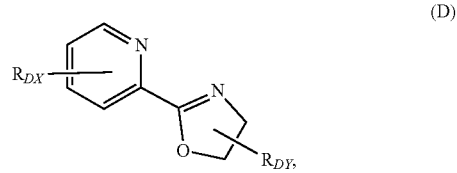
(D)

wherein R$_{DX}$ and R$_{DY}$ are independently selected from hydrogen, $C_1$-$C_4$ alkyl, $C_1$-$C_4$ haloalkyl, and $C_6$-$C_{10}$ aryl;

(iv) a compound represented by Formula E:

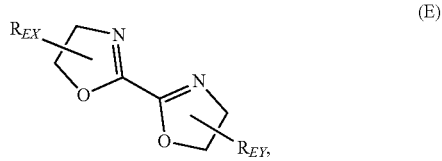
(E)

wherein R$_{EX}$ and R$_{EY}$ are independently selected from hydrogen, $C_1$-$C_4$ alkyl, $C_6$-$C_{10}$ aryl $C_1$-$C_6$ alkyl, and $C_6$-$C_{10}$ aryl;

(v) a compound represented by Formula F:

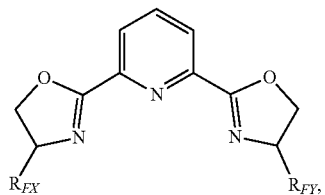

(F)

wherein $R_{FX}$ and $R_{FY}$ are independently selected from hydrogen, $C_1$-$C_4$ alkyl, and $C_6$-$C_{10}$ aryl; and (vi) a compound represented by Formula G:

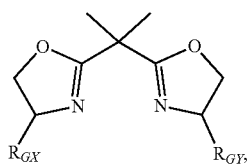

(G)

wherein $R_{GX}$ and $R_{GY}$ are independently selected from hydrogen, $C_1$-$C_4$ alkyl, $C_6$-$C_{10}$ aryl $C_1$-$C_6$ alkyl, and $C_6$-$C_{10}$ aryl.

12. The method of claim 9, wherein the catalyst is a complex of a metal and a ligand therefor, and the complex of a metal and a ligand therefor is selected from the group consisting of tetrakis(triphenylphosphine)nickel(O), bis(triphenylphosphine)nickel(II) dichloride, bis(tricyclohexylphosphine)nickel(II) dichloride, dibromobis(triphenylphosphine)nickel(II), bis[(2-dimethylamino)phenyl]aminenickel(II) chloride, cis-[2,2'-bis(diphenylphosphino)-1,1'-binaphthyl](2-methylphenyl)nickel(II) chloride, and [1,2-bis(diphenylphosphino)ethane]dichloronickel(II).

13. The method of claim 1, wherein the reducing agent is selected from the group consisting of zinc, manganese, iron, and magnesium.

14. The method of claim 1, wherein
(a) the compound represented by Formula II, the salt of the compound, or the solvate of the compound or the salt, the reducing agent, and $R_6$—X are mixed in the presence of the solvent and the catalyst, and then the additive is mixed therewith;
(b) the reducing agent and the additive are mixed in the presence of the solvent and the catalyst, and then the compound represented by Formula II, the salt of the compound, or the solvate of the compound or the salt, and $R_6$—X are mixed therewith; or
(c) the reducing agent is mixed with the solvent and the catalyst, and then the compound represented by Formula II, the salt of the compound, or the solvate of the compound or the salt, $R_6$—X, and the additive are mixed therewith.

15. The method of claim 1, wherein the catalyst is formed by mixing a metal and a ligand compound therefor, wherein the metal is nickel or a salt thereof, or a solvate of the nickel or salt thereof.

16. The method of claim 1, wherein the catalyst is formed by mixing a metal and a ligand compound therefor, wherein the metal is selected from the group consisting of $NiBr_2$, $NiI_2$, $NiCl_2$, $NiF_2$, $Ni(OAc)_2$, $Ni(acac)_2$, $Ni(OTf)_2$, $NiCO_3$, $Ni(NO_3)_2$, $NiSO_4$, $(NH_4)_2Ni(SO_4)_2$, allyl(cyclopentadienyl)nickel(II), bis(cyclopentadienyl)nickel, and bis(cyclooctadienyl)nickel, or is a solvate of these metals; and the ligand compound is selected from:
(i) a compound represented by Formula B:

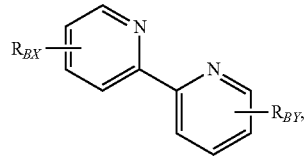

(B)

wherein $R_{BX}$ and $R_{BY}$ are independently selected from hydrogen, $C_1$-$C_4$ alkyl, $C_1$-$C_4$ alkoxy, heterocyclyl, and $C_6$-$C_{10}$ aryl;

(ii) a compound represented by Formula C:

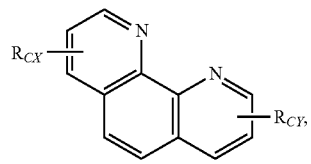

(C)

wherein $R_{CX}$ and $R_{CY}$ are independently selected from hydrogen, $C_1$-$C_4$ alkyl, $C_6$-$C_{10}$ aryl, and heteroaryl;

(iii) a compound represented by Formula D:

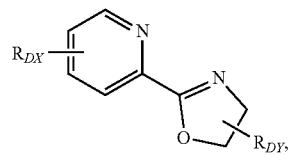

(D)

wherein $R_{DX}$ and $R_{DY}$ are independently selected from hydrogen, $C_1$-$C_4$ alkyl, $C_1$-$C_4$ haloalkyl, and $C_6$-$C_{10}$ aryl;

(iv) a compound represented by Formula E:

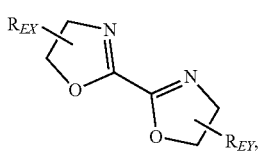

(E)

wherein $R_{EX}$ and $R_{EY}$ are independently selected from hydrogen, $C_1$-$C_4$ alkyl, $C_6$-$C_{10}$ aryl $C_1$-$C_6$ alkyl, and $C_6$-$C_{10}$ aryl;

(v) a compound represented by Formula F:

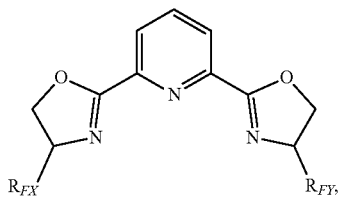
(F)

wherein $R_{FX}$ and $R_{FY}$ are independently selected from hydrogen, $C_1$-$C_4$ alkyl, and $C_6$-$C_{10}$ aryl; and (vi) a compound represented by Formula G:

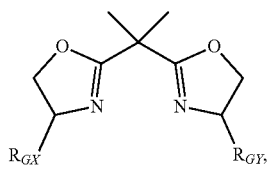
(G)

wherein $R_{GX}$ and $R_{GY}$ are independently selected from hydrogen, $C_1$-$C_4$ alkyl, $C_6$-$C_{10}$ aryl $C_1$-$C_6$ alkyl, and $C_6$-$C_{10}$ aryl.

17. The method of claim 16, wherein $R_1$ is a protecting group for an amino group.

18. The method of claim 16, wherein $R_3$ is a protecting group for a carboxyl group.

19. The method of claim 17, wherein $R_3$ is a protecting group for a carboxyl group.

20. The method of claim 1, wherein $R_1$ is a protecting group for an amino group, and the protecting group for an amino group is selected from the group consisting of Fmoc, Boc, Alloc, Cbz, Teoc, and trifluoroacetyl; and $R_3$ is a protecting group for a carboxyl group, and the protecting group for a carboxyl group is selected from the group consisting of methyl, ethyl, t-Bu, benzyl, trityl, cumyl, methoxytrityl, and 2-(trimethylsilyl)ethyl.

21. The method of claim 16, wherein $R_1$ is a protecting group for an amino group, and the protecting group for an amino group is selected from the group consisting of Fmoc, Boc, Alloc, Cbz, Teoc, and trifluoroacetyl; and $R_3$ is a protecting group for a carboxyl group, and the protecting group for a carboxyl group is selected from the group consisting of methyl, ethyl, t-Bu, benzyl, trityl, cumyl, methoxytrityl, and 2-(trimethylsilyl)ethyl.

22. The method of claim 16, wherein the reducing agent is zinc.

23. The method of claim 19, wherein the reducing agent is zinc.

24. The method of claim 21, wherein the reducing agent is zinc.

25. A method of producing a compound represented by Formula III, a salt of the compound, or a solvate of the compound or the salt, through a compound represented by Formula I, a salt of the compound, or a solvate of the compound or the salt:

Formula I

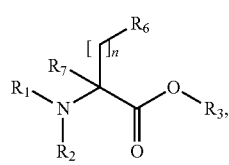
(I)

wherein $R_1$ is hydrogen or a protecting group for an amino group;

$R_2$ is hydrogen or $C_1$-$C_6$ alkyl, $R_3$ is a protecting group for a carboxyl group;

$R_6$ is optionally substituted $C_6$-$C_{10}$ aryl or optionally substituted heteroaryl;

$R_7$ is hydrogen or $C_1$-$C_4$ alkyl; and n is 1 or 2;

Formula III

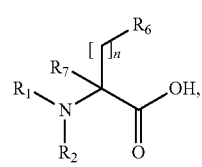
(III)

wherein $R_1$, $R_2$, $R_6$, $R_7$, and n are the same as $R_1$, $R_2$, $R_6$, $R_7$, and n of the compound represented by Formula I, respectively, the method comprising the steps of:

(1) mixing a compound represented by Formula II, a salt of the compound, or a solvate of the compound or the salt, with a reducing agent, an additive, and $R_6$—X, wherein $R_6$ is the same as $R_6$ of the compound represented by Formula I, and X is halogen, OTf, or OMs, in the presence of a solvent and a catalyst to obtain the compound represented by Formula I, the salt of the compound, or the solvate of the compound or the salt:

Formula II

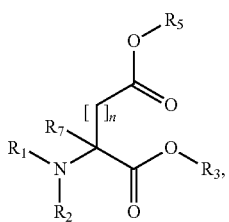
(II)

wherein

R$_1$, R$_2$, R$_3$, R$_7$, and n are the same as R$_1$, R$_2$, R$_3$, R$_7$, and n of the compound represented by Formula I, respectively;

R$_5$ is

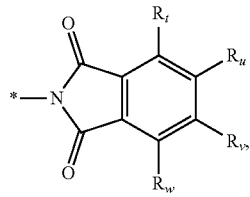

R$_t$, R$_u$, R$_v$, and R$_w$ are independently hydrogen, halogen, or nitro; and

* indicates a point of bonding wherein the additive is (a) a silyl compound represented by Formula A:

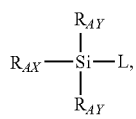

(A)

wherein

R$_{AX}$ and R$_{AY}$ are independently selected from the group consisting of C$_1$-C$_4$ alkyl, C$_1$-C$_4$ alkoxy, and phenyl; and L is selected from the group consisting of —Cl, —Br, —I, and —OTf, or (b) 1,2-dibromoethane; and (2) removing the protecting group R$_3$ from the compound represented by Formula I, the salt of the compound, or the solvate of the compound or the salt, to obtain the compound represented by Formula III, the salt of the compound, or the solvate of the compound or the salt.

26. The method of claim 25, wherein in step (1), the catalyst is formed by mixing a metal and a ligand compound therefor, wherein the metal is selected from the group consisting of NiBr$_2$, NiI$_2$, NiCl$_2$, NiF$_2$, Ni(OAc)$_2$, Ni(acac)$_2$, Ni(OTf)$_2$, NiCO$_3$, Ni(NO$_3$)$_2$, NiSO$_4$, (NH$_4$)$_2$Ni(SO$_4$)$_2$, allyl(cyclopentadienyl)nickel(II), bis(cyclopentadienyl)nickel, and bis(cyclooctadienyl)nickel, or is a solvate of these metals; and the ligand compound is selected from:

(i) a compound represented by Formula B:

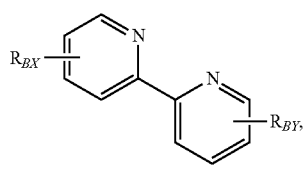

(B)

wherein R$_{BX}$ and R$_{BY}$ are independently selected from hydrogen, C$_1$-C$_4$ alkyl, C$_1$-C$_4$ alkoxy, heterocyclyl, and C$_6$-C$_{10}$ aryl;

(ii) a compound represented by Formula C:

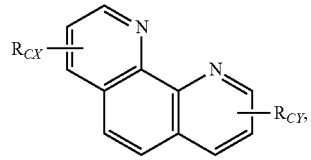

(C)

wherein R$_{CX}$ and R$_{CY}$ are independently selected from hydrogen, C$_1$-C$_4$ alkyl, C$_6$-C$_{10}$ aryl, and heteroaryl;

(iii) a compound represented by Formula D:

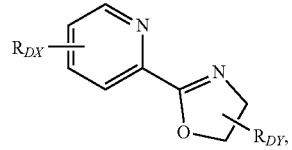

(D)

wherein R$_{DX}$ and R$_{DY}$ are independently selected from hydrogen, C$_1$-C$_4$ alkyl, C$_1$-C$_4$ haloalkyl, and C$_6$-C$_{10}$ aryl;

(iv) a compound represented by Formula E:

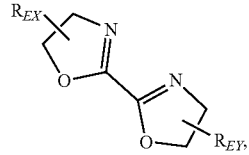

(E)

wherein R$_{EX}$ and R$_{EY}$ are independently selected from hydrogen, C$_1$-C$_4$ alkyl, C$_6$-C$_{10}$ aryl C$_1$-C$_6$ alkyl, and C$_6$-C$_{10}$ aryl;

(v) a compound represented by Formula F:

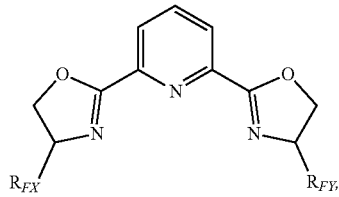

(F)

wherein R$_{FX}$ and R$_{FY}$ are independently selected from hydrogen, C$_1$-C$_4$ alkyl, and C$_6$-C$_{10}$ aryl; and (vi) a compound represented by Formula G:

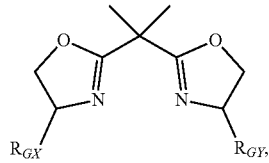

(G)

wherein $R_{GX}$ and $R_{GY}$ are independently selected from hydrogen, $C_1$-$C_4$ alkyl, $C_6$-$C_{10}$ aryl $C_1$-$C_6$ alkyl, and $C_6$-$C_{10}$ aryl.

27. The method of claim 26, wherein in step (1), the reducing agent is zinc.

28. The method of claim 27, wherein $R_1$ in Formula I and III is a protecting group for an amino group.

29. A method of producing a compound represented by Formula IV, a salt of the compound, or a solvate of the compound or the salt, through a compound represented by Formula I, a salt of the compound, or a solvate of the compound or the salt:

Formula I

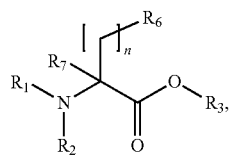

(1)

wherein
  $R_1$ is a protecting group for an amino group;
  $R_2$ is hydrogen or $C_1$-$C_6$ alkyl,
$R_3$ is a protecting group for a carboxyl group;
  $R_6$ is optionally substituted $C_6$-$C_{10}$ aryl or optionally substituted heteroaryl;
  $R_7$ is hydrogen or $C_1$-$C_4$ alkyl; and
  n is 1 or 2;
Formula IV:

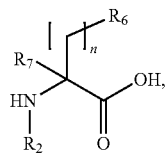

(IV)

wherein $R_2$, $R_6$, $R_7$, and n are the same as $R_2$, $R_6$, $R_7$, and n of the compound represented by Formula I, respectively, the method comprising the steps of:
  (1) mixing a compound represented by Formula II, a salt of the compound, or a solvate of the compound or the salt, with a reducing agent, an additive, and $R_6$—X, wherein $R_6$ is the same as $R_6$ of the compound represented by Formula I, and X is halogen, OTf, or OMs, in the presence of a solvent and a catalyst to obtain the compound represented by Formula I, the salt of the compound, or the solvate of the compound or the salt:

Formula II

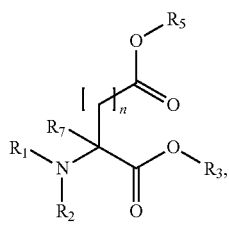

(II)

wherein
  $R_1$, $R_2$, $R_3$, $R_7$, and n are the same as $R_1$, $R_2$, $R_3$, $R_7$, and n of the compound represented by Formula I, respectively;
  $R_5$ is

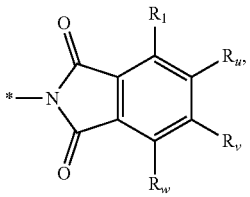

$R_t$, $R_u$, $R_v$, and $R_w$ are independently hydrogen, halogen, or nitro; and
  * indicates a point of bonding
wherein the additive is (a) a silyl compound represented by Formula A:

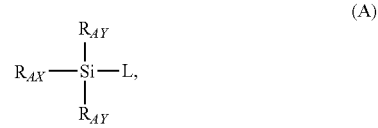

(A)

wherein
  $R_{AX}$ and $R_{AY}$ are independently selected from the group consisting of $C_1$-$C_4$ alkyl, $C_1$-$C_4$ alkoxy, and phenyl; and
  L is selected from the group consisting of —Cl, —Br, —I, and —OTf, or (b) 1,2-dibromoethane; and
  (2) removing the protecting groups $R_1$ and $R_3$ from the compound represented by Formula I, the salt of the compound, or the solvate of the compound or the salt, to obtain the compound represented by Formula IV, the salt of the compound, or the solvate of the compound or the salt.

30. The method of claim 29, wherein in step (1) the catalyst is formed by mixing a metal and a ligand compound therefor, wherein the metal is selected from the group consisting of $NiBr_2$, $NiI_2$, $NiCl_2$, $NiF_2$, $Ni(OAc)_2$, $Ni(acac)_2$, $Ni(OTf)_2$, $NiCO_3$, $Ni(NO_3)_2$, $NiSO_4$, $(NH_4)_2Ni(SO_4)_2$, allyl (cyclopentadienyl)nickel(II), bis(cyclopentadienyl)nickel, and bis(cyclooctadienyl)nickel, or is a solvate of these metals; and
  the ligand compound is selected from:
  (i) a compound represented by Formula B:

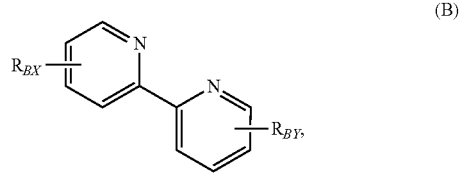

(B)

wherein $R_{BX}$ and $R_{BY}$ are independently selected from hydrogen, $C_1$-$C_4$ alkyl, $C_1$-$C_4$ alkoxy, heterocyclyl, and $C_6$-$C_{10}$ aryl;

(ii) a compound represented by Formula C:

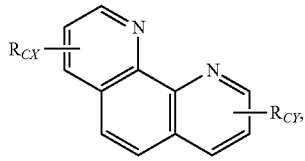
(C)

wherein $R_{CX}$ and $R_{CY}$ are independently selected from hydrogen, $C_1$-$C_4$ alkyl, $C_6$-$C_{10}$ aryl, and heteroaryl;

(iii) a compound represented by Formula D:

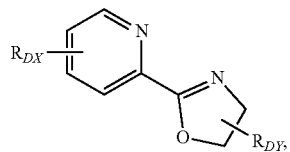
(D)

wherein $R_{DX}$ and $R_{DY}$ are independently selected from hydrogen, $C_1$-$C_4$ alkyl, $C_1$-$C_4$ haloalkyl, and $C_6$-$C_{10}$ aryl;

(iv) a compound represented by Formula E:

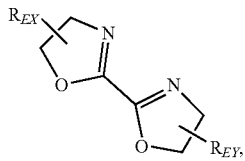
(E)

wherein $R_{EX}$ and $R_{EY}$ are independently selected from hydrogen, $C_1$-$C_4$ alkyl, $C_6$-$C_{10}$ aryl $C_1$-$C_6$ alkyl, and $C_6$-$C_{10}$ aryl;

(v) a compound represented by Formula F:

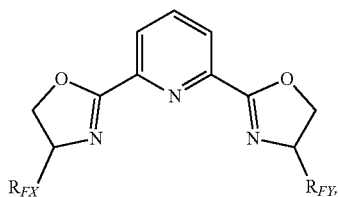
(F)

wherein $R_{FX}$ and $R_{FY}$ are independently selected from hydrogen, $C_1$-$C_4$ alkyl, and $C_6$-$C_{10}$ aryl; and (vi) a compound represented by Formula G:

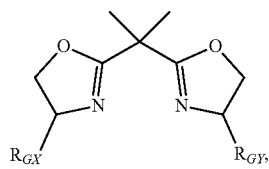
(G)

wherein $R_{GX}$ and $R_{GY}$ are independently selected from hydrogen, $C_1$-$C_4$ alkyl, $C_6$-$C_{10}$ aryl $C_1$-$C_6$ alkyl, and $C_6$-$C_{10}$ aryl.

31. The method of claim 30, wherein in step (1), the reducing agent is zinc.

\* \* \* \* \*